US012753225B2

(12) United States Patent
Sun et al.

(10) Patent No.: US 12,753,225 B2
(45) **Date of Patent: *Oct. 6, 2026**

(54) ANTI-MS4A4A ANTIBODIES AND METHODS OF USE THEREOF

(71) Applicant: Alector LLC, South San Francisco, CA (US)

(72) Inventors: Jeonghoon Sun, San Francisco, CA (US); Wei-Hsien Ho, Belmont, CA (US); Muhammad A. Alhawagri, San Francisco, CA (US); Philip Ling Kong, San Francisco, CA (US); Herve Rhinn, San Francisco, CA (US); Hua Long, San Carlos, CA (US); Karpagam Srinivasan, San Jose, CA (US); Ananya Mitra, Menlo Park, CA (US); Daniel P. Bermingham, San Francisco, CA (US); Klaus-Dieter Heger, San Mateo, CA (US); Santiago Viveros Salazar, San Carlos, CA (US); Francesca Cignarella, South San Francisco, CA (US); Ilaria Tassi, San Francisco, CA (US); Tina Schwabe, San Francisco, CA (US); Angie Grace Yee, San Francisco, CA (US); Arnon Rosenthal, Woodside, CA (US)

(73) Assignee: Alector LLC, South San Francisco, CA (US)

( * ) Notice: Subject to any disclaimer, the term of this patent is extended or adjusted under 35 U.S.C. 154(b) by 727 days.

This patent is subject to a terminal disclaimer.

(21) Appl. No.: 18/310,207

(22) Filed: May 1, 2023

(65) Prior Publication Data

US 2024/0076362 A1 Mar. 7, 2024

Related U.S. Application Data

(63) Continuation of application No. 16/943,123, filed on Jul. 30, 2020, now Pat. No. 11,667,699.

(60) Provisional application No. 63/057,142, filed on Jul. 27, 2020, provisional application No. 62/960,606, filed on Jan. 13, 2020, provisional application No. 62/947,449, filed on Dec. 12, 2019, provisional application No. 62/892,467, filed on Aug. 27, 2019, provisional application No. 62/881,187, filed on Jul. 31, 2019.

(51) Int. Cl.
*C07K 16/18* (2006.01)
*A61K 39/00* (2006.01)

(52) U.S. Cl.
CPC ........ *C07K 16/18* (2013.01); *A61K 2039/505* (2013.01); *C07K 2317/24* (2013.01); *C07K 2317/31* (2013.01); *C07K 2317/34* (2013.01); *C07K 2317/732* (2013.01); *C07K 2317/734* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 11,472,874 B2 | 10/2022 | Kong et al. | |
| 11,667,699 B2 | 6/2023 | Sun et al. | |
| 2009/0011409 A1 | 1/2009 | Sharma et al. | |
| 2010/0034736 A1* | 2/2010 | Sanchez-Garcia ... | C12Q 1/6881 435/7.1 |
| 2011/0286916 A1* | 11/2011 | Aste-Amezaga ........................ | G01N 33/57415 424/1.49 |
| 2016/0376359 A1 | 12/2016 | Wang et al. | |
| 2017/0355756 A1 | 12/2017 | Julien et al. | |
| 2018/0244770 A1 | 8/2018 | Monroe et al. | |
| 2021/0040200 A1 | 2/2021 | Kong et al. | |
| 2021/0122817 A1 | 4/2021 | Kong et al. | |
| 2022/0380455 A1 | 12/2022 | Kong et al. | |
| 2023/0126400 A1 | 4/2023 | Kong et al. | |
| 2023/0142579 A1 | 5/2023 | Kong et al. | |

FOREIGN PATENT DOCUMENTS

| | | | |
|---|---|---|---|
| CN | 101001879 | A | 7/2007 |
| CN | 101998992 | A | 3/2011 |
| CN | 105759057 | A | 7/2016 |
| CN | 105969901 | A | 9/2016 |
| CN | 110662765 | A | 1/2020 |
| JP | 2013534411 | A | 9/2013 |
| WO | WO-02062946 | A2 | 8/2002 |
| WO | WO-2003035689 | A1 | 5/2003 |
| WO | WO-2005040796 | A1 | 5/2005 |
| WO | WO-2005123779 | A2 | 12/2005 |

(Continued)

OTHER PUBLICATIONS

Edwards, B.M., et al., "The remarkable flexibility of the human antibody repertoire; isolation of over one thousand different antibodies to a single protein, BLyS," J Mol Biol 334(1):103-118, Elsevier, Netherlands (Nov. 2003).

(Continued)

*Primary Examiner* — Adam Weidner
(74) *Attorney, Agent, or Firm* — McNeill PLLC

(57) ABSTRACT

The present disclosure is generally directed to compositions that include antibodies, e.g., monoclonal antibodies, humanized antibodies and antibody fragments, that specifically bind a MS4A4A polypeptide, e.g., a mammalian MS4A4A or human MS4A4A, and use of such compositions in preventing, reducing risk, or treating an individual in need thereof.

27 Claims, 50 Drawing Sheets

Specification includes a Sequence Listing.

(56) References Cited

FOREIGN PATENT DOCUMENTS

| | | | |
|---|---|---|---|
| WO | WO-2008068048 | A2 | 6/2008 |
| WO | WO-2011147851 | A1 | 12/2011 |
| WO | WO-2017143036 | A1 | 8/2017 |
| WO | 2019028283 | A1 | 2/2019 |
| WO | WO-2019152706 | A1 | 8/2019 |
| WO | WO-2019152715 | A1 | 8/2019 |
| WO | WO-2020160468 | A1 | 8/2020 |
| WO | WO-2021022083 | A2 | 2/2021 |
| WO | WO-2021081101 | A1 | 4/2021 |
| WO | WO-2024086796 | A1 | 4/2024 |

OTHER PUBLICATIONS

NCBI, "Membrane-spanning 4-domains subfamily A member 4A isoform 1 [*Homo sapiens*]," Accession No. NP_683876, May 2, 2019, accessed at https://www.ncbi.nlm.nih.gov/protein/NP_683876.1/, 3 pages.

Al-Shawi, R., et al., "Neurotoxic and Neurotrophic Roles of ProNGF and the Receptor Sortilin in the Adult and Ageing Nervous System," *European Journal of Neuroscience 28*(9):2103-2114, Wiley-Blackwell Publishing Ltd., United Kingdom (Dec. 2008).

Allen, M., et al., "Novel late-onset Alzheimer disease loci variants associate with brain gene expression," *Neurology 79*(3):221-228, Lippincott Williams and Wilkins Ltd., United States (Jul. 2012).

Antúnez, C., et al., "The membrane-spanning 4-domains, subfamily A (MS4A) gene cluster contains a common variant associated with Alzheimer's disease," *Genome Medicine 3*:33, BioMed Central Ltd., United Kingdom (May 2011).

Arnett, M.J., et al., "Pro-NGF, Sortilin, and $p75^{NTR}$: Potential Mediators of Injury-induced Apoptosis in the Mouse Dorsal Root Ganglion," *Brain Research 1183*:32-42, Elsevier, Netherlands (Dec. 2007).

Barber, R.C., "The Genetics of Alzheimer's Disease," *Scientifica (Cairo)* 2012:246210, 14 pages, Hindawi Publishing Corporation, Egypt (Dec. 2012).

Beattie, M.S., et al., "ProNGF Induces p75-mediated Death of Oligodendrocytes Following Spinal Cord Injury," *Neuron 36*(3):375-386, Cell Press, United States (Oct. 2002).

Bubien, J.K., et al., "Transfection of the CD20 Cell Surface Molecule Into Ectopic Cell Types Generates a $Ca^{2+}$ Conductance Found Constitutively in B Lymphocytes," *The Journal of Cell Biology 121*(5):1121-1132, Rockefeller University Press, United States (Jun. 1993).

Cruse, G., et al., "The CD20 Homologue MS4A4 Directs Trafficking of KIT Toward Clathrin-independent Endocytosis Pathways and Thus Regulates Receptor Signaling and Recycling," *Molecular Biology of the Cell 26*(9):1711-1727, American Society for Cell Biology, United States (May 2015).

Deming, Y., et al., "The MS4A gene cluster is a key regulator of soluble TREM2 and Alzheimer disease risk," *Science Translational Medicine 11*(505):eaau2291, 34 pages, American Association for the Advancement of Science, United States (Aug. 14, 2019).

Denardo, D.G., et al., "Leukocyte Complexity Predicts Breast Cancer Survival and Functionally Regulates Response to Chemotherapy," *Cancer Discovery 1*(1):54-67, American Association for Cancer Research, United States (Jun. 2011).

Drake, A.W., and Klakamp, S.L., "A Rigorous Multiple Independent Binding Site Model for Determining Cell-based Equilibrium Dissociation Constants," *Journal of Immunological Methods 318*(1-2):147-152, Elsevier, Netherlands (Jan. 2007).

Efthymiou, A.G., and Goate, A.M., "Late Onset Alzheimer's Disease Genetics Implicates Microglial Pathways in Disease Risk," *Molecular Neurodegeneration 12*:43, BioMed Central Ltd., United Kingdom (May 2017).

Elias-Sonnenschein, L.S., et al., "Genetic loci associated with Alzheimer's disease and cerebrospinal fluid biomarkers in a Finnish case-control cohort," *PLoS One 8*(4):e59676, 9 pages, Public Library of Science, United States (Apr. 2013).

Engle, S.J., et al., "Best Practices For Translational Disease Modeling Using Human iPSC-derived Neurons," *Neuron 100*(4):783-797, Cell Press, United States (Nov. 2018).

Fahnestock, M., et al., "The Precursor Pro-nerve Growth Factor is the Predominant Form of Nerve Growth Factor in Brain and is Increased in Alzheimer's Disease," *Molecular and Cellular Neuroscience 18*(2):210-220, Academic Press, United States (Aug. 2001).

Fan, Y.J., et al., "Differential Effects of Pro-BDNF on Sensory Neurons After Sciatic Nerve Transection in Neonatal Rats," *European Journal of Neuroscience 27*(9):2380-2390, Wiley-Blackwell, France (May 2008).

Greer, P.L., et al., "A Family of Non-GPCR Chemosensors Defines an Alternative Logic for Mammalian Olfaction," *Cell 165*(7):1734-1748, Cell Press, United States (Jun. 2016).

Harrington, A.W., et al., "Secreted ProNGF is a Pathophysiological Death-inducing Ligand After Adult CNS Injury," *Proceedings of the National Academy of Sciences of the United States of America 101*(16):6226-6230, National Academy of Sciences, United States (Apr. 2004).

Hollingworth, P., et al., "Common Variants at ABCA7, MS4A6A/MS4A4E, EPHA1, CD33 and CD2AP Are Associated With Alzheimer's Disease," *Nature Genetics 43*(5):429-435, Nature Publishing Group, United Kingdom (May 2011).

Idusogie, E.E., et al., "Mapping of the C1q Binding Site on Rituxan, A Chimeric Antibody with a Human IgG1 Fc," *The Journal of Immunology 164*(8):4178-4184, American Association of Immunologists, United States (2000).

Ishibashi, K., et al., "Identification of a New Multigene Four-transmembrane Family (MS4A) Related to CD20, HTm4 and β Subunit of the High-affinity IgE Receptor," *Gene 264*(1):87-93, Elsevier, Netherlands (Feb. 2001).

International Search Report and Written Opinion for Application No. PCT/US2019/016156, European Patent Office, Netherlands, mailed on Apr. 23, 2019, 13 pages.

Jansen, P., et al., "Roles for the Pro-neurotrophin Receptor Sortilin in Neuronal Development, Aging and Brain Injury," *Nature Neuroscience 10*(11):1449-1457, Nature Publishing Group, United Kingdom (Nov. 2007).

Karch, C.M., et al., "Expression of novel Alzheimer's disease risk genes in control and Alzheimer's disease brains," *PLoS One 7*(11):e50976, Public Library of Science, United States (Nov. 2012).

Karch, C.M., et al., "Alzheimer's disease risk genes and mechanisms of disease pathogenesis," *Biol Psychiatry 77*(1):43-51, Elsevier Inc., Netherlands (Jan. 2015).

Kay, B.K., et al., "The Importance of Being Proline: the Interaction of Proline-rich Motifs in Signaling Proteins With Their Cognate Domains," *FASEB 14*(2):231-241, The Federation of American Societies for Experimental Biology, United States (Feb. 2000).

Koslowski, M., et al., "MS4A12 is a Colon-selective Store-operated Calcium Channel Promoting Malignant Cell Processes," *Cancer Research 68*(9):3458-3466, American Association for Cancer Research, United States (May 2008).

Kuek, L.E., et al., "The MS4A family: counting past 1, 2 and 3," *Immunology and Cell Biology 94*:11-23, American Society for Immunology Inc., United States (Apr. 2015).

Lambert, J.C., et al., "Meta-analysis of 74,046 Individuals Identifies 11 New Susceptibility Loci for Alzheimer's Disease," *Nature Genetics 45*(12):1452-1458, Nature Publishing Group, United Kingdom (Dec. 2013).

Liang, Y., and Tedder, T.F., "Identification of a CD20-, FcεRIβ-, and HTm4-related Gene Family: Sixteen New MS4A Family Members Expressed in Human and Mouse," *Genomics 72*(2):119-127, Academic Press, United States (Mar. 2001).

Liang, C.C., et al., "In Vitro Scratch Assay: a Convenient and Inexpensive Method for Analysis of Cell Migration in Vitro," *Nature Protocols 2*(2):329-333, Nature Publishing Group, United Kingdom (2007).

Ma, J., et al., "MS4A6A genotypes are associated with the atrophy rates of Alzheimer's disease related brain structures," *Oncotarget 7*(37):58779-58788, Impact Journals LLC, United States (Sep. 2016).

(56) References Cited

OTHER PUBLICATIONS

Murthy, M.N., et al., "Increased Brain Expression of GPNMB Is Associated with Genome Wide Significant Risk for Parkinson's Disease on Chromosome 7p15.3," *Neurogenetics 18*(3):121-133, Springer-Verlag, Germany (Jul. 2017).

Naj, A.C., et al., "Common Variants at MS4A4/MS4A6E, CD2AP, CD33 and EPHA1 Are Associated With Late-onset Alzheimer's Disease," *Nature Genetics 43*(5):436-441, Nature Publishing Group, United Kingdom (May 2011).

Nakamura, K., et al., "Intracellular Sortilin Expression Pattern Regulates ProNGF-induced Naturally Occurring Cell Death During Development," *Cell Death and Differentiation 14*(8):1552-1554, Nature Publishing Group, United Kingdom (Aug. 2007).

Nykjaer, A., et al., "Sortilin is Essential for ProNGF-induced Neuronal Cell Death," *Nature 427*(6977):843-848, Nature Publishing Group, United Kingdom (Feb. 2004).

Nykjaer, A., et al., "$P75^{NTR}$—Live or Let Die," *Current Opinion in Neurobiology 15*(1):49-57, Elsevier Ltd., Netherlands (Feb. 2005).

Peng, X., et al., "Preclinical Evaluation of 3D185, a Novel Potent Inhibitor of FGFR1/2/3 and CSF-1R, in FGFR-Dependent and Macrophage-Dominant Cancer models," *Journal of Experimental & Clinical Cancer Research 38*(1):372, BioMed Central, United Kingdom (Aug. 2019).

Piccio, L., et al., "Cerebrospinal Fluid Soluble TREM2 is Higher in Alzheimer Disease and Associated With Mutation Status," *Acta Neuropathologica 131*(6):925-933, Springer Verlag, Germany (Jun. 2016).

Pocock, J.M., et al., "Modelling Microglial Function With Induced Pluripotent Stem Cells: An Update," *Nature Reviews Neuroscience 19*(8):445-452, Nature Publishing Group, United Kingdom (Aug. 2018).

Provenzano, M.J., et al., "P75NTR and Sortilin Increase After Facial Nerve Injury," *Laryngoscope 118*(1):87-93, Wiley-Blackwell, United States (Jan. 2008).

Salimi, A., et al., "Comparison of Different Protocols for Neural Differentiation of Human Induced Pluripotent Stem Cells," *Molecular Biology Reports 41*(3):1713-1721, Springer, Netherlands (Mar. 2014).

Sanyal, R., et al., "MS4A4A: a novel cell surface marker for M2 macrophages and plasma cells," *Immunology and Cell Biology 95*(7):611-619, American Society for Immunology Inc., United States (Apr. 2017).

Shang, L., et al., "Selective Antibody Intervention of Toll-like Receptor 4 Activation through Fc $\gamma$ Receptor Tethering," *The Journal of Biological Chemistry 289*(22):15309-15318, American Society for Biochemistry and Molecular Biology, United States (May 2014).

Tcw, J., et al., "An Efficient Platform For Astrocyte Differentiation From Human Induced Pluripotent Stem Cells," *Stem Cell Reports 9*(2):600-614, Cell Press, United States (Aug. 2017).

Teng, H.K., et al., "ProBDNF Induces Neuronal Apoptosis via Activation of a Receptor Complex of $P75^{NTR}$ and Sortilin," *The Journal of Neuroscience 25*(22):5455-5463, Society for Neuroscience, United States (Jun. 2005).

Thornton, P., et al., "TREM2 shedding by cleavage at the H157-S158 bond is accelerated for the Alzheimer's disease-associated H157Y variant," *EMBO Mol Med 9*:1366-1378, Wiley-Blackwell, United Kingdom (Oct. 2017).

Tomay, F., "Regulation and function of the tetraspanin-like molecule MS4A4A in alternatively activated and tumor-associated macrophages," XP055578452, Retrieved from the Internet: https://air.unimi.it/retrieve/handle/2434/248877/338927/phd_unimi_R09505.pdf, Feb. 10, 2015, pp. 1-160.

Volosin, M., et al., "Interaction of Survival and Death Signaling in Basal Forebrain Neurons: Roles of Neurotrophins and Proneurotrophins," *The Journal of Neuroscience 26*(29):7756-7766, Society for Neuroscience, United States (Jul. 2006).

Volosin, M., et al., "Induction of Proneurotrophins and Activation of $P75^{NTR}$-mediated Apoptosis via Neurotrophin Receptor-interacting Factor in Hippocampal Neurons After Seizures," *The Journal of Neuroscience 28*(39):9870-9879, Society for Neuroscience, United States (Sep. 2008).

Wei, Y., et al., "Enhanced Protein Expressions of Sortilin and $P75^{NTR}$ in Retina of Rat Following Elevated Intraocular Pressure-induced Retinal Ischemia," *Neuroscience Letters 429*(2-3):169-174, Elsevier, Ireland (Dec. 2007).

Yano, H., et al., "Proneurotrophin-3 Is a Neuronal Apoptotic Ligand: Evidence for Retrograde-Directed Cell Killing," *The Journal of Neuroscience 29*(47):14790-14802, Society for Neuroscience, United States (Nov. 2009).

International Search Report and Written Opinion mailed Jan. 28, 2021, in Application No. PCT/US2020/044335, EPO, Netherlands, 15 pages.

International Search Report and Written Opinion mailed May 30, 2019, in Application No. PCT/US2019/016141, Korean Intellectual Property Office, Korea, 11 pages.

Proitsi, P., et al., "Alzheimer's disease susceptibility variants in the MS4A6A gene are associated with altered levels of MS4A6A expression in blood," Neurobiology of Aging 35:279-290, Elsevier, Netherlands (Sep. 2013).

Puri, M., et al., "The Evaluation of MS4A4A and MS4A8B Expression in Hematopoietic Cells," retrieved from: https://prism.ucalgary.ca/bitstream/handle/11023/1791/ucalgary2014purmandip.pdf;jsessionid=cda23b615634fb7f5836e43810707090?sequence=2, retrieved Oct. 21, 2020, Thesis, 160 pages (Sep. 2014).

Tomay, F., "Regulation and function of the tetraspanin-like molecule MS4A4A in alternatively activated and tumor-associated macrophages," XP055578452, Retrieved from the Internet: https://air.unimi.it/retrieve/handle/2434/248877/338927/phd_unimi_R09505.pdf, Thesis, Feb. 10, 2015, pp. 1-160.

Koeing, P., et al., "Mutational landscape of antibody variable domains reveals a switch modulating the interdomain conformational dynamics and antigen binding," PNAS 114(4):E486-E496, National Academy of Sciences, United States (2017).

Chen, C., et al., "Enhancement and destruction of antibody function by somatic mutation: unequal occurrence is controlled by V gene combinatorial associations," EMBO J 14(12):2784-2794, Wiley-Blackwell, Germany (Jun. 1995).

Kussie, P.H., et al., "A single engineered amino acid substitution changes antibody fine specificity," J Immunol 152(1):146-152, American Association of Immunologists, United States (Jan. 1994).

Reitz, C., "Toward precision medicine in Alzheimer's disease," Ann Transl Med 4(6): 107, AME Publishing Company, China (Mar. 2016).

Stanford, "Alzheimer's Prevention, Treatment and Research—A Q&A with Dr. Frank Longo" accessed from Stanfordhealthcare.org on May 3, 2016 (2016).

Office Action mailed Feb. 28, 2022, in U.S. Appl. No. 16/965,676, Kong, P., et al., filed Jul. 29, 2020, 16 pages.

Hu, X., et al., "Genome-wide association study identifies multiple novel loci associated with disease progression in subjects with mild cognitive impairment," Transl Psychiatry 1:e54, 9 pages, Macmillian Publishers Ltd., United Kingdom (Aug. 2011).

Lacher, S.E., et al., "A Hypermorphic Antioxidant Response Element is Associated With Increased MS4A6A Expression and Alzheimer's Disease," Redox Biology 14:686-693, Elsevier, B.V., Netherlands (Oct. 2017).

Ma, J., et al., "MS4A Cluster in Alzheimer's Disease," Molecular Neurobiology 51(3):1240-1248, Humana Press, United States (2015).

Maximov, A., et al., "Monitoring Synaptic Transmission in Primary Neuronal Cultures Using Local Extracellular Stimulation," Journal of Neuroscience Methods 161(1):75-87, Elsevier, Netherlands (Mar. 2007).

Office Action mailed Oct. 18, 2021, in U.S. Appl. No. 16/943,123, Sun, J., et al., filed Jul. 30, 2020, 15 pages.

Office Action mailed Jun. 16, 2022, in U.S. Appl. No. 16/943,123, Sun, J., et al., filed Jul. 30, 2020, 7 pages.

He Li, W., "Research progress in MS4A gene family and tumor," Tumor 36:345-350, China Academic Journal Electronic Publishing House, China (Mar. 2016).

He Li, W., "MS4A," Chin J Clin Lab Sci 34(3):202-204, Chinese Medical Journals Publishing House, China (Mar. 2016).

(56) References Cited

OTHER PUBLICATIONS

International Search Report and Written Opinion for International Application No. PCT/US2023/077418, European Patent Office, Netherlands, mailed Feb. 12, 2024, 13 pages.
You, S-F., et al., "MS4A4A modifies the risk of Alzheimer disease by regulating lipid metabolism and immune response in a unique microglia state," MedRxiv 10.1101/2023.02.06.23285545, accessed at https://www.medrixiv.org/content/10.1101/2023.02.06.23285545v1.full.pdf, accessed on Feb. 26, 2024, 31 pages, (Feb. 2023).
Dondelinger, M., et al., "Understanding the Significance and Implications of Antibody Numbering and Antigen-Binding Surface/Residue Definition," Front Immunol 9:2278, pp. 1-15, Frontiers Media SA., Switzerland (Oct. 2018).
Sela-Culang, I., et al., "The structural basis of antibody-antigen recognition," Front Immunol 4:302, pp. 1-13, Frontiers Media SA., Switzerland (Oct. 2013).
Sekine, S., "The Current State and the Issues of Antibody Drugs," Science and Technology Trends, 10:13-25 (Oct. 2009).
Morris, G.E., et al., "Epitope Mapping of Protein Antigens by Competition ELISA," The Protein Protocols Handbook, pp. 595-600, Humana Press, United States (1996).
Rudikoff, S., et al., "Single amino acid substitution altering antigen-binding specificity," Proc Natl Acad Sci USA 79(6):1979-1983, National Academy of Sciences, United States (Mar. 1982).

* cited by examiner

FIG. 1

*MHQTYSRHCRPEESTFSAAMTTMQGMEQAMPGAGPGVPQLGNMAVIHSHLWKGLQEKFLKGEP*
*K*VLGVVQILTALMSLSMGITMM*CMASNTYGSNPIS*VYIGYTIWGSVMFIISGSLSI*AAGIRTTKG*
*LVRGSLGMN*ITSSVLAASGILINTFSLAFY*SFHHPYCNYYGNSNNCHGTMS*ILMGLDGMVLLL
SVLEFCIAV*SLSAFGCKVLCCTPGGVVLILPSHSHMAETASPTPLNEV*

1P68 (SEQ ID NO:181)

MYGKLNDLLEDLQEVLKNLHKNWHGGKDNLHDVDNHLQNVIEDIHDFMQGGGSGGKLQE
MMKEFQQVLDELNNHLQGGKHTVHHIEQNIKEIFHHLEELVHR

1M6T (SEQ ID NO:182)

ADLEDNWETLNDNLKVIEKADNAAQVKDALTKMRAAALDAQKATPPKLEDKSPDSPEMKD
FRHGFDILVGQIDDALKLANEGKVKEAQAAAEQLKTTRNAYIQKYL

FIG. 3A

JS1 (SEQ ID NO:172)

MGWSCIILFLVATATGVHSMYGKLNDLLEDLQEVLKNLHKNCMASNTYGSNPISKDNLHD
VDNHLQNVIEDIHDFMQGGGSGGKLQEMMKEFQQVLDELNNH**SFHHPYCNYYGNSNNCH
GTMS**HTVHHIEQNIKEIFHHLEELVHRHHHHHHHHGGGLNDIFEAQKIEWHE

JS5 (SEQ ID NO:173)

MGWSCIILFLVATATGVHSADLEDNWETLNDNLKVIECMASNTYGSNPISAAQVKDALTKM
RAAALDAQKATPPKLEDKSPDSPEMKDFRHGFDILVGQIDDALKLAN**SFHHPYCNYYGNSN
NCHGTMS**VKEAQAAAEQLKTTRNAYIQKYLHHHHHHHHGGGLNDIFEAQKIEWHE

JS6 (SEQ ID NO:174)

MGWSCIILFLVATATGVHSADLEDNWETLNDNLKVIEGPCMASNTYGSNPISAAQVKDALT
KMRAAALDAQKATPPKLEDKSPDSPEMKDFRHGFDILVGQIDDALKLAN**SFHHPYCNYYG
NSNNCHGTMS**VKEAQAAAEQLKTTRNAYIQKYLHHHHHHHHGGGLNDIFEAQKIEWHE

FIG. 3B

JS4 (SEQ ID NO:175)

MGWSCIILFLVATATGVHSMYGKLNDLLEDLQEVLKNLHKNWHGGKDNLHDVDNHLQNVI
EDIHDFMQGGGSGGKLQEMMKEFQQVLDELNNHLQGGKHTVHHIEQNIKEIFHHLEELVHR
HHHHHHHHGGGLNDIFEAQKIEWHE

JS10 (SEQ ID NO:176)

MGWSCIILFLVATATGVHSADLEDNWETLNDNLKVIEKADNAAQVKDALTKMRAAALDAQ
KATPPKLEDKSPDSPEMKDFRHGFDILVGQIDDALKLANEGKVKEAQAAAEQLKTTRNAYIQ
KYLHHHHHHHHGGGLNDIFEAQKIEWHE

SEQUENCE LISTING

```
Sequence total quantity: 365
SEQ ID NO: 1            moltype = AA  length = 239
FEATURE                 Location/Qualifiers
source                  1..239
                        mol_type = protein
                        organism = Homo sapiens
SEQUENCE: 1
MHQTYSRHCR PEESTFSAAM TTMQGMEQAM PGAGPGVPQL GNMAVIHSHL WKGLQEKFLK  60
GEPKVLGVVQ ILTALMSLSM GITMMCMASN TYGSNPISVY IGYTIWGSVM FIISGSLSIA  120
AGIRTTKGLV RGSLGMNITS SVLAASGILI NTFSLAFYSF HHPYCNYYGN SNNCHGTMSI  180
LMGLDGMVLL LSVLEFCIAV SLSAFGCKVL CCTPGGVVLI LPSHSHMAET ASPTPLNEV   239

SEQ ID NO: 2            moltype = AA  length = 236
FEATURE                 Location/Qualifiers
source                  1..236
                        mol_type = protein
                        organism = Mus musculus
SEQUENCE: 2
MLVIQGTEQS ALEAGYGAQQ NGQPLYVNSH SWKRMTEKFL KGEPKILGIV QIVIAIMNLS  60
IGIMMIIATV STGEIPPSSV YIGYPIWGSL MFIISGSFSI VAGRRTTKGL VRSSLGLNIT  120
SSVFAFSGIV ISSLSPGIYS FHVYYCTYRG SSEGCHMTLS ILMGLDIVVV VLSVLEFCIG  180
VSLSAFGCRV MCCNPGGVMI IMPSNPTKAE TANPVTLQSG LMPPEHQERN VPENMH      236
```

```
SEQ ID NO: 3            moltype = AA  length = 238
FEATURE                 Location/Qualifiers
source                  1..238
                        mol_type = protein
                        organism = Macaca fascicularis
SEQUENCE: 3
HQTYRRHCRP EESTFSAAMT TMQGMEQATP GAGPGVPQLG NMAVVHSHLW KGLQEKFLKG  60
EPKVLGVVQI LIALMSLSMG ITMMCVAFSA YGHYPISVYI GYTIWGSVMF IISGSLSIAA  120
GIRTTKGLVR GSLGMNITSS VLAVSAILIN TISLTIYSFY HRYCNYYGNP NNCHGTVSIL  180
MGMDGMVLLL SVLEFCIAVS LSAFGCKAIC CTPGGVVLII PSNSHMAEAA PLTPLNEV    238

SEQ ID NO: 4            moltype = AA  length = 124
FEATURE                 Location/Qualifiers
source                  1..124
                        mol_type = protein
                        organism = synthetic construct
SEQUENCE: 4
QVQLQQSGAE LARPGASVKL SCKASGYTFT NYWMQWVKQR PGQGLEWIGA THPGHGDTRY  60
TQKFKGKATL SADKSSSTAY MQLSNLASED SAVYYCAREE VYYGFRSYWY FDVWGRGTLV  120
TVSS                                                               124

SEQ ID NO: 5            moltype = AA  length = 124
FEATURE                 Location/Qualifiers
source                  1..124
                        mol_type = protein
                        organism = synthetic construct
SEQUENCE: 5
QVQLVQSGAE VKKPGASVKV SCKASGYTFT NYWMQWVRQA PGQGLEWMGA THPGHGDTRY  60
AQKFQGRVTM TRDTSTSTVY MELSSLRSED TAVYYCAREE VYYGFRSYWY FDVWGRGTLV  120
TVSS                                                               124

SEQ ID NO: 6            moltype = AA  length = 124
FEATURE                 Location/Qualifiers
source                  1..124
                        mol_type = protein
                        organism = synthetic construct
SEQUENCE: 6
EVQLVQSGAE VKKPGESLKI SCKGSGYTFT NYWMQWVRQM PGKGLEWMGA THPGHGDTRY  60
SPSFQGQVTI SADKSISTAY LQWSSLKASD TAMYYCAREE VYYGFRSYWY FDVWGRGTLV  120
TVSS                                                               124

SEQ ID NO: 7            moltype = AA  length = 124
FEATURE                 Location/Qualifiers
source                  1..124
                        mol_type = protein
                        organism = synthetic construct
SEQUENCE: 7
EVQLVQSGAE VKKPGATVKI SCKVSGYTFT NYWMQWVQQA PGKGLEWMGA THPGHGDTRY  60
AEKFQGRVTI TADTSTDTAY MELSSLRSED TAVYYCAREE VYYGFRSYWY FDVWGRGTLV  120
TVSS                                                               124

SEQ ID NO: 8            moltype = AA  length = 124
FEATURE                 Location/Qualifiers
source                  1..124
                        mol_type = protein
                        organism = synthetic construct
SEQUENCE: 8
QVQLVQSGAE VKKPGASVKV SCKASGYTFT NYWMQWVRQA PGQGLEWMGA THPGHGDTRY  60
AQKFQGRVTM TADKSTSTVY MELSSLRSED TAVYYCAREE VYYGFRSYWY FDVWGRGTLV  120
TVSS                                                               124

SEQ ID NO: 9            moltype = AA  length = 124
FEATURE                 Location/Qualifiers
source                  1..124
                        mol_type = protein
                        organism = synthetic construct
SEQUENCE: 9
QVQLVQSGAE VKKPGASVKV SCKASGYTFT NYWMQWVRQA PGQGLEWMGA THPGHGDTRY  60
AQKFQGRVTM TADKSTSTAY MELSSLRSED TAVYYCAREE VYYGFRSYWY FDVWGRGTLV  120
TVSS                                                               124

SEQ ID NO: 10           moltype = AA  length = 124
FEATURE                 Location/Qualifiers
source                  1..124
                        mol_type = protein
                        organism = synthetic construct
SEQUENCE: 10
QVQLVQSGAE VKKPGASVKV SCKASGYTFT NYWMQWVRQA PGQGLEWMGA THPGHGDTRY  60
AQKFQGRVTL TADKSISTAY MELSRLRSDD TVVYYCAREE VYYGFRSYWY FDVWGRGTLV  120
```

```
TVSS                                                        124

SEQ ID NO: 11          moltype = AA  length = 124
FEATURE                Location/Qualifiers
source                 1..124
                       mol_type = protein
                       organism = synthetic construct
SEQUENCE: 11
EVQLVQSGAE VKKPGESLKI SCKGSGYTFT NYWMQWVRQM PGKGLEWMGA THPGHGDTRY  60
SPSFQGQVTI SADKSSSTAY LQWSSLKASD TAMYYCAREE VYYGFRSYWY FDVWGRGTLV  120
TVSS                                                        124

SEQ ID NO: 12          moltype = AA  length = 124
FEATURE                Location/Qualifiers
source                 1..124
                       mol_type = protein
                       organism = synthetic construct
SEQUENCE: 12
EVQLVQSGAE VKKPGATVKI SCKVSGYTFT NYWMQWVQQA PGKGLEWMGA THPGHGDTRY  60
AEKFQGRVTI TADKSTSTAY MELSSLRSED TAVYYCAREE VYYGFRSYWY FDVWGRGTLV  120
TVSS                                                        124

SEQ ID NO: 13          moltype = AA  length = 124
FEATURE                Location/Qualifiers
source                 1..124
                       mol_type = protein
                       organism = synthetic construct
SEQUENCE: 13
QVQLVQSGAE VKKPGASVKV SCKASGYTFT NYWMQWVRQA PGQGLEWMGA THPGHGDTRY  60
AQKFQGRVTM TRDTSTSTVY MELSSLRSED TAVYYCAREE VDYGFRSYWY FDVWGRGTLV  120
TVSS                                                        124

SEQ ID NO: 14          moltype = AA  length = 124
FEATURE                Location/Qualifiers
source                 1..124
                       mol_type = protein
                       organism = synthetic construct
SEQUENCE: 14
QVQLVQSGAE VKKPGASVKV SCKASGYTFT NYWMQWVRQA PGQGLEWMGA THPGHGDTRY  60
AQKFQGRVTM TRDTSTSTVY MELSSLRSED TAVYYCAREE VYYGFRSYWY FDLWGRGTLV  120
TVSS                                                        124

SEQ ID NO: 15          moltype = AA  length = 124
FEATURE                Location/Qualifiers
source                 1..124
                       mol_type = protein
                       organism = synthetic construct
SEQUENCE: 15
QVQLVQSGAE VKKPGASVKV SCKASGYTFT NYWMQWVRQA PGQGLEWMGT TLPGHGDTRY  60
AQKFQGRVTM TRDTSTSTVY MELSSLRSED TAVYYCAREE VYYGFRSYWY FDVWGRGTLV  120
TVSS                                                        124

SEQ ID NO: 16          moltype = AA  length = 111
FEATURE                Location/Qualifiers
source                 1..111
                       mol_type = protein
                       organism = synthetic construct
SEQUENCE: 16
DIVLTQSPAS LAVSLGQRAT ISCRASESVD NYGVSFMNWF QQKPGQPPKL LIYGASNQGS  60
GVPARFSGSG SGTDFSLNIH PMEEDDTAMY FCQQSKEVPP TFGGGTKLEI K         111

SEQ ID NO: 17          moltype = AA  length = 111
FEATURE                Location/Qualifiers
source                 1..111
                       mol_type = protein
                       organism = synthetic construct
SEQUENCE: 17
DIVMTQSPDS LAVSLGERAT INCRASESVD NYGVSFMNWY QQKPGQPPKL LIYGASNQGS  60
GVPDRFSGSG SGTDFTLTIS SLQAEDVAVY YCQQSKEVPP TFGGGTKVEI K         111

SEQ ID NO: 18          moltype = AA  length = 111
FEATURE                Location/Qualifiers
source                 1..111
                       mol_type = protein
                       organism = synthetic construct
SEQUENCE: 18
EIVLTQSPAT LSLSPGERAT LSCRASESVD NYGVSFMNWY QQKPGQAPRL LIYGASNQGS  60
GIPARFSGSG SGTDFTLTIS SLEPEDFAVY YCQQSKEVPP TFGGGTKVEI K         111
```

```
SEQ ID NO: 19          moltype = AA  length = 111
FEATURE                Location/Qualifiers
source                 1..111
                       mol_type = protein
                       organism = synthetic construct
SEQUENCE: 19
EIVLTQSPGT LSLSPGERAT LSCRASESVD NYGVSFMNWY QQKPGQAPRL LIYGASNQGS  60
GIPDRFSGSG SGTDFTLTIS RLEPEDFAVY YCQQSKEVPP TFGGGTKVEI K           111

SEQ ID NO: 20          moltype = AA  length = 111
FEATURE                Location/Qualifiers
source                 1..111
                       mol_type = protein
                       organism = synthetic construct
SEQUENCE: 20
DIQMTQSPSS LSASVGDRVT ITCRASESVD NYGVSFMNWY QQKPGKAPKL LIYGASNQGS  60
GVPSRFSGSG SGTDFTLTIS SLQPEDFATY YCQQSKEVPP TFGGGTKVEI K           111

SEQ ID NO: 21          moltype = AA  length = 111
FEATURE                Location/Qualifiers
source                 1..111
                       mol_type = protein
                       organism = synthetic construct
SEQUENCE: 21
EIVLTQSPAT LSLSPGERAT LSCRASESVD NYGVSFMNWY QQKPGQAPRL LIYGASNQQS  60
GIPARFSGSG SGTDFTLTIS SLEPEDFAVY YCQQSKEVPP TFGGGTKVEI K           111

SEQ ID NO: 22          moltype = AA  length = 111
FEATURE                Location/Qualifiers
source                 1..111
                       mol_type = protein
                       organism = synthetic construct
SEQUENCE: 22
EIVLTQSPAT LSLSPGERAT LSCRASESVD NYGVSRMNWY QQKPGQAPRL LIYGASNQGS  60
GIPARFSGSG SGTDFTLTIS SLEPEDFAVY YCQQSKEVPP TFGGGTKVEI K           111

SEQ ID NO: 23          moltype = AA  length = 120
FEATURE                Location/Qualifiers
source                 1..120
                       mol_type = protein
                       organism = synthetic construct
SEQUENCE: 23
QVQLQQPGTE LVKPGASVKL SCKASGYTFT SYWIHWVKQR PGQGLEWIGN INPTNGGTNY  60
NERFKSKATL TVDKSSSTAY MQLSSLTSED SAVYYCARAY YYGSSLFAYW GQGTLVTVSS  120

SEQ ID NO: 24          moltype = AA  length = 120
FEATURE                Location/Qualifiers
source                 1..120
                       mol_type = protein
                       organism = synthetic construct
SEQUENCE: 24
QVQLVQSGAE VKKPGASVKV SCKASGYTFT SYWIHWVRQA PGQGLEWMGN INPTNGGTNY  60
AQKFQGRVTM TRDTSTSTVY MELSSLRSED TAVYYCARAY YYGSSLFAYW GQGTLVTVSS  120

SEQ ID NO: 25          moltype = AA  length = 120
FEATURE                Location/Qualifiers
source                 1..120
                       mol_type = protein
                       organism = synthetic construct
SEQUENCE: 25
QVQLVQSGAE VKKPGASVKV SCKASGYTFT SYWIHWVRQA PGQGLEWMGN INPTNGGTNY  60
AQKFQGRVTM TVDKSTSTVY MELSSLRSED TAVYYCARAY YYGSSLFAYW GQGTLVTVSS  120

SEQ ID NO: 26          moltype = AA  length = 120
FEATURE                Location/Qualifiers
source                 1..120
                       mol_type = protein
                       organism = synthetic construct
SEQUENCE: 26
QVQLVQSGAE VKKPGASVKV SCKASGYTFT SYWIHWVRQA PGQGLEWMGN INPTNGGTNY  60
AQKFQGRVTM TVDKSTSTAY MELSSLRSED TAVYYCARAY YYGSSLFAYW GQGTLVTVSS  120

SEQ ID NO: 27          moltype = AA  length = 120
FEATURE                Location/Qualifiers
source                 1..120
                       mol_type = protein
                       organism = synthetic construct
SEQUENCE: 27
QVQLVQSGAE VKKPGASVKV SCKASGYTFT SYWIHWVRQA PGQGLEWMGN INPTNGGTNY  60
```

```
AQKFQGRVTS TRDTSISTAY MELSRLRSDD TVVYYCARAY YYGSSLFAYW GQGTLVTVSS  120

SEQ ID NO: 28          moltype = AA  length = 120
FEATURE                Location/Qualifiers
source                 1..120
                       mol_type = protein
                       organism = synthetic construct
SEQUENCE: 28
QVQLVQSGAE VKKPGASVKV SCKASGYTFT SYWIHWVRQA PGQGLEWMGN INPTNGGTNY  60
AQKFQGRVTS TVDKSISTAY MELSRLRSDD TVVYYCARAY YYGSSLFAYW GQGTLVTVSS  120

SEQ ID NO: 29          moltype = AA  length = 120
FEATURE                Location/Qualifiers
source                 1..120
                       mol_type = protein
                       organism = synthetic construct
SEQUENCE: 29
QVQLVQSGAE VKKPGASVKV SCKASGYTFT SYWIHWVRQA PGQRLEWMGN INPTNGGTNY  60
SQKFQGRVTI TRDTSASTAY MELSSLRSED TAVYYCARAY YYGSSLFAYW GQGTLVTVSS  120

SEQ ID NO: 30          moltype = AA  length = 120
FEATURE                Location/Qualifiers
source                 1..120
                       mol_type = protein
                       organism = synthetic construct
SEQUENCE: 30
QVQLVQSGAE VKKPGASVKV SCKASGYTFT SYWIHWVRQA PGQRLEWMGN INPTNGGTNY  60
SQKFQGRVTI TVDKSASTAY MELSSLRSED TAVYYCARAY YYGSSLFAYW GQGTLVTVSS  120

SEQ ID NO: 31          moltype = AA  length = 107
FEATURE                Location/Qualifiers
source                 1..107
                       mol_type = protein
                       organism = synthetic construct
SEQUENCE: 31
DIVMTQSQKF MSTTVGDRVS ITCKASQNVG TAVAWSQQKP GQSPKLLIYS ASYRHTGVPD  60
RFTGSGSGTD FTLTITNMQS EDLADYFCQQ YSTYPWTFGG GTKLEIK            107

SEQ ID NO: 32          moltype = AA  length = 107
FEATURE                Location/Qualifiers
source                 1..107
                       mol_type = protein
                       organism = synthetic construct
SEQUENCE: 32
DIVMTQSPSF LSASVGDRVT ITCKASQNVG TAVAWYQQKP GKAPKLLIYS ASYRHTGVPS  60
RFSGSGSGTE FTLTISSLQP EDFATYYCQQ YSTYPWTFGG GTKVEIK            107

SEQ ID NO: 33          moltype = AA  length = 108
FEATURE                Location/Qualifiers
source                 1..108
                       mol_type = protein
                       organism = synthetic construct
SEQUENCE: 33
DIQLTQSPSF LSASVGDRVT ITCKASQNVG TAVAWYQQKP GKAPKLLIYS ASYRHTGVPS  60
RFSGSGSGTE FTLTISSLQP EDFATYYCQQ YSTYPWTFGG GTKVEIKR           108

SEQ ID NO: 34          moltype = AA  length = 107
FEATURE                Location/Qualifiers
source                 1..107
                       mol_type = protein
                       organism = synthetic construct
SEQUENCE: 34
DIVMTQSPSS LSASVGDRVT ITCKASQNVG TAVAWYQQKP EKAPKSLIYS ASYRHTGVPS  60
RFSGSGSGTD FTLTISSLQP EDFATYYCQQ YSTYPWTFGG GTKVEIK            107

SEQ ID NO: 35          moltype = AA  length = 107
FEATURE                Location/Qualifiers
source                 1..107
                       mol_type = protein
                       organism = synthetic construct
SEQUENCE: 35
DIQMTQSPSS LSASVGDRVT ITCKASQNVG TAVAWYQQKP EKAPKSLIYS ASYRHTGVPS  60
RFSGSGSGTD FTLTISSLQP EDFATYYCQQ YSTYPWTFGG GTKVEIK            107

SEQ ID NO: 36          moltype = AA  length = 107
FEATURE                Location/Qualifiers
source                 1..107
                       mol_type = protein
                       organism = synthetic construct
```

```
SEQUENCE: 36
AIQMTQSPSS LSASVGDRVT ITCKASQNVG TAVAWYQQKP GKAPKLLIYS ASYRHTGVPS  60
RFSGSGSGTD FTLTISSLQP EDFATYYCQQ YSTYPWTFGG GTKVEIK                107

SEQ ID NO: 37          moltype = AA  length = 107
FEATURE                Location/Qualifiers
source                 1..107
                       mol_type = protein
                       organism = synthetic construct
SEQUENCE: 37
DIQLTQSPSF LSASVGDRVT ITCKASQNVG TAVAWYQQKP GKAPKLLIYS ASYRHTGVPS  60
RFSGSGSGTE FTLTISSLQP EDFATYYCQQ YSTYPWTFGG GTKVEIK                107

SEQ ID NO: 38          moltype = AA  length = 107
FEATURE                Location/Qualifiers
source                 1..107
                       mol_type = protein
                       organism = synthetic construct
SEQUENCE: 38
AIQLTQSPSS LSASVGDRVT ITCKASQNVG TAVAWYQQKP GKAPKLLIYS ASYRHTGVPS  60
RFSGSGSGTD FTLTISSLQP EDFATYYCQQ YSTYPWTFGG GTKVEIK                107

SEQ ID NO: 39          moltype = AA  length = 114
FEATURE                Location/Qualifiers
source                 1..114
                       mol_type = protein
                       organism = synthetic construct
SEQUENCE: 39
QIQLVQSGPE LKKPGETVKI SCKASGYIFT SYGLSWVKQT PGKGLKWMGW INTYSGVPTY  60
ANDFKGRFAF SLETSASTTY LRINNLKNDD TATYFCARSL VDYWGQGTPL TVSS        114

SEQ ID NO: 40          moltype = AA  length = 114
FEATURE                Location/Qualifiers
source                 1..114
                       mol_type = protein
                       organism = synthetic construct
SEQUENCE: 40
QVQLVQSGSE LKKPGASVKV SCKASGYIFT SYGLSWVRQA PGQGLEWMGW INTYSGVPTY  60
AQGFTGRFVF SLDTSVSTAY LQISSLKAED TAVYYCARSL VDYWGQGTLV TVSS        114

SEQ ID NO: 41          moltype = AA  length = 114
FEATURE                Location/Qualifiers
source                 1..114
                       mol_type = protein
                       organism = synthetic construct
SEQUENCE: 41
QVQLVQSGSE LKKPGASVKV SCKASGYIFT SYGLSWVRQA PGQGLEWMGW INTYSGVPTY  60
AQGFTGRFVF SLDTSVSTTY LQISSLKAED TAVYYCARSL VDYWGQGTLV TVSS        114

SEQ ID NO: 42          moltype = AA  length = 114
FEATURE                Location/Qualifiers
source                 1..114
                       mol_type = protein
                       organism = synthetic construct
SEQUENCE: 42
QVQLVQSGAE VKKPGASVKV SCKASGYIFT SYGLSWVRQA PGQRLEWMGW INTYSGVPTY  60
SQKFQGRVTI TLDTSASTTY MELSSLRSED TAVYYCARSL VDYWGQGTLV TVSS        114

SEQ ID NO: 43          moltype = AA  length = 114
FEATURE                Location/Qualifiers
source                 1..114
                       mol_type = protein
                       organism = synthetic construct
SEQUENCE: 43
QVQLVQSGAE VKKPGASVKV SCKASGYIFT SYGLSWVRQA PGQRLEWMGW INTYSGVPTY  60
SQKFQGRVTI TRDTSASTAY MELSSLRSED TAVYYCARSL VDYWGQGTLV TVSS        114

SEQ ID NO: 44          moltype = AA  length = 114
FEATURE                Location/Qualifiers
source                 1..114
                       mol_type = protein
                       organism = synthetic construct
SEQUENCE: 44
QIQLVQSGAE VKKPGASVKV SCKASGYIFT SYGLSWVRQA PGQGLEWMGW INTYSGVPTY  60
AQKFQGRVTM TRDTSTSTVY MELSSLRSED TAVYYCARSL VDYWGQGTLV TVSS        114

SEQ ID NO: 45          moltype = AA  length = 114
FEATURE                Location/Qualifiers
source                 1..114
```

```
                         mol_type = protein
                         organism = synthetic construct
SEQUENCE: 45
QIQLVQSGAE VKKPGASVKV SCKASGYIFT SYGLSWVRQA PGQGLEWMGW INTYSGVPTY  60
AQKFQGRVTM TLDTSTSTTY MELSSLRSED TAVYYCARSL VDYWGQGTLV TVSS        114

SEQ ID NO: 46            moltype = AA  length = 114
FEATURE                  Location/Qualifiers
source                   1..114
                         mol_type = protein
                         organism = synthetic construct
SEQUENCE: 46
QVQLVQSGAE VKKPGASVKV SCKASGYIFT SYGLSWVRQA PGQGLEWMGW INTYSGVPTY  60
AQKFQGRVTM TRDTSTSTVY MELSSLRSED TAVYYCARSL VDYWGQGTLV TVSS        114

SEQ ID NO: 47            moltype = AA  length = 114
FEATURE                  Location/Qualifiers
source                   1..114
                         mol_type = protein
                         organism = synthetic construct
SEQUENCE: 47
QVQLVQSGSE LKKPGASVKV SCKASGYIFT SYGLSWVRQA PGQGLEWMGW INTYSGVPTY  60
AQGFTGRFVF SLDTSVSTAY LQISSLKAED TAVYYCARTL ADYWGQGTLV TVSS        114

SEQ ID NO: 48            moltype = AA  length = 114
FEATURE                  Location/Qualifiers
source                   1..114
                         mol_type = protein
                         organism = synthetic construct
SEQUENCE: 48
QVQLVQSGSE LKKPGASVKV SCKASGYTFT SYGLSWIRQA PGQGLEWMGW INTYSGVPTY  60
AQGFTGRFVF SLDTSVSTAY LQISSLKAED TAVYYCARTM VDYWGQGTLV TVSS        114

SEQ ID NO: 49            moltype = AA  length = 114
FEATURE                  Location/Qualifiers
source                   1..114
                         mol_type = protein
                         organism = synthetic construct
SEQUENCE: 49
QVQLVQSGSE LKKPGASVKV SCKASGYIFT SYGLSWVRQA PGQGLEWMGW INTYSGVPTY  60
AQGFTGRFVF SLDTSVSTAY LQISSLKAED TAVYYCARTL GDYWGQGTLV TVSS        114

SEQ ID NO: 50            moltype = AA  length = 114
FEATURE                  Location/Qualifiers
source                   1..114
                         mol_type = protein
                         organism = synthetic construct
SEQUENCE: 50
QVQLVQSGSE LKKPGASVKV SCKASGYIFT SYGLSWVRQA PGQGLEWMGW INTYSGVPTY  60
AQGFTGRFVF SLDTSVSTAY LQISSLKAED TAVYYCARTL VDYWGQGTLV TVSS        114

SEQ ID NO: 51            moltype = AA  length = 114
FEATURE                  Location/Qualifiers
source                   1..114
                         mol_type = protein
                         organism = synthetic construct
SEQUENCE: 51
QVQLVQSGSE LKKPGASVKV SCKASGYIFT SYGLSWVRQA PGQGLEWMGW INTYSGVPTY  60
AQGFAGRFVF SLDTSVSTAY LQISSLKAED TAVYYCARTL VDYWGQGTLV TVSS        114

SEQ ID NO: 52            moltype = AA  length = 114
FEATURE                  Location/Qualifiers
source                   1..114
                         mol_type = protein
                         organism = synthetic construct
SEQUENCE: 52
QVQLVQSGSE LKKPGASVKV SCKASGYIFT SYGLSWVRQA PGQGLEWMGW INTYSGVPTY  60
AQGFTGRFVF SLDTSVSTAY LQISSLKAED TAVYYCARSL ADYWGQGTLV TVSS        114

SEQ ID NO: 53            moltype = AA  length = 114
FEATURE                  Location/Qualifiers
source                   1..114
                         mol_type = protein
                         organism = synthetic construct
SEQUENCE: 53
QVQLVQSGSE LKKPGASVKV SCKASGYIFT SYGLSWVRQA PGQGLEWMGW INTYSGVPTY  60
AQGFTGRFVF SLDTSVSTAY LQISSLKAED TAVYYCARSM ADYWGQGTLV TVSS        114

SEQ ID NO: 54            moltype = AA  length = 112
```

```
FEATURE                Location/Qualifiers
source                 1..112
                       mol_type = protein
                       organism = synthetic construct
SEQUENCE: 54
DVVMTQTPFT LSVTIGQSAS ISCKSSQSLL YSDGKTYLSW LLQRPGQSPK RLIYLVSKLD  60
SGVPDRFTGS GSGTDFTLKI SRVEAEDLGV YYCWQGIDFH QTFGGGTKLE IK          112

SEQ ID NO: 55          moltype = AA  length = 112
FEATURE                Location/Qualifiers
source                 1..112
                       mol_type = protein
                       organism = synthetic construct
SEQUENCE: 55
DVVMTQSPLS LPVTLGQPAS ISCKSSQSLL YSDGKTYLSW FQQRPGQSPR RLIYLVSKLD  60
SGVPDRFSGS GSGTDFTLKI SRVEAEDVGV YYCWQGIDFH QTFGGGTKVE IK          112

SEQ ID NO: 56          moltype = AA  length = 112
FEATURE                Location/Qualifiers
source                 1..112
                       mol_type = protein
                       organism = synthetic construct
SEQUENCE: 56
DIVMTQTPLS SPVTLGQPAS ISCKSSQSLL YSDGKTYLSW LQQRPGQPPR LLIYLVSKLD  60
SGVPDRFSGS GAGTDFTLKI SRVEAEDVGV YYCWQGIDFH QTFGGGTKVE IK          112

SEQ ID NO: 57          moltype = AA  length = 112
FEATURE                Location/Qualifiers
source                 1..112
                       mol_type = protein
                       organism = synthetic construct
SEQUENCE: 57
DVVMTQTPLS SPVTLGQPAS ISCKSSQSLL YSDGKTYLSW LQQRPGQPPR LLIYLVSKLD  60
SGVPDRFSGS GAGTDFTLKI SRVEAEDVGV YYCWQGIDFH QTFGGGTKVE IK          112

SEQ ID NO: 58          moltype = AA  length = 112
FEATURE                Location/Qualifiers
source                 1..112
                       mol_type = protein
                       organism = synthetic construct
SEQUENCE: 58
DVVMTQTPLS SPVTLGQPAS ISCKSSQSLL YSDGKTYLSW LQQRPGQPPR RLIYLVSKLD  60
SGVPDRFSGS GAGTDFTLKI SRVEAEDVGV YYCWQGIDFH QTFGGGTKVE IK          112

SEQ ID NO: 59          moltype = AA  length = 112
FEATURE                Location/Qualifiers
source                 1..112
                       mol_type = protein
                       organism = synthetic construct
SEQUENCE: 59
DVVMTQTPLS LSVTPGQPAS ISCKSSQSLL YSDGKTYLSW YLQKPGQPPQ LLIYLVSKLD  60
SGVPDRFSGS GSGTDFTLKI SRVEAEDVGV YYCWQGIDFH QTFGGGTKVE IK          112

SEQ ID NO: 60          moltype = AA  length = 112
FEATURE                Location/Qualifiers
source                 1..112
                       mol_type = protein
                       organism = synthetic construct
SEQUENCE: 60
DVVMTQTPLS LSVTPGQPAS ISCKSSQSLL YSDGKTYLSW YLQKPGQPPQ RLIYLVSKLD  60
SGVPDRFSGS GSGTDFTLKI SRVEAEDVGV YYCWQGIDFH QTFGGGTKVE IK          112

SEQ ID NO: 61          moltype = AA  length = 112
FEATURE                Location/Qualifiers
source                 1..112
                       mol_type = protein
                       organism = synthetic construct
SEQUENCE: 61
DIVMTQTPLS LSVTPGQPAS ISCKSSQSLL YSDGKTYLSW YLQKPGQPPQ LLIYLVSKLD  60
SGVPDRFSGS GSGTDFTLKI SRVEAEDVGV YYCWQGIDFH QTFGGGTKVE IK          112

SEQ ID NO: 62          moltype = AA  length = 112
FEATURE                Location/Qualifiers
source                 1..112
                       mol_type = protein
                       organism = synthetic construct
SEQUENCE: 62
DVVMTQSPLS LPVTLGQPAS ISCKSSRSLL YSDGKTYLSW FQQRPGQSPR RLIYLVSKLD  60
SGVPDRFSGS GSGTDFTLKI SRVEAEDVGV YYCWQGIDFH QTFGGGTKVE IK          112
```

```
SEQ ID NO: 63          moltype = AA  length = 112
FEATURE                Location/Qualifiers
source                 1..112
                       mol_type = protein
                       organism = synthetic construct
SEQUENCE: 63
DVVMTQSPLS LPVTLGQPAS ISCKSSRSLL YSGGKTYLSW FQQRPGQSPR RLIYLVSKLD  60
SGVPDRFSGS GSGTDFTLKI SRVEAEDVGV YYCWQGIDFH QTFGGGTKVE IK          112

SEQ ID NO: 64          moltype = AA  length = 112
FEATURE                Location/Qualifiers
source                 1..112
                       mol_type = protein
                       organism = synthetic construct
SEQUENCE: 64
DVVMTQSPLS LPVTLGQPAS ISCKSSRSLL YSEGKTYLSW FQQRPGQSPR RLIYLVSKLD  60
SGVPDRFSGS GSGTDFTLKI SRVEAEDVGV YYCWQGIDFH QTFGGGTKVE IK          112

SEQ ID NO: 65          moltype = AA  length = 112
FEATURE                Location/Qualifiers
source                 1..112
                       mol_type = protein
                       organism = synthetic construct
SEQUENCE: 65
DVVMTQSPLS LPVTLGQPAS ISCKSSRSLL YSAGKTYLSW FQQRPGQSPR RLIYLVSKLD  60
SGVPDRFSGS GSGTDFTLKI SRVEAEDVGV YYCWQGIDFH QTFGGGTKVE IK          112

SEQ ID NO: 66          moltype = AA  length = 112
FEATURE                Location/Qualifiers
source                 1..112
                       mol_type = protein
                       organism = synthetic construct
SEQUENCE: 66
DVVMTQSPLS LPVTLGQPAS ISCKSSRSLL YSSGKTYLSW FQQRPGQSPR RLIYLVSKLD  60
SGVPDRFSGS GSGTDFTLKI SRVEAEDVGV YYCWQGIDFH QTFGGGTKVE IK          112

SEQ ID NO: 67          moltype = AA  length = 112
FEATURE                Location/Qualifiers
source                 1..112
                       mol_type = protein
                       organism = synthetic construct
SEQUENCE: 67
DVVMTQSPLS LPVTLGQPAS ISCKSSRSLL YSQGKTYLSW FQQRPGQSPR RLIYLVSKLD  60
SGVPDRFSGS GSGTDFTLKI SRVEAEDVGV YYCWQGIDFH QTFGGGTKVE IK          112

SEQ ID NO: 68          moltype = AA  length = 112
FEATURE                Location/Qualifiers
source                 1..112
                       mol_type = protein
                       organism = synthetic construct
SEQUENCE: 68
DVVMTQSPLS LPVTLGQPAS ISCKSSQSLL YSDGKTYLSW FQQRPGQSPR RLIYEVSKLD  60
SGVPDRFSGS GSGTDFTLKI SRVEAEDVGV YYCWQGIDFH QTFGGGTKVE IK          112

SEQ ID NO: 69          moltype = AA  length = 112
FEATURE                Location/Qualifiers
source                 1..112
                       mol_type = protein
                       organism = synthetic construct
SEQUENCE: 69
DVVMTQSPLS LPVTLGQPAS ISCKSSQSLL YSDGKTYLSW FQQRPGQSPR RLIYLVSKLD  60
SGVPDRFSGS GSGTDFTLKI SRVEAEDVGV YYCWQGIRFH QTFGGGTKVE IK          112

SEQ ID NO: 70          moltype = AA  length = 112
FEATURE                Location/Qualifiers
source                 1..112
                       mol_type = protein
                       organism = synthetic construct
SEQUENCE: 70
DVVMTQSPLS LPVTLGQPAS ISCKASQSLL YSDGKTYLSW FQQRPGQSPR RLIYLVSKLD  60
SGVPDRFSGS GSGADFTLKI SRVEAEDVGV YYCWQGIDFH QTFGGGTKVE IK          112

SEQ ID NO: 71          moltype = AA  length = 112
FEATURE                Location/Qualifiers
source                 1..112
                       mol_type = protein
                       organism = synthetic construct
SEQUENCE: 71
```

```
DVVMTQSPLS LPVTLGQPAS ISCKSGQSLL YSDGKTYLSW FQQRPGQSPR RLIYLVSRLD  60
SGVPDRFSGS GSGTDFTLKI SRVEAEDVGV YYCWQGIDFH QTFGGGTKVE IK          112

SEQ ID NO: 72          moltype = AA  length = 112
FEATURE                Location/Qualifiers
source                 1..112
                       mol_type = protein
                       organism = synthetic construct
SEQUENCE: 72
DVVMTQSPLS LPVTLGQPAS ISCKSSQSLL YSDGKTYLSW FQQRPGQSPR RLIYLVSKLE  60
SGVPDRFSGS GSGTDFTLKI SRVEAEDVGV YYCWQGIDFH QTFGGGTKVE IK          112

SEQ ID NO: 73          moltype = AA  length = 112
FEATURE                Location/Qualifiers
source                 1..112
                       mol_type = protein
                       organism = synthetic construct
SEQUENCE: 73
DVVMTQSPLS LPVTLGQPAS ISCKSSQSLL YSDGKTYLSW FQQRPGQSPR RLIYLVSRLD  60
SGVPDRFSGS GSGTDFTLKI SRVEAEDVGV YYCWQGIDFH QTFGGGTKVE IK          112

SEQ ID NO: 74          moltype = AA  length = 112
FEATURE                Location/Qualifiers
source                 1..112
                       mol_type = protein
                       organism = synthetic construct
SEQUENCE: 74
DVVMTQSPLS LPVTLGQPAS ISCKSSQSLL YSDGKTYLSW FQQRPGQSPR RLIYLVSKLS  60
SGVPDRFSGS GSGTDFTLKI SRVEAEDVGV YYCWQGIDFH QTFGGGTKVE IK          112

SEQ ID NO: 75          moltype = AA  length = 120
FEATURE                Location/Qualifiers
source                 1..120
                       mol_type = protein
                       organism = synthetic construct
SEQUENCE: 75
QVTLKESGPG ILQPSQTLSL TCSFSGFSLR TSDMGVGWVR QPSGEGLEWL ADIWWDDNKY  60
YNPSLKSRLT ISKDTSSNQV FLKITSVDTA DTATYYCARR ANYGNLFDYW GQGTAVTVSS  120

SEQ ID NO: 76          moltype = AA  length = 120
FEATURE                Location/Qualifiers
source                 1..120
                       mol_type = protein
                       organism = synthetic construct
SEQUENCE: 76
QVTLKESGPA LVQPTQTLTL TCTFSGFSLR TSDMGVSWIR QPPGEALEWL ALIWWDDNKY  60
YSTSLKTRLT ISKDTSSNQV VLTMTNMDPV DTATYYCARR ANYGNLFDYW GQGTAVTVSS  120

SEQ ID NO: 77          moltype = AA  length = 120
FEATURE                Location/Qualifiers
source                 1..120
                       mol_type = protein
                       organism = synthetic construct
SEQUENCE: 77
QVTLKESGPT LVQPTQTLTL TCTFSGFSLR TSDMGVGWIR QPPGKALEWL ALIWWDDNKY  60
YSPSLKSRLT ISKDTSSNQV VLTMTNMDPV DTATYYCARR ANYGNLFDYW GQGTLVTVSS  120

SEQ ID NO: 78          moltype = AA  length = 120
FEATURE                Location/Qualifiers
source                 1..120
                       mol_type = protein
                       organism = synthetic construct
SEQUENCE: 78
QVTLRESGPA LVQPTQTLTL TCTFSGFSLR TSDMGVSWIR QPPGEALEWL ALIWWDDNKY  60
YSTSLKTRLT ISKDTSSNQV VLTMTNMDPV DTATYYCARR ANYGNLFDYW GQGTLVTVSS  120

SEQ ID NO: 79          moltype = AA  length = 120
FEATURE                Location/Qualifiers
source                 1..120
                       mol_type = protein
                       organism = synthetic construct
SEQUENCE: 79
QVTLKESGPT LVKPTQTLTL TCTFSGFSLR TSDMGVGWIR QPPGKALEWL ALIWWDDNKY  60
YSPSLKSRLT ITKDTSSNQV VLTMTNMDPV DTATYYCARR ANYGNLFDYW GQGTLVTVSS  120

SEQ ID NO: 80          moltype = AA  length = 120
FEATURE                Location/Qualifiers
source                 1..120
                       mol_type = protein
```

```
                         organism = synthetic construct
SEQUENCE: 80
QVTLKESGPG LVQPTETLTL TCTFSGFSLR TSDMGVSWIR QPPGKALEWL AHIWWDDNKS  60
YSTSLKSRLT ISKDTSSNQV VLTMTNMDPV DTATYYCARR ANYGNLFDYW GQGTLVTVSS  120

SEQ ID NO: 81            moltype = AA  length = 120
FEATURE                  Location/Qualifiers
source                   1..120
                         mol_type = protein
                         organism = synthetic construct
SEQUENCE: 81
QVTLKESGPV LVKPTETLTL TCTFSGFSLR TSDMGVSWIR QPSGKALEWL AHIWWDDNKS  60
YSTSLKSRLT ISKDTSKNQV VLTMTNMDPV DTATYYCARR ANYGNLFDYW GQGTLVTVSS  120

SEQ ID NO: 82            moltype = AA  length = 120
FEATURE                  Location/Qualifiers
source                   1..120
                         mol_type = protein
                         organism = synthetic construct
SEQUENCE: 82
QVTLKESGPV LVKPTETLTL TCTFSGFSLR TSDMGVSWIR QPSGEGLEWL AHIWWDDNKS  60
YSTSLKSRLT ISKDTSKNQV VLTMTNMDPV DTATYYCARR ANYGNLFDYW GQGTLVTVSS  120

SEQ ID NO: 83            moltype = AA  length = 120
FEATURE                  Location/Qualifiers
source                   1..120
                         mol_type = protein
                         organism = synthetic construct
SEQUENCE: 83
QVTLQESGPG LVKPSETLSL TCAVSGFSLR TSDMGVGWIR QPPGEGLEWI GSIWWDDNKY  60
YNPSLKSRVT ISKDTSKNQV SLKLSSVDAA DTAVYYCARR ANYGNLFDYW GQGTLVTVSS  120

SEQ ID NO: 84            moltype = AA  length = 120
FEATURE                  Location/Qualifiers
source                   1..120
                         mol_type = protein
                         organism = synthetic construct
SEQUENCE: 84
QVQLQESGPG LVQPSETLSL TCAVSGFSLR TSDMGVGWIR QPPGKGLEWI GSIWYDDNKY  60
YNPSLKSRVT ISKDTSSNQF SLKLSSVTAA DTAVYYCARR ANYGNLFDYW GQGTLVTVSS  120

SEQ ID NO: 85            moltype = AA  length = 106
FEATURE                  Location/Qualifiers
source                   1..106
                         mol_type = protein
                         organism = synthetic construct
SEQUENCE: 85
DIVMTQSLKF MSTSVGDRVS ITCKASQNVR SAVAWYQQKP GQSPKVLIYW ASNRHTGVPD  60
RFTGSGSGTD FTLTISNVQS EDLADYFCLQ HWNYLTFGSG TKLEIK                106

SEQ ID NO: 86            moltype = AA  length = 106
FEATURE                  Location/Qualifiers
source                   1..106
                         mol_type = protein
                         organism = synthetic construct
SEQUENCE: 86
DIVLTQSPSS LSASVGDRVT ITCRASQNVR SALAWYQQKP GQAPKVLIYW ASNRHSGVPS  60
RFSGSGSGTD FTLTISSLQP EDFATYYCQQ HWNYLTFGGG TKVEIK                106

SEQ ID NO: 87            moltype = AA  length = 106
FEATURE                  Location/Qualifiers
source                   1..106
                         mol_type = protein
                         organism = synthetic construct
SEQUENCE: 87
DIVLTQSPSS LSASVGDRVT ITCRASQNVR SALAWYQQKP GQAPKLLIYW ASNRHSGVPS  60
RFSGSGSGTD FTLTISSLQP EDFATYYCQQ HWNYLTFGGG TKVEIK                106

SEQ ID NO: 88            moltype = AA  length = 106
FEATURE                  Location/Qualifiers
source                   1..106
                         mol_type = protein
                         organism = synthetic construct
SEQUENCE: 88
DIVMTQSPSS MSASVGDRVT ITCQASQNVR SAVAWYQQKP GKAPKLLIYW ASNRHTGVPS  60
RFSGSGSGTD FTFTISSLQP EDIATYYCQQ HWNYLTFGGG TKVEIK                106

SEQ ID NO: 89            moltype = AA  length = 106
FEATURE                  Location/Qualifiers
```

```
source                  1..106
                        mol_type = protein
                        organism = synthetic construct
SEQUENCE: 89
DIVMTQSPSS LSTSVGDRVT ITCRASQNVR SALAWYQQKP EKAPKSLIYW ASNRHSGVPS  60
RFSGSGSGTD FTLTISSLQP EDFATYYCQQ HWNYLTFGGG TKVEIK                106

SEQ ID NO: 90           moltype = AA  length = 106
FEATURE                 Location/Qualifiers
source                  1..106
                        mol_type = protein
                        organism = synthetic construct
SEQUENCE: 90
DIVMTQSPSS LSASVGDRVT ITCRASQNVR SALAWYQQKP EQAPKSLIYW ASNRHSGVPS  60
RFSGSGSGTD FTLTISSLQP EDFATYYCQQ HWNYLTFGGG TKVEIK                106

SEQ ID NO: 91           moltype = AA  length = 106
FEATURE                 Location/Qualifiers
source                  1..106
                        mol_type = protein
                        organism = synthetic construct
SEQUENCE: 91
DIVMTQSPSS LSASVGDRVT ITCQASQNVR SALNWYQQKP GKAPKLLIYW ASNRHTGVPS  60
RFSGSGSGTD FTFTISSLQS EDIATYYCQQ HWNYLTFGGG TKVEIK                106

SEQ ID NO: 92           moltype = AA  length = 106
FEATURE                 Location/Qualifiers
source                  1..106
                        mol_type = protein
                        organism = synthetic construct
SEQUENCE: 92
DIQMTQSPSS LSASVGDRVT ITCRASQNVR SALAWYQQKP EQAPKSLIYW ASSLQSGVPS  60
RFSGSGSGTD FTLTISNRHP EDFATYYCQQ HWNYLTFGGG TKVEIK                106

SEQ ID NO: 93           moltype = AA  length = 106
FEATURE                 Location/Qualifiers
source                  1..106
                        mol_type = protein
                        organism = synthetic construct
SEQUENCE: 93
DIQMTQSPSS LSTSVGDRVT ITCQASQNVR SALNWYQQKP GKAPKLLIYW ASNRHTGVPS  60
RFSGSGSGTD FTFTISSLQS EDIATYYCQQ HWNYLTFGGG TKVEIK                106

SEQ ID NO: 94           moltype = AA  length = 5
FEATURE                 Location/Qualifiers
source                  1..5
                        mol_type = protein
                        organism = synthetic construct
SEQUENCE: 94
NYWMQ                                                             5

SEQ ID NO: 95           moltype = AA  length = 17
FEATURE                 Location/Qualifiers
source                  1..17
                        mol_type = protein
                        organism = synthetic construct
SEQUENCE: 95
ATHPGHGDTR YTQKFKG                                                17

SEQ ID NO: 96           moltype = AA  length = 17
FEATURE                 Location/Qualifiers
source                  1..17
                        mol_type = protein
                        organism = synthetic construct
SEQUENCE: 96
ATHPGHGDTR YAQKFQG                                                17

SEQ ID NO: 97           moltype = AA  length = 17
FEATURE                 Location/Qualifiers
source                  1..17
                        mol_type = protein
                        organism = synthetic construct
SEQUENCE: 97
ATHPGHGDTR YSPSFQG                                                17

SEQ ID NO: 98           moltype = AA  length = 17
FEATURE                 Location/Qualifiers
source                  1..17
                        mol_type = protein
```

```
                        organism = synthetic construct
SEQUENCE: 98
ATHPGHGDTR YAEKFQG                                                      17

SEQ ID NO: 99           moltype = AA  length = 17
FEATURE                 Location/Qualifiers
source                  1..17
                        mol_type = protein
                        organism = synthetic construct
SEQUENCE: 99
TTLPGHGDTR YAQKFQG                                                      17

SEQ ID NO: 100          moltype = AA  length = 15
FEATURE                 Location/Qualifiers
source                  1..15
                        mol_type = protein
                        organism = synthetic construct
SEQUENCE: 100
EEVYYGFRSY WYFDV                                                        15

SEQ ID NO: 101          moltype = AA  length = 15
FEATURE                 Location/Qualifiers
source                  1..15
                        mol_type = protein
                        organism = synthetic construct
SEQUENCE: 101
EEVDYGFRSY WYFDV                                                        15

SEQ ID NO: 102          moltype = AA  length = 15
FEATURE                 Location/Qualifiers
source                  1..15
                        mol_type = protein
                        organism = synthetic construct
SEQUENCE: 102
EEVYYGFRSY WYFDL                                                        15

SEQ ID NO: 103          moltype = AA  length = 15
FEATURE                 Location/Qualifiers
source                  1..15
                        mol_type = protein
                        organism = synthetic construct
SEQUENCE: 103
RASESVDNYG VSFMN                                                        15

SEQ ID NO: 104          moltype = AA  length = 15
FEATURE                 Location/Qualifiers
source                  1..15
                        mol_type = protein
                        organism = synthetic construct
SEQUENCE: 104
RASESVDNYG VSRMN                                                        15

SEQ ID NO: 105          moltype = AA  length = 7
FEATURE                 Location/Qualifiers
source                  1..7
                        mol_type = protein
                        organism = synthetic construct
SEQUENCE: 105
GASNQGS                                                                 7

SEQ ID NO: 106          moltype = AA  length = 7
FEATURE                 Location/Qualifiers
source                  1..7
                        mol_type = protein
                        organism = synthetic construct
SEQUENCE: 106
GASNQQS                                                                 7

SEQ ID NO: 107          moltype = AA  length = 9
FEATURE                 Location/Qualifiers
source                  1..9
                        mol_type = protein
                        organism = synthetic construct
SEQUENCE: 107
QQSKEVPPT                                                               9

SEQ ID NO: 108          moltype = AA  length = 5
FEATURE                 Location/Qualifiers
source                  1..5
```

```
                        mol_type = protein
                        organism = synthetic construct
SEQUENCE: 108
SYWIH                                                        5

SEQ ID NO: 109          moltype = AA  length = 17
FEATURE                 Location/Qualifiers
source                  1..17
                        mol_type = protein
                        organism = synthetic construct
SEQUENCE: 109
NINPTNGGTN YNERFKS                                           17

SEQ ID NO: 110          moltype = AA  length = 17
FEATURE                 Location/Qualifiers
source                  1..17
                        mol_type = protein
                        organism = synthetic construct
SEQUENCE: 110
NINPTNGGTN YAQKFQG                                           17

SEQ ID NO: 111          moltype = AA  length = 17
FEATURE                 Location/Qualifiers
source                  1..17
                        mol_type = protein
                        organism = synthetic construct
SEQUENCE: 111
NINPTNGGTN YSQKFQG                                           17

SEQ ID NO: 112          moltype = AA  length = 11
FEATURE                 Location/Qualifiers
source                  1..11
                        mol_type = protein
                        organism = synthetic construct
SEQUENCE: 112
AYYYGSSLFA Y                                                 11

SEQ ID NO: 113          moltype = AA  length = 11
FEATURE                 Location/Qualifiers
source                  1..11
                        mol_type = protein
                        organism = synthetic construct
SEQUENCE: 113
KASQNVGTAV A                                                 11

SEQ ID NO: 114          moltype = AA  length = 7
FEATURE                 Location/Qualifiers
source                  1..7
                        mol_type = protein
                        organism = synthetic construct
SEQUENCE: 114
SASYRHT                                                      7

SEQ ID NO: 115          moltype = AA  length = 9
FEATURE                 Location/Qualifiers
source                  1..9
                        mol_type = protein
                        organism = synthetic construct
SEQUENCE: 115
QQYSTYPWT                                                    9

SEQ ID NO: 116          moltype = AA  length = 5
FEATURE                 Location/Qualifiers
source                  1..5
                        mol_type = protein
                        organism = synthetic construct
SEQUENCE: 116
SYGLS                                                        5

SEQ ID NO: 117          moltype = AA  length = 17
FEATURE                 Location/Qualifiers
source                  1..17
                        mol_type = protein
                        organism = synthetic construct
SEQUENCE: 117
WINTYSGVPT YANDFKG                                           17

SEQ ID NO: 118          moltype = AA  length = 17
FEATURE                 Location/Qualifiers
```

```
source                  1..17
                        mol_type = protein
                        organism = synthetic construct
SEQUENCE: 118
WINTYSGVPT YAQGFTG                                                17

SEQ ID NO: 119          moltype = AA  length = 17
FEATURE                 Location/Qualifiers
source                  1..17
                        mol_type = protein
                        organism = synthetic construct
SEQUENCE: 119
WINTYSGVPT YSQKFQG                                                17

SEQ ID NO: 120          moltype = AA  length = 16
FEATURE                 Location/Qualifiers
source                  1..16
                        mol_type = protein
                        organism = synthetic construct
SEQUENCE: 120
INTYSGVPTY AQKFQG                                                 16

SEQ ID NO: 121          moltype = AA  length = 17
FEATURE                 Location/Qualifiers
source                  1..17
                        mol_type = protein
                        organism = synthetic construct
SEQUENCE: 121
WINTYSGVPT YAQKFQG                                                17

SEQ ID NO: 122          moltype = AA  length = 17
FEATURE                 Location/Qualifiers
source                  1..17
                        mol_type = protein
                        organism = synthetic construct
SEQUENCE: 122
WINTYSGVPT YAQGFAG                                                17

SEQ ID NO: 123          moltype = AA  length = 5
FEATURE                 Location/Qualifiers
source                  1..5
                        mol_type = protein
                        organism = synthetic construct
SEQUENCE: 123
SLVDY                                                             5

SEQ ID NO: 124          moltype = AA  length = 5
FEATURE                 Location/Qualifiers
source                  1..5
                        mol_type = protein
                        organism = synthetic construct
SEQUENCE: 124
TLADY                                                             5

SEQ ID NO: 125          moltype = AA  length = 5
FEATURE                 Location/Qualifiers
source                  1..5
                        mol_type = protein
                        organism = synthetic construct
SEQUENCE: 125
TMVDY                                                             5

SEQ ID NO: 126          moltype = AA  length = 5
FEATURE                 Location/Qualifiers
source                  1..5
                        mol_type = protein
                        organism = synthetic construct
SEQUENCE: 126
TLGDY                                                             5

SEQ ID NO: 127          moltype = AA  length = 5
FEATURE                 Location/Qualifiers
source                  1..5
                        mol_type = protein
                        organism = synthetic construct
SEQUENCE: 127
TLVDY                                                             5

SEQ ID NO: 128          moltype = AA  length = 5
```

```
FEATURE                 Location/Qualifiers
source                  1..5
                        mol_type = protein
                        organism = synthetic construct
SEQUENCE: 128
SLADY                                                                       5

SEQ ID NO: 129          moltype = AA  length = 5
FEATURE                 Location/Qualifiers
source                  1..5
                        mol_type = protein
                        organism = synthetic construct
SEQUENCE: 129
SMADY                                                                       5

SEQ ID NO: 130          moltype = AA  length = 16
FEATURE                 Location/Qualifiers
source                  1..16
                        mol_type = protein
                        organism = synthetic construct
SEQUENCE: 130
KSSQSLLYSD GKTYLS                                                           16

SEQ ID NO: 131          moltype = AA  length = 16
FEATURE                 Location/Qualifiers
source                  1..16
                        mol_type = protein
                        organism = synthetic construct
SEQUENCE: 131
KSSRSLLYSD GKTYLS                                                           16

SEQ ID NO: 132          moltype = AA  length = 16
FEATURE                 Location/Qualifiers
source                  1..16
                        mol_type = protein
                        organism = synthetic construct
SEQUENCE: 132
KSSRSLLYSG GKTYLS                                                           16

SEQ ID NO: 133          moltype = AA  length = 16
FEATURE                 Location/Qualifiers
source                  1..16
                        mol_type = protein
                        organism = synthetic construct
SEQUENCE: 133
KSSRSLLYSE GKTYLS                                                           16

SEQ ID NO: 134          moltype = AA  length = 16
FEATURE                 Location/Qualifiers
source                  1..16
                        mol_type = protein
                        organism = synthetic construct
SEQUENCE: 134
KSSRSLLYSA GKTYLS                                                           16

SEQ ID NO: 135          moltype = AA  length = 16
FEATURE                 Location/Qualifiers
source                  1..16
                        mol_type = protein
                        organism = synthetic construct
SEQUENCE: 135
KSSRSLLYSS GKTYLS                                                           16

SEQ ID NO: 136          moltype = AA  length = 16
FEATURE                 Location/Qualifiers
source                  1..16
                        mol_type = protein
                        organism = synthetic construct
SEQUENCE: 136
KSSRSLLYSQ GKTYLS                                                           16

SEQ ID NO: 137          moltype = AA  length = 16
FEATURE                 Location/Qualifiers
source                  1..16
                        mol_type = protein
                        organism = synthetic construct
SEQUENCE: 137
KASQSLLYSD GKTYLS                                                           16
```

```
SEQ ID NO: 138          moltype = AA  length = 16
FEATURE                 Location/Qualifiers
source                  1..16
                        mol_type = protein
                        organism = synthetic construct
SEQUENCE: 138
KSGQSLLYSD GKTYLS                                              16

SEQ ID NO: 139          moltype = AA  length = 7
FEATURE                 Location/Qualifiers
source                  1..7
                        mol_type = protein
                        organism = synthetic construct
SEQUENCE: 139
LVSKLDS                                                        7

SEQ ID NO: 140          moltype = AA  length = 7
FEATURE                 Location/Qualifiers
source                  1..7
                        mol_type = protein
                        organism = synthetic construct
SEQUENCE: 140
EVSKLDS                                                        7

SEQ ID NO: 141          moltype = AA  length = 7
FEATURE                 Location/Qualifiers
source                  1..7
                        mol_type = protein
                        organism = synthetic construct
SEQUENCE: 141
LVSRLDS                                                        7

SEQ ID NO: 142          moltype = AA  length = 7
FEATURE                 Location/Qualifiers
source                  1..7
                        mol_type = protein
                        organism = synthetic construct
SEQUENCE: 142
LVSKLES                                                        7

SEQ ID NO: 143          moltype = AA  length = 7
FEATURE                 Location/Qualifiers
source                  1..7
                        mol_type = protein
                        organism = synthetic construct
SEQUENCE: 143
LVSKLSS                                                        7

SEQ ID NO: 144          moltype = AA  length = 9
FEATURE                 Location/Qualifiers
source                  1..9
                        mol_type = protein
                        organism = synthetic construct
SEQUENCE: 144
WQGIDFHQT                                                      9

SEQ ID NO: 145          moltype = AA  length = 9
FEATURE                 Location/Qualifiers
source                  1..9
                        mol_type = protein
                        organism = synthetic construct
SEQUENCE: 145
WQGIRFHQT                                                      9

SEQ ID NO: 146          moltype = AA  length = 7
FEATURE                 Location/Qualifiers
source                  1..7
                        mol_type = protein
                        organism = synthetic construct
SEQUENCE: 146
TSDMGVG                                                        7

SEQ ID NO: 147          moltype = AA  length = 7
FEATURE                 Location/Qualifiers
source                  1..7
                        mol_type = protein
                        organism = synthetic construct
SEQUENCE: 147
TSDMGVS                                                        7
```

```
SEQ ID NO: 148          moltype = AA  length = 16
FEATURE                 Location/Qualifiers
source                  1..16
                        mol_type = protein
                        organism = synthetic construct
SEQUENCE: 148
DIWWDDNKYY NPSLKS                                                   16

SEQ ID NO: 149          moltype = AA  length = 16
FEATURE                 Location/Qualifiers
source                  1..16
                        mol_type = protein
                        organism = synthetic construct
SEQUENCE: 149
LIWWDDNKYY STSLKT                                                   16

SEQ ID NO: 150          moltype = AA  length = 16
FEATURE                 Location/Qualifiers
source                  1..16
                        mol_type = protein
                        organism = synthetic construct
SEQUENCE: 150
LIWWDDNKYY SPSLKS                                                   16

SEQ ID NO: 151          moltype = AA  length = 16
FEATURE                 Location/Qualifiers
source                  1..16
                        mol_type = protein
                        organism = synthetic construct
SEQUENCE: 151
HIWWDDNKSY STSLKS                                                   16

SEQ ID NO: 152          moltype = AA  length = 16
FEATURE                 Location/Qualifiers
source                  1..16
                        mol_type = protein
                        organism = synthetic construct
SEQUENCE: 152
SIWWDDNKYY NPSLKS                                                   16

SEQ ID NO: 153          moltype = AA  length = 16
FEATURE                 Location/Qualifiers
source                  1..16
                        mol_type = protein
                        organism = synthetic construct
SEQUENCE: 153
SIWYDDNKYY NPSLKS                                                   16

SEQ ID NO: 154          moltype = AA  length = 10
FEATURE                 Location/Qualifiers
source                  1..10
                        mol_type = protein
                        organism = synthetic construct
SEQUENCE: 154
RANYGNLFDY                                                          10

SEQ ID NO: 155          moltype = AA  length = 11
FEATURE                 Location/Qualifiers
source                  1..11
                        mol_type = protein
                        organism = synthetic construct
SEQUENCE: 155
KASQNVRSAV A                                                        11

SEQ ID NO: 156          moltype = AA  length = 11
FEATURE                 Location/Qualifiers
source                  1..11
                        mol_type = protein
                        organism = synthetic construct
SEQUENCE: 156
RASQNVRSAL A                                                        11

SEQ ID NO: 157          moltype = AA  length = 11
FEATURE                 Location/Qualifiers
source                  1..11
                        mol_type = protein
                        organism = synthetic construct
SEQUENCE: 157
```

```
QASQNVRSAV A                                                        11

SEQ ID NO: 158          moltype = AA  length = 11
FEATURE                 Location/Qualifiers
source                  1..11
                        mol_type = protein
                        organism = synthetic construct
SEQUENCE: 158
QASQNVRSAL N                                                        11

SEQ ID NO: 159          moltype = AA  length = 7
FEATURE                 Location/Qualifiers
source                  1..7
                        mol_type = protein
                        organism = synthetic construct
SEQUENCE: 159
WASNRHT                                                             7

SEQ ID NO: 160          moltype = AA  length = 7
FEATURE                 Location/Qualifiers
source                  1..7
                        mol_type = protein
                        organism = synthetic construct
SEQUENCE: 160
WASNRHS                                                             7

SEQ ID NO: 161          moltype = AA  length = 7
FEATURE                 Location/Qualifiers
source                  1..7
                        mol_type = protein
                        organism = synthetic construct
SEQUENCE: 161
WASSLQS                                                             7

SEQ ID NO: 162          moltype = AA  length = 7
FEATURE                 Location/Qualifiers
source                  1..7
                        mol_type = protein
                        organism = synthetic construct
SEQUENCE: 162
QHWNYLT                                                             7

SEQ ID NO: 163          moltype = AA  length = 8
FEATURE                 Location/Qualifiers
source                  1..8
                        mol_type = protein
                        organism = synthetic construct
SEQUENCE: 163
QQHWNYLT                                                            8

SEQ ID NO: 164          moltype = AA  length = 124
FEATURE                 Location/Qualifiers
source                  1..124
                        mol_type = protein
                        organism = synthetic construct
SEQUENCE: 164
QVQLQQSGAE LARPGASVKL SCKASGYTFT NYWMQWVKQR PGQGLEWIGA THPGHGDTRY  60
TQKFKGKATL SADKSSSTAY MQLSNLASED SAVYYCAREE VYYGFRSYWY FDVWGRGTLV  120
TVSS                                                                124

SEQ ID NO: 165          moltype = AA  length = 111
FEATURE                 Location/Qualifiers
source                  1..111
                        mol_type = protein
                        organism = synthetic construct
SEQUENCE: 165
DIVLTQSPAS LAVSLGQRAT ISCRASESVD NYGVSFMNWF QQKPGQPPKL LIYGASNQGS  60
GVPARFSGSG SGTDFSLNIH PMEEDDTAMY FCQQSKEVPP TFGGGTKLEI K           111

SEQ ID NO: 166          moltype = AA  length = 120
FEATURE                 Location/Qualifiers
source                  1..120
                        mol_type = protein
                        organism = synthetic construct
SEQUENCE: 166
QVQLQQPGTE LVKPGASVKL SCKASGYTFT SYWIHWVKQR PGQGLEWIGN INPTNGGTNY  60
NERFKSKATL TVDKSSSTAY MQLSSLTSED SAVYYCARAY YYGSSLFAYW GQGTLVTVSS  120

SEQ ID NO: 167          moltype = AA  length = 107
```

```
FEATURE                 Location/Qualifiers
source                  1..107
                        mol_type = protein
                        organism = synthetic construct
SEQUENCE: 167
DIVMTQSQKF MSTTVGDRVS ITCKASQNVG TAVAWSQQKP GQSPKLLIYS ASYRHTGVPD  60
RFTGSGSGTD FTLTITNMQS EDLADYFCQQ YSTYPWTFGG GTKLEIK                107

SEQ ID NO: 168          moltype = AA  length = 114
FEATURE                 Location/Qualifiers
source                  1..114
                        mol_type = protein
                        organism = synthetic construct
SEQUENCE: 168
QIQLVQSGPE LKKPGETVKI SCKASGYIFT SYGLSWVKQT PGKGLKWMGW INTYSGVPTY  60
ANDFKGRFAF SLETSASTTY LRINNLKNDD TATYFCARSL VDYWGQGTPL TVSS        114

SEQ ID NO: 169          moltype = AA  length = 112
FEATURE                 Location/Qualifiers
source                  1..112
                        mol_type = protein
                        organism = synthetic construct
SEQUENCE: 169
DVVMTQTPFT LSVTIGQSAS ISCKSSQSLL YSDGKTYLSW LLQRPGQSPK RLIYLVSKLD  60
SGVPDRFTGS GSGTDFTLKI SRVEAEDLGV YYCWQGIDFH QTFGGGTKLE IK          112

SEQ ID NO: 170          moltype = AA  length = 120
FEATURE                 Location/Qualifiers
source                  1..120
                        mol_type = protein
                        organism = synthetic construct
SEQUENCE: 170
QVTLKESGPG ILQPSQTLSL TCSFSGFSLR TSDMGVGWVR QPSGEGLEWL ADIWWDDNKY  60
YNPSLKSRLT ISKDTSSNQV FLKITSVDTA DTATYYCARR ANYGNLFDYW GQGTAVTVSS  120

SEQ ID NO: 171          moltype = AA  length = 106
FEATURE                 Location/Qualifiers
source                  1..106
                        mol_type = protein
                        organism = synthetic construct
SEQUENCE: 171
DIVMTQSLKF MSTSVGDRVS ITCKASQNVR SAVAWYQQKP GQSPKVLIYW ASNRHTGVPD  60
RFTGSGSGTD FTLTISNVQS EDLADYFCLQ HWNYLTFGSG TKLEIK                 106

SEQ ID NO: 172          moltype = AA  length = 171
FEATURE                 Location/Qualifiers
source                  1..171
                        mol_type = protein
                        organism = synthetic construct
SEQUENCE: 172
MGWSCIILFL VATATGVHSM YGKLNDLLED LQEVLKNLHK NCMASNTYGS NPISKDNLHD  60
VDNHLQNVIE DIHDFMQGGG SGGKLQEMMK EFQQVLDELN NHSFHHPYCN YYGNSNNCHG  120
TMSHTVHHIE QNIKEIFHHL EELVHRHHHH HHHHGGGLND IFEAQKIEWH E           171

SEQ ID NO: 173          moltype = AA  length = 177
FEATURE                 Location/Qualifiers
source                  1..177
                        mol_type = protein
                        organism = synthetic construct
SEQUENCE: 173
MGWSCIILFL VATATGVHSA DLEDNWETLN DNLKVIECMA SNTYGSNPIS AAQVKDALTK  60
MRAAALDAQK ATPPKLEDKS PDSPEMKDFR HGFDILVGQI DDALKLANSF HHPYCNYYGN  120
SNNCHGTMSV KEAQAAAEQL KTTRNAYIQK YLHHHHHHHH GGGLNDIFEA QKIEWHE     177

SEQ ID NO: 174          moltype = AA  length = 179
FEATURE                 Location/Qualifiers
source                  1..179
                        mol_type = protein
                        organism = synthetic construct
SEQUENCE: 174
MGWSCIILFL VATATGVHSA DLEDNWETLN DNLKVIEGPC MASNTYGSNP ISAAQVKDAL  60
TKMRAAALDA QKATPPKLED KSPDSPEMKD FRHGFDILVG QIDDALKLAN SFHHPYCNYY  120
GNSNNCHGTM SVKEAQAAAE QLKTTRNAYI QKYLHHHHHH HHGGGLNDIF EAQKIEWHE   179

SEQ ID NO: 175          moltype = AA  length = 146
FEATURE                 Location/Qualifiers
source                  1..146
                        mol_type = protein
                        organism = synthetic construct
```

```
SEQUENCE: 175
MGWSCIILFL VATATGVHSM YGKLNDLLED LQEVLKNLHK NWHGGKDNLH DVDNHLQNVI  60
EDIHDFMQGG GSGGKLQEMM KEFQQVLDEL NNHLQGGKHT VHHIEQNIKE IFHHLEELVH  120
RHHHHHHHHG GGLNDIFEAQ KIEWHE                                       146

SEQ ID NO: 176         moltype = AA  length = 150
FEATURE                Location/Qualifiers
source                 1..150
                       mol_type = protein
                       organism = synthetic construct
SEQUENCE: 176
MGWSCIILFL VATATGVHSA DLEDNWETLN DNLKVIEKAD NAAQVKDALT KMRAAALDAQ  60
KATPPKLEDK SPDSPEMKDF RHGFDILVGQ IDDALKLANE GKVKEAQAAA EQLKTTRNAY  120
IQKYLHHHHH HHHGGGLNDI FEAQKIEWHE                                   150

SEQ ID NO: 177         moltype = AA  length = 13
FEATURE                Location/Qualifiers
source                 1..13
                       mol_type = protein
                       organism = Homo sapiens
SEQUENCE: 177
CMASNTYGSN PIS                                                     13

SEQ ID NO: 178         moltype = AA  length = 21
FEATURE                Location/Qualifiers
source                 1..21
                       mol_type = protein
                       organism = Homo sapiens
SEQUENCE: 178
SFHHPYCNYY GNSNNCHGTM S                                            21

SEQ ID NO: 179         moltype = AA  length = 117
FEATURE                Location/Qualifiers
source                 1..117
                       mol_type = protein
                       organism = synthetic construct
SEQUENCE: 179
EVKLEESGGG LVQPGRSMKL SCVASGFTFS NYWMNWVRQS PEKGLEWVAE IRLKSNNYAT  60
HYAESVKGRF TISRDDSKSS VYLQMNNLRA EDTGIYYCSS MIIVDYWGQG TTVTVSS     117

SEQ ID NO: 180         moltype = AA  length = 111
FEATURE                Location/Qualifiers
source                 1..111
                       mol_type = protein
                       organism = synthetic construct
SEQUENCE: 180
DIVLTQSPAS LTVSLGQRAT ISCRASQSVS SSTYSYLHWY QQRPGQPPKL LIKYASNLES  60
GVPARFSGSG SGTVFTLNIH PVEEEDTATY YCQHSWEIPL TFGAGTKLEM K           111

SEQ ID NO: 181         moltype = AA  length = 102
FEATURE                Location/Qualifiers
source                 1..102
                       mol_type = protein
                       organism = synthetic construct
SEQUENCE: 181
MYGKLNDLLE DLQEVLKNLH KNWHGGKDNL HDVDNHLQNV IEDIHDFMQG GGSGGKLQEM  60
MKEFQQVLDE LNNHLQGGKH TVHHIEQNIK EIFHHLEELV HR                     102

SEQ ID NO: 182         moltype = AA  length = 106
FEATURE                Location/Qualifiers
source                 1..106
                       mol_type = protein
                       organism = synthetic construct
SEQUENCE: 182
ADLEDNWETL NDNLKVIEKA DNAAQVKDAL TKMRAAALDA QKATPPKLED KSPDSPEMKD  60
FRHGFDILVG QIDDALKLAN EGKVKEAQAA AEQLKTTRNA YIQKYL                 106

SEQ ID NO: 183         moltype = AA  length = 21
FEATURE                Location/Qualifiers
source                 1..21
                       mol_type = protein
                       organism = synthetic construct
SEQUENCE: 183
SFHHAYCNYY GNSNNCHGTM S                                            21

SEQ ID NO: 184         moltype = AA  length = 21
FEATURE                Location/Qualifiers
source                 1..21
                       mol_type = protein
```

```
                         organism = synthetic construct
SEQUENCE: 184
SFHHPYCNYY GNSANCHGTM S                                                21

SEQ ID NO: 185          moltype =   length =
SEQUENCE: 185
000

SEQ ID NO: 186          moltype =   length =
SEQUENCE: 186
000

SEQ ID NO: 187          moltype =   length =
SEQUENCE: 187
000

SEQ ID NO: 188          moltype =   length =
SEQUENCE: 188
000

SEQ ID NO: 189          moltype =   length =
SEQUENCE: 189
000

SEQ ID NO: 190          moltype =   length =
SEQUENCE: 190
000

SEQ ID NO: 191          moltype =   length =
SEQUENCE: 191
000

SEQ ID NO: 192          moltype =   length =
SEQUENCE: 192
000

SEQ ID NO: 193          moltype =   length =
SEQUENCE: 193
000

SEQ ID NO: 194          moltype =   length =
SEQUENCE: 194
000

SEQ ID NO: 195          moltype =   length =
SEQUENCE: 195
000

SEQ ID NO: 196          moltype =   length =
SEQUENCE: 196
000

SEQ ID NO: 197          moltype =   length =
SEQUENCE: 197
000

SEQ ID NO: 198          moltype =   length =
SEQUENCE: 198
000

SEQ ID NO: 199          moltype =   length =
SEQUENCE: 199
000

SEQ ID NO: 200          moltype =   length =
SEQUENCE: 200
000

SEQ ID NO: 201          moltype =   length =
SEQUENCE: 201
000

SEQ ID NO: 202          moltype =   length =
SEQUENCE: 202
000

SEQ ID NO: 203          moltype =   length =
SEQUENCE: 203
000
```

SEQ ID NO: 204 moltype = length =
SEQUENCE: 204
000

SEQ ID NO: 205 moltype = length =
SEQUENCE: 205
000

SEQ ID NO: 206 moltype = length =
SEQUENCE: 206
000

SEQ ID NO: 207 moltype = length =
SEQUENCE: 207
000

SEQ ID NO: 208 moltype = length =
SEQUENCE: 208
000

SEQ ID NO: 209 moltype = length =
SEQUENCE: 209
000

SEQ ID NO: 210 moltype = length =
SEQUENCE: 210
000

SEQ ID NO: 211 moltype = length =
SEQUENCE: 211
000

SEQ ID NO: 212 moltype = length =
SEQUENCE: 212
000

SEQ ID NO: 213 moltype = length =
SEQUENCE: 213
000

SEQ ID NO: 214 moltype = length =
SEQUENCE: 214
000

SEQ ID NO: 215 moltype = length =
SEQUENCE: 215
000

SEQ ID NO: 216 moltype = length =
SEQUENCE: 216
000

SEQ ID NO: 217 moltype = length =
SEQUENCE: 217
000

SEQ ID NO: 218 moltype = length =
SEQUENCE: 218
000

SEQ ID NO: 219 moltype = length =
SEQUENCE: 219
000

SEQ ID NO: 220 moltype = length =
SEQUENCE: 220
000

SEQ ID NO: 221 moltype = length =
SEQUENCE: 221
000

SEQ ID NO: 222 moltype = length =
SEQUENCE: 222
000

SEQ ID NO: 223 moltype = length =
SEQUENCE: 223

000

SEQ ID NO: 224 moltype = length =
SEQUENCE: 224
000

SEQ ID NO: 225 moltype = length =
SEQUENCE: 225
000

SEQ ID NO: 226 moltype = length =
SEQUENCE: 226
000

SEQ ID NO: 227 moltype = length =
SEQUENCE: 227
000

SEQ ID NO: 228 moltype = length =
SEQUENCE: 228
000

SEQ ID NO: 229 moltype = length =
SEQUENCE: 229
000

SEQ ID NO: 230 moltype = length =
SEQUENCE: 230
000

SEQ ID NO: 231 moltype = length =
SEQUENCE: 231
000

SEQ ID NO: 232 moltype = length =
SEQUENCE: 232
000

SEQ ID NO: 233 moltype = length =
SEQUENCE: 233
000

SEQ ID NO: 234 moltype = length =
SEQUENCE: 234
000

SEQ ID NO: 235 moltype = length =
SEQUENCE: 235
000

SEQ ID NO: 236 moltype = length =
SEQUENCE: 236
000

SEQ ID NO: 237 moltype = length =
SEQUENCE: 237
000

SEQ ID NO: 238 moltype = length =
SEQUENCE: 238
000

SEQ ID NO: 239 moltype = length =
SEQUENCE: 239
000

SEQ ID NO: 240 moltype = length =
SEQUENCE: 240
000

SEQ ID NO: 241 moltype = length =
SEQUENCE: 241
000

SEQ ID NO: 242 moltype = length =
SEQUENCE: 242
000

SEQ ID NO: 243 moltype = length =

```
SEQUENCE: 243
000

SEQ ID NO: 244          moltype =   length =
SEQUENCE: 244
000

SEQ ID NO: 245          moltype =   length =
SEQUENCE: 245
000

SEQ ID NO: 246          moltype =   length =
SEQUENCE: 246
000

SEQ ID NO: 247          moltype =   length =
SEQUENCE: 247
000

SEQ ID NO: 248          moltype =   length =
SEQUENCE: 248
000

SEQ ID NO: 249          moltype =   length =
SEQUENCE: 249
000

SEQ ID NO: 250          moltype =   length =
SEQUENCE: 250
000

SEQ ID NO: 251          moltype =   length =
SEQUENCE: 251
000

SEQ ID NO: 252          moltype =   length =
SEQUENCE: 252
000

SEQ ID NO: 253          moltype =   length =
SEQUENCE: 253
000

SEQ ID NO: 254          moltype =   length =
SEQUENCE: 254
000

SEQ ID NO: 255          moltype = AA  length = 13
FEATURE                 Location/Qualifiers
source                  1..13
                        mol_type = protein
                        organism = synthetic construct
SEQUENCE: 255
SMASNTYGSN PIS                                                    13

SEQ ID NO: 256          moltype = AA  length = 13
FEATURE                 Location/Qualifiers
source                  1..13
                        mol_type = protein
                        organism = synthetic construct
SEQUENCE: 256
CAASNTYGSN PIS                                                    13

SEQ ID NO: 257          moltype = AA  length = 13
FEATURE                 Location/Qualifiers
source                  1..13
                        mol_type = protein
                        organism = synthetic construct
SEQUENCE: 257
CMSSNTYGSN PIS                                                    13

SEQ ID NO: 258          moltype = AA  length = 13
FEATURE                 Location/Qualifiers
source                  1..13
                        mol_type = protein
                        organism = synthetic construct
SEQUENCE: 258
CMAANTYGSN PIS                                                    13
```

```
SEQ ID NO: 259          moltype = AA  length = 13
FEATURE                 Location/Qualifiers
source                  1..13
                        mol_type = protein
                        organism = synthetic construct
SEQUENCE: 259
CMASATYGSN PIS                                                     13

SEQ ID NO: 260          moltype = AA  length = 13
FEATURE                 Location/Qualifiers
source                  1..13
                        mol_type = protein
                        organism = synthetic construct
SEQUENCE: 260
CMASNAYGSN PIS                                                     13

SEQ ID NO: 261          moltype = AA  length = 13
FEATURE                 Location/Qualifiers
source                  1..13
                        mol_type = protein
                        organism = synthetic construct
SEQUENCE: 261
CMASNTAGSN PIS                                                     13

SEQ ID NO: 262          moltype = AA  length = 13
FEATURE                 Location/Qualifiers
source                  1..13
                        mol_type = protein
                        organism = synthetic construct
SEQUENCE: 262
CMASNTYASN PIS                                                     13

SEQ ID NO: 263          moltype = AA  length = 13
FEATURE                 Location/Qualifiers
source                  1..13
                        mol_type = protein
                        organism = synthetic construct
SEQUENCE: 263
CMASNTYGAN PIS                                                     13

SEQ ID NO: 264          moltype = AA  length = 13
FEATURE                 Location/Qualifiers
source                  1..13
                        mol_type = protein
                        organism = synthetic construct
SEQUENCE: 264
CMASNTYGSA PIS                                                     13

SEQ ID NO: 265          moltype = AA  length = 13
FEATURE                 Location/Qualifiers
source                  1..13
                        mol_type = protein
                        organism = synthetic construct
SEQUENCE: 265
CMASNTYGSN AIS                                                     13

SEQ ID NO: 266          moltype = AA  length = 13
FEATURE                 Location/Qualifiers
source                  1..13
                        mol_type = protein
                        organism = synthetic construct
SEQUENCE: 266
CMASNTYGSN PAS                                                     13

SEQ ID NO: 267          moltype = AA  length = 13
FEATURE                 Location/Qualifiers
source                  1..13
                        mol_type = protein
                        organism = synthetic construct
SEQUENCE: 267
CMASNTYGSN PIA                                                     13

SEQ ID NO: 268          moltype = AA  length = 21
FEATURE                 Location/Qualifiers
source                  1..21
                        mol_type = protein
                        organism = synthetic construct
SEQUENCE: 268
AFHHPYCNYY GNSNNCHGTM S                                            21
```

```
SEQ ID NO: 269          moltype = AA  length = 21
FEATURE                 Location/Qualifiers
source                  1..21
                        mol_type = protein
                        organism = synthetic construct
SEQUENCE: 269
SAHHPYCNYY GNSNNCHGTM S                                              21

SEQ ID NO: 270          moltype = AA  length = 21
FEATURE                 Location/Qualifiers
source                  1..21
                        mol_type = protein
                        organism = synthetic construct
SEQUENCE: 270
SFAHPYCNYY GNSNNCHGTM S                                              21

SEQ ID NO: 271          moltype = AA  length = 21
FEATURE                 Location/Qualifiers
source                  1..21
                        mol_type = protein
                        organism = synthetic construct
SEQUENCE: 271
SFHAPYCNYY GNSNNCHGTM S                                              21

SEQ ID NO: 272          moltype = AA  length = 21
FEATURE                 Location/Qualifiers
source                  1..21
                        mol_type = protein
                        organism = synthetic construct
SEQUENCE: 272
SFHHPACNYY GNSNNCHGTM S                                              21

SEQ ID NO: 273          moltype = AA  length = 21
FEATURE                 Location/Qualifiers
source                  1..21
                        mol_type = protein
                        organism = synthetic construct
SEQUENCE: 273
SFHHPYSNYY GNSNNCHGTM S                                              21

SEQ ID NO: 274          moltype = AA  length = 21
FEATURE                 Location/Qualifiers
source                  1..21
                        mol_type = protein
                        organism = synthetic construct
SEQUENCE: 274
SFHHPYCAYY GNSNNCHGTM S                                              21

SEQ ID NO: 275          moltype = AA  length = 21
FEATURE                 Location/Qualifiers
source                  1..21
                        mol_type = protein
                        organism = synthetic construct
SEQUENCE: 275
SFHHPYCNAY GNSNNCHGTM S                                              21

SEQ ID NO: 276          moltype = AA  length = 21
FEATURE                 Location/Qualifiers
source                  1..21
                        mol_type = protein
                        organism = synthetic construct
SEQUENCE: 276
SFHHPYCNYA GNSNNCHGTM S                                              21

SEQ ID NO: 277          moltype = AA  length = 21
FEATURE                 Location/Qualifiers
source                  1..21
                        mol_type = protein
                        organism = synthetic construct
SEQUENCE: 277
SFHHPYCNYY ANSNNCHGTM S                                              21

SEQ ID NO: 278          moltype = AA  length = 21
FEATURE                 Location/Qualifiers
source                  1..21
                        mol_type = protein
                        organism = synthetic construct
SEQUENCE: 278
```

```
SFHHPYCNYY GASNNCHGTM S                                            21

SEQ ID NO: 279          moltype = AA  length = 21
FEATURE                 Location/Qualifiers
source                  1..21
                        mol_type = protein
                        organism = synthetic construct
SEQUENCE: 279
SFHHPYCNYY GNANNCHGTM S                                            21

SEQ ID NO: 280          moltype = AA  length = 21
FEATURE                 Location/Qualifiers
source                  1..21
                        mol_type = protein
                        organism = synthetic construct
SEQUENCE: 280
SFHHPYCNYY GNSNACHGTM S                                            21

SEQ ID NO: 281          moltype = AA  length = 21
FEATURE                 Location/Qualifiers
source                  1..21
                        mol_type = protein
                        organism = synthetic construct
SEQUENCE: 281
SFHHPYCNYY GNSNNSHGTM S                                            21

SEQ ID NO: 282          moltype = AA  length = 21
FEATURE                 Location/Qualifiers
source                  1..21
                        mol_type = protein
                        organism = synthetic construct
SEQUENCE: 282
SFHHPYCNYY GNSNNCAGTM S                                            21

SEQ ID NO: 283          moltype = AA  length = 21
FEATURE                 Location/Qualifiers
source                  1..21
                        mol_type = protein
                        organism = synthetic construct
SEQUENCE: 283
SFHHPYCNYY GNSNNCHATM S                                            21

SEQ ID NO: 284          moltype = AA  length = 21
FEATURE                 Location/Qualifiers
source                  1..21
                        mol_type = protein
                        organism = synthetic construct
SEQUENCE: 284
SFHHPYCNYY GNSNNCHGAM S                                            21

SEQ ID NO: 285          moltype = AA  length = 21
FEATURE                 Location/Qualifiers
source                  1..21
                        mol_type = protein
                        organism = synthetic construct
SEQUENCE: 285
SFHHPYCNYY GNSNNCHGTA S                                            21

SEQ ID NO: 286          moltype = AA  length = 21
FEATURE                 Location/Qualifiers
source                  1..21
                        mol_type = protein
                        organism = synthetic construct
SEQUENCE: 286
SFHHPYCNYY GNSNNCHGTM A                                            21

SEQ ID NO: 287          moltype = AA  length = 18
FEATURE                 Location/Qualifiers
source                  1..18
                        mol_type = protein
                        organism = synthetic construct
SEQUENCE: 287
SFHHPYCNYY NNCHGTMS                                                18

SEQ ID NO: 288          moltype = AA  length = 16
FEATURE                 Location/Qualifiers
source                  1..16
                        mol_type = protein
                        organism = synthetic construct
```

```
SEQUENCE: 288
SFHHPYCNNN CHGTMS                                                    16

SEQ ID NO: 289          moltype = AA  length = 13
FEATURE                 Location/Qualifiers
source                  1..13
                        mol_type = protein
                        organism = Homo sapiens
SEQUENCE: 289
CMASNTYGSN PIS                                                       13

SEQ ID NO: 290          moltype = AA  length = 21
FEATURE                 Location/Qualifiers
source                  1..21
                        mol_type = protein
                        organism = synthetic construct
SEQUENCE: 290
SFHHPYCNYY GNSNNCHGTM S                                              21

SEQ ID NO: 291          moltype =   length =
SEQUENCE: 291
000

SEQ ID NO: 292          moltype = AA  length = 15
FEATURE                 Location/Qualifiers
source                  1..15
                        mol_type = protein
                        organism = Homo sapiens
SEQUENCE: 292
ITMMCMASNT YGSNP                                                     15

SEQ ID NO: 293          moltype = AA  length = 15
FEATURE                 Location/Qualifiers
source                  1..15
                        mol_type = protein
                        organism = Homo sapiens
SEQUENCE: 293
MMCMASNTYG SNPIS                                                     15

SEQ ID NO: 294          moltype = AA  length = 15
FEATURE                 Location/Qualifiers
source                  1..15
                        mol_type = protein
                        organism = Homo sapiens
SEQUENCE: 294
CMASNTYGSN PISVY                                                     15

SEQ ID NO: 295          moltype = AA  length = 15
FEATURE                 Location/Qualifiers
source                  1..15
                        mol_type = protein
                        organism = Homo sapiens
SEQUENCE: 295
ASNTYGSNPI SVYIG                                                     15

SEQ ID NO: 296          moltype = AA  length = 15
FEATURE                 Location/Qualifiers
source                  1..15
                        mol_type = protein
                        organism = Homo sapiens
SEQUENCE: 296
LAFYSFHHPY CNYYG                                                     15

SEQ ID NO: 297          moltype = AA  length = 15
FEATURE                 Location/Qualifiers
source                  1..15
                        mol_type = protein
                        organism = Homo sapiens
SEQUENCE: 297
FYSFHHPYCN YYGNS                                                     15

SEQ ID NO: 298          moltype = AA  length = 15
FEATURE                 Location/Qualifiers
source                  1..15
                        mol_type = protein
                        organism = Homo sapiens
SEQUENCE: 298
SFHHPYCNYY GNSNN                                                     15
```

```
SEQ ID NO: 299         moltype = AA  length = 15
FEATURE                Location/Qualifiers
source                 1..15
                       mol_type = protein
                       organism = Homo sapiens
SEQUENCE: 299
HHPYCNYYGN SNNCH                                                   15

SEQ ID NO: 300         moltype = AA  length = 15
FEATURE                Location/Qualifiers
source                 1..15
                       mol_type = protein
                       organism = Homo sapiens
SEQUENCE: 300
PYCNYYGNSN NCHGT                                                   15

SEQ ID NO: 301         moltype = AA  length = 15
FEATURE                Location/Qualifiers
source                 1..15
                       mol_type = protein
                       organism = Homo sapiens
SEQUENCE: 301
CNYYGNSNNC HGTMS                                                   15

SEQ ID NO: 302         moltype = AA  length = 15
FEATURE                Location/Qualifiers
source                 1..15
                       mol_type = protein
                       organism = Homo sapiens
SEQUENCE: 302
YYGNSNNCHG TMSIL                                                   15

SEQ ID NO: 303         moltype = AA  length = 15
FEATURE                Location/Qualifiers
source                 1..15
                       mol_type = protein
                       organism = Homo sapiens
SEQUENCE: 303
GNSNNCHGTM SILMG                                                   15

SEQ ID NO: 304         moltype = AA  length = 114
FEATURE                Location/Qualifiers
source                 1..114
                       mol_type = protein
                       organism = synthetic construct
SEQUENCE: 304
QVQLVQSGSE LKKPGASVKV SCKASGYAFT SYGLSWVRQA PGQGLEWMGW INTYSGVPTY  60
AQGFTGRFVF SLDTSVSTAY LQISSLKAED TAVYYCARTM ADYWGQGTLV TVSS        114

SEQ ID NO: 305         moltype = AA  length = 112
FEATURE                Location/Qualifiers
source                 1..112
                       mol_type = protein
                       organism = synthetic construct
SEQUENCE: 305
DVVMTQSPLS LPVTLGQPAS ISCKSSRSLL YSAGKTYLSW FQQRPGQSPR RLIYLVSKLD  60
SGVPDRFSGS GSGTDFTLKI SRVEAEDVGV YYCWQGIDFH QTFGGGTKVE IK          112

SEQ ID NO: 306         moltype = AA  length = 114
FEATURE                Location/Qualifiers
source                 1..114
                       mol_type = protein
                       organism = synthetic construct
SEQUENCE: 306
QVQLVQSGSE LKKPGASVKV SCKASGYRFT SYGLSWVRQA PGQGLEWMGW INTYSGVPTY  60
AQGFKGRFVF SLDTSVSTAY LQISSLKAED TAVYYCARTM ADYWGQGTLV TVSS        114

SEQ ID NO: 307         moltype = AA  length = 112
FEATURE                Location/Qualifiers
source                 1..112
                       mol_type = protein
                       organism = synthetic construct
SEQUENCE: 307
DVVMTQSPLS LPVTLGQPAS ISCKSSRSLL YSAGKTYLSW FQQRPGQSPR RLIYLVSKLD  60
SGVPDRFSGS GSGTDFTLKI SRVEAEDVGV YYCWQGIDFH QTFGGGTKVE IK          112

SEQ ID NO: 308         moltype = AA  length = 5
FEATURE                Location/Qualifiers
source                 1..5
```

```
                        mol_type = protein
                        organism = synthetic construct
SEQUENCE: 308
SYGLS                                                                       5

SEQ ID NO: 309          moltype = AA  length = 17
FEATURE                 Location/Qualifiers
source                  1..17
                        mol_type = protein
                        organism = synthetic construct
SEQUENCE: 309
WINTYSGVPT YAQGFTG                                                          17

SEQ ID NO: 310          moltype = AA  length = 5
FEATURE                 Location/Qualifiers
source                  1..5
                        mol_type = protein
                        organism = synthetic construct
SEQUENCE: 310
TMADY                                                                       5

SEQ ID NO: 311          moltype = AA  length = 5
FEATURE                 Location/Qualifiers
source                  1..5
                        mol_type = protein
                        organism = synthetic construct
SEQUENCE: 311
SYGLS                                                                       5

SEQ ID NO: 312          moltype = AA  length = 17
FEATURE                 Location/Qualifiers
source                  1..17
                        mol_type = protein
                        organism = synthetic construct
SEQUENCE: 312
WINTYSGVPT YAQGFKG                                                          17

SEQ ID NO: 313          moltype = AA  length = 5
FEATURE                 Location/Qualifiers
source                  1..5
                        mol_type = protein
                        organism = synthetic construct
SEQUENCE: 313
TMADY                                                                       5

SEQ ID NO: 314          moltype = AA  length = 16
FEATURE                 Location/Qualifiers
source                  1..16
                        mol_type = protein
                        organism = synthetic construct
SEQUENCE: 314
KSSRSLLYSA GKTYLS                                                           16

SEQ ID NO: 315          moltype = AA  length = 7
FEATURE                 Location/Qualifiers
source                  1..7
                        mol_type = protein
                        organism = synthetic construct
SEQUENCE: 315
LVSKLDS                                                                     7

SEQ ID NO: 316          moltype = AA  length = 9
FEATURE                 Location/Qualifiers
source                  1..9
                        mol_type = protein
                        organism = synthetic construct
SEQUENCE: 316
WQGIDFHQT                                                                   9

SEQ ID NO: 317          moltype = AA  length = 16
FEATURE                 Location/Qualifiers
source                  1..16
                        mol_type = protein
                        organism = synthetic construct
SEQUENCE: 317
KSSRSLLYSA GKTYLS                                                           16

SEQ ID NO: 318          moltype = AA  length = 7
FEATURE                 Location/Qualifiers
```

```
source                  1..7
                        mol_type = protein
                        organism = synthetic construct
SEQUENCE: 318
LVSKLDS                                                     7

SEQ ID NO: 319          moltype = AA  length = 9
FEATURE                 Location/Qualifiers
source                  1..9
                        mol_type = protein
                        organism = synthetic construct
SEQUENCE: 319
WQGIDFHQT                                                   9

SEQ ID NO: 320          moltype = AA  length = 444
FEATURE                 Location/Qualifiers
source                  1..444
                        mol_type = protein
                        organism = synthetic construct
SEQUENCE: 320
QVQLVQSGSE LKKPGASVKV SCKASGYAFT SYGLSWVRQA PGQGLEWMGW INTYSGVPTY  60
AQGFTGRFVF SLDTSVSTAY LQISSLKAED TAVYYCARTM ADYWGQGTLV TVSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK KVEPKSCDKT HTCPPCPAPE LLGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SRDELTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGK                                   444

SEQ ID NO: 321          moltype = AA  length = 443
FEATURE                 Location/Qualifiers
source                  1..443
                        mol_type = protein
                        organism = synthetic construct
SEQUENCE: 321
QVQLVQSGSE LKKPGASVKV SCKASGYAFT SYGLSWVRQA PGQGLEWMGW INTYSGVPTY  60
AQGFTGRFVF SLDTSVSTAY LQISSLKAED TAVYYCARTM ADYWGQGTLV TVSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK KVEPKSCDKT HTCPPCPAPE LLGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SRDELTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPG                                    443

SEQ ID NO: 322          moltype = AA  length = 444
FEATURE                 Location/Qualifiers
source                  1..444
                        mol_type = protein
                        organism = synthetic construct
SEQUENCE: 322
QVQLVQSGSE LKKPGASVKV SCKASGYAFT SYGLSWVRQA PGQGLEWMGW INTYSGVPTY  60
AQGFTGRFVF SLDTSVSTAY LQISSLKAED TAVYYCARTM ADYWGQGTLV TVSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK KVEPKSCDKT HTCPPCPAPE LLGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPASIE KTISKAKGQP REPQVYTLPP SRDELTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGK                                   444

SEQ ID NO: 323          moltype = AA  length = 443
FEATURE                 Location/Qualifiers
source                  1..443
                        mol_type = protein
                        organism = synthetic construct
SEQUENCE: 323
QVQLVQSGSE LKKPGASVKV SCKASGYAFT SYGLSWVRQA PGQGLEWMGW INTYSGVPTY  60
AQGFTGRFVF SLDTSVSTAY LQISSLKAED TAVYYCARTM ADYWGQGTLV TVSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK KVEPKSCDKT HTCPPCPAPE LLGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPASIE KTISKAKGQP REPQVYTLPP SRDELTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPG                                    443

SEQ ID NO: 324          moltype = AA  length = 444
FEATURE                 Location/Qualifiers
source                  1..444
                        mol_type = protein
                        organism = synthetic construct
```

```
SEQUENCE: 324
QVQLVQSGSE LKKPGASVKV SCKASGYAFT SYGLSWVRQA PGQGLEWMGW INTYSGVPTY  60
AQGFTGRFVF SLDTSVSTAY LQISSLKAED TAVYYCARTM ADYWGQGTLV TVSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK KVEPKSCDKT HTCPPCPAPE LLGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SSKAFPAPIE KTISKAKGQP REPQVYTLPP SRDELTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGK                                        444

SEQ ID NO: 325         moltype = AA  length = 443
FEATURE                Location/Qualifiers
source                 1..443
                       mol_type = protein
                       organism = synthetic construct
SEQUENCE: 325
QVQLVQSGSE LKKPGASVKV SCKASGYAFT SYGLSWVRQA PGQGLEWMGW INTYSGVPTY  60
AQGFTGRFVF SLDTSVSTAY LQISSLKAED TAVYYCARTM ADYWGQGTLV TVSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK KVEPKSCDKT HTCPPCPAPE LLGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SSKAFPAPIE KTISKAKGQP REPQVYTLPP SRDELTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPG                                         443

SEQ ID NO: 326         moltype = AA  length = 444
FEATURE                Location/Qualifiers
source                 1..444
                       mol_type = protein
                       organism = synthetic construct
SEQUENCE: 326
QVQLVQSGSE LKKPGASVKV SCKASGYAFT SYGLSWVRQA PGQGLEWMGW INTYSGVPTY  60
AQGFTGRFVF SLDTSVSTAY LQISSLKAED TAVYYCARTM ADYWGQGTLV TVSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK KVEPKSCDKT HTCPPCPAPE LLGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCAV SNKALPAPIE KTISKAKGQP REPQVYTLPP SRDELTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGK                                        444

SEQ ID NO: 327         moltype = AA  length = 443
FEATURE                Location/Qualifiers
source                 1..443
                       mol_type = protein
                       organism = synthetic construct
SEQUENCE: 327
QVQLVQSGSE LKKPGASVKV SCKASGYAFT SYGLSWVRQA PGQGLEWMGW INTYSGVPTY  60
AQGFTGRFVF SLDTSVSTAY LQISSLKAED TAVYYCARTM ADYWGQGTLV TVSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK KVEPKSCDKT HTCPPCPAPE LLGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCAV SNKALPAPIE KTISKAKGQP REPQVYTLPP SRDELTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPG                                         443

SEQ ID NO: 328         moltype = AA  length = 444
FEATURE                Location/Qualifiers
source                 1..444
                       mol_type = protein
                       organism = synthetic construct
SEQUENCE: 328
QVQLVQSGSE LKKPGASVKV SCKASGYRFT SYGLSWVRQA PGQGLEWMGW INTYSGVPTY  60
AQGFKGRFVF SLDTSVSTAY LQISSLKAED TAVYYCARTM ADYWGQGTLV TVSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK KVEPKSCDKT HTCPPCPAPE LLGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SRDELTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGK                                        444

SEQ ID NO: 329         moltype = AA  length = 443
FEATURE                Location/Qualifiers
source                 1..443
                       mol_type = protein
                       organism = synthetic construct
SEQUENCE: 329
QVQLVQSGSE LKKPGASVKV SCKASGYRFT SYGLSWVRQA PGQGLEWMGW INTYSGVPTY  60
AQGFKGRFVF SLDTSVSTAY LQISSLKAED TAVYYCARTM ADYWGQGTLV TVSSASTKGP  120
SVFPLAPSSK STSGGTAALG CLVKDYFPEP VTVSWNSGAL TSGVHTFPAV LQSSGLYSLS  180
```

```
SVVTVPSSSL GTQTYICNVN HKPSNTKVDK KVEPKSCDKT HTCPPCPAPE LLGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SRDELTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPG                                         443

SEQ ID NO: 330          moltype = AA  length = 444
FEATURE                 Location/Qualifiers
source                  1..444
                        mol_type = protein
                        organism = synthetic construct
SEQUENCE: 330
QVQLVQSGSE LKKPGASVKV SCKASGYRFT SYGLSWVRQA PGQGLEWMGW INTYSGVPTY  60
AQGFKGRFVF SLDTSVSTAY LQISSLKAED TAVYYCARTM ADYWGQGTLV TVSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK KVEPKSCDKT HTCPPCPAPE LLGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPASIE KTISKAKGQP REPQVYTLPP SRDELTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGK                                        444

SEQ ID NO: 331          moltype = AA  length = 443
FEATURE                 Location/Qualifiers
source                  1..443
                        mol_type = protein
                        organism = synthetic construct
SEQUENCE: 331
QVQLVQSGSE LKKPGASVKV SCKASGYRFT SYGLSWVRQA PGQGLEWMGW INTYSGVPTY  60
AQGFKGRFVF SLDTSVSTAY LQISSLKAED TAVYYCARTM ADYWGQGTLV TVSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK KVEPKSCDKT HTCPPCPAPE LLGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPASIE KTISKAKGQP REPQVYTLPP SRDELTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPG                                         443

SEQ ID NO: 332          moltype = AA  length = 444
FEATURE                 Location/Qualifiers
source                  1..444
                        mol_type = protein
                        organism = synthetic construct
SEQUENCE: 332
QVQLVQSGSE LKKPGASVKV SCKASGYRFT SYGLSWVRQA PGQGLEWMGW INTYSGVPTY  60
AQGFKGRFVF SLDTSVSTAY LQISSLKAED TAVYYCARTM ADYWGQGTLV TVSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK KVEPKSCDKT HTCPPCPAPE LLGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SSKAFPAPIE KTISKAKGQP REPQVYTLPP SRDELTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGK                                        444

SEQ ID NO: 333          moltype = AA  length = 443
FEATURE                 Location/Qualifiers
source                  1..443
                        mol_type = protein
                        organism = synthetic construct
SEQUENCE: 333
QVQLVQSGSE LKKPGASVKV SCKASGYRFT SYGLSWVRQA PGQGLEWMGW INTYSGVPTY  60
AQGFKGRFVF SLDTSVSTAY LQISSLKAED TAVYYCARTM ADYWGQGTLV TVSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK KVEPKSCDKT HTCPPCPAPE LLGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SSKAFPAPIE KTISKAKGQP REPQVYTLPP SRDELTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPG                                         443

SEQ ID NO: 334          moltype = AA  length = 444
FEATURE                 Location/Qualifiers
source                  1..444
                        mol_type = protein
                        organism = synthetic construct
SEQUENCE: 334
QVQLVQSGSE LKKPGASVKV SCKASGYRFT SYGLSWVRQA PGQGLEWMGW INTYSGVPTY  60
AQGFKGRFVF SLDTSVSTAY LQISSLKAED TAVYYCARTM ADYWGQGTLV TVSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK KVEPKSCDKT HTCPPCPAPE LLGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCAV SNKALPAPIE KTISKAKGQP REPQVYTLPP SRDELTKNQV  360
SLTCLVKGFY PSDIAVEWES NGQPENNYKT TPPVLDSDGS FFLYSKLTVD KSRWQQGNVF  420
```

```
SCSVMHEALH NHYTQKSLSL SPGK                                      444

SEQ ID NO: 335          moltype = AA  length = 443
FEATURE                 Location/Qualifiers
source                  1..443
                        mol_type = protein
                        organism = synthetic construct
SEQUENCE: 335
QVQLVQSGSE LKKPGASVKV SCKASGYRFT SYGLSWVRQA PGQGLEWMGW INTYSGVPTY  60
AQGFKGRFVF SLDTSVSTAY LQISSLKAED TAVYYCARTM ADYWGQGTLV TVSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK KVEPKSCDKT HTCPPCPAPE LLGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCAV SNKALPAPIE KTISKAKGQP REPQVYTLPP SRDELTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPG                                       443

SEQ ID NO: 336          moltype = AA  length = 330
FEATURE                 Location/Qualifiers
source                  1..330
                        mol_type = protein
                        organism = synthetic construct
SEQUENCE: 336
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                330

SEQ ID NO: 337          moltype = AA  length = 329
FEATURE                 Location/Qualifiers
source                  1..329
                        mol_type = protein
                        organism = synthetic construct
SEQUENCE: 337
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                 329

SEQ ID NO: 338          moltype = AA  length = 330
FEATURE                 Location/Qualifiers
source                  1..330
                        mol_type = protein
                        organism = synthetic construct
SEQUENCE: 338
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPASIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                330

SEQ ID NO: 339          moltype = AA  length = 329
FEATURE                 Location/Qualifiers
source                  1..329
                        mol_type = protein
                        organism = synthetic construct
SEQUENCE: 339
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPASIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                 329

SEQ ID NO: 340          moltype = AA  length = 330
FEATURE                 Location/Qualifiers
source                  1..330
                        mol_type = protein
                        organism = synthetic construct
SEQUENCE: 340
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSSKA FPAPIEKTIS KAKGQPREPQ VYTLPPSRDE  240
```

```
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 341          moltype = AA  length = 329
FEATURE                 Location/Qualifiers
source                  1..329
                        mol_type = protein
                        organism = synthetic construct
SEQUENCE: 341
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSSKA FPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 342          moltype = AA  length = 330
FEATURE                 Location/Qualifiers
source                  1..330
                        mol_type = protein
                        organism = synthetic construct
SEQUENCE: 342
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCAVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 343          moltype = AA  length = 329
FEATURE                 Location/Qualifiers
source                  1..329
                        mol_type = protein
                        organism = synthetic construct
SEQUENCE: 343
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCAVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 344          moltype = AA  length = 107
FEATURE                 Location/Qualifiers
source                  1..107
                        mol_type = protein
                        organism = synthetic construct
SEQUENCE: 344
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 345          moltype = DNA  length = 20
FEATURE                 Location/Qualifiers
source                  1..20
                        mol_type = other DNA
                        note = Non-targeting 2
                        organism = synthetic construct
SEQUENCE: 345
gtaggcgcgc cgctctctac                                             20

SEQ ID NO: 346          moltype = DNA  length = 20
FEATURE                 Location/Qualifiers
source                  1..20
                        mol_type = other DNA
                        note = Non-targeting 2
                        organism = synthetic construct
SEQUENCE: 346
aacccctgat tgtatccgca                                             20

SEQ ID NO: 347          moltype = DNA  length = 20
FEATURE                 Location/Qualifiers
source                  1..20
                        mol_type = other DNA
                        note = MS4A4A-specific guideRNA #1
                        organism = synthetic construct
SEQUENCE: 347
aattgtgtac ccgatataca                                             20

SEQ ID NO: 348          moltype = DNA  length = 20
```

```
FEATURE                 Location/Qualifiers
source                  1..20
                        mol_type = other DNA
                        note = MS4A4A-specific guideRNA #2
                        organism = synthetic construct
SEQUENCE: 348
aaccatgcaa ggaatggaac                                                20

SEQ ID NO: 349          moltype = DNA  length = 20
FEATURE                 Location/Qualifiers
source                  1..20
                        mol_type = other DNA
                        note = MS4A4A-specific guideRNA #3
                        organism = synthetic construct
SEQUENCE: 349
tattcattcc tagactacct                                                20

SEQ ID NO: 350          moltype = DNA  length = 20
FEATURE                 Location/Qualifiers
source                  1..20
                        mol_type = other DNA
                        note = MS4A4A-specific guideRNA #4
                        organism = synthetic construct
SEQUENCE: 350
gctctgtact ggctgcatca                                                20

SEQ ID NO: 351          moltype = DNA  length = 20
FEATURE                 Location/Qualifiers
source                  1..20
                        mol_type = other DNA
                        note = TREM2 #1
                        organism = synthetic construct
SEQUENCE: 351
gccatcacag acgataccct                                                20

SEQ ID NO: 352          moltype = DNA  length = 20
FEATURE                 Location/Qualifiers
source                  1..20
                        mol_type = other DNA
                        note = TREM2 #2
                        organism = synthetic construct
SEQUENCE: 352
ataggggcaa gacacctgca                                                20

SEQ ID NO: 353          moltype = DNA  length = 20
FEATURE                 Location/Qualifiers
source                  1..20
                        mol_type = other DNA
                        note = TREM2 #3
                        organism = synthetic construct
SEQUENCE: 353
cagcatcccg gtgatccagg                                                20

SEQ ID NO: 354          moltype = DNA  length = 20
FEATURE                 Location/Qualifiers
source                  1..20
                        mol_type = other DNA
                        note = TREM2 #4
                        organism = synthetic construct
SEQUENCE: 354
tggagatctc tggttccccg                                                20

SEQ ID NO: 355          moltype = AA  length = 454
FEATURE                 Location/Qualifiers
source                  1..454
                        mol_type = protein
                        note = 4A-313 (huIgG1) sequence
                        organism = synthetic construct
SEQUENCE: 355
QVQLVQSGAE VKKPGASVKV SCKASGYTFT NYWMQWVRQA PGQGLEWMGA THPGHGDTRY  60
AQKFQGRVTM TRDTSTSTVY MELSSLRSED TAVYYCAREE VYYGFRSYWY FDLWGRGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SRDELTKNQV SLTCLVKGFY PSDIAVEWES NGQPENNYKT TPPVLDSDGS FFLYSKLTVD  420
KSRWQQGNVF SCSVMHEALH NHYTQKSLSL SPGK                                454

SEQ ID NO: 356          moltype = AA  length = 453
```

```
FEATURE                Location/Qualifiers
source                 1..453
                       mol_type = protein
                       note = 4A-313 (huIgG1 heavy chain without C-terminal K)
                        sequence
                       organism = synthetic construct
SEQUENCE: 356
QVQLVQSGAE VKKPGASVKV SCKASGYTFT NYWMQWVRQA PGQGLEWMGA THPGHGDTRY  60
AQKFQGRVTM TRDTSTSTVY MELSSLRSED TAVYYCAREE VYYGFRSYWY FDLWGRGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SRDELTKNQV SLTCLVKGFY PSDIAVEWES NGQPENNYKT TPPVLDSDGS FFLYSKLTVD  420
KSRWQQGNVF SCSVMHEALH NHYTQKSLSL SPG                              453

SEQ ID NO: 357         moltype = AA  length = 454
FEATURE                Location/Qualifiers
source                 1..454
                       mol_type = protein
                       note = 4A-313 (hIgG1 heavy chain P331S) sequence
                       organism = synthetic construct
SEQUENCE: 357
QVQLVQSGAE VKKPGASVKV SCKASGYTFT NYWMQWVRQA PGQGLEWMGA THPGHGDTRY  60
AQKFQGRVTM TRDTSTSTVY MELSSLRSED TAVYYCAREE VYYGFRSYWY FDLWGRGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPASIE KTISKAKGQP REPQVYTLPP  360
SRDELTKNQV SLTCLVKGFY PSDIAVEWES NGQPENNYKT TPPVLDSDGS FFLYSKLTVD  420
KSRWQQGNVF SCSVMHEALH NHYTQKSLSL SPGK                             454

SEQ ID NO: 358         moltype = AA  length = 453
FEATURE                Location/Qualifiers
source                 1..453
                       mol_type = protein
                       note = 4A-313 (hIgG1 heavy chain P331S without C-terminal K)
                       organism = synthetic construct
SEQUENCE: 358
QVQLVQSGAE VKKPGASVKV SCKASGYTFT NYWMQWVRQA PGQGLEWMGA THPGHGDTRY  60
AQKFQGRVTM TRDTSTSTVY MELSSLRSED TAVYYCAREE VYYGFRSYWY FDLWGRGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPASIE KTISKAKGQP REPQVYTLPP  360
SRDELTKNQV SLTCLVKGFY PSDIAVEWES NGQPENNYKT TPPVLDSDGS FFLYSKLTVD  420
KSRWQQGNVF SCSVMHEALH NHYTQKSLSL SPG                              453

SEQ ID NO: 359         moltype = AA  length = 454
FEATURE                Location/Qualifiers
source                 1..454
                       mol_type = protein
                       note = 4A-313 (huIgG1 heavy chain N325S/L328F) sequence
                       organism = synthetic construct
SEQUENCE: 359
QVQLVQSGAE VKKPGASVKV SCKASGYTFT NYWMQWVRQA PGQGLEWMGA THPGHGDTRY  60
AQKFQGRVTM TRDTSTSTVY MELSSLRSED TAVYYCAREE VYYGFRSYWY FDLWGRGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SSKAFPAPIE KTISKAKGQP REPQVYTLPP  360
SRDELTKNQV SLTCLVKGFY PSDIAVEWES NGQPENNYKT TPPVLDSDGS FFLYSKLTVD  420
KSRWQQGNVF SCSVMHEALH NHYTQKSLSL SPGK                             454

SEQ ID NO: 360         moltype = AA  length = 453
FEATURE                Location/Qualifiers
source                 1..453
                       mol_type = protein
                       note = 4A-313 (hIgG1 heavy chain N325S/L328F without
                        C-terminal K)
                       organism = synthetic construct
SEQUENCE: 360
QVQLVQSGAE VKKPGASVKV SCKASGYTFT NYWMQWVRQA PGQGLEWMGA THPGHGDTRY  60
AQKFQGRVTM TRDTSTSTVY MELSSLRSED TAVYYCAREE VYYGFRSYWY FDLWGRGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SSKAFPAPIE KTISKAKGQP REPQVYTLPP  360
SRDELTKNQV SLTCLVKGFY PSDIAVEWES NGQPENNYKT TPPVLDSDGS FFLYSKLTVD  420
```

```
KSRWQQGNVF SCSVMHEALH NHYTQKSLSL SPG                              453

SEQ ID NO: 361         moltype = AA  length = 454
FEATURE                Location/Qualifiers
source                 1..454
                       mol_type = protein
                       note = 4A-313 (huIgG1 heavy chain K322A) sequence
                       organism = synthetic construct
SEQUENCE: 361
QVQLVQSGAE VKKPGASVKV SCKASGYTFT NYWMQWVRQA PGQGLEWMGA THPGHGDTRY  60
AQKFQGRVTM TRDTSTSTVY MELSSLRSED TAVYYCAREE VYYGFRSYWY FDLWGRGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLMI SRTPEVTCVV VDVSHEDPEV KFNWYVDGVE VHNAKTKPRE  300
EQYNSTYRVV SVLTVLHQDW LNGKEYKCAV SNKALPAPIE KTISKAKGQP REPQVYTLPP  360
SRDELTKNQV SLTCLVKGFY PSDIAVEWES NGQPENNYKT TPPVLDSDGS FFLYSKLTVD  420
KSRWQQGNVF SCSVMHEALH NHYTQKSLSL SPGK                             454

SEQ ID NO: 362         moltype = AA  length = 453
FEATURE                Location/Qualifiers
source                 1..453
                       mol_type = protein
                       note = 4A-313 (huIgG1 heavy chain K322A without C-terminal
                        K) sequence
                       organism = synthetic construct
SEQUENCE: 362
QVQLVQSGAE VKKPGASVKV SCKASGYTFT NYWMQWVRQA PGQGLEWMGA THPGHGDTRY  60
AQKFQGRVTM TRDTSTSTVY MELSSLRSED TAVYYCAREE VYYGFRSYWY FDLWGRGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLMI SRTPEVTCVV VDVSHEDPEV KFNWYVDGVE VHNAKTKPRE  300
EQYNSTYRVV SVLTVLHQDW LNGKEYKCAV SNKALPAPIE KTISKAKGQP REPQVYTLPP  360
SRDELTKNQV SLTCLVKGFY PSDIAVEWES NGQPENNYKT TPPVLDSDGS FFLYSKLTVD  420
KSRWQQGNVF SCSVMHEALH NHYTQKSLSL SPG                              453

SEQ ID NO: 363         moltype = AA  length = 219
FEATURE                Location/Qualifiers
source                 1..219
                       mol_type = protein
                       note = 4A-450 - full length light chain
                       organism = synthetic construct
SEQUENCE: 363
DVVMTQSPLS LPVTLGQPAS ISCKSSRSLL YSAGKTYLSW FQQRPGQSPR RLIYLVSKLD  60
SGVPDRFSGS GSGTDFTLKI SRVEAEDVGV YYCWQGIDFH QTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 364         moltype = AA  length = 219
FEATURE                Location/Qualifiers
source                 1..219
                       mol_type = protein
                       note = 4A-419 - full length light chain
                       organism = synthetic construct
SEQUENCE: 364
DVVMTQSPLS LPVTLGQPAS ISCKSSRSLL YSAGKTYLSW FQQRPGQSPR RLIYLVSKLD  60
SGVPDRFSGS GSGTDFTLKI SRVEAEDVGV YYCWQGIDFH QTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 365         moltype = AA  length = 218
FEATURE                Location/Qualifiers
source                 1..218
                       mol_type = protein
                       note = 4A-313 - full length light chain
                       organism = synthetic construct
SEQUENCE: 365
EIVLTQSPAT LSLSPGERAT LSCRASESVD NYGVSRMNWY QQKPGQAPRL LIYGASNQGS  60
GIPARFSGSG SGTDFTLTIS SLEPEDFAVY YCQQSKEVPP TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                         218
```

ANTI-MS4A4A ANTIBODIES AND METHODS OF USE THEREOF

CROSS-REFERENCE TO RELATED APPLICATIONS

This application is a continuation of U.S. application Ser. No. 16/943,123, now U.S. Pat. No. 11,667,699, issued Jun. 6, 2023, which claims the priority benefit of U.S. Provisional Application No. 62/881,187, filed Jul. 31, 2019, U.S. Provisional Application No. 62/892,467, filed Aug. 27, 2019, U.S. Provisional Application No. 62/947,449, filed Dec. 12, 2019, U.S. Provisional Application No. 62/960,606, filed Jan. 13, 2020, and U.S. Provisional Application No. 63/057,142, filed Jul. 27, 2020.

SUBMISSION OF SEQUENCE LISTING ON XML FILE

The content of the following submission on XML file is incorporated herein by reference in its entirety: a computer readable form (CRF) of the Sequence Listing (Name: 4503_0080008_SequenceListing_ST26.xml; Size: 301,315 bytes; Date of Creation: Apr. 28, 2023).

FIELD OF THE PRESENT DISCLOSURE

The present disclosure relates to anti-MS4A4A antibodies and therapeutic uses of such antibodies.

BACKGROUND OF THE PRESENT DISCLOSURE

The membrane-spanning 4-domain subfamily A (MS4A) gene cluster is present on chromosome 11g12 and includes eighteen genes. The MS4A gene family encodes membrane proteins typically having tetra-spanning topology (Ishibashi et al, 2001, Gene, 265:87-93; Liang and Tedder, 2001, Genomics, 72:119-127; Efthymiou and Goate, 2017, Molecular Neurodegeneration, 12:43). The membrane spanning domains are interconnected by one intracellular loop and two extracellular loops with both N- and C-termini residing within the cytosol. Most MS4A proteins share amino acid sequence homology to that of MS4A1 (CD20) (20-30% similarity), with the highest degree of sequence identity occurring in the first three transmembrane domains. The highly conserved motifs within these transmembrane regions across different MS4A proteins suggest that the membrane spanning domains have an important general role in MS4A protein function. The regions of greatest variation between MS4A proteins occur within their N- and C-terminal cytoplasmic domains and the putative second extracellular loop (Ishibashi et al, 2001, Gene, 265:87-93), suggesting that these regions impart unique functional properties.

Despite this diversity, the MS4A domains possess some shared elements. For instance, one notable feature conserved in MS4A proteins (with the exception of MS4A8B and MS4A12) is the conservation of two cysteine residues in the putative second extracellular loop that may form a disulfide bridge. The N- and C-terminal domains of MS4A proteins are also rich in proline residues, although the functional significance of this remains to be elucidated (Hulett et al, 2001, Genomics, 72:119-127). Proline rich regions are, however, commonly involved in various cellular processes such as cytoskeletal rearrangement, initiation of transcription, signaling cascades, and association with SH3 domains as part of an adaptor system to facilitate protein-protein interactions (Kay et al, 2000, FASEB J, 14:231-241).

The MS4A protein family is relatively uncharacterized functionally, with some important exceptions: MS4A1 (CD20) is expressed exclusively in B lymphocytes, where the protein has a function in signaling by the B cell antigen receptor, and calcium influx. CD20 is the target of immunotherapeutic antibodies used to deplete pathogenic B cells in chronic lymphocytic leukemia, lymphomas, autoimmune diseases, and in solid organ transplantation. MS4A2 (FcERβ) is a signaling subunit of the high affinity IgE receptor (FIERI) and the low affinity IgG receptor (FcERIII) on mast cells, having a key role in hypersensitivity and allergic reactions. MS4A2 is an ITAM-domain protein that amplifies signals through a 4-protein high affinity IgE receptor complex. MS4A3 (Htm4) is expressed on intracellular membranes of lymphoid and myeloid cells, and functions as an adaptor protein in cell cycle regulation.

While the majority of MS4A family members are uncharacterized, reports suggest MS4A proteins act as chemosensors and chemoreceptors for a variety of exogenous and endogenous ligands, including fatty acids, peptides, and sulfated steroids, and have been implicated in mediating calcium influx, regulating endocytosis, trafficking, and may act as adapters for signal transduction complexes (Cruse et al, 2015, Mol Biol Cell, 26:1711-1727; Greer et al, 2016, Cell, 165:1734-1748; Eon Kuek et al, 2016, Cell, 165:1734-1748; Koslowski et al, 2008, Cancer Res, 68:3458-3466; Bubien et al, 1993; J Cell Biol, 121:1121-1132).

Certain MS4A genes have been genetically linked to various disorders and diseases, in particular neurodegenerative disorders. For example, genome-wide significance association analyses have identified the MS4A gene cluster, located on chromosome 11q12, as one of the most significant Alzheimer's disease loci. One gene of particular interest identified is MS4A4A (Lambert et al, 2013, Nat Genet, 45:1452-1458; Hollingworth et al, 2011, Nat Genet, 43:429-435; Naj et al, 2011, Nat Genet, 43:436-441).

Accordingly, there is a need for therapies targeting MS4A4A, including antibodies that specifically bind to MS4A4A, and/or therapies that are capable of modulating (e.g., inhibiting or reducing; activating or enhancing) the activity of MS4A4A, such as by reducing or increasing MS4A4A protein levels or activity, in order to treat various diseases, disorders, and conditions associated with MS4A4A activity.

All references cited herein, including patent applications and publications, are hereby incorporated by reference in their entirety.

SUMMARY OF THE PRESENT DISCLOSURE

The present disclosure is generally directed to anti-MS4A4A antibodies and methods of using such antibodies. The methods provided herein find use in preventing, reducing risk, or treating an individual having a neurodegenerative disease, disorder, or condition. In some embodiments, the present disclosure provides a method for preventing, reducing risk, or treating an individual having a neurodegenerative disease, disorder, or condition selected from Alzheimer's disease, late onset Alzheimer's disease, dementia, and cognitive impairment, the method including administering to the individual in need thereof a therapeutically effective amount of an anti-MS4A4A antibody. In some embodiments, the present disclosure provides a method for preventing, reducing risk, or treating an individual having a disease, disorder, or condition associated with increased expression or activity of MS4A4A, the method including administering to the individual in need thereof a therapeutically effective amount of an anti-MS4A4A antibody.

In one aspect, the present disclosure relates to an isolated antibody that binds to a MS4A4A protein, wherein the antibody includes a heavy chain variable region and a light chain variable region, wherein the heavy chain variable region includes: an HVR-H1 including an amino acid sequence selected from SEQ ID NOs: 94, 108, 116, 146, 147, 308, and 311; an HVR-H2 including an amino acid sequence selected from SEQ ID NOs: 96, 97, 98, 99, 110, 111, 118, 119, 120, 121, 122, 149, 150, 151, 152, 153, 309, and 312; and an HVR-H3 including an amino acid sequence selected from SEQ ID NOs: 100, 101, 102, 112, 123, 124, 125, 126, 127, 128, 129, 154, 310, and 313; and the light chain variable region includes: an HVR-L1 including an amino acid sequence selected from SEQ ID NOs: 103, 104, 113, 130, 131, 132, 133, 134, 135, 136, 137, 138, 156, 157, 158, 314, and 317; an HVR-L2 including an amino acid sequence selected from SEQ ID NOs: 105, 106, 114, 139, 140, 141, 142, 143, 159, 160, 161, 315, and 318; and an HVR-L3 including an amino acid sequence selected from SEQ ID NOs: 107, 115, 144, 145, 163, 316, and 319.

In some embodiments that may be combined with any of the embodiments herein, an anti-MS4A4A antibody of the present disclosure is an isolated antibody that binds to a MS4A4A protein, wherein the antibody includes a heavy chain variable region and a light chain variable region, wherein the heavy chain variable region includes: an HVR-H1 including the amino acid sequence of SEQ ID NO: 94; an HVR-H2 including an amino acid sequence selected from SEQ ID NOs: 96-99; and an HVR-H3 including an amino acid sequence selected from SEQ ID NOs: 100-102; and the light chain variable region includes: an HVR-L1 including an amino acid sequence selected from SEQ ID NOs: 103-104; an HVR-L2 including an amino acid sequence selected from SEQ ID NOs: 105-106; and an HVR-L3 including the amino acid sequence of SEQ ID NO: 107.

In some embodiments that may be combined with any of the embodiments herein, an anti-MS4A4A antibody of the present disclosure is an isolated antibody that binds to a MS4A4A protein, wherein the antibody includes a heavy chain variable region and a light chain variable region, wherein the heavy chain variable region includes: an HVR-H1 including the amino acid sequence of SEQ ID NO: 308; an HVR-H2 including the amino acid sequence of SEQ ID NO: 309; and an HVR-H3 including the amino acid sequence of SEQ ID NO: 310; and the light chain variable region includes: an HVR-L1 including the amino acid sequence of SEQ ID NO: 314; an HVR-L2 including the amino acid sequence of SEQ ID NO: 315; and an HVR-L3 including the amino acid sequence of SEQ ID NO: 316.

In some embodiments that may be combined with any of the embodiments herein, an anti-MS4A4A antibody of the present disclosure is an isolated antibody that binds to a MS4A4A protein, wherein the antibody includes a heavy chain variable region and a light chain variable region, wherein the heavy chain variable region includes: an HVR-H1 including the amino acid sequence of SEQ ID NO: 311; an HVR-H2 including the amino acid sequence of SEQ ID NO: 312; and an HVR-H3 including the amino acid sequence of SEQ ID NO: 313; and the light chain variable region includes: an HVR-L1 including the amino acid sequence of SEQ ID NO: 317; an HVR-L2 including the amino acid sequence of SEQ ID NO: 318; and an HVR-L3 including the amino acid sequence of SEQ ID NO: 319.

In some embodiments that may be combined with any of the embodiments herein, an anti-MS4A4A antibody of the present disclosure is an isolated antibody that binds to a MS4A4A protein, wherein the antibody includes a heavy chain variable region and a light chain variable region, wherein the heavy chain variable region includes: an HVR-H1 including the amino acid sequence of SEQ ID NO: 108; an HVR-H2 including an amino acid sequence selected from SEQ ID NOs: 110-111; and an HVR-H3 including the amino acid sequence of SEQ ID NO: 112; and the light chain variable region includes: an HVR-L1 including the amino acid sequence of SEQ ID NO: 113; an HVR-L2 including the amino acid sequence of SEQ ID NO: 114; and an HVR-L3 including the amino acid sequence of SEQ ID NO: 115.

In some embodiments that may be combined with any of the embodiments herein, an anti-MS4A4A antibody of the present disclosure is an isolated antibody that binds to a MS4A4A protein, wherein the antibody includes a heavy chain variable region and a light chain variable region, wherein the heavy chain variable region includes: an HVR-H1 including the amino acid sequence of SEQ ID NO: 116; an HVR-H2 including an amino acid sequence selected from SEQ ID NOs: 118-122; and an HVR-H3 including an amino acid sequence selected from SEQ ID NOs: 123-129; and the light chain variable region includes: an HVR-L1 including an amino acid sequence selected from SEQ ID NOs: 130-138; an HVR-L2 including an amino acid sequence selected from SEQ ID NOs: 139-143; and an HVR-L3 including an amino acid sequence selected from SEQ ID NOs: 144-145.

In some embodiments that may be combined with any of the embodiments herein, an anti-MS4A4A antibody of the present disclosure is an isolated antibody that binds to a MS4A4A protein, wherein the antibody includes a heavy chain variable region and a light chain variable region, wherein the heavy chain variable region includes: an HVR-H1 including an amino acid sequence selected from SEQ ID NOs: 146-147; an HVR-H2 including an amino acid sequence selected from SEQ ID NOs: 149-153; and an HVR-H3 including the amino acid sequence of SEQ ID NO: 154; and the light chain variable region includes: an HVR-L1 including an amino acid sequence selected from SEQ ID NOs: 156-158; an HVR-L2 including an amino acid sequence selected from SEQ ID NOs: 159-161; and an HVR-L3 including the amino acid sequence of SEQ ID NO: 163.

In some embodiments that may be combined with any of the embodiments herein, an anti-MS4A4A antibody of the present disclosure is an isolated antibody that binds to a MS4A4A protein, wherein the antibody includes a heavy chain variable region, wherein the heavy chain variable region includes an amino acid sequence selected from SEQ ID NOs: 5-15, 304, and 306. In some embodiments that may be combined with any of the embodiments herein, an anti-MS4A4A antibody of the present disclosure is an isolated antibody that binds to a MS4A4A protein, wherein the antibody includes a heavy chain variable region, wherein the heavy chain variable region includes an amino acid sequence selected from SEQ ID NOs: 24-30. In some embodiments that may be combined with any of the embodiments herein, an anti-MS4A4A antibody of the present disclosure is an isolated antibody that binds to a MS4A4A protein, wherein the antibody includes a heavy chain variable region, wherein the heavy chain variable region includes an amino acid sequence selected from SEQ ID NOs: 40-53. In some embodiments that may be combined with any of the embodiments herein, an anti-MS4A4A antibody of the present disclosure is an isolated antibody that binds to a MS4A4A protein, wherein the antibody includes a heavy chain variable region, wherein the heavy chain variable region includes an amino acid sequence selected from SEQ ID NOs: 76-84.

In some embodiments that may be combined with any of the embodiments herein, an anti-MS4A4A antibody of the present disclosure is an isolated antibody that binds to a MS4A4A protein, wherein the antibody includes a light chain variable region, wherein the light chain variable region includes an amino acid sequence selected from SEQ ID NOs: 17-22, 305, and 307. In some embodiments that may be combined with any of the embodiments herein, an anti-MS4A4A antibody of the present disclosure is an isolated antibody that binds to a MS4A4A protein, wherein the antibody includes a light chain variable region, wherein the light chain variable region includes an amino acid sequence selected from SEQ ID NOs: 32-36. In some embodiments that may be combined with any of the embodiments herein, an anti-MS4A4A antibody of the present disclosure is an isolated antibody that binds to a MS4A4A protein, wherein the antibody includes a light chain variable region, wherein the light chain variable region includes an amino acid sequence selected from SEQ ID NOs: 55-74. In some embodiments that may be combined with any of the embodiments herein, an anti-MS4A4A antibody of the present disclosure is an isolated antibody that binds to a MS4A4A protein, wherein the antibody includes a light chain variable region, wherein the light chain variable region includes an amino acid sequence selected from SEQ ID NOs: 86-93.

In some embodiments that may be combined with any of the embodiments herein, an anti-MS4A4A antibody of the present disclosure is an isolated antibody that binds to a MS4A4A protein, wherein the antibody includes a heavy chain variable region and a light chain variable region, wherein the heavy chain variable region includes an amino acid sequence selected from SEQ ID NOs: 5-15, 304, and 306, and the light chain variable region includes an amino acid sequence selected from SEQ ID NOs: 17-22, 305, and 307. In some embodiments that may be combined with any of the embodiments herein, an anti-MS4A4A antibody of the present disclosure is an isolated antibody that binds to a MS4A4A protein, wherein the antibody includes a heavy chain variable region and a light chain variable region, wherein the heavy chain variable region includes an amino acid sequence selected from SEQ ID NOs: 24-30, and the light chain variable region includes an amino acid sequence selected from SEQ ID NOs: 32-36. In some embodiments that may be combined with any of the embodiments herein, an anti-MS4A4A antibody of the present disclosure is an isolated antibody that binds to a MS4A4A protein, wherein the antibody includes a heavy chain variable region and a light chain variable region, wherein the heavy chain variable region includes an amino acid sequence selected from SEQ ID NOs: 40-53, and the light chain variable region includes an amino acid sequence selected from SEQ ID NOs: 55-74. In some embodiments that may be combined with any of the embodiments herein, an anti-MS4A4A antibody of the present disclosure is an isolated antibody that binds to a MS4A4A protein, wherein the antibody includes a heavy chain variable region and a light chain variable region, wherein the heavy chain variable region includes an amino acid sequence selected from SEQ ID NOs: 76-84, and the light chain variable region includes an amino acid sequence selected from SEQ ID NOs: 86-93.

In some embodiments that may be combined with any of the embodiments herein, an anti-MS4A4A antibody of the present disclosure is an isolated antibody that binds to a MS4A4A protein, wherein the antibody includes a heavy chain and a light chain, wherein the heavy chain includes an amino acid sequence selected from SEQ ID NOs: 320-343. In some embodiments, the heavy chain includes an amino acid sequence selected from SEQ ID NOs: 336-343 (optionally wherein the light chain comprises a light chain variable region comprising the amino acid sequence of SEQ ID NO: 22, further optionally wherein the light chain further comprises a constant region comprising the amino acid sequence of SEQ ID NO: 344). In some embodiments, the heavy chain includes an amino acid sequence selected from SEQ ID NOs: 320-327 (optionally wherein the light chain comprises a light chain variable region comprising the amino acid sequence of SEQ ID NO: 304, further optionally wherein the light chain further comprises a constant region comprising the amino acid sequence of SEQ ID NO: 344). In some embodiments, the heavy chain includes an amino acid sequence selected from SEQ ID NOs: 328-335 (optionally wherein the light chain comprises a light chain variable region comprising the amino acid sequence of SEQ ID NO: 305, further optionally wherein the light chain further comprises a constant region comprising the amino acid sequence of SEQ ID NO: 344).

In some embodiments that may be combined with any of the embodiments herein, an anti-MS4A4A antibody of the present disclosure is an isolated antibody that binds to a MS4A4A protein, wherein the antibody comprises a heavy chain variable region and a light chain variable region, wherein the heavy chain variable region comprises an HVR-H1 comprising the amino acid sequence of SEQ ID NO: 94, an HVR-H2 comprising the amino acid sequence of SEQ ID NO: 96, and an HVR-H3 comprising the amino acid sequence of SEQ ID NO: 102; and the light chain variable region comprises an HVR-L1 comprising the amino acid sequence of SEQ ID NO: 104, an HVR-L2 comprising the amino acid sequence of SEQ ID NO: 105, and an HVR-L3 comprising the amino acid sequence of SEQ ID NO: 107. In some embodiments that may be combined with any of the embodiments herein, an anti-MS4A4A antibody of the present disclosure is an isolated antibody that binds to a MS4A4A protein, wherein the antibody comprises a heavy chain variable region and a light chain variable region, wherein the heavy chain variable region comprises the amino acid sequence of SEQ ID NO: 14, and the light chain variable region comprises the amino acid sequence of SEQ ID NO: 22. In some embodiments that may be combined with any of the embodiments herein, an anti-MS4A4A antibody of the present disclosure is an isolated antibody that binds to a MS4A4A protein, wherein the antibody comprises a heavy chain and a light chain wherein the heavy chain comprises the amino acid sequence of SEQ ID NO: 359 or 360, and the light chain comprises the amino acid sequence of SEQ ID NO: 365.

In some embodiments that may be combined with any of the embodiments herein, an anti-MS4A4A antibody of the present disclosure is an isolated antibody that binds to a MS4A4A protein, wherein the antibody comprises a heavy chain variable region and a light chain variable region, wherein the heavy chain variable region comprises: an HVR-H1 comprising the amino acid sequence of SEQ ID NO: 308; an HVR-H2 comprising the amino acid sequence of SEQ ID NO: 309; and an HVR-H3 comprising the amino acid sequence of SEQ ID NO: 310; and the light chain variable region comprises: an HVR-L1 comprising the amino acid sequence of SEQ ID NO: 314; an HVR-L2 comprising the amino acid sequence of SEQ ID NO: 315;

and an HVR-L3 comprising the amino acid sequence of SEQ ID NO: 316. In some embodiments that may be combined with any of the embodiments herein, an anti-MS4A4A antibody of the present disclosure is an isolated antibody that binds to a MS4A4A protein, wherein the antibody comprises a heavy chain variable region and a light chain variable region, wherein the heavy chain variable region comprises the amino acid sequence of SEQ ID NO: 304, and the light chain variable region comprises the amino acid sequence of SEQ ID NO: 305. In some embodiments that may be combined with any of the embodiments herein, an anti-MS4A4A antibody of the present disclosure is an isolated antibody that binds to a MS4A4A protein, wherein the antibody comprises a heavy chain and a light chain wherein the heavy chain comprises the amino acid sequence of SEQ ID NO: 324 or 325, and the light chain comprises the amino acid sequence of SEQ ID NO: 363.

In some embodiments that may be combined with any of the embodiments herein, an anti-MS4A4A antibody of the present disclosure is an isolated antibody that binds to a MS4A4A protein, wherein the antibody comprises a heavy chain variable region and a light chain variable region, wherein the heavy chain variable region comprises: an HVR-H1 comprising the amino acid sequence of SEQ ID NO: 311; an HVR-H2 comprising the amino acid sequence of SEQ ID NO: 312; and an HVR-H3 comprising the amino acid sequence of SEQ ID NO: 313; and the light chain variable region comprises: an HVR-L1 comprising the amino acid sequence of SEQ ID NO: 317; an HVR-L2 comprising the amino acid sequence of SEQ ID NO: 318; and an HVR-L3 comprising the amino acid sequence of SEQ ID NO: 319. In some embodiments that may be combined with any of the embodiments herein, an anti-MS4A4A antibody of the present disclosure is an isolated antibody that binds to a MS4A4A protein, wherein the antibody comprises a heavy chain variable region and a light chain variable region, wherein the heavy chain variable region comprises the amino acid sequence of SEQ ID NO: 306, and the light chain variable region comprises the amino acid sequence of SEQ ID NO: 307. In some embodiments that may be combined with any of the embodiments herein, an anti-MS4A4A antibody of the present disclosure is an isolated antibody that binds to a MS4A4A protein, wherein the antibody comprises a heavy chain and a light chain wherein the heavy chain comprises the amino acid sequence of SEQ ID NO: 332 or 333, and the light chain comprises the amino acid sequence of SEQ ID NO: 364.

In one aspect, the present disclosure relates to an isolated antibody that binds to a MS4A4A protein, wherein the antibody competitively inhibits binding with one or more of the antibodies of any of the embodiments herein for binding to MS4A4A.

In another aspect, the present disclosure relates to an isolated antibody that binds to a MS4A4A protein, wherein the antibody binds essentially the same or an overlapping epitope on MS4A4A as the antibody of any of the embodiments herein.

In some embodiments that may be combined with any of the embodiments herein, an anti-MS4A4A antibody of the present disclosure is an isolated antibody that binds to a MS4A4A protein, wherein the antibody binds to extracellular domain 1 of human MS4A4A. In some embodiments that may be combined with any of the embodiments herein, an anti-MS4A4A antibody of the present disclosure is an isolated antibody that binds to a MS4A4A protein, wherein the antibody binds to one or more amino acid residues within the amino acid sequence CMASNTYGSNPIS (SEQ ID NO: 177) of SEQ ID NO: 1. In some embodiments that may be combined with any of the embodiments herein, an anti-MS4A4A antibody of the present disclosure is an isolated antibody that binds to a MS4A4A protein, wherein the antibody binds to extracellular domain 2 of human MS4A4A. In some embodiments that may be combined with any of the embodiments herein, an anti-MS4A4A antibody of the present disclosure is an isolated antibody that binds to a MS4A4A protein, wherein the antibody binds to one or more amino acid residues within the amino acid sequence SFHHPYCNYYGNSNNCHGTMS (SEQ ID NO: 178) of SEQ ID NO: 1. In some embodiments that may be combined with any of the embodiments herein, an anti-MS4A4A antibody of the present disclosure is an isolated antibody that binds to a MS4A4A protein, wherein the antibody binds to one or more amino acid residues within the amino acid sequence SFHHPYCNYYGNSNNCHGTMS (SEQ ID NO: 178) of SEQ ID NO: 1, and further wherein the antibody does not bind to amino acid residue proline 163 (P163) of SEQ ID NO: 1. In some embodiments that may be combined with any of the embodiments herein, the anti-MS4A4A antibody is a human anti-MS4A4A antibody or a humanized anti-MS4A4A antibody.

In some embodiments that may be combined with any of the embodiments herein, an anti-MS4A4A antibody of the present disclosure is an isolated antibody that binds to a MS4A4A protein, wherein the antibody decreases cell surface levels of MS4A4A or decreases intracellular levels of MS4A4A.

In certain embodiments that may be combined with any of the embodiments herein, the MS4A4A protein is a mammalian protein or a human protein. In certain embodiments that may be combined with any of the embodiments herein, the MS4A4A protein is a wild-type protein. In certain embodiments that may be combined with any of the embodiments herein, the MS4A4A protein is a naturally occurring variant.

In some embodiments that may be combined with any of the embodiments herein, an anti-MS4A4A antibody of the present disclosure increases soluble TREM2 levels, increases membrane TREM2 levels, or increases soluble TREM2 and increases membrane TREM2 levels in myeloid cells. In some embodiments that may be combined with any of the embodiments herein, an anti-MS4A4A antibody of the present disclosure increases soluble TREM2 levels. In some embodiments that may be combined with any of the embodiments herein, an anti-MS4A4A antibody of the present disclosure increases membrane TREM2 levels. In some embodiments that may be combined with any of the embodiments herein, an anti-MS4A4A antibody of the present disclosure increases soluble TREM2 levels and membrane TREM2 levels. In some embodiments that may be combined with any of the embodiments herein, an anti-MS4A4A antibody of the present disclosure increases soluble TREM2 levels in vivo. In some embodiments that may be combined with any of the embodiments herein, an anti-MS4A4A antibody of the present disclosure increases soluble TREM2 levels in serum in vivo. In some embodiments that may be combined with any of the embodiments herein, an anti-MS4A4A antibody of the present disclosure increases soluble TREM2 levels in cerebrospinal fluid (CSF) in vivo. In some embodiments that may be combined with any of the embodiments herein, an anti-MS4A4A antibody of the present disclosure increases soluble TREM2 levels in serum and in CSF in vivo.

In some embodiments that may be combined with any of the embodiments herein, an anti-MS4A4A antibody of the present disclosure reduces expression of M2 cell surface markers (e.g., receptors) on myeloid cells. In some embodiments that may be combined with any of the embodiments herein, an anti-MS4A4A antibody of the present disclosure decreases or reduces the levels of M2 cell surface markers in a myeloid cell, e.g., a macrophage.

In some embodiments that may be combined with any of the embodiments herein, an anti-MS4A4A antibody of the present disclosure reduces expression of CD200R, Dectin-1, or CD163 on myeloid cells. In some embodiments that may be combined with any of the embodiments herein, an anti-MS4A4A antibody of the present disclosure decreases or reduces cell surface levels of CD200R, Dectin-1, and/or CD163 in myeloid cells, e.g., a macrophage.

In some embodiments that may be combined with any of the embodiments herein, an anti-MS4A4A antibody of the present disclosure increases mRNA and/or protein expression of gelsolin and/or osteopontin on myeloid cells. In some embodiments that may be combined with any of the embodiments herein, an anti-MS4A4A antibody of the present disclosure increases mRNA and/or protein levels of IL1RN on myeloid cells. In some embodiments that may be combined with any of the embodiments herein, an anti-MS4A4A antibody of the present disclosure increases mRNA and/or protein levels of CSF1R on myeloid cells. In some embodiments that may be combined with any of the embodiments herein, an anti-MS4A4A antibody of the present disclosure decreases mRNA and/or protein levels of purinergic receptor P2RY12 and/or CX3C chemokine receptor 1 (CX3CR1) on myeloid cells. In some embodiments that may be combined with any of the embodiments herein, an anti-MS4A4A antibody of the present disclosure increases mRNA and/or protein levels of 1-phosphotidylinositol-4,5-bisphosphate phosphodiesterase gamma-2 (PLCG2), C-type lectin domain family 7 member A (CLEC7A), inositol 1,4,5-triphosphate receptor 2 (ITPR2), and/or antigen KI-67 (MK167) on myeloid cells. In some embodiments that may be combined with any of the embodiments herein, an anti-MS4A4A antibody of the present disclosure decreases mRNA and/or protein levels of transmembrane glycoprotein NMB (GPNMB) on myeloid cells.

In one aspect, the present disclosure relates to an isolated antibody that binds to a MS4A4A protein, wherein the antibody increases mRNA and/or protein expression of gelsolin and/or osteopontin on myeloid cells. In some embodiments that may be combined with any of the embodiments herein, the myeloid cells are human macrophages. In certain embodiments that may be combined with any of the embodiments herein, the isolated antibody that binds to a MS4A4A protein is human or humanized. In certain embodiments that may be combined with any of the embodiments herein, the isolated antibody that binds to a MS4A4A protein is a human antibody, a humanized antibody, a bispecific antibody, a monoclonal antibody, a multivalent antibody, a conjugated antibody, or a chimeric antibody. In certain embodiments that may be combined with any of the embodiments herein, the isolated antibody that binds to a MS4A4A protein binds to the same epitope as an antibody selected from 4A-18, 4A-25, 4A-214, 4A-21 and 4A-202. In certain embodiments that may be combined with any of the embodiments herein, the isolated antibody that binds to a MS4A4A protein reduces expression of M2 markers on myeloid cells. In certain embodiments that may be combined with any of the embodiments herein, the myeloid cells are human macrophages. In certain embodiments that may be combined with any of the embodiments herein, the M2 markers are CD200R, Dectin-1, and/or CD163. In certain embodiments that may be combined with any of the embodiments herein, the isolated antibody that binds to a MS4A4A protein increases plasma-membrane or cell surface TREM2 on human macrophages by at least 50%, 90%, 100%, 150%, 200% or 250%. In certain embodiments that may be combined with any of the embodiments herein, the isolated antibody that binds to a MS4A4A protein increases soluble TREM2 in human macrophage supernatant by at least 15%, 20%, 25%, 30%, 40%, 50%, 60%, or 70%.

In certain embodiments that may be combined with any of the embodiments herein, the anti-MS4A4A antibody is a bispecific antibody recognizing a first antigen and a second antigen. In certain embodiments that may be combined with any of the embodiments herein, the first antigen is MS4A4A and the second antigen is an antigen facilitating transport across the blood-brain-barrier. In certain embodiments that may be combined with any of the embodiments herein, the second antigen is selected from MS4A4A, transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, basigin, Glut1, and CD98hc, and ANG1005.

In some embodiments that may be combined with any of the embodiments herein, the anti-MS4A4A antibody of the present disclosure is a monoclonal antibody. In some embodiments that may be combined with any of the embodiments herein, the antibody is a human antibody. In some embodiments that may be combined with any of the embodiments herein, the antibody is a humanized antibody. In some embodiments that may be combined with any of the embodiments herein, the antibody is a bispecific antibody. In some embodiments that may be combined with any of the embodiments herein, the antibody is a multivalent antibody. In some embodiments that may be combined with any of the embodiments herein, the antibody is a chimeric antibody.

In some embodiments that may be combined with any of the embodiments herein, the anti-MS4A4A antibody of the present disclosure is of the IgG class, the IgM class, or the IgA class. In some embodiments, the antibody is of the IgG class and has an IgG1, IgG2, or IgG4 isotype. In certain embodiments that may be combined with any of the embodiments herein, the antibody is an antibody fragment. In certain embodiments that may be combined with any of the embodiments herein, antibody is an antibody fragment that binds to an epitope including amino acid residues on human MS4A4A or a mammalian MS4A4A protein. In certain embodiments that may be combined with any of the embodiments herein, the antibody fragment is a Fab, Fab', Fab'-SH, F(ab')2, Fv, or scFv fragment.

In some embodiments that may be combined with any of the embodiments herein, the antibody is a bispecific antibody recognizing a first antigen and a second antigen. In some embodiments that may be combined with any of the embodiments herein, the first antigen is MS4A4A and the second antigen is:

(a) an antigen facilitating transport across the blood-brain-barrier;
(b) an antigen facilitating transport across the blood-brain-barrier selected from transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopeptide, and ANG1005;

(c) a disease-causing agent selected from disease-causing peptides or proteins or, disease-causing nucleic acids, wherein the disease-causing nucleic acids are antisense GGCCCC (G2C4) repeat-expansion RNA, the disease-causing proteins are selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading; frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides;

(d) ligands and/or proteins expressed on immune cells, wherein the ligands and/or proteins selected from CD40, OX40, ICOS, CD28, CD137/4-1BB, CD27, GITR, PD-L1, CTLA-4, PD-L2, PD-1, B7-H3, B7-H4, HVEM, BTLA, KIR, GALS, TIM3, A2AR, LAG-3, and phosphatidylserine; or (e) a protein, lipid, polysaccharide, or glycolipid expressed on one or more tumor cells.

In another aspect, the present disclosure relates to an isolated nucleic acid including a nucleic acid sequence encoding the antibody of any of the preceding embodiments. In some embodiments, the present disclosure relates to a vector including the nucleic acid of any of the preceding embodiments. In some embodiments, the present disclosure relates to an isolated host cell including the vector of any of the preceding embodiments.

In another aspect, the present disclosure relates to a method of producing an antibody that binds to human MS4A4A antibody, including culturing the host cell of any of the preceding embodiments so that the anti-MS4A4A antibody is produced. In certain embodiments, the method further includes recovering the anti-MS4A4A antibody produced by the cell.

In another aspect, the present disclosure relates to a pharmaceutical composition including the antibody of any one of the preceding embodiments and a pharmaceutically acceptable carrier.

In one aspect, the present disclosure relates to a method of preventing, reducing risk, or treating an individual having a disease, disorder, or injury selected from Alzheimer's disease, late onset Alzheimer's disease, and cognitive impairment, the method including administering to an individual in need thereof a therapeutically effective amount of the antibody of any one of the preceding embodiments. In another aspect, the present disclosure relates to a method of preventing, reducing risk, or treating an individual having a disease, disorder, condition, or injury caused by or associated with over expression or increased activity of MS4A4A, the method including administering to an individual in need thereof a therapeutically effective amount of the antibody of any one of the preceding embodiments. In some embodiments of the present disclosure, the method further includes detecting levels of osteopontin, gelsolin, plasma-membrane or cell surface TREM2, and/or soluble TREM2 before and/or after the administration of the antibody.

In one aspect, the present disclosure relates to a method of preventing, reducing risk, or treating an individual having a CSF1R-deficient disease or disorder, the method including administering to an individual in need thereof a therapeutically effective amount of the antibody of any one of the preceding embodiments. In some embodiments, the CSF1R-deficient disease or disorder is adult-onset leukoencephalopathy with axonal spheroids and pigmented glia (ALSP) or hereditary diffuse leukoencephalopathy (HDLS).

Other aspects of the present disclosure relate to an isolated anti-MS4A4A antibody produced by the method of any of the preceding embodiments. Other aspects of the present disclosure relate to a pharmaceutical composition including the anti-MS4A4A antibody of any of the preceding embodiments, and a pharmaceutically acceptable carrier.

In another aspect, the present disclosure relates to an antibody that binds to a MS4A4A protein, wherein the antibody includes a heavy chain variable region and a light chain variable region, wherein the heavy chain variable region includes the HVR-H1, HVR-H2, and HVR-H3 of antibody 4A-301, 4A-302, 4A-303, 4A-304, 4A-305, 4A-306, 4A-307, 4A-308, 4A-309, 4A-310, 4A-311, 4A-312, 4A-313, 4A-314, 4A-419, or 4A-450 (as shown in Table 1, Table 5, Table 30, and Table 31).

In another aspect, the present disclosure relates to an antibody that binds to a MS4A4A protein, wherein the antibody includes a heavy chain variable region and a light chain variable region, wherein the light chain variable region includes the HVR-L1, HVR-L2, and HVR-L3 of antibody 4A-301, 4A-302, 4A-303, 4A-304, 4A-305, 4A-306, 4A-307, 4A-308, 4A-309, 4A-310, 4A-311, 4A-312, 4A-313, 4A-314, 4A-419, or 4A-450 (as shown in Table 1, Table 5, Table 30, and Table 31).

In another aspect, the present disclosure relates to an antibody that bind to a MS4A4A protein, wherein the antibody includes a heavy chain variable region including an HVR-H1, HVR-H2, and HVR-H3 and a light chain variable region including an HVR-L1, HVR-L2, and HVR-L3, wherein the antibody includes the HVR-H1, HVR-H2, HVR-H3, HVR-L1, HVR-L2, and HVR-L3 of antibody 4A-301, 4A-302, 4A-303, 4A-304, 4A-305, 4A-306, 4A-307, 4A-308, 4A-309, 4A-310, 4A-311, 4A-312, 4A-313, 4A-314, 4A-419, or 4A-450 (as shown in Table 1, Table 5, Table 30, and Table 31).

In another aspect, the present disclosure relates to an antibody that binds to a MS4A4A protein, wherein the antibody includes a heavy chain variable region and a light chain variable region, wherein the heavy chain variable region includes the HVR-H1, HVR-H2, and HVR-H3 of antibody 4A-315, 4A-316, 4A-317, 4A-318, 4A-319, 4A-320, 4A-321, 4A-322, 4A-323, 4A-324, 4A-325, 4A-326, 4A-327, 4A-328, 4A-329, 4A-330, or 4A-331 (as shown in Table 2 and Table 6).

In another aspect, the present disclosure relates to an antibody that binds to a MS4A4A protein, wherein the antibody includes a heavy chain variable region and a light chain variable region, wherein the light chain variable region includes the HVR-L1, HVR-L2, and HVR-L3 of antibody 4A-315, 4A-316, 4A-317, 4A-318, 4A-319, 4A-320, 4A-321, 4A-322, 4A-323, 4A-324, 4A-325, 4A-326, 4A-327, 4A-328, 4A-329, 4A-330, or 4A-331 (as shown in Table 2 and Table 6).

In another aspect, the present disclosure relates to an antibody that bind to a MS4A4A protein, wherein the antibody includes a heavy chain variable region including an HVR-H1, HVR-H2, and HVR-H3 and a light chain variable region including an HVR-L1, HVR-L2, and HVR-L3, wherein the antibody includes the HVR-H1, HVR-H2, HVR-H3, HVR-L1, HVR-L2, and HVR-L3 of antibody 4A-315, 4A-316, 4A-317, 4A-318, 4A-319, 4A-320, 4A-321, 4A-322, 4A-323, 4A-324, 4A-325, 4A-326, 4A-327, 4A-328, 4A-329, 4A-330, or 4A-331 (as shown in Table 2 and Table 6).

In another aspect, the present disclosure relates to an antibody that binds to a MS4A4A protein, wherein the antibody includes a heavy chain variable region and a light chain variable region, wherein the heavy chain variable region includes the HVR-H1, HVR-H2, and HVR-H3 of antibody 4A-332, 4A-333, 4A-334, 4A-335, 4A-336, 4A-337, 4A-338, 4A-339, 4A-340, 4A-341, 4A-342, 4A-343, 4A-344, 4A-345, 4A-346, 4A-347, 4A-348, 4A-349, 4A-350, 4A-351, 4A-352, 4A-353, 4A-354, 4A-355, 4A-356, 4A-357, 4A-358, 4A-359, 4A-360, 4A-361, 4A-361, 4A-363, 4A-364, 4A-365, 4A-366, 4A-367, 4A-368, 4A-369, 4A-370, 4A-371, 4A-372, 4A-373, 4A-374, 4A-375, 4A-376, 4A-377, 4A-378, 4A-379, 4A-380, or 4A-381 (as shown in Table 3 and Table 7).

In another aspect, the present disclosure relates to an antibody that binds to a MS4A4A protein, wherein the antibody includes a heavy chain variable region and a light chain variable region, wherein the light chain variable region includes the HVR-L1, HVR-L2, and HVR-L3 of antibody 4A-332, 4A-333, 4A-334, 4A-335, 4A-336, 4A-337, 4A-338, 4A-339, 4A-340, 4A-341, 4A-342, 4A-343, 4A-344, 4A-345, 4A-346, 4A-347, 4A-348, 4A-349, 4A-350, 4A-351, 4A-352, 4A-353, 4A-354, 4A-355, 4A-356, 4A-357, 4A-358, 4A-359, 4A-360, 4A-361, 4A-361, 4A-363, 4A-364, 4A-365, 4A-366, 4A-367, 4A-368, 4A-369, 4A-370, 4A-371, 4A-372, 4A-373, 4A-374, 4A-375, 4A-376, 4A-377, 4A-378, 4A-379, 4A-380, or 4A-381 (as shown in Table 3 and Table 7).

In another aspect, the present disclosure relates to an antibody that bind to a MS4A4A protein, wherein the antibody includes a heavy chain variable region including an HVR-H1, HVR-H2, and HVR-H3 and a light chain variable region including an HVR-L1, HVR-L2, and HVR-L3, wherein the antibody includes the HVR-H1, HVR-H2, HVR-H3, HVR-L1, HVR-L2, and HVR-L3 of antibody 4A-332, 4A-333, 4A-334, 4A-335, 4A-336, 4A-337, 4A-338, 4A-339, 4A-340, 4A-341, 4A-342, 4A-343, 4A-344, 4A-345, 4A-346, 4A-347, 4A-348, 4A-349, 4A-350, 4A-351, 4A-352, 4A-353, 4A-354, 4A-355, 4A-356, 4A-357, 4A-358, 4A-359, 4A-360, 4A-361, 4A-361, 4A-363, 4A-364, 4A-365, 4A-366, 4A-367, 4A-368, 4A-369, 4A-370, 4A-371, 4A-372, 4A-373, 4A-374, 4A-375, 4A-376, 4A-377, 4A-378, 4A-379, 4A-380, or 4A-381 (as shown in Table 3 and Table 7).

In another aspect, the present disclosure relates to an antibody that binds to a MS4A4A protein, wherein the antibody includes a heavy chain variable region and a light chain variable region, wherein the heavy chain variable region includes the HVR-H1, HVR-H2, and HVR-H3 of antibody 4A-382, 4A-383, 4A-384, 4A-385, 4A-386, 4A-387, 4A-388, 4A-389, or 4A-390 (as shown in Table 4 and Table 8).

In another aspect, the present disclosure relates to an antibody that binds to a MS4A4A protein, wherein the antibody includes a heavy chain variable region and a light chain variable region, wherein the light chain variable region includes the HVR-L1, HVR-L2, and HVR-L3 of antibody 4A-382, 4A-383, 4A-384, 4A-385, 4A-386, 4A-387, 4A-388, 4A-389, or 4A-390 (as shown in Table 4 and Table 8).

In another aspect, the present disclosure relates to an antibody that bind to a MS4A4A protein, wherein the antibody includes a heavy chain variable region including an HVR-H1, HVR-H2, and HVR-H3 and a light chain variable region including an HVR-L1, HVR-L2, and HVR-L3, wherein the antibody includes the HVR-H1, HVR-H2, HVR-H3, HVR-L1, HVR-L2, and HVR-L3 of antibody 4A-382, 4A-383, 4A-384, 4A-385, 4A-386, 4A-387, 4A-388, 4A-389, or 4A-390 (as shown in Table 4 and Table 8).

In certain embodiments that may be combined with any of the embodiments herein, the present disclosure relates to an antibody that binds to a MS4A4A protein, wherein the antibody increases mRNA and/or protein expression of gelsolin and/or osteopontin on myeloid cells. In some embodiments, the myeloid cells are macrophages.

In certain embodiments that may be combined with any of the embodiments herein, the anti-MS4A4A antibody binds specifically to human MS4A4A, mouse MS4A4A, cyno MS4A4A, or a combination thereof.

It is to be understood that one, some, or all of the properties of the various embodiments described herein may be combined to form other embodiments of the present disclosure. These and other aspects of the disclosure will become apparent to one of skill in the art. These and other embodiments of the disclosure are further described by the detailed description that follows.

BRIEF DESCRIPTION OF THE DRAWINGS

FIG. 1 shows the primary amino acid sequence of human MS4A4A (SEQ ID NO: 1). Intracellular domains are italicized, transmembrane domains are underlined, extracellular loops are bold italicized.

FIG. 3A shows the primary amino acid sequences of soluble four helix bundle scaffolds JS1, JS5, and JS6, into which the two extracellular loops of human MS4A4A were added (shown as bold underlined). FIG. 3B shows the primary amino acid sequences of soluble four helix bundle scaffolds JS4 and JS10 used as negative control variants.

FIG. 10A provides the levels (ng/mL) of sTREM2 in the serum of cynomolgus monkeys at the indicated times (hours) following administration of anti-MS4A4A antibody 4A-202 or isotype control antibody (huIgG1), both at a dose of 80 mg/kg. FIG. 10B provides the levels of sTREM2 (percent of baseline) in the serum of cynomolgus monkeys at the indicated times (hours) following administration of anti-MS4A4A antibody 4A-202 or isotype control antibody (huIgG1), both at a dose of 80 mg/kg.

FIG. 11A provides the levels (ng/mL) of sTREM2 in the CSF of cynomolgus monkeys at the indicated times (hours) following administration of anti-MS4A4A antibody 4A-202 or isotype control antibody (huIgG1), both at a dose of 80 mg/kg. FIG. 11B provides the levels of sTREM2 (percent of baseline) in the CSF of cynomolgus monkeys at the indicated times (hours) following administration of anti-MS4A4A antibody 4A-202 or isotype control antibody (huIgG1), both at a dose of 80 mg/kg.

DETAILED DESCRIPTION OF THE PRESENT DISCLOSURE

Figures 2A, 2B, 2C:
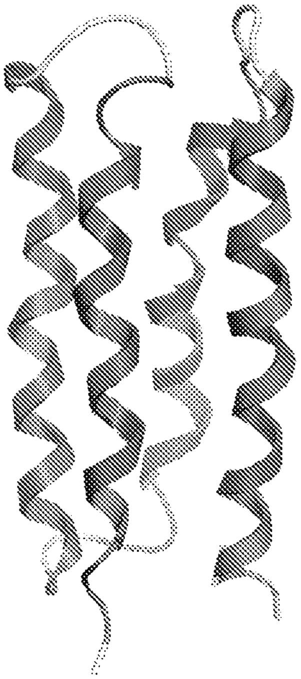
FIG. 2A shows a structure schematic of a soluble four helix bundle scaffold (PDB_ID:1P68) obtained from the RCSB Protein Data Bank having four transmembrane domains shown as helical ribbons in the structure.
FIG. 2B and FIG. 2C show the primary amino acid sequence of soluble four helix bundle scaffold PDB-ID: 1P68 and PDB_ID: 1M6T, respectively; the four transmembrane domains are underlined in the amino acid sequences.

The present disclosure relates to anti-MS4A4A antibodies (e.g., monoclonal antibodies); methods of making and using such antibodies; pharmaceutical compositions comprising such antibodies; nucleic acids encoding such antibodies; and host cells comprising nucleic acids encoding such antibodies.

The techniques and procedures described or referenced herein are generally well understood and commonly employed using conventional methodology by those skilled in the art, such as, for example, the widely utilized methodologies such as those described in Sambrook et al. *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003); *Monoclonal Antibodies: A Practical Approach* (P. Shepherd and C. Dean, eds., Oxford University Press, 2000).

I. Definitions

The terms "MS4A4A" or "MS4A4A polypeptide" are used interchangeably herein refer herein to any native MS4A4A from any vertebrate source, including mammals such as primates (e.g., humans and cynos) and rodents (e.g., mice and rats), unless otherwise indicated. In some embodiments, the term encompasses both wild-type sequences and naturally occurring variant sequences, e.g., splice variants or allelic variants. In some embodiments, the term encompasses "full-length," unprocessed MS4A4A as well as any form of MS4A4A that results from processing in the cell. In some embodiments, the MS4A4A is human MS4A4A. In some embodiments, the amino acid sequence of an exemplary MS4A4A is Uniprot Accession No. Q96JQ5 as of Dec. 1, 2001. In some embodiments, the amino acid sequence of an exemplary human MS4A4A is SEQ ID NO: 1.

The terms "anti-MS4A4A antibody," an "antibody that binds to MS4A4A," and "antibody that specifically binds MS4A4A" refer to an antibody that is capable of binding MS4A4A with sufficient affinity such that the antibody is useful as a diagnostic and/or therapeutic agent in targeting MS4A4A. In one embodiment, the extent of binding of an anti-MS4A4A antibody to an unrelated, non-MS4A4A polypeptide is less than about 10% of the binding of the antibody to MS4A4A as measured, e.g., by a radioimmunoassay (RIA). In certain embodiments, an antibody that binds to MS4A4A has a dissociation constant (KD) of <1 μM, <100 nM, <10 nM, <1 nM, <0.1 nM, <0.01 nM, or <0.001 nM (e.g., $10^{-8}$ M or less, e.g. from $10^{-8}$ M to $10^{-13}$ M, e.g., from $10^{-9}$ M to $10^{-13}$ M). In certain embodiments, an anti-MS4A4A antibody binds to an epitope of MS4A4A that is conserved among MS4A4A from different species.

With regard to the binding of an antibody to a target molecule, the term "specific binding" or "specifically binds" or is "specific for" a particular polypeptide or an epitope on a particular polypeptide target means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a KD for the target of about any of $10^{-4}$ M or lower, $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, $10^{-12}$ M or lower or a KD in the range of $10^{-4}$ M to $10^{-6}$ M or $10^{-6}$ M to $10^{-10}$ M or $10^{-7}$ M to $10^{-9}$ M. As will be appreciated by the skilled artisan, affinity and KD values are inversely related. A high affinity for an antigen is measured by a low KD value. In one embodiment, the term "specific binding" refers to binding where a molecule binds to a particular polypeptide or epitope on a particular polypeptide without substantially binding to any other polypeptide or polypeptide epitope.

The term "immunoglobulin" (Ig) is used interchangeably with "antibody" herein. The term "antibody" herein is used in the broadest sense and specially covers monoclonal antibodies, polyclonal antibodies, multispecific antibodies (e.g., bispecific antibodies) including those formed from at least two intact antibodies, and antibody fragments so long as they exhibit the desired biological activity.

"Native antibodies" are usually heterotetrameric glycoproteins of about 150,000 Daltons, composed of two identical Light ("L") chains and two identical heavy ("H") chains. Each light chain is linked to a heavy chain by one covalent disulfide bond, while the number of disulfide linkages varies among the heavy chains of different immunoglobulin isotypes. Each heavy and light chain also has regularly spaced intra-chain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

For the structure and properties of the different classes of antibodies, see, e.g., Basic and Clinical Immunology, 8th Ed., Daniel P. Stites, Abba I. Ten and Tristram G. Parslow (eds.), Appleton & Lange, Norwalk, C T, 1994, page 71 and Chapter 6.

The light chain from any vertebrate species can be assigned to one of two clearly distinct types, called kappa ("K") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("δ"), epsilon ("ε"), gamma ("γ"), and mu ("μ"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three-dimensional configurations of different classes of immunoglobulins are well known and described generally in, for example, Abbas et al., Cellular and Molecular Immunology, $4^{th}$ ed. (W. B. Saunders Co., 2000).

The "variable region" or "variable domain" of an antibody, such as an anti-MS4A4A antibody of the present disclosure, refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies, such as anti-MS4A4A antibodies of the present disclosure. The variable domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., Sequences of Immunological Interest, Fifth Edition, National Institute of Health, Bethesda, MD (1991)). The constant domains are not involved directly in the binding of antibody to an antigen, but exhibit various effector functions, such as participation of the antibody in antibody-dependent-cellular toxicity.

The term "monoclonal antibody" as used herein refers to an antibody, such as a monoclonal anti-MS4A4A antibody of the present disclosure, obtained from a population of substantially homogeneous antibodies, i.e., the individual antibodies comprising the population are identical except for possible naturally occurring mutations and/or post-translation modifications (e.g., isomerizations, amidations, etc.) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including, for example, the hybridoma method, recombinant DNA methods, and technologies for producing human or human-like antibodies in animals that have parts or all of the human immunoglobulin loci or genes encoding human immunoglobulin sequences.

The terms "full-length antibody," "intact antibody" or "whole antibody" are used interchangeably to refer to an antibody, such as an anti-MS4A4A antibody of the present disclosure, in its substantially intact form, as opposed to an antibody fragment. Specifically, whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" refers to a molecule other than an intact antibody that comprises a portion of an intact antibody that binds the antigen to which the intact antibody binds. Examples of antibody fragments include Fab, Fab', F(ab')2 and Fv fragments; diabodies; linear antibodies (see U.S. Pat. No. 5,641,870, Example 2; Zapata et al., *Protein Eng.* 8(10):1057-1062 (1995)); single-chain antibody molecules and multispecific antibodies formed from antibody fragments.

Papain digestion of antibodies, such as anti-MS4A4A antibodies of the present disclosure, produces two identical antigen-binding fragments, called "Fab" fragments, and a residual "Fc" fragment, a designation reflecting the ability to crystallize readily. The Fab fragment consists of an entire light chain along with the variable region domain of the heavy chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The Fc fragment comprises the carboxy-terminal portions of both heavy chains held together by disulfides. The effector functions of antibodies are determined by sequences in the Fc region, the region which is also recognized by Fc receptors (FcR) found on certain types of cells.

"Functional fragments" of antibodies, such as anti-MS4A4A antibodies of the present disclosure, comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the variable domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains.

As used herein, a "chimeric antibody" refers to an antibody (immunoglobulin), such as a chimeric anti-MS4A4A antibody of the present disclosure, in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity. Chimeric antibodies of interest herein include PRIMATIZED ° antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies, such as humanized forms of anti-MS4A4A antibodies of the present disclosure, are chimeric antibodies comprising amino acid residues from non-human HVRs and amino acid residues from human FRs. In certain embodiments, a humanized antibody will comprise substantially all of at least one, and typically two, variable domains, in which all or substantially all of each HVR (e.g., CDRs) correspond to those of a non-human antibody, and all or substantially all of each FR correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is an antibody, such as an anti-MS4A4A antibody of the present disclosure, possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries and yeast-display libraries. Human antibodies can be prepared by administering the antigen to a transgenic animal that has been modified to produce such antibodies in response to antigenic challenge, but whose endogenous loci have been disabled, e.g., immunized xenomice as well as generated via a human B-cell hybridoma technology.

The term "hypervariable region," "HVR," or "HV," when used herein refers to the regions of an antibody-variable domain, such as that of an anti-MS4A4A antibody of the present disclosure, that are hypervariable in sequence and/or form structurally defined loops. Generally, antibodies comprise six HVRs; three in the $V_H$ (H1, H2, H3), and three in the $V_L$ (L1, L2, L3). In native antibodies, H3 and L3 display the most diversity of the six HVRs, and H3 in particular is believed to play a unique role in conferring fine specificity to antibodies. Naturally occurring camelid antibodies consisting of a heavy chain only are functional and stable in the absence of light chain.

A number of HVR delineations are in use and are encompassed herein. In some embodiments, the HVRs may be Kabat complementarity-determining regions (CDRs) based on sequence variability and are the most commonly used (Kabat et al., supra). In some embodiments, the HVRs may be Chothia CDRs. Chothia refers instead to the location of the structural loops (Chothia and Lesk *J. Mol. Biol.* 196: 901-917 (1987)). In some embodiments, the HVRs may be AbM HVRs. The AbM HVRs represent a compromise between the Kabat CDRs and Chothia structural loops, and are used by Oxford Molecular's AbM antibody-modeling software. In some embodiments, the HVRs may be "contact" HVRs. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the $V_L$, and 26-35 (H1), 50-65 or 49-65 (a preferred embodiment) (H2), and 93-102, 94-102, or 95-102 (H3) in the $V_H$. The variable-domain residues are numbered according to Kabat et al., supra, for each of these extended-HVR definitions.

"Framework" or "FR" residues are those variable domain residues other than the HVR residues as herein defined.

An "acceptor human framework" as used herein is a framework comprising the amino acid sequence of a $V_L$ or $V_H$ framework derived from a human immunoglobulin framework or a human consensus framework. An acceptor human framework "derived from" a human immunoglobulin framework or a human consensus framework may comprise the same amino acid sequence thereof, or it may comprise pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a $V_H$, preferable those changes occur at only three, two, or one of positions 71H, 73H and 78H; for instance, the amino acid residues at those positions may by 71A, 73T and/or 78A. In one embodiment, the $V_L$ acceptor human framework is identical in sequence to the $V_L$ human immunoglobulin framework sequence or human consensus framework sequence.

A "human consensus framework" is a framework that represents the most commonly occurring amino acid residues in a selection of human immunoglobulin $V_L$ or $V_H$ framework sequences. Generally, the selection of human immunoglobulin $V_L$ or $V_H$ framework sequences is from a subgroup of variable domain sequences. Generally, the subgroup of sequences is a subgroup as in Kabat et al., *Sequences of Proteins of Immunological Interest,* $5^{th}$ Ed. Public Health Service, National Institutes of Health, Bethesda, MD (1991). Examples include for the $V_L$, the subgroup may be subgroup kappa I, kappa II, kappa III or kappa IV as in Kabat et al., supra. Additionally, for the $V_H$, the subgroup may be subgroup I, subgroup II, or subgroup III as in Kabat et al., supra.

An "amino-acid modification" at a specified position, e.g., of an anti-MS4A4A antibody of the present disclosure, refers to the substitution or deletion of the specified residue, or the insertion of at least one amino acid residue adjacent the specified residue. "Adjacent" to a specified residue means insertion within one to two residues thereof. The insertion may be N-terminal or C-terminal to the specified residue. A preferred amino acid modification herein is a substitution.

An "affinity-matured" antibody, such as an affinity matured anti-MS4A4A antibody of the present disclosure, is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al. *Bio/Technology* 10:779-783 (1992) describes affinity maturation by $V_H$- and $V_L$-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155: 1994-2004 (1995); Jackson et al. *J. Immunol.* 154(7):3310-9 (1995); and Hawkins et al, *J. Mol. Biol.* 226:889-896 (1992).

"Fv" is the minimum antibody fragment which comprises a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains, which enables the sFv to form the desired structure for antigen binding.

Antibody "effector functions" refer to those biological activities attributable to the Fc region (a native sequence Fc region or amino acid sequence variant Fc region) of an antibody, and vary with the antibody isotype.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the present disclosure include human IgG1, IgG2, IgG3 and IgG4.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain. Other FcRs, including those to be identified in the future, are encompassed by the term "FcR" herein. FcRs can also increase the serum half-life of antibodies.

As used herein, "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full-length of the sequences being compared.

The term "compete" when used in the context of antibodies (e.g., neutralizing antibodies) that compete for the same epitope means competition between antibody as determined by an assay in which the antibody being tested prevents or inhibits (e.g., reduces) specific binding of a reference molecule (e.g., a ligand, or a reference antibody) to a common antigen (e.g., MS4A4A or a fragment thereof). Numerous types of competitive binding assays can be used to determine if antibody competes with another, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol.

32:77-82). Typically, such an assay involves the use of purified antigen bound to a solid surface or cells bearing either of these, an unlabelled test antibody and a labeled reference antibody. Competitive inhibition is measured by determining the amount of label bound to the solid surface or cells in the presence of the test antibody. Usually the test antibody is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Additional details regarding methods for determining competitive binding are provided in the examples herein. Usually, when a competing antibody is present in excess, it will inhibit (e.g., reduce) specific binding of a reference antibody to a common antigen by at least 20%, 30%, 40%, 50%, 60%, 70%, 80%, 85%, 90%, 95%, 97.5%, and/or near 100%.

As used herein, an "interaction" between a MS4A4A polypeptide and a second polypeptide encompasses, without limitation, protein-protein interaction, a physical interaction, a chemical interaction, binding, covalent binding, and ionic binding. As used herein, an antibody "inhibits interaction" between two polypeptides when the antibody disrupts, reduces, or completely eliminates an interaction between the two polypeptides. An antibody of the present disclosure, thereof, "inhibits interaction" between two polypeptides when the antibody thereof binds to one of the two polypeptides. In some embodiments, the interaction can be inhibited by at least about any of 20%, 30%, 40%, 50%, 60%, 70%, 80%, 85%, 90%, 95%, 97.5%, and/or near 100%.

The term "epitope" includes any determinant capable of being bound by an antibody. An epitope is a region of an antigen that is bound by an antibody that targets that antigen, and when the antigen is a polypeptide, includes specific amino acids that directly contact the antibody. Most often, epitopes reside on polypeptides, but in some instances, can reside on other kinds of molecules, such as nucleic acids. Epitope determinants can include chemically active surface groupings of molecules such as amino acids, sugar side chains, phosphoryl or sulfonyl groups, and can have specific three dimensional structural characteristics, and/or specific charge characteristics. Generally, antibodies specific for a particular target antigen will preferentially recognize an epitope on the target antigen in a complex mixture of polypeptides and/or macromolecules.

An "agonist" antibody or an "activating" antibody is an antibody that induces (e.g., increases) one or more activities or functions of the antigen after the antibody binds the antigen.

An "antagonist" antibody or a "blocking" antibody or an "inhibitory" antibody is an antibody that reduces, inhibits, and/or eliminates (e.g., decreases) antigen binding to one or more ligand after the antibody binds the antigen, and/or that reduces, inhibits, and/or eliminates (e.g., decreases) one or more activities or functions of the antigen after the antibody binds the antigen. In some embodiments, antagonist antibodies, or blocking antibodies, or inhibitory antibodies substantially or completely inhibit antigen binding to one or more ligand and/or one or more activities or functions of the antigen.

An "isolated" antibody, such as an isolated anti-MS4A4A antibody of the present disclosure, is one that has been identified, separated and/or recovered from a component of its production environment (e.g., naturally or recombinantly). Preferably, the isolated antibody is free of association with all other contaminant components from its production environment. Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In preferred embodiments, the antibody will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant T-cells since at least one component of the antibody's natural environment will not be present. Ordinarily, however, an isolated polypeptide or antibody will be prepared by at least one purification step.

An "isolated" nucleic acid molecule encoding an antibody, such as an anti-MS4A4A antibody of the present disclosure, is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of the present disclosure.

The terms "membrane TREM2", "plasma membrane TREM2", and "cell surface TREM2", as used herein, are used interchangeably.

"Carriers" as used herein include pharmaceutically acceptable carriers, excipients, or stabilizers that are non-toxic to the cell or mammal being exposed thereto at the dosages and concentrations employed.

As used herein, the term "preventing" includes providing prophylaxis with respect to occurrence or recurrence of a particular disease, disorder, or condition in an individual. An individual may be predisposed to, susceptible to a particular disease, disorder, or condition, or at risk of developing such a disease, disorder, or condition, but has not yet been diagnosed with the disease, disorder, or condition.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic or prophylactic result. An effective amount can be provided in one or more administrations. An effective amount herein may vary according to factors such as the disease state, age, sex, and weight of the individual, and the ability of the treatment to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

An "individual" for purposes of treatment, prevention, or reduction of risk refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. In some embodiments, the individual is human.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration. In some embodiments, administration in conjunction is administration as a part of the same treatment regimen.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspect and embodiments of the present disclosure described herein include "comprising," "consisting," and "consisting essentially of" aspects and embodiments.

I. Anti-MS4A4A Antibodies

Provided herein are anti-MS4A4A antibodies. Antibodies provided herein are useful, e.g., for the diagnosis or treatment of MS4A4A-associated disorders.

In one aspect, the present disclosure provides isolated (e.g., monoclonal) antibodies that bind to an epitope within a MS4A4A protein of the present disclosure. MS4A4A proteins of the present disclosure include, without limitation, a mammalian MS4A4A protein, human MS4A4A protein, mouse MS4A4A protein, and cyno MS4A4A protein. MS4A4A proteins of the present disclosure include naturally-occurring variants of MS4A4A.

Human MS4A4A is a 239-amino acid protein that encodes a membrane glycoprotein. The amino acid sequence of human MS4A4A is set forth in SEQ ID NO: 1:

```
MHQTYSRHCRPEESTFSAAMTTMQGMEQAMPGAGPGVPQLGNMAVIHSHL
WKGLQEKFLKGEPKVLGVVQILTALMSLSMGITMMCMASNTYGSNPISVY
IGYTIWGSVMFIISGSLSIAAGIRTTKGLVRGSLGMNITSSVLAASGILI
NTFSLAFYSFHHPYCNYYGNSNNCHGTMSILMGLDGMVLLLSVLEFCIAV
SLSAFGCKVLCCTPGGVVLILPSHSHMAETASPTPLNEV
```

Additionally, the amino acid sequence of mouse MS4A4A is set forth in SEQ ID NO: 2:

```
MLVIQGTEQSALEAGYGAQQNGQPLYVNSHSWKRMTEKFLKGEPKILGIV

QIVIAIMNLSIGIMMIIATVSTGEIPPSSVYIGYPIWGSLMFIISGSFSI

VAGRRTTKGLVRSSLGLNITSSVFAFSGIVISSLSPGIYSFHVYYCTYRG

SSEGCHMTLSILMGLDIVVVVLSVLEFCIGVSLSAFGCRVMCCNPGGVMI

IMPSNPTKAETANPVTLQSGLMPPEHQERNVPENMH
```

Additionally, the amino acid sequence of cynomolgus (cyno) MS4A4A is set forth in SEQ ID NO: 3:

```
HQTYRRHCRPEESTFSAAMTTMQGMEQATPGAGPGVPQLGNMAVVHSHLW

KGLQEKFLKGEPKVLGVVQILIALMSLSMGITMMCVAFSAYGHYPISVYI

GYTIWGSVMFIISGSLSIAAGIRTTKGLVRGSLGMNITSSVLAVSAILIN

TISLTIYSFYHRYCNYYGNPNNCHGTVSILMGMDGMVLLLSVLEFCIAVS

LSAFGCKAICCTPGGVVLIIPSNSHMAEAAPLTPLNEV
```

In some embodiments, MS4A4A is expressed in a cell. In some embodiments, MS4A4A is expressed in myeloid cells. In some embodiments, MS4A4A is expressed in brain cells. In some embodiments, MS4A4A is expressed in astrocytes, including without limitation mature astrocytes. In some embodiments, MS4A4A is expressed in oligodendrocytes. In some embodiments, MS4A4A is expressed in microglial cells. In some embodiments, MS4A4A is expressed in immune cells, including without limitation, macrophages, eosinophils, mast cells, dendritic cells, natural killer cells, neutrophils, and T cells. In some embodiment, MS4A4A is expressed in olfactory cells. In some embodiments, MS4A4A is expressed on the cell surface.

MS4A4A proteins of the present disclosure include several domains, including without limitation, a cytoplasmic domain (amino acid residues 1-64 of human MS4A4A; see SEQ ID NO: 1); a transmembrane domain (amino acid residues 65-85 of human MS4A4A); an extracellular domain (extracellular domain 1; ECL1), corresponding to amino acid residues 86-98 of human MS4A4A; a transmembrane domain (amino acid residues 99-119 of human MS4A4A); a cytoplasmic domain (amino acid residues 120-137 of human MS4A4A); a transmembrane domain (amino acid residues 138-158 of human MS4A4A); an extracellular domain (extracellular domain 2; ECL2), corresponding to amino acid residues 159-179; a transmembrane domain (amino acid residues 180-200 of human MS4A4A); and a cytoplasmic domain (amino acid residues 201-239 of human MS4A4A). Additionally, MS4A4A proteins of the present disclosure are expressed in a number of tissues and cells, including without limitation, the brain, neurons, glial cells, endothelial cells, perivascular cells, pericytes, etc.

MS4A4A in Macrophage and Microglial Cell Function

Macrophages and myeloid cells of the central nervous system (CNS), such as microglia, are inherently plastic in their phenotype and function. Macrophages in vitro can be divided into M1 macrophages and M2 macrophages, which have differing phagocytic and inflammatory potentials, phenotypes, and activities. For example, in peripheral organs, macrophages having an M1 phenotype are considered to have pro-inflammatory and anti-microbial phenotype and function, while macrophages having an M2 phenotype are considered to be in a more homeostatic state, having an anti-inflammatory phenotype and function.

Microglia associated with healthy, homeostatic conditions express more M2 markers on their cell surface (e.g., CD200R, CD163 and CD115) compared to that of M1 markers (e.g., CD16, MHC Class II, CD86) (Ginhoux and Prinz, 2015, Cold Spring Harb Perspect Biol, 7:a020537). However, disease associated microglia (DAM) in both mouse models of Alzheimer's disease and in human Alzheimer's disease are in a proinflammatory or activated state. Disease associated microglia in proinflammatory or activated states are considered beneficial by playing an active role in reducing the pathology associated with Alzheimer's disease and other neurodegenerative disorders.

MS4A4A expression is elevated in M2 macrophages in vitro, and it has been suggested that MS4A4A is a novel cell surface marker for M2 macrophages. Additionally, MS4A4A has also been shown to regulate cell surface transport of cKit on mast cells, suggesting a role of MS4A4A in modulating mast cell degranulation and survival (Cruse et al, 2015, Molecular Biol Cell, 26:1711-1727). Taken together, these reported findings suggest that targeting MS4A4A may affect the recycling, expression, and/or degradation of various macrophage cell surface receptors associated with M1 and M2 macrophage phenotypes, thus affecting their functions and activities.

Anti-MS4A4A antibodies of the present disclosure affect the expression of M2 macrophage cell surface markers. In particular, anti-MS4A4A antibodies of the present disclosure reduce the cell surface expression of CD200R, Dectin-1, and CD163 in macrophages, suggesting that anti-MS4A4A antibodies modulate macrophage polarization, function, and/or activity by reducing expression of M2 macrophage cell surface receptors. Anti-MS4A4A antibodies of the present disclosure reduce M2 macrophage cell surface receptors, suggesting that anti-MS4A4A antibodies of the present disclosure are effective at altering the physiological state of microglial cells to that of a more protective phenotype, such as to a more proinflammatory or activated state (e.g., to a more M1 phenotype). Accordingly, anti-MS4A4A antibodies of the present disclosure are useful in treating Alzheimer's disease and other neurodegenerative disorders, in part, by altering the phenotype of macrophages and microglia to a proinflammatory and activated state.

Anti-MS4A4A antibodies of the present disclosure affect the activation state of microglia. Anti-MS4A4A antibodies of the present disclosure increased mRNA levels of proteins associated with microglia activation (e.g., C-type lectin domain family 7 member A (CLEC7A)), microglia migration (e.g., inositol 1,4,5-triphosphate receptor 2 (ITPR2)), and microglia proliferation (e.g., antigen KI-67 (MKI67)) in vivo. Additionally, anti-MS4A4A antibodies of the present disclosure increased mRNA levels of microglia activation markers IL1RN, SPP1, and PLCG2. Anti-MS4A4A antibodies of the present dislsoure also decreased mRNA levels of homeostatic microglia markers purinergic receptor P2RY12 and CX3C chemokine receptor 1 (CX3CR1). Accordingly, anti-MS4A4A antibodies of the present disclosure are effective at activating microglia in vivo as evidenced by increases in various mRNA levels of proteins associated with microglia activation, migration, and proliferation; and by decreases in various mRNA levels of proteins associated with microglia homeostasis.

MS4A4A and TREM2 Expression

Neurodegenerative diseases are characterized, in part, by defective immune function in the central nervous system (CNS). For example, a decrease in viability and function in the CNS myeloid cell compartment, including but not restricted to microglia, is thought to contribute to susceptibility to neurodegenerative disorders, such as Alzheimer's disease. Pharmacological intervention that enhances viability and/or function of myeloid cells would provide effective treatment to ameliorate the onset, severity, or progression of such neurodegenerative diseases and disorders.

Triggering receptor expressed on myeloid cells-2 (TREM2) is an immunoglobulin-like receptor that is expressed primarily on myeloid cells, such as macrophages, dendritic cells, monocytes, Langerhans cells of skin, Kupffer cells, osteoclasts, and microglia. TREM2 is highly expressed on microglia and infiltrating macrophages in the CNS during experimental autoimmune encephalomyelitis and Alzheimer's disease (Piccio et al, 2007, Eur J Immunol, 37:1290-1301; Wang, 2015, Cell, 160:1061-1071). The TREM2 pathway is considered a key modulator of CNS myeloid cell viability and function.

Data from human genetics studies have suggested strong genetic links between MS4A4A and TREM2 and with susceptibility to Alzheimer's disease (Piccio et al., 2016, Acta Neuropathol, 131:925-9330). In particular, MS4A4A alleles protective for Alzheimer's disease are linked to increased sTREM2 levels in the cerebrospinal fluid in patients.

Anti-MS4A4A antibodies of the present invention increase cellular ATP levels in macrophages, indicating that anti-MA4A4A antibodies are effective at increasing, maintaining, or enhancing cell (e.g., macrophages, myeloid cells, microglia) viability and function. Additionally, anti-MS4A4A antibodies of the present invention increased sTREM2 and mTREM2 levels in macrophages, in contrast to that previously reported in which commercially available anti-MS4A4A antibody 5C12 reduced sTREM2 levels in supernatants of cultured human macrophages (Deming et al, 2018, bioRxiv, doi: dx doi org/As MS4A4A protective alleles for Alzheimer's disease are linked to increased sTREM2 levels, the results provided herein indicated that anti-MS4A4A antibodies of the present invention mimic or replicate a protective phenotype in neurodegenerative diseases and disorders, such as Alzheimer's disease, by increasing sTREM2 and mTREM2 levels. In some embodiments, an anti-MS4A4A antibody of the present disclosure increases cell surface expression of TREM2 in myeloid cells (e.g., macrophages, human macrophages, microglia) by at least 10%, by at least 20%, by at least 25%, by at least 50%, by at least 75%, by at least 90%, by at least 100%, by at least 125%, by at least 150%, by at least 200%, or by at least 250%. In some embodiments, an anti-MS4A4A antibody of the present disclosure increases soluble TREM2 levels in myeloid cells (e.g., macrophages, human macrophages, microglia) by at least 10%, by at least 20%, by at least 30%, by at least 40%, by at least 50%, by at least 60%, by at least 70%, by at least 80%, by at least 90%, or by at least 100%.

In some embodiments, an anti-MS4A4A antibody of the present disclosure increases mTREM protein levels in myeloid cells (e.g., macrophages, human macrophages, microglia) with an EC50 of about μg/ml to about 0.039 μg/ml. In some embodiments, an anti-MS4A4A antibody of the present disclosure increases sTREM protein levels in myeloid cells (e.g., macrophages, human macrophages, microglia) with an EC50 of about 0.025 μg/ml to about 0.069 μg/ml. In yet other embodiments, an anti-MS4A4A antibody of the present disclosure increases ATP levels in myeloid cells (e.g., macrophages, human macrophages, microglia) with an EC50 of about 0.010 μg/ml to about 0.021 μg/ml. In some embodiments, an anti-MS4A4A antibody of the present disclosure increases ATP levels in myeloid cells (e.g., macrophages, human macrophages, microglia) by about 1.2-fold, about 1.4-fold, or about 1.7-fold over the level of ATP in such cells in the absence of anti-MS4A4A antibody.

In some embodiments, an anti-MS4A4A antibody of the present disclosure increases soluble TREM2 levels in vivo (e.g., in a non-human primate or in a human). In some embodiments, an anti-MS4A4A antibody of the present disclosure increases soluble TREM2 levels in serum in vivo by at least 10%, by at least 20%, by at least 25%, by at least 50%, by at least 75%, by at least 90%, by at least 100%, by at least 125%, or by at least 150% from the baseline soluble TREM2 levels in serum in vivo prior to administration of an anti-MS4A4A antibody of the present disclosure. In some embodiments, an anti-MS4A4A antibody of the present disclosure increases soluble TREM2 levels in serum in vivo by about 50% from the baseline soluble TREM2 levels in serum in vivo prior to administration of an anti-MS4A4A antibody of the present disclosure.

In some embodiments, an anti-MS4A4A antibody of the present disclosure increases soluble TREM2 levels in serum in vivo by at least 1.1-fold, by at least 1.2-fold, by at least 1.3-fold, by at least 1.4-fold, by at least 1.5-fold, by at least 1.6-fold, by at least 1.7-fold, by at least 1.8-fold, by at least 1.9-fold, or by at least 2-fold relative to the soluble TREM2 levels in serum in vivo prior to administration of an anti-MS4A4A antibody of the present disclosure. In some embodiments, an anti-MS4A4A antibody of the present disclosure increases soluble TREM2 levels in serum in vivo by about 1.5-fold relative to the soluble TREM2 levels in serum in vivo prior to administration of an anti-MS4A4A antibody of the present disclosure.

In some embodiments, an anti-MS4A4A antibody of the present disclosure increases soluble TREM2 levels in serum in vivo compared to the soluble TREM2 levels in serum in vivo prior to administration of an anti-MS4A4A antibody of the present disclosure for at least 1 day, at least 2 days, at least 3 days, at least 4 days, at least 5 days, at least 6 days, at least 7 days, at least 8 days, at least 9 days, at lead 10 days, at least 11 days, at least 12 days, at least 13 days, at least 14 days, at least 15, at least 16 days, at least 17 days, at least 18 days, at least 19 days, or at least 20 days. In some embodiments, an anti-MS4A4A antibody of the present disclosure increases soluble TREM2 levels in serum in vivo compared to the soluble TREM2 levels in serum in vivo prior to administration of an anti-MS4A4A antibody of the present disclosure for at least 20 days. In some embodiments, an anti-MS4A4A antibody of the present disclosure increases soluble TREM2 levels in serum in vivo compared to the soluble TREM2 levels in serum in vivo prior to administration of an anti-MS4A4A antibody of the present disclosure for at least 24 hours, at least 48 hours, at least 72 hours, at least 96 hours, at least 120 hours, at least 144 hours, at least 168 hours, at least 192 hours, at least 216 hours, at least 240 hours, at least 264 hours, at least 288 hours, at least 312 hours, at least 336 hours, at least 360 hours, at least 384 hours, at least 408 hours, at 432 hours, at least 456 hours, or at least 480 hours. In some embodiments, an anti-MS4A4A antibody of the present disclosure increases soluble TREM2 levels in serum in vivo compared to the soluble TREM2 levels in serum in vivo prior to administration of an anti-MS4A4A antibody of the present disclosure for at least 480 hours.

In some embodiments, an anti-MS4A4A antibody of the present disclosure increases soluble TREM2 levels in CSF in vivo by at least 10%, by at least 20%, by at least 25%, by at least 50%, by at least 75%, by at least 90%, by at least 100%, by at least 125%, by at least 150%, by at least 200%, by at least 225%, by at least 250%, by at least 275%, by at least 300%, by at least 325%, by at least 350%, by at least 375%, or by at least 400% from the baseline soluble TREM2 levels in CSF in vivo prior to administration of an anti-MS4A4A antibody of the present disclosure. In some embodiments, an anti-MS4A4A antibody of the present disclosure increases soluble TREM2 levels in CSF in vivo by about 300% from the baseline soluble TREM2 levels in CSF in vivo prior to administration of an anti-MS4A4A antibody of the present disclosure.

In some embodiments, an anti-MS4A4A antibody of the present disclosure increases soluble TREM2 levels in CSF in vivo by at least 1.4-fold, by at least 1.6-fold, by at least 1.8-fold, by at least 2.0-fold, by at least 2.2-fold, by at least 2.4-fold, by at least 2.6-fold, by at least 2.8-fold, by at least 3.0-fold, by at least 3.2-fold, by at least 3.4-fold, by at least 3.6-fold, by at least 3.8-fold, or by at least 4.0-fold relative to the soluble TREM2 levels in CSF in vivo prior to administration of an anti-MS4A4A antibody of the present disclosure. In some embodiments, an anti-MS4A4A antibody of the present disclosure increases soluble TREM2 levels in CSF in vivo by between about 2-fold to about 4-fold relative to the soluble TREM2 levels in CSF in vivo prior to administration of an anti-MS4A4A antibody of the present disclosure.

In some embodiments, an anti-MS4A4A antibody of the present disclosure increases soluble TREM2 levels in CSF in vivo compared to the soluble TREM2 levels in CSF in vivo prior to administration of an anti-MS4A4A antibody of the present disclosure for at least 1 day, at least 2 days, at least 3 days, or at least 4 days. In some embodiments, an anti-MS4A4A antibody of the present disclosure increases soluble TREM2 levels in CSF in vivo compared to the soluble TREM2 levels in CSF in vivo prior to administration of an anti-MS4A4A antibody of the present disclosure for at least 4 days. In some embodiments, an anti-MS4A4A antibody of the present disclosure increases soluble TREM2 levels in CSF in vivo compared to the soluble TREM2 levels in CSF in vivo prior to administration of an anti-MS4A4A antibody of the present disclosure for at least 24 hours, at least 48 hours, at least 72 hours, or at least 96 hours. In some embodiments, an anti-MS4A4A antibody of the present disclosure increases soluble TREM2 levels in CSF in vivo compared to the soluble TREM2 levels in CSF in vivo prior to administration of an anti-MS4A4A antibody of the present disclosure for at least 96 hours.

The evidence provided herein demonstrates that the anti-MS4A4A antibodies of the present disclosure affect TREM2, but does not exclude the antibodies acting through other pathways.

Antagonist Antibodies

In some embodiments, antibodies that bind a MS4A4A protein may include antagonist antibodies that bind MS4A4A inhibit one or more MS4A4A activities, either by preventing interaction between MS4A4A and its ligand(s), or by preventing the transduction of signal of MS4A4A into the cell cytoplasm in the presence of ligand. In some embodiments, antagonist antibodies of the present disclosure may have the epitope specificity of an agonist antibody of the present disclosure, but have an Fc domain that is not capable of binding Fcg receptors and thus is unable to, for example, cluster MS4A4A receptor.

In some embodiments, an antibody of the present disclosure is an antagonist antibody. In some embodiments, the antagonist antibody inhibits one or more MS4A4A activities. In some embodiments, the antagonist antibody decreases activity of one or more MS4A4A-dependent genes. In some embodiments, the antagonist antibody inhibits interaction between MS4A4A and one or more MS4A4A ligands. In some embodiments, the antagonist antibody inhibits MS4A4A signal transduction. In some embodiments, the antagonist antibody inhibits interaction between MS4A4A and one or more MS4A4A ligands and inhibits MS4A4A signal transduction.

In some embodiments, down-regulation of MS4A4A protein levels or reducing MS4A4A activity is accomplished by an anti-MS4A4A antibody that down-regulates or reduces MS4A4A protein levels in a cell. In some embodiments, down-regulation of MS4A4A protein levels or reducing MS4A4A activity is accomplished by down-regulation of MS4A4A nucleic acid expression or levels, by, e.g., use of antisense methodologies, gene therapy, etc, using methods known and available to one of skill in the art. Accordingly, in some embodiments, reducing MS4A4A protein levels or activity is accomplished with an anti-MS4A4A antibody of the present disclosure or by reducing MS4A4A nucleic acid (e.g., mRNA) expression or levels.

In some embodiments, antibody cross-linking is required for agonist antibody function. Antibody cross-linking can occur through binding to a secondary antibody in vitro or through binding to Fc receptors in vivo. For example, antagonistic antibodies can be converted to agonistic antibodies via biotin/streptavidin cross-linking or secondary antibody binding in vitro (see for example Gravestein et al., 1996, J. Exp. Med. 184:675-685; Gravestein et al., 1994, International Immunol, 7:551-557). Agonistic antibodies may exert their activity by mimicking the biological activity of the receptor ligand or by enhancing receptor aggregation, thereby activating receptor signaling. In some embodiments, the absence of antibody cross-linking is required for antagonistic activity. Antagonistic antibodies may exert their activity by blocking receptor-ligand interactions.

Gelsolin, Osteopontin, and Phenocopy of Alzheimer's Disease Protective Allele

There are three SNPs in the MS4A gene cluster that have been associated with an increased risk of late-onset Alzheimer's disease. These include rs4938933 in MS4A4A, rs670139 in MS4A4E, and rs610932 in MS4A6A (Hollingworth et al, 2011, Nat Genetics, 43:429-435; Naj et al, 2011, Nature Genetics, 43:436-441; Antunez et al, 2011, Genome Medicine, 3, article 33). Additionally, MS4A4A locus SNPs (rs2304933 and rs2304935) are associated with higher levels of MS4A4A and increased Alzheimer's disease risk, including late-onset Alzheimer's disease (LOAD) (Allen et al, 2012, Neurology, 79:221-228).

Alzheimer's disease-associated genetic variants (SNPs) associated with the MS4A gene cluster have been identified. One of those variant alleles is rs1582763, which is associated with elevated CSF sTREM2 levels and with reduced Alzheimer's disease risk and delayed age-at-onset, and thus considered a protective allele. (Deming et al, 2018, bioRxiv, doi: dx doi org/10.1101/352179). The rs1582763 protective allele is associated with decreased MS4A4A mRNA levels in blood. These findings further suggest that the rs1582763 allele performs a protective role by reducing MS4A4A levels, and decreasing Alzheimer's disease risk or severity. The protective rs1582763 is associated also with increased expression levels of osteopontin and with increased levels of gelsolin. Anti-MS4A4A antibodies of the present invention are effective at phenocopying these aspects of the protective alleles, at least with respect to decreasing MS4A4A expression, increasing osteopontin expression, increasing gelsolin expression, and/or increasing sTREM levels. In some aspects of the present disclosure, anti-MS4A4A antibodies are provided wherein the antibodies phenocopy one or more alleles of MS4A that are associated with reduced Alzheimer's disease risk and/or delayed age-at-onset of Alzheimer's disease.

Anti-MS4A4A antibodies of the present disclosure increased mRNA levels of osteopontin (SPP1) and increased mRNA levels of gelsolin (GSN) in human peripheral blood mononuclear cell-derived macrophages. In some embodiments, anti-MS4A4A antibodies of the present disclosure increase mRNA and/or protein levels of osteopontin. In some embodiments, anti-MS4A4A antibodies of the present disclosure increase mRNA and/or protein levels of gelsolin. In some embodiments, an anti-MS4A4A antibody of the present disclosure increases mRNA and/or protein levels of osteopontin in myeloid cells (e.g., macrophages, human macrophages, microglia) by at least 10%, by at least 20%, by at least 25%, by at least 30%, by at least 40%, by at least 50%, by at least 60%, by at least 70%, by at least 75%, by at least 80%, by at least 90%, by at least 100%, by at least 125%, by at least 150%, by at least 200%, or by at least 250%. In some embodiments, an anti-MS4A4A antibody of the present disclosure increases gelsolin mRNA and/or protein levels in myeloid cells (e.g., macrophages, human macrophages, microglia) by at least 10%, by at least 20%, by at least 25%, by at least 30%, by at least 40%, by at least 50%, by at least 60%, by at least 70%, by at least 75%, by at least 80%, by at least 90%, by at least 100%, by at least 125%, by at least 150%, by at least 200%, or by at least 250%.

Anti-MS4A4A antibodies of the present disclosure increased osteopontin (SSP1) levels in non-human primates. In some embodiments, anti-MS4A4A antibodies of the present disclosure increase mRNA and/or protein levels of osteopontin in vivo (e.g., in non-human primates or in humans). In some embodiments, an anti-MS4A4A antibody of the present disclosure increases mRNA and/or protein levels of osteopontin in serum and/or in CSF. In some embodiments, an anti-MS4A4A antibody of the present disclosure increases mRNA and/or protein levels of osteopontin in serum and/or in CSF by at least 10%, by at least 20%, by at least 25%, by at least 30%, by at least 40%, by at least 50%, by at least 60%, by at least 70%, by at least 75%, by at least 80%, by at least 90%, by at least 100%, by at least 125%, by at least 150%, by at least 200%, or by at least 250%. In some embodiments, an anti-MS4A4A antibody of the present disclosure increases protein levels of osteopontin in the brain. In some embodiments, an anti-MS4A4A antibody of the present disclosure increases protein levels of osteopontin in the frontal cortex and/or in the hippocampus.

In some embodiments, anti-MS4A4A antibodies of the present disclosure phenocopy the protective rs1582763 allele with respect to increasing expression of osteopontin and gelsolin. In other aspects, anti-MS4A4A antibodies of the present disclosure are effective at increasing expression of osteopontin, of gelsolin, and/or of sTREM2 and are biologically active in decreasing Alzhemier's disease risk and/or severity, similar to that of the protective rs1582763 allele. The data indicated that SPP1 and GSN are pharmacodynamic markers for the protective biological activity associated with the rs158273 allele.

CSFR1 and 11,1RN Expression

Anti-MS4A4A antibodies of the present disclosure increased CSF1R levels in non-human primates. In some embodiments, anti-MS4A4A antibodies of the present disclosure increase mRNA and/or protein levels of CSF1R in vivo (e.g., in non-human primates or in humans). In some embodiments, an anti-MS4A4A antibody of the present disclosure increases mRNA and/or protein levels of CSF1R in serum and/or in CSF. In some embodiments, an anti-MS4A4A antibody of the present disclosure increases mRNA and/or protein levels of CSF1R in serum and/or in CSF by at least 10%, by at least 20%, by at least 25%, by at least 30%, by at least 40%, by at least 50%, by at least 60%, by at least 70%, by at least 75%, by at least 80%, by at least 90%, by at least 100%, by at least 125%, by at least 150%, by at least 200%, or by at least 250%. In some embodiments, an anti-MS4A4A antibody of the present disclosure increases protein levels of CSF1R in the brain. In some embodiments, an anti-MS4A4A antibody of the present disclosure increases protein levels of CSF1R in the frontal cortex and/or in the hippocampus.

CSF1R deficiency negatively impacts the development of microglia in the brain (Swerdlow et al (2000) Neurology, 111:300-311; Baba et al (2006) Acta Neuropath, 111:300-311) and recent research has linked mutations in the CSF1R gene to various disorders, including adult-onset leukoencephalopathy with axonal spheroids and pigmented glia (ALSP) and hereditary diffuse leukoencephalopathy with spheroids (HDLS) (Oosterhof et al (2019) Am J Hum Genet, 104:936-947; Rademaker et al (2011) Nat Genet, 44:200-205; Nicholson et al (2013) Neurology, 80:1033-1040). Anti-MS4A4A antibodies of the present disclosure reduced cell death and sustained survival of human macrophages following CSF1R inhibition. Accordingly, in some embodiments, anti-MS4A4A antibodies of the present disclosure are useful for treating an individual having a CSF1R-deficient disease or disorder, such as ALSP or HDLS.

Anti-MS4A4A antibodies of the present disclosure increased IL1RN levels in human peripheral blood mononuclear cell-derived macrophages. In some embodiments, anti-MS4A4A antibodies of the present disclosure increase mRNA and/or protein levels of IL1RN. In some embodiments, anti-MS4A4A antibodies of the present disclosure increase mRNA and/or protein levels of IL1RN. In some embodiments, an anti-MS4A4A antibody of the present disclosure increases mRNA and/or protein levels of IL1RN in myeloid cells (e.g., macrophages, human macrophages, microglia) by at least 10%, by at least 20%, by at least 25%, by at least 30%, by at least 40%, by at least 50%, by at least 60%, by at least 70%, by at least 75%, by at least 80%, by at least 90%, by at least 100%, by at least 125%, by at least 150%, by at least 200%, or by at least 250%.

GPNMB Expression

GPNMB (glycoprotein nonmetastatic melanoma protein B); is a surface glycoprotein expressed in multiple cell types including tissue macrophages and microglia. Several genetic variants have been associated with Parkinson's disease (PD) risk. GPNMB protein levels are elevated in the substantia nigra of PD patients and GPNMB levels are increased following lysosomal stress (Moloney et. al., 2018, Neurobio Dis. 120: 1-11). Additionally, increased expression of GPNMB was linked to SNP rs199347, this risk SNP being located withing the GPNMB gene (Murthy et al, Neurogenetics, 2017, 18:121-133).

Anti-MS4A4A antibodies of the present disclosure reduced GPNMB cell surface protein levels in human primary macrophages. In some embodiments, an anti-MS4A4A antibody of the present disclosure decreases GPNMB cell surface protein levels in myeoid cells (e.g., macrophages, human macrophages, microglia) by at least 10%, by at least 20%, by at least 30%, by at least 40%, or by at least 50%. As increased GPNMB levels are associated with risk alleles for PD, a reduction in GPNMB following anti-MS4A4A antibody addition may provide a means for treatment of PD.

A. Exemplary Antibodies and Certain Other Antibody Embodiments

In some embodiments, provided herein are anti-MS4A4A antibodies comprising at least one, two, three, four, five, or six HVRs selected from: (a) HVR-H1 comprising an amino acid sequence selected from the group consisting of SEQ ID NOs: 94, 108, 116, 146, 147, 308, and 311, or an amino acid with at least about 95% homology to an amino acid selected from the group consisting of SEQ ID NOs: 94, 108, 116, 146, 147, 308, and 311; (b) HVR-H2 comprising an amino acid sequence selected from the group consisting of SEQ ID NOs: 96, 97, 98, 99, 110, 111, 118, 119, 120, 121, 122, 149, 150, 151, 152, 153, 309, and 312, or an amino acid with at least about 95% homology to an amino acid selected from the group consisting of SEQ ID NOs: 96, 97, 98, 99, 110, 111, 118, 119, 120, 121, 122, 149, 150, 151, 152, 153, 309, and 312; (c) HVR-H3 comprising an amino acid sequence selected from the group consisting of SEQ ID NOs: 100, 101, 102, 112, 123, 124, 125, 126, 127, 128, 129, 154, 310, and 313, or an amino acid with at least about 95% homology to an amino acid selected from the group consisting of SEQ ID NOs: 100, 101, 102, 112, 123, 124, 125, 126, 127, 128, 129, 154, 310, and 313; (d) HVR-L1 comprising an amino acid sequence selected from the group consisting of SEQ ID NOs: 103, 104, 113, 130, 131, 132, 133, 134, 135, 136, 137, 138, 156, 157, 158, 314, and 317, or an amino acid with at least about 95% homology to an amino acid selected from the group consisting of SEQ ID NOs: 103, 104, 113, 130, 131, 132, 133, 134, 135, 136, 137, 138, 156, 157, 158, 314, and 317; (e) HVR-L2 comprising an amino acid sequence selected from the group consisting of SEQ ID NOs: 105, 106, 114, 139, 140, 141, 142, 143, 160, 161, 315, and 318, or an amino acid with at least about 95% homology to an amino acid selected from the group consisting of SEQ ID NOs: 105, 106, 114, 139, 140, 141, 142, 143, 160, 161, 315, and 318; and (f) HVR-L3 comprising an amino acid sequence selected from the group consisting of SEQ ID NOs: 107, 115, 144, 145, 163, 316, and 319, or an amino acid with at least about 95% homology to an amino acid selected from the group consisting of SEQ ID Nos:107, 115, 144, 145, 163, 316, and 319.

In some embodiments, provided herein are anti-MS4A4A antibodies comprising at least one, two, three, four, five, or six HVRs selected from: (a) HVR-H1 comprising the amino acid sequence selected from the group consisting of SEQ ID NO: 94 and 308, or an amino acid with at least about 95% homology to the amino acid sequence selected from the group consisting of SEQ ID NO: 94 and 308; (b) HVR-H2 comprising an amino acid sequence selected from the group consisting of SEQ ID NOs: 96, 97, 98, 99, and 309, or an amino acid with at least about 95% homology to an amino acid selected from the group consisting of SEQ ID NOs: 96, 97, 98, 99, and 309; (c) HVR-H3 comprising an amino acid sequence selected from the group consisting of SEQ ID NOs: 100, 101, 102, and 310, or an amino acid with at least about 95% homology to an amino acid selected from the group consisting of SEQ ID NOs: 100, 101, 102, and 310; (d) HVR-L1 comprising an amino acid sequence selected from the group consisting of SEQ ID NOs: 103 104, and 314, or an amino acid with at least about 95% homology to an amino acid selected from the group consisting of SEQ ID NOs: 103, 104, and 314; (e) HVR-L2 comprising an amino acid sequence selected from the group consisting of SEQ ID NOs: 105, 106, and 315, or an amino acid with at least about 95% homology to an amino acid selected from the group consisting of SEQ ID NOs: 105, 106, and 315; and (f) HVR-L3 comprising the amino acid sequence selected from the group consisting of SEQ ID NO: 107 and 316, or an amino acid with at least about 95% homology to an amino acid sequence selected from the group consisting of SEQ ID NO: 107 and 316.

In some embodiments, provided herein are anti-MS4A4A antibodies comprising at least one, two, three, four, five, or six HVRs selected from: (a) HVR-H1 comprising the amino acid sequence of SEQ ID NO: 108, or an amino acid with at least about 95% homology to the amino acid of SEQ ID NO: 108; (b) HVR-H2 comprising an amino acid sequence selected from the group consisting of SEQ ID NOs: 110 and 111, or an amino acid with at least about 95% homology to an amino acid selected from the group consisting of SEQ ID NOs: 110 and 111; (c) HVR-H3 comprising the amino acid sequence of SEQ ID NO: 112, or an amino acid with at least about 95% homology to the amino acid of SEQ ID NO: 112; (d) HVR-L1 comprising the amino acid sequence of SEQ ID NO: 113, or an amino acid with at least about 95% homology to the amino acid of SEQ ID NO: 113; (e) HVR-L2 comprising the amino acid sequence of SEQ ID NO: 114, or an amino acid with at least about 95% homology to the amino acid of SEQ ID NO: 114; and (f) HVR-L3 comprising the amino acid sequence of SEQ ID NO: 115, or an amino acid with at least about 95% homology to the amino acid of SEQ ID NO: 115.

In some embodiments, provided herein are anti-MS4A4A antibodies comprising at least one, two, three, four, five, or six HVRs selected from: (a) HVR-H1 comprising the amino acid sequence of SEQ ID NO: 116, or an amino acid with at least about 95% homology to the amino acid of SEQ ID NO: 116; (b) HVR-H2 comprising an amino acid sequence selected from the group consisting of SEQ ID NOs: 118, 119, 120, 121, and 122, or an amino acid with at least about 95% homology to an amino acid selected from the group consisting of SEQ ID NOs: 118, 119, 120, 121, and 122; (c) HVR-H3 comprising an amino acid sequence selected from the group consisting of SEQ ID NOs: 123, 124, 125, 126, 127, 128, and 129, or an amino acid with at least about 95% homology to an amino acid selected from the group consisting of SEQ ID NOs: 123, 124, 125, 126, 127, 128, and 129; (d) HVR-L1 comprising an amino acid sequence selected from the group consisting of SEQ ID NOs: 130, 131, 132, 133, 134, 135, 136, 137, and 138, or an amino acid with at least about 95% homology to an amino acid selected from the group consisting of SEQ ID NOs: 130, 131, 132, 133, 134, 135, 136, 137, and 138; (e) HVR-L2 comprising an amino acid sequence selected from the group consisting of SEQ ID NOs: 139, 140, 141, 142, and 143, or an amino acid with at least about 95% homology to an amino acid selected from the group consisting of SEQ ID NOs: 139, 140, 141, 142, and 143; and (f) HVR-L3 comprising an amino acid sequence selected from the group consisting of SEQ ID Nos:144 and 145, or an amino acid with at least about 95% homology to an amino acid selected from the group consisting of SEQ ID Nos:144 and 145.

In some embodiments, provided herein are anti-MS4A4A antibodies comprising at least one, two, three, four, five, or six HVRs selected from: (a) HVR-H1 comprising an amino acid sequence selected from the group consisting of SEQ ID NOs: 146 and 147, or an amino acid with at least about 95% homology to an amino acid selected from the group consisting of SEQ ID NOs: 146 and 147; (b) HVR-H2 comprising an amino acid sequence selected from the group consisting of SEQ ID NOs: 149, 150, 151, 152, and 153, or an amino acid with at least about 95% homology to an amino acid selected from the group consisting of SEQ ID NOs: 149, 150, 151, 152, and 153; (c) HVR-H3 comprising the amino acid sequence of SEQ ID NO: 154, or an amino acid with at least about 95% homology to the amino acid of SEQ ID NO: 154; (d) HVR-L1 comprising an amino acid sequence selected from the group consisting of SEQ ID NOs: 156, 157, and 158, or an amino acid with at least about 95% homology to an amino acid selected from the group consisting of SEQ ID NOs: 156, 157, and 158; (e) HVR-L2 comprising an amino acid sequence selected from the group consisting of SEQ ID NOs: 159, 160, and 161, or an amino acid with at least about 95% homology to an amino acid selected from the group consisting of SEQ ID NOs: 159, 160, and 161; and (f) HVR-L3 comprising the amino acid sequence selected from the group consisting of SEQ ID NO: 163, or an amino acid with at least about 95% homology to the amino acid selected from the group consisting of SEQ ID NO: 163.

In some embodiments, provided herein are anti-MS4A4A antibodies comprising: (a) HVR-H1 comprising the amino acid sequence of SEQ ID NO: 94; (b) HVR-H2 comprising the amino acid sequence of SEQ ID NO: 96; (c) HVR-H3 comprising the amino acid sequence of SEQ ID NO: 100; (d) HVR-L1 comprising the amino acid sequence of SEQ ID NO: 103; (e) HVR-L2 comprising the amino acid sequence of SEQ ID NO: 105; and (f) HVR-L3 comprising the amino acid sequence of SEQ ID NO: 107; (a) HVR-H1 comprising the amino acid sequence of SEQ ID NO: 94; (b) HVR-H2 comprising the amino acid sequence of SEQ ID NO: 97; (c) HVR-H3 comprising the amino acid sequence of SEQ ID NO: 100; (d) HVR-L1 comprising the amino acid sequence of SEQ ID NO: 103; (e) HVR-L2 comprising the amino acid sequence of SEQ ID NO: 105; and (f) HVR-L3 comprising the amino acid sequence of SEQ ID NO: 107; (a) HVR-H1 comprising the amino acid sequence of SEQ ID NO: 94; (b) HVR-H2 comprising the amino acid sequence of SEQ ID NO: 98; (c) HVR-H3 comprising the amino acid sequence of SEQ ID NO: 100; (d) HVR-L1 comprising the amino acid sequence of SEQ ID NO: 103; (e) HVR-L2 comprising the amino acid sequence of SEQ ID NO: 105; and (f) HVR-L3 comprising the amino acid sequence of SEQ ID NO: 107; (a) HVR-H1 comprising the amino acid sequence of SEQ ID NO: 94; (b) HVR-H2 comprising the amino acid sequence of SEQ ID NO: 96; (c) HVR-H3 comprising the amino acid sequence of SEQ ID NO: 101; (d) HVR-L1 comprising the amino acid sequence of SEQ ID NO: 103; (e) HVR-L2 comprising the amino acid sequence of SEQ ID NO: 106; and (f) HVR-L3 comprising the amino acid sequence of SEQ ID NO: 107; (a) HVR-H1 comprising the amino acid sequence of SEQ ID NO: 94; (b) HVR-H2 comprising the amino acid sequence of SEQ ID NO: 96; (c) HVR-H3 comprising the amino acid sequence of SEQ ID NO: 102; (d) HVR-L1 comprising the amino acid sequence of SEQ ID NO: 104; (e) HVR-L2 comprising the amino acid sequence of SEQ ID NO: 105; and (f) HVR-L3 comprising the amino acid sequence of SEQ ID NO: 107; or (a) HVR-H1 comprising the amino acid sequence of SEQ ID NO: 94; (b) HVR-H2 comprising the amino acid sequence of SEQ ID NO: 99; (c) HVR-H3 comprising the amino acid sequence of SEQ ID NO: 100; (d) HVR-L1 comprising the amino acid sequence of SEQ ID NO: 104; (e) HVR-L2 comprising the amino acid sequence of SEQ ID NO: 105; and (f) HVR-L3 comprising the amino acid sequence of SEQ ID NO: 107.

In some embodiments, provided herein are anti-MS4A4A antibodies comprising: (a) HVR-H1 comprising the amino acid sequence of SEQ ID NO: 308; (b) HVR-H2 comprising the amino acid sequence of SEQ ID NO: 309; (c) HVR-H3 comprising the amino acid sequence of SEQ ID NO: 310; (d) HVR-L1 comprising the amino acid sequence of SEQ ID NO: 314; (e) HVR-L2 comprising the amino acid sequence of SEQ ID NO: 315; and (f) HVR-L3 comprising the amino acid sequence of SEQ ID NO: 316; or (a) HVR-H1 comprising the amino acid sequence of SEQ ID NO: 311; (b) HVR-H2 comprising the amino acid sequence of SEQ ID NO: 312; (c) HVR-H3 comprising the amino acid sequence of SEQ ID NO: 313; (d) HVR-L1 comprising the amino acid sequence of SEQ ID NO: 317; (e) HVR-L2 comprising the amino acid sequence of SEQ ID NO: 318; and (f) HVR-L3 comprising the amino acid sequence of SEQ ID NO: 319.

In some embodiments, provided herein are anti-MS4A4A antibodies comprising: (a) HVR-H1 comprising the amino acid sequence of SEQ ID NO: 108; (b) HVR-H2 comprising the amino acid sequence of SEQ ID NO: 110; (c) HVR-H3 comprising the amino acid sequence of SEQ ID NO: 112; (d) HVR-L1 comprising the amino acid sequence of SEQ ID NO: 113; (e) HVR-L2 comprising the amino acid sequence of SEQ ID NO: 114; and (f) HVR-L3 comprising the amino acid sequence of SEQ ID NO: 115; or (a) HVR-H1 comprising the amino acid sequence of SEQ ID NO: 108; (b) HVR-H2 comprising the amino acid sequence of SEQ ID NO: 111; (c) HVR-H3 comprising the amino acid sequence of SEQ ID NO: 112; (d) HVR-L1 comprising the amino acid sequence of SEQ ID NO: 113; (e) HVR-L2 comprising the amino acid sequence of SEQ ID NO: 114; and (f) HVR-L3 comprising the amino acid sequence of SEQ ID NO: 115.

In some embodiments, provided herein are anti-MS4A4A antibodies comprising: (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 123; (d) HVR-L1 comprising the amino acid sequence of SEQ ID NO: 130; (e) HVR-L2 comprising the amino acid sequence of SEQ ID NO: 139; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 119; (c) HVR-H3 comprising the amino acid sequence of SEQ ID NO: 123; (d) HVR-L1 comprising the amino acid sequence of SEQ ID NO: 130; (e) HVR-L2 comprising the amino acid sequence of SEQ ID NO: 139; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 120; (c) HVR-H3 comprising the amino acid sequence of SEQ ID NO: 123; (d) HVR-L1 comprising the amino acid sequence of SEQ ID NO: 130; (e) HVR-L2 comprising the amino acid sequence of SEQ ID NO: 139; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 121; (c) HVR-H3 comprising the amino acid sequence of SEQ ID NO: 123; (d) HVR-L1 comprising the amino acid sequence of SEQ ID NO: 130; (e) HVR-L2 comprising the amino acid sequence of SEQ ID NO: 139; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 124; (d) HVR-L1 comprising the amino acid sequence of SEQ ID NO: 130; (e) HVR-L2 comprising the amino acid sequence of SEQ ID NO: 139; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 124; (d) HVR-L1 comprising the amino acid sequence of SEQ ID NO: 131; (e) HVR-L2 comprising the amino acid sequence of SEQ ID NO: 139; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 124; (d) HVR-L1 comprising the amino acid sequence of SEQ ID NO: 132; (e) HVR-L2 comprising the amino acid sequence of SEQ ID NO: 139; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 124; (d) HVR-L1 comprising the amino acid sequence of SEQ ID NO: 133; (e) HVR-L2 comprising the amino acid sequence of SEQ ID NO: 139; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 124; (d) HVR-L1 comprising the amino acid sequence of SEQ ID NO: 134; (e) HVR-L2 comprising the amino acid sequence of SEQ ID NO: 139; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 124; (d) HVR-L1 comprising the amino acid sequence of SEQ ID NO: 135; (e) HVR-L2 comprising the amino acid sequence of SEQ ID NO: 139; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 124; (d) HVR-L1 comprising the amino acid sequence of SEQ ID NO: 136; (e) HVR-L2 comprising the amino acid sequence of SEQ ID NO: 139; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 124; (d) HVR-L1 comprising the amino acid sequence of SEQ ID NO: 130; (e) HVR-L2 comprising the amino acid sequence of SEQ ID NO: 140; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 124; (d) HVR-L1 comprising the amino acid sequence of SEQ ID NO: 130; (e) HVR-L2 comprising the amino acid sequence of SEQ ID NO: 139; and (f) HVR-L3 comprising the amino acid sequence of SEQ ID NO: 145; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 124; (d) HVR-L1 comprising the amino acid sequence of SEQ ID NO: 137; (e) HVR-L2 comprising the amino acid sequence of SEQ ID NO: 139; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 124; (d) HVR-L1 comprising the amino acid sequence of SEQ ID NO: 138; (e) HVR-L2 comprising the amino acid sequence of SEQ ID NO: 141; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 124; (d) HVR-L1 comprising the amino acid sequence of SEQ ID NO: 130; (e) HVR-L2 comprising the amino acid sequence of SEQ ID NO: 142; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 124; (d) HVR-L 1 comprising the amino acid sequence of SEQ ID NO: 130; (e) HVR-L2 comprising the amino acid sequence of SEQ ID NO: 141; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 124; (d) HVR-L1 comprising the amino acid sequence of SEQ ID NO: 130; (e) HVR-L2 comprising the amino acid sequence of SEQ ID NO: 143; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 125; (d) HVR-L1 comprising the amino acid sequence of SEQ ID NO: 137; (e) HVR-L2 comprising the amino acid sequence of SEQ ID NO: 139; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 125; (d) HVR-L1 comprising the amino acid sequence of SEQ ID NO: 130; (e) HVR-L2 comprising the amino acid sequence of SEQ ID NO: 143; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 125; (d) HVR-L1 comprising the amino acid sequence of SEQ ID NO: 131; (e) HVR-L2 comprising the amino acid sequence of SEQ ID NO: 139; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 125; (d) HVR-L1 comprising the amino acid sequence of SEQ ID NO: 130; (e) HVR-L2 comprising the amino acid sequence of SEQ ID NO: 139; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 125; (d) HVR-L1 comprising the amino acid sequence of SEQ ID NO: 130; (e) HVR-L2 comprising the amino acid sequence of SEQ ID NO: 142; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 125; (d) HVR-L1 comprising the amino acid sequence of SEQ ID NO: 130; (e) HVR-L2 comprising the amino acid sequence of SEQ ID NO: 139; and (f) HVR-L3 comprising the amino acid sequence of SEQ ID NO: 145; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 126; (d) HVR-L1 comprising the amino acid sequence of SEQ ID NO: 138; (e) HVR-L2 comprising the amino acid sequence of SEQ ID NO: 141; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 126; (d) HVR-L1 comprising the amino acid sequence of SEQ ID NO: 130; (e) HVR-L2 comprising the amino acid sequence of SEQ ID NO: 139; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 126; (d) HVR-L1 comprising the amino acid sequence of SEQ ID NO: 130; (e) HVR-L2 comprising the amino acid sequence of SEQ ID NO: 141; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 127; (d) HVR-L1 comprising the amino acid sequence of SEQ ID NO: 131; (e) HVR-L2 comprising the amino acid sequence of SEQ ID NO: 139; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 122; (c) HVR-H3 comprising the amino acid sequence of SEQ ID NO: 127; (d) HVR-L1 comprising the amino acid sequence of SEQ ID NO: 131; (e) HVR-L2 comprising the amino acid sequence of SEQ ID NO: 139; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 128; (d) HVR-L1 comprising the amino acid sequence of SEQ ID NO: 131; (e) HVR-L2 comprising the amino acid sequence of SEQ ID NO: 139; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 129; (d) HVR-L1 comprising the amino acid sequence of SEQ ID NO: 131; (e) HVR-L2 comprising the amino acid sequence of SEQ ID NO: 139; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 129; (d) HVR-L1 comprising the amino acid sequence of SEQ ID NO: 132; (e) HVR-L2 comprising the amino acid sequence of SEQ ID NO: 139; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 129; (d) HVR-L1 comprising the amino acid sequence of SEQ ID NO: 133; (e) HVR-L2 comprising the amino acid sequence of SEQ ID NO: 139; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 129; (d) HVR-L1 comprising the amino acid sequence of SEQ ID NO: 134; (e) HVR-L2 comprising the amino acid sequence of SEQ ID NO: 139; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 129; (d) HVR-L1 comprising the amino acid sequence of SEQ ID NO: 135; (e) HVR-L2 comprising the amino acid sequence of SEQ ID NO: 139; and (f) HVR-L3 comprising the amino acid sequence of SEQ ID NO: 144; (a) HVR-H1 comprising the amino acid sequence of SEQ ID NO: 116; (b) HVR-H2 comprising the amino acid sequence of SEQ ID NO: 118; (c) HVR-H3 comprising the amino acid sequence of SEQ ID NO: 129; (d) HVR-L1 comprising the amino acid sequence of SEQ ID NO: 136; (e) HVR-L2 comprising the amino acid sequence of SEQ ID NO: 139; and (f) HVR-L3 comprising the amino acid sequence of SEQ ID NO: 144.

In some embodiments, provided herein are anti-MS4A4A antibodies comprising: (a) HVR-H1 comprising the amino acid sequence of SEQ ID NO: 147; (b) HVR-H2 comprising the amino acid sequence of SEQ ID NO: 149; (c) HVR-H3 comprising the amino acid sequence of SEQ ID NO: 154; (d) HVR-L1 comprising the amino acid sequence of SEQ ID NO: 156; (e) HVR-L2 comprising the amino acid sequence of SEQ ID NO: 160; and (f) HVR-L3 comprising the amino acid sequence of SEQ ID NO: 163; (a) HVR-H1 comprising the amino acid sequence of SEQ ID NO: 146; (b) HVR-H2 comprising the amino acid sequence of SEQ ID NO: 150; (c) HVR-H3 comprising the amino acid sequence of SEQ ID NO: 154; (d) HVR-L1 comprising the amino acid sequence of SEQ ID NO: 156; (e) HVR-L2 comprising the amino acid sequence of SEQ ID NO: 160; and (f) HVR-L3 comprising the amino acid sequence of SEQ ID NO: 163; (a) HVR-H1 comprising the amino acid sequence of SEQ ID NO: 147; (b) HVR-H2 comprising the amino acid sequence of SEQ ID NO: 149; (c) HVR-H3 comprising the amino acid sequence of SEQ ID NO: 154; (d) HVR-L1 comprising the amino acid sequence of SEQ ID NO: 157; (e) HVR-L2 comprising the amino acid sequence of SEQ ID NO: 159; and (f) HVR-L3 comprising the amino acid sequence of SEQ ID NO: 163; (a) HVR-H1 comprising the amino acid sequence of SEQ ID NO: 147; (b) HVR-H2 comprising the amino acid sequence of SEQ ID NO: 151; (c) HVR-H3 comprising the amino acid sequence of SEQ ID NO: 154; (d) HVR-L1 comprising the amino acid sequence of SEQ ID NO: 156; (e) HVR-L2 comprising the amino acid sequence of SEQ ID NO: 160; and (f) HVR-L3 comprising the amino acid sequence of SEQ ID NO: 163; (a) HVR-H1 comprising the amino acid sequence of SEQ ID NO: 147; (b) HVR-H2 comprising the amino acid sequence of SEQ ID NO: 151; (c) HVR-H3 comprising the amino acid sequence of SEQ ID NO: 154; (d) HVR-L1 comprising the amino acid sequence of SEQ ID NO: 158; (e) HVR-L2 comprising the amino acid sequence of SEQ ID NO: 159; and (f) HVR-L3 comprising the amino acid sequence of SEQ ID NO: 163; (a) HVR-H1 comprising the amino acid sequence of SEQ ID NO: 146; (b) HVR-H2 comprising the amino acid sequence of SEQ ID NO: 152; (c)

HVR-H3 comprising the amino acid sequence of SEQ ID NO: 154; (d) HVR-L1 comprising the amino acid sequence of SEQ ID NO: 156; (e) HVR-L2 comprising the amino acid sequence of SEQ ID NO: 161; and (f) HVR-L3 comprising the amino acid sequence of SEQ ID NO: 163; (a) HVR-H1 comprising the amino acid sequence of SEQ ID NO: 146; (b) HVR-H2 comprising the amino acid sequence of SEQ ID NO: 153; (c) HVR-H3 comprising the amino acid sequence of SEQ ID NO: 154; (d) HVR-L1 comprising the amino acid sequence of SEQ ID NO: 158; (e) HVR-L2 comprising the amino acid sequence of SEQ ID NO: 159; and (f) HVR-L3 comprising the amino acid sequence of SEQ ID NO: 163.

In some embodiments, provided herein are anti-MS4A4A antibodies comprising at least one, at least two, or all three $V_H$ HVR sequences selected from (a) HVR-H1 comprising the amino acid sequence of SEQ ID NO: 94, or an amino acid sequence with at least about 95% homology to the amino acid sequence of SEQ ID NO: 94; (b) HVR-H2 comprising an amino acid sequence selected from the group consisting of SEQ ID NOs: 96, 97, 98, and 99, or an amino acid sequence with at least about 95% homology to an amino acid sequence selected from the group consisting of SEQ ID Nos:96, 97, 98, and 99; and (c) HVR-H3 comprising an amino acid sequence selected from the group consisting of SEQ ID NOs: 100, 101, and 102, or an amino acid sequence with at least about 95% homology to an amino acid sequence selected from the group consisting of SEQ ID NOs: 100, 101, and 102.

In some embodiments, provided herein are anti-MS4A4A antibodies comprising at least one, at least two, or all three $V_H$ HVR sequences selected from (a) HVR-H1 comprising the amino acid sequence of SEQ ID NO: 308, or an amino acid sequence with at least about 95% homology to the amino acid sequence of SEQ ID NO: 308; (b) HVR-H2 comprising the amino acid sequence of SEQ ID NO: 309, or an amino acid sequence with at least about 95% homology to the amino acid sequence of SEQ ID No:309; and (c) HVR-H3 comprising the amino acid sequence of SEQ ID NO: 310, or an amino acid sequence with at least about 95% homology to the amino acid sequence of SEQ ID NO: 310.

In some embodiments, provided herein are anti-MS4A4A antibodies comprising at least one, at least two, or all three $V_H$ HVR sequences selected from (a) HVR-H1 comprising the amino acid sequence of SEQ ID NO: 311, or an amino acid sequence with at least about 95% homology to the amino acid sequence of SEQ ID NO: 311; (b) HVR-H2 comprising the amino acid sequence of SEQ ID NO: 312, or an amino acid sequence with at least about 95% homology to the amino acid sequence of SEQ ID No:312; and (c) HVR-H3 comprising the amino acid sequence of SEQ ID NO: 313, or an amino acid sequence with at least about 95% homology to the amino acid sequence of SEQ ID NO: 313.

In some embodiments, provided herein are anti-MS4A4A antibodies comprising at least one, at least two, or all three $V_L$ HVR sequences selected from (a) HVR-L1 comprising an amino acid sequence selected from the group consisting of SEQ ID NOs: 103 and 104, or an amino acid sequence with at least about 95% homology to an amino acid sequence selected from the group consisting of SEQ ID NOs: 103 and 104; (b) HVR-L2 comprising an amino acid sequence selected from the group consisting of SEQ ID NOs: 105 and 106, or an amino acid sequence with at least about 95% homology to an amino acid sequence selected from the group consisting of SEQ ID NOs: 105 and 106; and (c) HVR-L3 comprising the amino acid sequence of SEQ ID NO: 107, or an amino acid sequence with at least about 95% homology to the amino acid sequence of SEQ ID NO: 107.

In some embodiments, provided herein are anti-MS4A4A antibodies comprising at least one, at least two, or all three $V_L$ HVR sequences selected from (a) HVR-L1 comprising the amino acid sequence selected of SEQ ID NO: 314, or an amino acid sequence with at least about 95% homology to the amino acid sequence selected of SEQ ID NO: 314; (b) HVR-L2 comprising the amino acid sequence of SEQ ID NO: 315, or an amino acid sequence with at least about 95% homology to the amino acid sequence of SEQ ID NO: 315; and (c) HVR-L3 comprising the amino acid sequence of SEQ ID NO: 316, or an amino acid sequence with at least about 95% homology to the amino acid sequence of SEQ ID NO: 316.

In some embodiments, provided herein are anti-MS4A4A antibodies comprising at least one, at least two, or all three $V_L$ HVR sequences selected from (a) HVR-L1 comprising the amino acid sequence selected of SEQ ID NO: 317, or an amino acid sequence with at least about 95% homology to the amino acid sequence selected of SEQ ID NO: 317; (b) HVR-L2 comprising the amino acid sequence of SEQ ID NO: 318, or an amino acid sequence with at least about 95% homology to the amino acid sequence of SEQ ID NO: 318; and (c) HVR-L3 comprising the amino acid sequence of SEQ ID NO: 319, or an amino acid sequence with at least about 95% homology to the amino acid sequence of SEQ ID NO: 319.

In some embodiments, provided herein are anti-MS4A4A antibodies comprising (a) a $V_H$ domain comprising at least one, at least two, or all three $V_H$ HVR sequences selected from (i) HVR-H1 comprising the amino acid sequence of SEQ ID NO: 94, or an amino acid sequence with at least about 95% homology to the amino acid sequence of SEQ ID NO: 94, (ii) HVR-H2 comprising an amino acid sequence selected from the group consisting of SEQ ID NOs: 96, 97, 98, and 99, or an amino acid sequence with at least about 95% homology to an amino acid sequence selected from the group consisting of SEQ ID NOs: 96, 97, 98, and 99, and (iii) HVR-H3 comprising an amino acid sequence selected from the group consisting of SEQ ID NOs: 100, 101, and 102, or an amino acid sequence with at least about 95% homology to an amino acid sequence selected from the group consisting of SEQ ID NOs: 100, 101, and 102, and (b) a $V_L$ domain comprising at least one, at least two, or all three $V_L$ HVR sequences selected from (i) HVR-L1 comprising an amino acid sequence selected from the group consisting of SEQ ID NOs: 103 and 104, or an amino acid sequence with at least about 95% homology to an amino acid sequence selected from the group consisting of SEQ ID NOs: 103 and 104, (ii) HVR-L2 comprising an amino acid sequence selected from the group consisting of SEQ ID NOs: 105 and 106, or an amino acid sequence with at least about 95% homology to an amino acid sequence selected from the group consisting of SEQ ID NOs: 105 and 106, and (iii) HVR-L3 comprising the amino acid sequence of SEQ ID NO: 107, or an amino acid sequence with at least about 95% homology to the amino acid sequence of SEQ ID NO: 107.

In some embodiments, provided herein are anti-MS4A4A antibodies comprising (a) a $V_H$ domain comprising at least one, at least two, or all three $V_H$ HVR sequences selected from (i) HVR-H1 comprising the amino acid sequence of SEQ ID NO: 308, or an amino acid sequence with at least about 95% homology to the amino acid sequence of SEQ ID NO: 308, (ii) HVR-H2 comprising the amino acid of SEQ ID NO: 309, or an amino acid sequence with at least about 95% homology to the amino acid sequence of SEQ ID NO: 309, and (iii) HVR-H3 comprising the amino acid sequence of SEQ ID NO: 310, or an amino acid sequence with at least about 95% homology to the amino acid sequence of SEQ ID NO: 310, and (b) a $V_L$ domain comprising at least one, at least two, or all three $V_L$ HVR sequences selected from (i) HVR-L1 comprising the amino acid sequence of SEQ ID NO: 314, or an amino acid sequence with at least about 95% homology to the amino acid sequence of SEQ ID NO: 314 (ii) HVR-L2 comprising the amino acid sequence of SEQ ID NO: 315, or an amino acid sequence with at least about 95% homology to the amino acid sequence selected of SEQ ID NO: 315, and (iii) HVR-L3 comprising the amino acid sequence of SEQ ID NO: 316, or an amino acid sequence with at least about 95% homology to the amino acid sequence of SEQ ID NO: 316.

In some embodiments, provided herein are anti-MS4A4A antibodies comprising (a) a $V_H$ domain comprising at least one, at least two, or all three $V_H$ HVR sequences selected from (i) HVR-H1 comprising the amino acid sequence of SEQ ID NO: 311, or an amino acid sequence with at least about 95% homology to the amino acid sequence of SEQ ID NO: 311, (ii) HVR-H2 comprising the amino acid of SEQ ID NO: 312, or an amino acid sequence with at least about 95% homology to the amino acid sequence of SEQ ID NO: 312, and (iii) HVR-H3 comprising the amino acid sequence of SEQ ID NO: 313, or an amino acid sequence with at least about 95% homology to the amino acid sequence of SEQ ID NO: 313, and (b) a $V_L$ domain comprising at least one, at least two, or all three $V_L$ HVR sequences selected from (i) HVR-L1 comprising the amino acid sequence of SEQ ID NO: 317, or an amino acid sequence with at least about 95% homology to the amino acid sequence of SEQ ID NO: 317 (ii) HVR-L2 comprising the amino acid sequence of SEQ ID NO: 318, or an amino acid sequence with at least about 95% homology to the amino acid sequence selected of SEQ ID NO: 318, and (iii) HVR-L3 comprising the amino acid sequence of SEQ ID NO: 316, or an amino acid sequence with at least about 95% homology to the amino acid sequence of SEQ ID NO: 316.

In some embodiments, provided herein are anti-MS4A4A antibodies comprising at least one, at least two, or all three $V_H$ HVR sequences selected from (a) HVR-H1 comprising an amino acid sequence selected from the group consisting of SEQ ID NOs: 24, 25, 26, 27, 28, 29, and 30, or an amino acid sequence with at least about 95% homology to an amino acid sequence selected from the group consisting of SEQ ID NOs: 24, 25, 26, 27, 28, 29, and 30; (b) HVR-H2 comprising an amino acid sequence selected from the group consisting of SEQ ID NOs: 110 and 111, or an amino acid sequence with at least about 95% homology to an amino acid sequence selected from the group consisting of SEQ ID NOs: 110 and 111; and (c) HVR-H3 comprising the amino acid sequence of SEQ ID NO: 112, or an amino acid sequence with at least about 95% homology to the amino acid sequence of SEQ ID NO: 112.

In some embodiments, provided herein are anti-MS4A4A antibodies comprising at least one, at least two, or all three $V_L$ HVR sequences selected from (a) HVR-L1 comprising the amino acid sequence of SEQ ID NO: 113, or an amino acid sequence with at least about 95% homology to the amino acid sequence of SEQ ID NO: 113; (b) HVR-L2 comprising the amino acid sequence of SEQ ID NO: 114, or an amino acid sequence with at least about 95% homology to the amino acid sequence of SEQ ID NO: 114; and (c) HVR-L3 comprising the amino acid sequence of SEQ ID NO: 115, or an amino acid sequence with at least about 95% homology to the amino acid sequence of SEQ ID NO: 115.

In some embodiments, provided herein are anti-MS4A4A antibodies comprising (a) a $V_H$ domain comprising at least one, at least two, or all three $V_H$ HVR sequences selected from (i) HVR-H1 comprising the amino acid sequence of SEQ ID NO: 108, or an amino acid sequence with at least about 95% homology to the amino acid sequence of SEQ ID NO: 108, (ii) HVR-H2 comprising an amino acid sequence selected from the group consisting of SEQ ID NOs: 110 and 111, or an amino acid sequence with at least about 95% homology to an amino acid sequence selected from the group consisting of SEQ ID NOs: 110 and 111, and (iii) HVR-H3 comprising the amino acid sequence of SEQ ID NO: 112, or an amino acid sequence with at least about 95% homology to the amino acid sequence of SEQ ID NO: 112, and (b) a $V_L$ domain comprising at least one, at least two, or all three $V_L$ HVR sequences selected from (i) HVR-L1 comprising the amino acid sequence of SEQ ID NO: 113, or an amino acid sequence with at least about 95% homology to the amino acid sequence of SEQ ID NO: 113, (ii) HVR-L2 comprising the amino acid sequence of SEQ ID NO: 114, or an amino acid sequence with at least about 95% homology to the amino acid sequence of SEQ ID NO: 114, and (iii) HVR-L3 comprising the amino acid sequence of SEQ ID NO: 115, or an amino acid sequence with at least about 95% homology to the amino acid sequence of SEQ ID NO: 115.

In some embodiments, provided herein are anti-MS4A4A antibodies comprising at least one, at least two, or all three $V_H$ HVR sequences selected from (a) HVR-H1 comprising the amino acid sequence of SEQ ID NO: 116, or an amino acid sequence with at least about 95% homology to the amino acid sequence of SEQ ID NO: 116; (b) HVR-H2 comprising an amino acid sequence selected from the group consisting of SEQ ID NOs: 118, 119, 120, 121, and 122, or an amino acid sequence with at least about 95% homology to an amino acid sequence selected from the group consisting of SEQ ID NOs: 118, 119, 120 121, and 122; and (c) HVR-H3 comprising an amino acid sequence selected from the group consisting of SEQ ID NOs: 123, 124, 125, 126, 127, 128, and 129, or an amino acid sequence with at least about 95% homology to an amino acid sequence selected from the group consisting of SEQ ID NOs: 123, 124, 125, 126, 127, 128, and 129.

In some embodiments, provided herein are anti-MS4A4A antibodies comprising at least one, at least two, or all three $V_L$ HVR sequences selected from (a) HVR-L1 comprising an amino acid sequence selected from the group consisting of SEQ ID NOs: 130, 131, 132, 133, 134, 135, 136, 137, and 138, or an amino acid sequence with at least about 95% homology to an amino acid sequence selected from the group consisting of SEQ ID NOs: 130, 131, 132, 133, 134, 135, 136, 137, and 138; (b) HVR-L2 comprising an amino acid sequence selected from the group consisting of SEQ ID NOs: 139, 140, 141, 142, and 143, or an amino acid sequence with at least about 95% homology to an amino acid sequence selected from the group consisting of SEQ ID NOs: 139, 140, 141, 142, and 143; and (c) HVR-L3 comprising an amino acid sequence selected from the group consisting of SEQ ID NOs: 144 and 145, or an amino acid sequence with at least about 95% homology to an amino acid sequence selected from the group consisting of SEQ ID NOs: 144 and 145.

In some embodiments, provided herein are anti-MS4A4A antibodies comprising (a) a $V_H$ domain comprising at least one, at least two, or all three $V_H$ HVR sequences selected from (i) HVR-H1 comprising the amino acid sequence of SEQ ID NO: 116, or an amino acid sequence with at least about 95% homology to the amino acid sequence of SEQ ID NO: 116, (ii) HVR-H2 comprising an amino acid sequence selected from the group consisting of SEQ ID NOs: 118, 119, 120, 121, and 122, or an amino acid sequence with at least about 95% homology to an amino acid sequence selected from the group consisting of SEQ ID NOs: 118, 119, 120, 121, and 122, and (iii) HVR-H3 comprising an amino acid sequence selected from the group consisting of SEQ ID NOs: 123, 124, 125, 126, 127, 128, and 129, or an amino acid sequence with at least about 95% homology to an amino acid sequence selected from the group consisting of SEQ ID NOs: 123, 124, 125, 126, 127, 128, and 129, and (b) a $V_L$ domain comprising at least one, at least two, or all three $V_L$ HVR sequences selected from (i) HVR-L1 comprising an amino acid sequence selected from the group consisting of SEQ ID NOs: 130, 131, 132, 133, 134, 135, 136, 137, and 138, or an amino acid sequence with at least about 95% homology to an amino acid sequence selected from the group consisting of SEQ ID NOs: 130, 131, 132, 133, 134, 135, 136, 137, and 138, (ii) HVR-L2 comprising an amino acid sequence selected from the group consisting of SEQ ID NOs: 139, 140, 141, 142, and 143, or an amino acid sequence with at least about 95% homology to an amino acid sequence selected from the group consisting of SEQ ID NOs: 139, 140, 141, 142, and 143, and (iii) HVR-L3 comprising an amino acid sequence selected from the group consisting of SEQ ID NOs: 144 and 145, or an amino acid sequence with at least about 95% homology to an amino acid sequence selected from the group consisting of SEQ ID NOs: 144 and 145.

In some embodiments, provided herein are anti-MS4A4A antibodies comprising at least one, at least two, or all three $V_H$ HVR sequences selected from (a) HVR-H1 comprising an amino acid sequence selected from the group consisting of SEQ ID NOs: 146 and 147, or an amino acid sequence with at least about 95% homology to an amino acid sequence selected from the group consisting of SEQ ID NOs: 146 and 147; (b) HVR-H2 comprising an amino acid sequence selected from the group consisting of SEQ ID NOs: 149, 150, 151, 152, and 153, or an amino acid sequence with at least about 95% homology to an amino acid sequence selected from the group consisting of SEQ ID NOs: 149, 150, 151, 152, and 153; and (c) HVR-H3 comprising the amino acid sequence of SEQ ID NO: 154, or an amino acid sequence with at least about 95% homology to the amino acid sequence of SEQ ID NO: 154.

In some embodiments, provided herein are anti-MS4A4A antibodies comprising at least one, at least two, or all three $V_L$ HVR sequences selected from (a) HVR-L1 comprising an amino acid sequence selected from the group consisting of SEQ ID NOs: 156, 157, and 158, or an amino acid sequence with at least about 95% homology to an amino acid sequence selected from the group consisting of SEQ ID NOs: 156, 157, and 158; (b) HVR-L2 comprising an amino acid sequence selected from the group consisting of SEQ ID NOs: 160 and 161, or an amino acid sequence with at least about 95% homology to an amino acid sequence selected from the group consisting of SEQ ID NOs: 160 and 161; and (c) HVR-L3 comprising the amino acid sequence of SEQ ID NO: 163, or an amino acid sequence with at least about 95% homology to the amino acid sequence of SEQ ID NO: 163.

In some embodiments, provided herein are anti-MS4A4A antibodies comprising (a) a $V_H$ domain comprising at least one, at least two, or all three $V_H$ HVR sequences selected from (i) HVR-H1 comprising an amino acid sequence selected from the group consisting of SEQ ID NOs: 146 and 147, or an amino acid sequence with at least about 95% homology to an amino acid sequence selected from the group consisting of SEQ ID NOs: 146 and 147, (ii) HVR-H2 comprising an amino acid sequence selected from the group consisting of SEQ ID NOs: 149, 150, 151, 152, and 153, or an amino acid sequence with at least about 95% homology to an amino acid sequence selected from the group consisting of SEQ ID NOs: 149, 150, 151, 152, and 153, and (iii) HVR-H3 comprising the amino acid sequence of SEQ ID NO: 154, or an amino acid sequence with at least about 95% homology to the amino acid sequence of SEQ ID NO: 154, and (b) a $V_L$ domain comprising at least one, at least two, or all three $V_L$ HVR sequences selected from (i) HVR-L1 comprising an amino acid sequence selected from the group consisting of SEQ ID NOs: 156, 157, and 158, or an amino acid sequence with at least about 95% homology to an amino acid sequence selected from the group consisting of SEQ ID NOs: 156, 157, and 158, (ii) HVR-L2 comprising an amino acid sequence selected from the group consisting of SEQ ID NOs: 160 and 161, or an amino acid sequence with at least about 95% homology to an amino acid sequence selected from the group consisting of SEQ ID NOs: 160 and 161, and (iii) HVR-L3 comprising the amino acid sequence of SEQ ID NO: 163, or an amino acid sequence with at least about 95% homology to the amino acid sequence of SEQ ID NO: 163.

In another aspect, an anti-MS4A4A antibody comprises a heavy chain variable domain ($V_H$) sequence having at least 90%, 91%, 92%, 93%, 94%, 95%, 96%, 97%, 98%, 99%, or 100% sequence identity to an amino acid sequence selected from the group consisting of SEQ ID NOs: 5, 6, 7, 8, 9, 10, 11, 12, 13, 14, 15, 24, 25, 26, 27, 28, 29, 30, 40, 41, 42, 43, 44, 45, 46, 47, 48, 49, 50, 51, 52, 53, 76, 77, 78, 79, 80, 81, 82, 83, 84, 304, and 306. In certain embodiments, a $V_H$ sequence having at least 90%, 91%, 92%, 93%, 94%, 95%, 96%, 97%, 98%, or 99% identity to an amino acid sequence selected from the group consisting of SEQ ID NOs: 5, 6, 7, 8, 9, 10, 11, 12, 13, 14, 15, 24, 25, 26, 27, 28, 29, 30, 40, 41, 42, 43, 44, 45, 46, 47, 48, 49, 50, 51, 52, 53, 76, 77, 78, 79, 80, 81, 82, 83, 84, 304, and 306 contains substitutions (e.g., conservative substitutions), insertions, or deletions relative to the reference sequence, but an anti-MS4A4A antibody comprising that sequence retains the ability to bind to MS4A4A. In certain embodiments, a total of 1 to 10 amino acids have been substituted, inserted, and/or deleted in SEQ ID NO: 6, 7, 8, 9, 10, 11, 12, 13, 14, 15, 24, 25, 26, 27, 28, 29, 30, 40, 41, 42, 43, 44, 45, 46, 47, 48, 49, 50, 51, 52, 53, 76, 77, 78, 79, 80, 81, 82, 83, 84, 304, or 306. In certain embodiments, a total of 1 to 5 amino acids have been substituted, inserted and/or deleted in SEQ ID NO: 5, 6, 7, 8, 9, 10, 11, 12, 13, 14, 15, 24, 25, 26, 27, 28, 29, 30, 40, 41, 42, 43, 44, 45, 46, 47, 48, 49, 50, 51, 52, 53, 76, 77, 78, 79, 80, 81, 82, 83, 84, 304, or 306. In certain embodiments, substitutions, insertions, or deletions occur in regions outside the HVRs (i.e., in the FRs). Optionally, the anti-MS4A4A antibody comprises the $V_H$ sequence of SEQ ID NO: 5, 6, 7, 8, 9, 10, 11, 12, 13, 14, 15, 24, 25, 26, 27, 28, 29, 30, 40, 41, 42, 43, 44, 45, 46, 47, 48, 49, 50, 51, 52, 53, 76, 77, 78, 79, 80, 81, 82, 83, 84, 304, or 306. including post-translational modifications of that sequence. In a particular embodiment, the $V_H$ comprises one, two or three HVRs selected from: (a) HVR-H1 comprising an amino acid sequence selected from the group consisting of SEQ ID NOs: 94, 108, 116, 146, 147, and 308, and 311, (b) HVR-H2 comprising an amino acid sequence selected from the group consisting of SEQ ID NOs: 96, 97, 98, 99, 110, 111, 118, 119, 120, 121, 122, 149, 150, 151, 152, 153, 309, and 312, and (c) HVR-H3 comprising an amino acid sequence selected from the group consisting of SEQ ID NOs: 100, 101, 102, 112, 123, 124, 125, 126, 127, 128, 129, 154, 310, and 313.

In another aspect, an anti-MS4A4A antibody is provided, wherein the antibody comprises a light chain variable domain ($V_L$) having at least 90%, 91%, 92%, 93%, 94%, 95%, 96%, 97%, 98%, 99%, or 100% sequence identity to an amino acid sequence selected from the group consisting of SEQ ID NOs: 17, 18, 19, 20, 21, 22, 32, 33, 34, 35, 36, 55, 56, 57, 58, 59, 60, 61, 62, 63, 64, 65, 66, 67, 68, 69, 70, 71, 72, 73, 74, 86, 87, 88, 89, 90, 91, 92, 93, 305, and 307. In certain embodiments, a $V_L$ sequence having at least 90%, 91%, 92%, 93%, 94%, 95%, 96%, 97%, 98%, or 99% identity to an amino acid sequence selected from the group consisting of SEQ ID NOs: 17, 18, 19, 20, 21, 22, 32, 33, 34, 35, 36, 55, 56, 57, 58, 59, 60, 61, 62, 63, 64, 65, 66, 67, 68, 69, 70, 71, 72, 73, 74, 86, 87, 88, 89, 90, 91, 92, 93, 305, and 307 and contains substitutions (e.g., conservative substitutions), insertions, or deletions relative to the reference sequence, but an anti-MS4A4A antibody comprising that sequence retains the ability to bind to MS4A4A. In some embodiments, a total of 1 to 10 amino acids have been substituted, inserted and/or deleted in SEQ ID NO: 17, 18, 19, 20, 21, 22, 32, 33, 34, 35, 36, 55, 56, 57, 58, 59, 60, 61, 62, 63, 64, 65, 66, 67, 68, 69, 70, 71, 72, 73, 74, 86, 87, 88, 89, 90, 91, 92, 93, 305, or 307. In certain embodiments, a total of 1 to 5 amino acids have been substituted, inserted and/or deleted in SEQ ID NO: 17, 18, 19, 20, 21, 22, 32, 33, 34, 35, 36, 55, 56, 57, 58, 59, 60, 61, 62, 63, 64, 65, 66, 67, 68, 69, 70, 71, 72, 73, 74, 86, 87, 88, 89, 90, 91, 92, 93, 305, or 307. In certain embodiments, the substitutions, insertions, or deletions occur in regions outside the HVRs (i.e., in the FRs). Optionally, the anti-MS4A4A antibody comprises the $V_L$ sequence of SEQ ID NO: 17, 18, 19, 20, 21, 22, 32, 33, 34, 35, 36, 55, 56, 57, 58, 59, 60, 61, 62, 63, 64, 65, 66, 67, 68, 69, 70, 71, 72, 73, 74, 86, 87, 88, 89, 90, 91, 92, 93, 305, or 307, including post-translational modifications of that sequence. In a particular embodiment, the $V_L$ comprises one, two or three HVRs selected from (a) HVR-L1 comprising an amino acid sequence selected from the group consisting of SEQ ID NOs: 103, 104, 113, 130, 131, 132, 133, 134, 135, 136, 137, 138, 156, 157, 158, 314 and 317, (b) HVR-L2 comprising an amino acid sequence selected from the group consisting of SEQ ID NOs: 105, 106, 114, 139, 140, 141, 142, 143, 160, 161, 315 and 318, and (c) HVR-L3 comprising an amino acid sequence selected from the group consisting of SEQ ID NOs: 107, 115, 144, 145, 163, 316 and 319.

In some embodiments, an anti-MS4A4A antibody is provided, wherein the antibody comprises a $V_H$ as in any of the embodiments provided above, and a $V_L$ as in any of the embodiments provided above. In some embodiments, provided herein are anti-MS4A4A antibodies, wherein the antibody comprises a $V_H$ as in any of the embodiments provided above, and a $V_L$ as in any of the embodiments provided above. In one embodiment, the antibody comprises the $V_H$ and $V_L$ sequences in SEQ ID NOs: 5-15 and SEQ ID NOs: 17-22, respectively, including post-translational modifications of those sequences. In one embodiment, the antibody comprises the $V_H$ and $V_L$ sequences in SEQ ID NOs: 24-30 and SEQ ID NOs: 32-36, respectively, including post-translational modifications of those sequences. In one embodiment, the antibody comprises the $V_H$ and $V_L$ sequences in SEQ ID NOs: 40-53 and SEQ ID NOs: 55-74, respectively, including post-translational modifications of those sequences. In one embodiment, the antibody comprises the $V_H$ and $V_L$ sequences in SEQ ID NOs: 76-84 and SEQ ID NOs: 86-93, respectively, including post-translational modifications of those sequences. In one embodiment, the antibody comprises the $V_H$ and $V_L$ sequences in SEQ ID NO: 304 and SEQ ID NO: 305, respectively, including post-translational modifications of those sequences. In one embodiment, the antibody comprises the $V_H$ and $V_L$ sequences in SEQ ID NO: 306 and SEQ ID NO: 307, respectively, including post-translational modifications of those sequences.

In some embodiments, provided herein are anti-MS4A4A antibodies comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO: 5 and $V_L$ comprising the amino acid sequence of SEQ ID NO: 17; $V_H$ comprising the amino acid sequence of SEQ ID NO: 5 and $V_L$ comprising the amino acid sequence of SEQ ID NO: 18; $V_H$ comprising the amino acid sequence of SEQ ID NO: 6 and $V_L$ comprising the amino acid sequence of SEQ ID NO: 17; $V_H$ comprising the amino acid sequence of SEQ ID NO: 5 and $V_L$ comprising the amino acid sequence of SEQ ID NO: 19; $V_H$ comprising the amino acid sequence of SEQ ID NO: 7 and $V_L$ comprising the amino acid sequence of SEQ ID NO: 17; $V_H$ comprising the amino acid sequence of SEQ ID NO: 5 and $V_L$ comprising the amino acid sequence of SEQ ID NO: 20; $V_H$ comprising the amino acid sequence of SEQ ID NO: 8 and $V_L$ comprising the amino acid sequence of SEQ ID NO: 17; $V_H$ comprising the amino acid sequence of SEQ ID NO: 9 and $V_L$ comprising the amino acid sequence of SEQ ID NO: 17; $V_H$ comprising the amino acid sequence of SEQ ID NO: 10 and $V_L$ comprising the amino acid sequence of SEQ ID NO: 18; $V_H$ comprising the amino acid sequence of SEQ ID NO: 11 and $V_L$ comprising the amino acid sequence of SEQ ID NO: 17; V H comprising the amino acid sequence of SEQ ID NO: 12 and $V_L$ comprising the amino acid sequence of SEQ ID NO: 17; $V_H$ comprising the amino acid sequence of SEQ ID NO: 13 and $V_L$ comprising the amino acid sequence of SEQ ID NO: 21; $V_H$ comprising the amino acid sequence of SEQ ID NO: 14 and $V_L$ comprising the amino acid sequence of SEQ ID NO: 22; $V_H$ comprising the amino acid sequence of SEQ ID NO: 15 and $V_L$ comprising the amino acid sequence of SEQ ID NO: 122; $V_H$ comprising the amino acid sequence of SEQ ID NO: 304 and $V_L$ comprising the amino acid sequence of SEQ ID NO: 305; and $V_H$ comprising the amino acid sequence of SEQ ID NO: 306 and $V_L$ comprising the amino acid sequence of SEQ ID NO: 307.

In some embodiments, provided herein are anti-MS4A4A antibodies comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO: 24 and $V_L$ comprising the amino acid sequence of SEQ ID NO: 32; $V_H$ comprising the amino acid sequence of SEQ ID NO: 25 and $V_L$ comprising the amino acid sequence of SEQ ID NO: 33; $V_H$ comprising the amino acid sequence of SEQ ID NO: 25 and $V_L$ comprising the amino acid sequence of SEQ ID NO: 32; $V_H$ comprising the amino acid sequence of SEQ ID NO: 26 and $V_L$ comprising the amino acid sequence of SEQ ID NO: 33; $V_H$ comprising the amino acid sequence of SEQ ID NO: 26 and $V_L$ comprising the amino acid sequence of SEQ ID NO: 32; $V_H$ comprising the amino acid sequence of SEQ ID NO: 27 and $V_L$ comprising the amino acid sequence of SEQ ID NO: 32; $V_H$ comprising the amino acid sequence of SEQ ID NO: 27 and $V_L$ comprising the amino acid sequence of SEQ ID NO: 34; $V_H$ comprising the amino acid sequence of SEQ ID NO: 28 and $V_L$ comprising the amino acid sequence of SEQ ID NO: 33; $V_H$ comprising the amino acid sequence of SEQ ID NO: 28 and $V_L$ comprising the amino acid sequence of SEQ ID NO: 32; V H comprising the amino acid sequence of SEQ ID NO: 28 and $V_L$ comprising the amino acid sequence of SEQ ID NO: 35; $V_H$ comprising the amino acid sequence of SEQ ID NO: 28 and $V_L$ comprising the amino acid sequence of SEQ ID NO: 34; $V_H$ comprising the amino acid sequence of SEQ ID NO: 29 and $V_L$ comprising the amino acid sequence of SEQ ID NO: 32; $V_H$ comprising the amino acid sequence of SEQ ID NO: 29 and $V_L$ comprising the amino acid sequence of SEQ ID NO: 36; $V_H$ comprising the amino acid sequence of SEQ ID NO: 30 and $V_L$ comprising the amino acid sequence of SEQ ID NO: 37; $V_H$ comprising the amino acid sequence of SEQ ID NO: 30 and $V_L$ comprising the amino acid sequence of SEQ ID NO: 32; $V_H$ comprising the amino acid sequence of SEQ ID NO: 30 and $V_L$ comprising the amino acid sequence of SEQ ID NO: 38; and $V_H$ comprising the amino acid sequence of SEQ ID NO: 30 and $V_L$ comprising the amino acid sequence of SEQ ID NO: 36.

In some embodiments, provided herein are anti-MS4A4A antibodies comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO: 40 and $V_L$ comprising the amino acid sequence of SEQ ID NO: 55; $V_H$ comprising the amino acid sequence of SEQ ID NO: 41 and $V_L$ comprising the amino acid sequence of SEQ ID NO: 55; $V_H$ comprising the amino acid sequence of SEQ ID NO: 40 and $V_L$ comprising the amino acid sequence of SEQ ID NO: 56; $V_H$ comprising the amino acid sequence of SEQ ID NO: 40 and $V_L$ comprising the amino acid sequence of SEQ ID NO: 57; V H comprising the amino acid sequence of SEQ ID NO: 40 and $V_L$ comprising the amino acid sequence of SEQ ID NO: 58; $V_H$ comprising the amino acid sequence of SEQ ID NO: 41 and $V_L$ comprising the amino acid sequence of SEQ ID NO: 56; $V_H$ comprising the amino acid sequence of SEQ ID NO: 41 and $V_L$ comprising the amino acid sequence of SEQ ID NO: 57; $V_H$ comprising the amino acid sequence of SEQ ID NO: 41 and $V_L$ comprising the amino acid sequence of SEQ ID NO: 58; $V_H$ comprising the amino acid sequence of SEQ ID NO: 42 and $V_L$ comprising the amino acid sequence of SEQ ID NO: 59; $V_H$ comprising the amino acid sequence of SEQ ID NO: 43 and $V_L$ comprising the amino acid sequence of SEQ ID NO: 59; $V_H$ comprising the amino acid sequence of SEQ ID NO: 44 and $V_L$ comprising the amino acid sequence of SEQ ID NO: 60; $V_H$ comprising the amino acid sequence of SEQ ID NO: 45 and $V_L$ comprising the amino acid sequence of SEQ ID NO: 60; $V_H$ comprising the amino acid sequence of SEQ ID NO: 46 and $V_L$ comprising the amino acid sequence of SEQ ID NO: 60; $V_H$ comprising the amino acid sequence of SEQ ID NO: 43 and $V_L$ comprising the amino acid sequence of SEQ ID NO: 61; $V_H$ comprising the amino acid sequence of SEQ ID NO: 46 and $V_L$ comprising the amino acid sequence of SEQ ID NO: 61; $V_H$ comprising the amino acid sequence of SEQ ID NO: 42 and $V_L$ comprising the amino acid sequence of SEQ ID NO: 61; $V_H$ comprising the amino acid sequence of SEQ ID NO: 44 and $V_L$ comprising the amino acid sequence of SEQ ID NO: 61; $V_H$ comprising the amino acid sequence of SEQ ID NO: 45 and $V_L$ comprising the amino acid sequence of SEQ ID NO: 61; $V_H$ comprising the amino acid sequence of SEQ ID NO: 47 and $V_L$ comprising the amino acid sequence of SEQ ID NO: 55; V H comprising the amino acid sequence of SEQ ID NO: 47 and $V_L$ comprising the amino acid sequence of SEQ ID NO: 62; $V_H$ comprising the amino acid sequence of SEQ ID NO: 47 and $V_L$ comprising the amino acid sequence of SEQ ID NO: 63; $V_H$ comprising the amino acid sequence of SEQ ID NO: 47 and $V_L$ comprising the amino acid sequence of SEQ ID NO: 64; $V_H$ comprising the amino acid sequence of SEQ ID NO: 47 and $V_L$ comprising the amino acid sequence of SEQ ID NO: 65; $V_H$ comprising the amino acid sequence of SEQ ID NO: 47 and $V_L$ comprising the amino acid sequence of SEQ ID NO: 66; $V_H$ comprising the amino acid sequence of SEQ ID NO: 47 and $V_L$ comprising the amino acid sequence of SEQ ID NO: 67; $V_H$ comprising the amino acid sequence of SEQ ID NO: 47 and $V_L$ comprising the amino acid sequence of SEQ ID NO: 68; $V_H$ comprising the amino acid sequence of SEQ ID NO: 47 and $V_L$ comprising the amino acid sequence of SEQ ID NO: 69; $V_H$ comprising the amino acid sequence of SEQ ID NO: 47 and $V_L$ comprising the amino acid sequence of SEQ ID NO: 70; $V_H$ comprising the amino acid sequence of SEQ ID NO: 47 and $V_L$ comprising the amino acid sequence of SEQ ID NO: 71; $V_H$ comprising the amino acid sequence of SEQ ID NO: 47 and $V_L$ comprising the amino acid sequence of SEQ ID NO: 72; $V_H$ comprising the amino acid sequence of SEQ ID NO: 47 and $V_L$ comprising the amino acid sequence of SEQ ID NO: 73; $V_H$ comprising the amino acid sequence of SEQ ID NO: 47 and $V_L$ comprising the amino acid sequence of SEQ ID NO: 74; $V_H$ comprising the amino acid sequence of SEQ ID NO: 48 and $V_L$ comprising the amino acid sequence of SEQ ID NO: 70; $V_H$ comprising the amino acid sequence of SEQ ID NO: 48 and $V_L$ comprising the amino acid sequence of SEQ ID NO: 74; V H comprising the amino acid sequence of SEQ ID NO: 48 and $V_L$ comprising the amino acid sequence of SEQ ID NO: 62; $V_H$ comprising the amino acid sequence of SEQ ID NO: 48 and $V_L$ comprising the amino acid sequence of SEQ ID NO: 55; $V_H$ comprising the amino acid sequence of SEQ ID NO: 48 and $V_L$ comprising the amino acid sequence of SEQ ID NO: 72; $V_H$ comprising the amino acid sequence of SEQ ID NO: 48 and $V_L$ comprising the amino acid sequence of SEQ ID NO: 69; $V_H$ comprising the amino acid sequence of SEQ ID NO: 49 and $V_L$ comprising the amino acid sequence of SEQ ID NO: 71; $V_H$ comprising the amino acid sequence of SEQ ID NO: 49 and $V_L$ comprising the amino acid sequence of SEQ ID NO: 55; $V_H$ comprising the amino acid sequence of SEQ ID NO: 49 and $V_L$ comprising the amino acid sequence of SEQ ID NO: 73; $V_H$ comprising the amino acid sequence of SEQ ID NO: 50 and $V_L$ comprising the amino acid sequence of SEQ ID NO: 62; $V_H$ comprising the amino acid sequence of SEQ ID NO: 51 and $V_L$ comprising the amino acid sequence of SEQ ID NO: 62; $V_H$ comprising the amino acid sequence of SEQ ID NO: 52 and $V_L$ comprising the amino acid sequence of SEQ ID NO: 62; $V_H$ comprising the amino acid sequence of SEQ ID NO: 53 and $V_L$ comprising the amino acid sequence of SEQ ID NO: 62; $V_H$ comprising the amino acid sequence of SEQ ID NO: 53 and $V_L$ comprising the amino acid sequence of SEQ ID NO: 63; $V_H$ comprising the amino acid sequence of SEQ ID NO: 53 and $V_L$ comprising the amino acid sequence of SEQ ID NO: 64; $V_H$ comprising the amino acid sequence of SEQ ID NO: 53 and $V_L$ comprising the amino acid sequence of SEQ ID NO: 65; $V_H$ comprising the amino acid sequence of SEQ ID NO: 53 and $V_L$ comprising the amino acid sequence of SEQ ID NO: 66; and V H comprising the amino acid sequence of SEQ ID NO: 53 and $V_L$ comprising the amino acid sequence of SEQ ID NO: 67.

In some embodiments, provided herein are anti-MS4A4A antibodies comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO: 76 and $V_L$ comprising the amino acid sequence of SEQ ID NO: 86; $V_H$ comprising the amino acid sequence of SEQ ID NO: 77 and $V_L$ comprising the amino acid sequence of SEQ ID NO: 87; $V_H$ comprising the amino acid sequence of SEQ ID NO: 78 and $V_L$ comprising the amino acid sequence of SEQ ID NO: 88; $V_H$ comprising the amino acid sequence of SEQ ID NO: 79 and $V_L$ comprising the amino acid sequence of SEQ ID NO: 89; $V_H$ comprising the amino acid sequence of SEQ ID NO: 80 and $V_L$ comprising the amino acid sequence of SEQ ID NO: 90; $V_H$ comprising the amino acid sequence of SEQ ID NO: 81 and $V_L$ comprising the amino acid sequence of SEQ ID NO: 91; $V_H$ comprising the amino acid sequence of SEQ ID NO: 82 and $V_L$ comprising the amino acid sequence of SEQ ID NO: 91; $V_H$ comprising the amino acid sequence of SEQ ID NO: 83 and $V_L$ comprising the amino acid sequence of SEQ ID NO: 92; and $V_H$ comprising the amino acid sequence of SEQ ID NO: 84 and $V_L$ comprising the amino acid sequence of SEQ ID NO: 93.

In another aspect, an anti-MS4A4A antibody comprises a heavy chain variable domain ($V_H$) sequence having at least 90%, 91%, 92%, 93%, 94%, 95%, 96%, 97%, 98%, 99%, or 100% sequence identity to an amino acid sequence selected from the group consisting of SEQ ID NOs: 5, 6, 7, 8, 9, 10, 11, 12, 13, 14, 15, 304, and 306. In certain embodiments, a $V_H$ sequence having at least 90%, 91%, 92%, 93%, 94%, 95%, 96%, 97%, 98%, or 99% identity to an amino acid sequence selected from the group consisting of SEQ ID NOs: 5, 6, 7, 8, 9, 10, 11, 12, 13, 14, 15, 304, and 306 contains substitutions (e.g., conservative substitutions), insertions, or deletions relative to the reference sequence, but an anti-MS4A4A antibody comprising that sequence retains the ability to bind to MS4A4A. In certain embodiments, a total of 1 to 10 amino acids have been substituted, inserted, and/or deleted in SEQ ID NO: 5, 6, 7, 8, 9, 10, 11, 12, 13, 14, 304, or 306. In certain embodiments, a total of 1 to 5 amino acids have been substituted, inserted and/or deleted in SEQ ID NO: 5, 6, 7, 8, 9, 10, 11, 12, 13, 14, 15, 304, or 306. In certain embodiments, substitutions, insertions, or deletions occur in regions outside the HVRs (i.e., in the FRs). Optionally, the anti-MS4A4A antibody comprises the $V_H$ sequence of SEQ ID NO: 5, 6, 7, 8, 9, 10, 11, 12, 13, 14, 15, 304, or 306, including post-translational modifications of that sequence. In a particular embodiment, the $V_H$ comprises one, two or three HVRs selected from: (a) HVR-H1 comprising the amino acid sequence selected from the group consisting of SEQ ID NO: 94 and 308, (b) HVR-H2 comprising an amino acid sequence selected from the group consisting of SEQ ID NOs: 96, 97, 98, 99, and 309, and (c) HVR-H3 comprising an amino acid sequence selected from the group consisting of SEQ ID NOs: 100, 101, 102, and 310.

In another aspect, an anti-MS4A4A antibody is provided, wherein the antibody comprises a light chain variable domain ($V_L$) having at least 90%, 91%, 92%, 93%, 94%, 95%, 96%, 97%, 98%, 99%, or 100% sequence identity to an amino acid sequence selected from the group consisting of SEQ ID NOs: 17, 18, 19, 20, 21, 22, 305, and 307. In certain embodiments, a $V_L$ sequence having at least 90%, 91%, 92%, 93%, 94%, 95%, 96%, 97%, 98%, or 99% identity to an amino acid sequence selected from the group consisting of SEQ ID NOs: 17, 18, 19, 20, 21, 22, 305, and 307, and contains substitutions (e.g., conservative substitutions), insertions, or deletions relative to the reference sequence, but an anti-MS4A4A antibody comprising that sequence retains the ability to bind to MS4A4A. In some embodiments, a total of 1 to 10 amino acids have been substituted, inserted and/or deleted in SEQ ID NO: 17, 18, 19, 20, 21, 22, 305 or 307. In certain embodiments, a total of 1 to 5 amino acids have been substituted, inserted and/or deleted in SEQ ID NO: 17, 18, 19, 20, 21, 22, 305 or 307. In certain embodiments, the substitutions, insertions, or deletions occur in regions outside the HVRs (i.e., in the FRs). Optionally, the anti-MS4A4A antibody comprises the $V_L$ sequence of SEQ ID NO: 17, 18, 19, 20, 21, 22, 305, or 307, including post-translational modifications of that sequence. In a particular embodiment, the $V_L$ comprises one, two or three HVRs selected from (a) HVR-L1 comprising an amino acid sequence selected from the group consisting of SEQ ID NOs: 103, 104, and 314, (b) HVR-L2 comprising an amino acid sequence selected from the group consisting of SEQ ID NOs: 105, 106, and 315, and (c) HVR-L3 comprising the amino acid sequence selected from the group consisting of SEQ ID NO: 107 and 316.

In another aspect, an anti-MS4A4A antibody comprises a heavy chain variable domain ($V_H$) sequence having at least 90%, 91%, 92%, 93%, 94%, 95%, 96%, 97%, 98%, 99%, or 100% sequence identity to an amino acid sequence selected from the group consisting of SEQ ID NOs: 24, 25, 26, 27, 28, 29, and 30. In certain embodiments, a $V_H$ sequence having at least 90%, 91%, 92%, 93%, 94%, 95%, 96%, 97%, 98%, or 99% identity to an amino acid sequence selected from the group consisting of SEQ ID NOs: 24, 25, 26, 27, 28, 29, and 30 contains substitutions (e.g., conservative substitutions), insertions, or deletions relative to the reference sequence, but an anti-MS4A4A antibody comprising that sequence retains the ability to bind to MS4A4A. In certain embodiments, a total of 1 to 10 amino acids have been substituted, inserted, and/or deleted in SEQ ID NO: 24, 25, 26, 27, 28, 29, or 30. In certain embodiments, a total of 1 to 5 amino acids have been substituted, inserted and/or deleted in SEQ ID NO: 24, 25, 26, 27, 28, 29, or 30. In certain embodiments, substitutions, insertions, or deletions occur in regions outside the HVRs (i.e., in the FRs). Optionally, the anti-MS4A4A antibody comprises the $V_H$ sequence of SEQ ID NO: 24, 26, 27, 28, 29, or 30, including post-translational modifications of that sequence. In a particular embodiment, the $V_H$ comprises one, two or three HVRs selected from: (a) HVR-H1 comprising the amino acid sequence of SEQ ID NO: 108, (b) HVR-H2 comprising an amino acid sequence selected from the group consisting of SEQ ID NOs: 110 and 111, and (c) HVR-H3 comprising the amino acid sequence of SEQ ID NO: 112.

In another aspect, an anti-MS4A4A antibody is provided, wherein the antibody comprises a light chain variable domain ($V_L$) having at least 90%, 91%, 92%, 93%, 94%, 95%, 96%, 97%, 98%, 99%, or 100% sequence identity to an amino acid sequence selected from the group consisting of SEQ ID NOs: 32, 33, 34, 35 and 36. In certain embodiments, a $V_L$ sequence having at least 90%, 91%, 92%, 93%, 94%, 95%, 96%, 97%, 98%, or 99% identity to an amino acid sequence selected from the group consisting of SEQ ID NOs: 32, 33, 34, 35, and 36, and contains substitutions (e.g., conservative substitutions), insertions, or deletions relative to the reference sequence, but an anti-MS4A4A antibody comprising that sequence retains the ability to bind to MS4A4A. In some embodiments, a total of 1 to 10 amino acids have been substituted, inserted and/or deleted in SEQ ID NO: 32, 33, 34, 35, or 36. In certain embodiments, a total of 1 to 5 amino acids have been substituted, inserted and/or deleted in SEQ ID NO: 32, 33, 34, 35, or 36. In certain embodiments, the substitutions, insertions, or deletions occur in regions outside the HVRs (i.e., in the FRs). Optionally, the anti-MS4A4A antibody comprises the $V_L$ sequence of SEQ ID NO: 32, 33, 34, 35, or 36, including post-translational modifications of that sequence. In a particular embodiment, the $V_L$ comprises one, two or three HVRs selected from (a) HVR-L1 comprising the amino acid sequence of SEQ ID NO: 113, (b) HVR-L2 comprising the amino acid sequence of SEQ ID NO: 114, and (c) HVR-L3 comprising the amino acid sequence of SEQ ID NO: 115.

In another aspect, an anti-MS4A4A antibody comprises a heavy chain variable domain ($V_H$) sequence having at least 90%, 91%, 92%, 93%, 94%, 95%, 96%, 97%, 98%, 99%, or 100% sequence identity to an amino acid sequence selected from the group consisting of SEQ ID NOs: 40, 41, 42, 43, 44, 46, 47, 48, 49, 50, 51, 52, and 53. In certain embodiments, a $V_H$ sequence having at least 90%, 91%, 92%, 93%, 94%, 95%, 96%, 97%, 98%, or 99% identity to an amino acid sequence selected from the group consisting of SEQ ID NOs: 40, 41, 42, 43, 44, 45, 46, 47, 48, 49, 50, 51, 52, and 53 contains substitutions (e.g., conservative substitutions), insertions, or deletions relative to the reference sequence, but an anti-MS4A4A antibody comprising that sequence retains the ability to bind to MS4A4A. In certain embodiments, a total of 1 to 10 amino acids have been substituted, inserted, and/or deleted in SEQ ID NO: 41, 42, 43, 44, 45, 46, 47, 48, 49, 50, 51, 52, or 53. In certain embodiments, a total of 1 to 5 amino acids have been substituted, inserted and/or deleted in SEQ ID NO: 40, 41, 42, 43, 44, 45, 46, 47, 48, 49, 51, 52, or 53. In certain embodiments, substitutions, insertions, or deletions occur in regions outside the HVRs (i.e., in the FRs). Optionally, the anti-MS4A4A antibody comprises the $V_H$ sequence of SEQ ID NO: 40, 41, 42, 43, 44, 45, 46, 47, 48, 49, 50, 51, 52, or 53, including post-translational modifications of that sequence. In a particular embodiment, the $V_H$ comprises one, two or three HVRs selected from: (a) HVR-H1 comprising the amino acid sequence of SEQ ID NO: 116, (b) HVR-H2 comprising an amino acid sequence selected from the group consisting of SEQ ID NOs: 118, 119, 120, 121, and 122, and (c) I—WR-H3 comprising an amino acid sequence selected from the group consisting of SEQ ID NOs: 123, 124, 125, 126, 127, 128, and 129.

In another aspect, an anti-MS4A4A antibody is provided, wherein the antibody comprises a light chain variable domain ($V_L$) having at least 90%, 91%, 92%, 93%, 94%, 95%, 96%, 97%, 98%, 99%, or 100% sequence identity to an amino acid sequence selected from the group consisting of SEQ ID NOs: 55, 56, 57, 58, 59, 60, 61, 62, 63, 64, 65, 66, 67, 68, 69, 70, 71, 72, 73, and 74. In certain embodiments, a $V_L$ sequence having at least 90%, 91%, 92%, 93%, 94%, 95%, 96%, 97%, 98%, or 99% identity to an amino acid sequence selected from the group consisting of SEQ ID NOs: 55, 56, 57, 58, 59, 60, 61, 62, 63, 64, 66, 67, 68, 69, 70, 71, 72, 73, and 74, and contains substitutions (e.g., conservative substitutions), insertions, or deletions relative to the reference sequence, but an anti-MS4A4A antibody comprising that sequence retains the ability to bind to MS4A4A. In some embodiments, a total of 1 to 10 amino acids have been substituted, inserted and/or deleted in SEQ ID NO: 55, 56, 57, 58, 59, 60, 61, 62, 63, 64, 65, 66, 67, 68, 69, 70, 71, 72, 73, or 74. In certain embodiments, a total of 1 to 5 amino acids have been substituted, inserted and/or deleted in SEQ ID NO: 55, 56, 57, 58, 59, 60, 61, 62, 63, 64, 65, 66, 67, 68, 69, 70, 71, 72, 73, or 74. In certain embodiments, the substitutions, insertions, or deletions occur in regions outside the HVRs (i.e., in the FRs). Optionally, the anti-MS4A4A antibody comprises the $V_L$ sequence of SEQ ID NO: 55, 56, 57, 58, 59, 60, 61, 62, 63, 64, 65, 66, 67, 68, 69, 70, 71, 72, 73, or 74, including post-translational modifications of that sequence. In a particular embodiment, the $V_L$ comprises one, two or three HVRs selected from (a) HVR-L1 comprising an amino acid sequence selected from the group consisting of SEQ ID NOs: 130, 131, 132, 133, 134, 135, 136, 137, and 138, (b) HVR-L2 comprising an amino acid sequence selected from the group consisting of SEQ ID NOs: 139, 140, 141, 142, and 143, and (c) HVR-L3 comprising an amino acid sequence selected from the group consisting of SEQ ID NOs: 144 and 145.

In another aspect, an anti-MS4A4A antibody comprises a heavy chain variable domain ($V_H$) sequence having at least 90%, 91%, 92%, 93%, 94%, 95%, 96%, 97%, 98%, 99%, or 100% sequence identity to an amino acid sequence selected from the group consisting of SEQ ID NOs: 76, 77, 78, 79, 80, 81, 82, 83, and 84. In certain embodiments, a $V_H$ sequence having at least 90%, 91%, 92%, 93%, 94%, 95%, 96%, 97%, 98%, or 99% identity to an amino acid sequence selected from the group consisting of SEQ ID NOs: 76, 77, 78, 79, 80, 81, 82, 83, and 84 contains substitutions (e.g., conservative substitutions), insertions, or deletions relative to the reference sequence, but an anti-MS4A4A antibody comprising that sequence retains the ability to bind to MS4A4A. In certain embodiments, a total of 1 to 10 amino acids have been substituted, inserted, and/or deleted in SEQ ID NO: 76, 77, 78, 79, 80, 81, 82, 83, or 84. In certain embodiments, a total of 1 to 5 amino acids have been substituted, inserted and/or deleted in SEQ ID NO: 76, 77, 78, 79, 80, 81, 82, 83, or 84. In certain embodiments, substitutions, insertions, or deletions occur in regions outside the HVRs (i.e., in the FRs). Optionally, the anti-MS4A4A antibody comprises the $V_H$ sequence of SEQ ID NO: 76, 77, 78, 79, 80, 81, 82, 83, or 84, including post-translational modifications of that sequence. In a particular embodiment, the $V_H$ comprises one, two or three HVRs selected from: (a) HVR-H1 comprising an amino acid sequence selected from the group consisting of SEQ ID NOs: 146 and 147, (b) HVR-H2 comprising an amino acid sequence selected from the group consisting of SEQ ID NOs: 149, 150, 151, 152, and 153, and (c) HVR-H3 comprising the amino acid sequence of SEQ ID NO: 154.

In another aspect, an anti-MS4A4A antibody is provided, wherein the antibody comprises a light chain variable domain ($V_L$) having at least 90%, 91%, 92%, 93%, 94%, 95%, 96%, 97%, 98%, 99%, or 100% sequence identity to an amino acid sequence selected from the group consisting of SEQ ID NOs: 86, 87, 88, 89, 90, 91, 92, and 93. In certain embodiments, a $V_L$ sequence having at least 90%, 91%, 92%, 93%, 94%, 95%, 96%, 97%, 98%, or 99% identity to an amino acid sequence selected from the group consisting of SEQ ID NOs: 86, 87, 88, 89, 90, 91, 92, and 93, and contains substitutions (e.g., conservative substitutions), insertions, or deletions relative to the reference sequence, but an anti-MS4A4A antibody comprising that sequence retains the ability to bind to MS4A4A. In some embodiments, a total of 1 to 10 amino acids have been substituted, inserted and/or deleted in SEQ ID NO: 86, 87, 88, 89, 90, 91, 92, or 93. In certain embodiments, a total of 1 to 5 amino acids have been substituted, inserted and/or deleted in SEQ ID NO: 86, 87, 88, 89, 90, 91, 92, or 93. In certain embodiments, the substitutions, insertions, or deletions occur in regions outside the HVRs (i.e., in the FRs). Optionally, the anti-MS4A4A antibody comprises the $V_L$ sequence of SEQ ID NO: 86, 87, 88, 89, 90, 91, 92, or 93, including post-translational modifications of that sequence. In a particular embodiment, the $V_L$ comprises one, two or three HVRs selected from (a) HVR-L1 comprising an amino acid sequence selected from the group consisting of SEQ ID NOs: 156, 157, and 158, (b) HVR-L2 comprising an amino acid sequence selected from the group consisting of SEQ ID NOs: 160 and 161, and (c) HVR-L3 comprising the amino acid sequence of SEQ ID NO: 163.

In another aspect, an anti-MS4A4A antibody comprises a full length heavy chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 320-335 and 355-362. In certain embodiments, a full length heavy chain amino acid sequence having at least 90%, 91%, 92%, 93%, 94%, 95%, 96%, 97%, 98%, or 99% identity to an amino acid sequence selected from the group consisting of SEQ ID NOs: 320-335 and 355-362 contains substitutions (e.g., conservative substitutions), insertions, or deletions relative to the reference sequence, but an anti-MS4A4A antibody comprising that sequence retains the ability to bind to MS4A4A. In certain embodiments, a total of 1 to 10 amino acids have been substituted, inserted, and/or deleted in SEQ ID NO: 320-335 and 355-362. In certain embodiments, a total of 1 to 5 amino acids have been substituted, inserted and/or deleted in SEQ ID NO: 320-335 and 355-362. In certain embodiments, substitutions, insertions, or deletions occur in regions outside the HVRs (i.e., in the FRs).

In another aspect, an anti-MS4A4A antibody comprises a full length light chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 363-365. In certain embodiments, a full length heavy chain amino acid sequence having at least 90%, 91%, 92%, 93%, 94%, 95%, 96%, 97%, 98%, or 99% identity to an amino acid sequence selected from the group consisting of SEQ ID NOs: 363-365 contains substitutions (e.g., conservative substitutions), insertions, or deletions relative to the reference sequence, but an anti-MS4A4A antibody comprising that sequence retains the ability to bind to MS4A4A. In certain embodiments, a total of 1 to 10 amino acids have been substituted, inserted, and/or deleted in SEQ ID NO: 363-365. In certain embodiments, a total of 1 to 5 amino acids have been substituted, inserted and/or deleted in SEQ ID NO: 363-365. In certain embodiments, substitutions, insertions, or deletions occur in regions outside the LVRs (i.e., in the FRs).

In some embodiments, the anti-MS4A4A antibody comprises a full length heavy chain amino acid sequence of SEQ ID NOs: 355-362 and a full length light chain amino acid sequence of SEQ ID NO: 365. In some embodiments, the anti-MS4A4A antibody comprises a full length heavy chain amino acid sequence of SEQ ID NOs: 320-327 and a full length light chain amino acid sequence of SEQ ID NO: 363. In some embodiments, the anti-MS4A4A antibody comprises a full length heavy chain amino acid sequence of SEQ ID NOs: 328-335 and a full length light chain amino acid sequence of SEQ ID NO: 364.

In some embodiments, an anti-MS4A4A antibody of the present disclosure competitively inhibits binding of at least one reference antibody selected from 4A-202, 4A-301, 4A-302, 4A-303, 4A-304, 4A-305, 4A-306, 4A-307, 4A-308, 4A-309, 4A-310, 4A-311, 4A-312, 4A-313, 4A-314, 4A-419, and 4A-450. In some embodiments, an anti-MS4A4A antibody of the present disclosure competitively inhibits binding of at least one reference antibody selected from 4A-18, 4A-315, 4A-316, 4A-317, 4A-318, 4A-319, 4A-320, 4A-321, 4A-322, 4A-323, 4A-324, 4A-325, 4A-326, 4A-327, 4A-328, 4A-329, 4A-330, and 4A-331. In some embodiments, an anti-MS4A4A antibody of the present disclosure competitively inhibits binding of at least one reference antibody selected from 4A-21, 4A-332, 4A-333, 4A-334, 4A-335, 4A-336, 4A-337, 4A-338, 4A-339, 4A-340, 4A-341, 4A-342, 4A-343, 4A-344, 4A-345, 4A-346, 4A-347, 4A-348, 4A-349, 4A-350, 4A-351, 4A-352, 4A-353, 4A-354, 4A-355, 4A-356, 4A-357, 4A-358, 4A-359, 4A-360, 4A-361, 4A-361, 4A-363, 4A-364, 4A-365, 4A-366, 4A-367, 4A-368, 4A-369, 4A-370, 4A-371, 4A-372, 4A-373, 4A-374, 4A-375, 4A-376, 4A-377, 4A-378, 4A-379, 4A-380, and 4A-381. In some embodiments, an anti-MS4A4A antibody of the present disclosure competitively inhibits binding of at least one reference antibody selected from 4A-25, 4A-382, 4A-383, 4A-384, 4A-385, 4A-386, 4A-387, 4A-388, 4A-389, 4A-390.

In some embodiments, an anti-MS4A4A antibody of the present disclosure binds to an epitope of human MS4A4A that is the same as or overlaps with the MS4A4A epitope bound by at least one reference antibody selected from 4A-202, 4A-301, 4A-302, 4A-303, 4A-304, 4A-305, 4A-306, 4A-307, 4A-308, 4A-309, 4A-310, 4A-311, 4A-312, 4A-313, 4A-314, 4A-18, 4A-315, 4A-316, 4A-317, 4A-318, 4A-319, 4A-320, 4A-321, 4A-322, 4A-323, 4A-324, 4A-325, 4A-326, 4A-327, 4A-328, 4A-329, 4A-330, 4A-331, 4A-21, 4A-332, 4A-333, 4A-334, 4A-335, 4A-336, 4A-337, 4A-338, 4A-339, 4A-340, 4A-341, 4A-342, 4A-343, 4A-344, 4A-345, 4A-346, 4A-347, 4A-348, 4A-349, 4A-350, 4A-351, 4A-352, 4A-353, 4A-354, 4A-355, 4A-356, 4A-357, 4A-358, 4A-359, 4A-360, 4A-361, 4A-361, 4A-363, 4A-364, 4A-365, 4A-366, 4A-367, 4A-368, 4A-369, 4A-370, 4A-371, 4A-372, 4A-373, 4A-374, 4A-375, 4A-376, 4A-377, 4A-378, 4A-379, 4A-380, 4A-381, 4A-25, 4A-382, 4A-383, 4A-384, 4A-385, 4A-386, 4A-387, 4A-388, 4A-389, 4A-390, 4A-419, and 4A-450. Detailed exemplary methods for mapping an epitope to which an antibody binds are provided in Morris (1996) "Epitope Mapping Protocols," in Methods in Molecular Biology vol. 66 (Humana Press, Totowa, NJ).

In some embodiments, an anti-MS4A4A antibody of the present disclosure competitively inhibits binding of at least one reference antibody selected from 4A-202, 4A-301, 4A-302, 4A-303, 4A-304, 4A-305, 4A-306, 4A-307, 4A-308, 4A-309, 4A-310, 4A-311, 4A-312, 4A-313, 4A-314, 4A-419, and 4A-450, and any combination thereof, for binding to MS4A4A. In some embodiments, an anti-MS4A4A antibody of the present disclosure competitively inhibits binding of at least one reference antibody selected from 4A-18, 4A-315, 4A-316, 4A-317, 4A-318, 4A-319, 4A-320, 4A-321, 4A-322, 4A-323, 4A-324, 4A-325, 4A-326, 4A-327, 4A-328, 4A-329, 4A-330, and 4A-331, and any combination thereof, for binding to MS4A4A. In some embodiments, an anti-MS4A4A antibody of the present disclosure competitively inhibits binding of at least one reference antibody selected from 4A-21, 4A-332, 4A-333, 4A-334, 4A-335, 4A-336, 4A-337, 4A-338, 4A-339, 4A-340, 4A-341, 4A-342, 4A-343, 4A-344, 4A-345, 4A-346, 4A-347, 4A-348, 4A-349, 4A-350, 4A-351, 4A-352, 4A-353, 4A-354, 4A-355, 4A-356, 4A-357, 4A-358, 4A-359, 4A-360, 4A-361, 4A-361, 4A-363, 4A-364, 4A-365, 4A-366, 4A-367, 4A-368, 4A-369, 4A-370, 4A-371, 4A-372, 4A-373, 4A-374, 4A-375, 4A-376, 4A-377, 4A-378, 4A-379, 4A-380, and 4A-381, and any combination thereof, for binding to MS4A4A. In some embodiments, an anti-MS4A4A antibody of the present disclosure competitively inhibits binding of at least one reference antibody selected from 4A-25, 4A-382, 4A-383, 4A-384, 4A-385, 4A-386, 4A-387, 4A-388, 4A-389, or 4A-390, and any combination thereof, for binding to MS4A4A.

In some embodiments, an anti-MS4A4A antibody of the present disclosure has the same or overlapping epitope on MS4A4A as at least one reference antibody selected from 4A-202, 4A-301, 4A-302, 4A-303, 4A-304, 4A-305, 4A-306, 4A-307, 4A-308, 4A-309, 4A-310, 4A-311, 4A-312, 4A-313, 4A-314, 4A-419, and 4A-450, and any combination thereof, for binding to MS4A4A. In some embodiments, an anti-MS4A4A antibody of the present disclosure has the same or overlapping epitope on MS4A4A as at least one reference antibody selected from 4A-18, 4A-315, 4A-316, 4A-317, 4A-318, 4A-319, 4A-320, 4A-321, 4A-322, 4A-323, 4A-324, 4A-325, 4A-326, 4A-327, 4A-328, 4A-329, 4A-330, and 4A-331, and any combination thereof, for binding to MS4A4A. In some embodiments, an anti-MS4A4A antibody of the present disclosure has the same or overlapping epitope on MS4A4A as at least one reference antibody selected from 4A-21, 4A-332, 4A-333, 4A-334, 4A-335, 4A-336, 4A-337, 4A-338, 4A-339, 4A-340, 4A-341, 4A-342, 4A-343, 4A-344, 4A-345, 4A-346, 4A-347, 4A-348, 4A-349, 4A-350, 4A-351, 4A-352, 4A-353, 4A-354, 4A-355, 4A-356, 4A-357, 4A-358, 4A-359, 4A-360, 4A-361, 4A-361, 4A-363, 4A-364, 4A-365, 4A-366, 4A-367, 4A-368, 4A-369, 4A-370, 4A-371, 4A-372, 4A-373, 4A-374, 4A-375, 4A-376, 4A-377, 4A-378, 4A-379, 4A-380, and 4A-381, and any combination thereof, for binding to MS4A4A. In some embodiments, an anti-MS4A4A antibody of the present disclosure has the same or overlapping epitope on MS4A4A as at least one reference antibody selected from 4A-25, 4A-382, 4A-383, 4A-384, 4A-385, 4A-386, 4A-387, 4A-388, 4A-389, and 4A-390, and any combination thereof, for binding to MS4A4A.

In some embodiments, an anti-MS4A4A antibody of the present disclosure binds to extracellular domain 1 (ECL1) of MS4A4A. In some embodiments, an anti-MS4A4A antibody of the present disclosure binds to one or more amino acids within the amino acid sequence CMASNTYGSNPIS (SEQ ID NO: 177) of SEQ ID NO: 1. In some embodiments, an anti-MS4A4A antibody of the present disclosure binds to extracellular domain 2 (ECL2) of MS4A4A. In some embodiments, an anti-MS4A4A antibody of the present disclosure binds to one or more amino acids within the amino acid sequence SFFIHPYCNYYGNSNNCHGTMS (SEQ ID NO: 178) of SEQ ID NO: 1

Any suitable competition assay or MS4A4A binding assay known in the art, such as BIAcore analysis, ELISA assays, or flow cytometry, may be utilized to determine whether an anti-MS4A4A antibody competes with (or competitively inhibits the binding of) one or more reference antibodies selected from 4A-202, 4A-301, 4A-302, 4A-303, 4A-304, 4A-305, 4A-306, 4A-307, 4A-308, 4A-309, 4A-310, 4A-311, 4A-312, 4A-313, 4A-314, 4A-18, 4A-315, 4A-316, 4A-317, 4A-318, 4A-319, 4A-320, 4A-321, 4A-322, 4A-323, 4A-324, 4A-325, 4A-326, 4A-327, 4A-328, 4A-329, 4A-330, 4A-331, 4A-21, 4A-332, 4A-333, 4A-334, 4A-335, 4A-336, 4A-337, 4A-338, 4A-339, 4A-340, 4A-341, 4A-342, 4A-343, 4A-344, 4A-345, 4A-346, 4A-347, 4A-348, 4A-349, 4A-350, 4A-351, 4A-352, 4A-353, 4A-354, 4A-355, 4A-356, 4A-357, 4A-358, 4A-359, 4A-360, 4A-361, 4A-361, 4A-363, 4A-364, 4A-365, 4A-366, 4A-367, 4A-368, 4A-369, 4A-370, 4A-371, 4A-372, 4A-373, 4A-374, 4A-375, 4A-376, 4A-377, 4A-378, 4A-379, 4A-380, 4A-381, 4A-25, 4A-382, 4A-383, 4A-384, 4A-385, 4A-386, 4A-387, 4A-388, 4A-389, 4A-390, 4A-419, and 4A-450, and any combination thereof for binding to MS4A4A. In an exemplary competition assay, immobilized MS4A4A or cells expressing MS4A4A on the cell surface are incubated in a solution comprising a first labeled antibody that binds to MS4A4A (e.g., human or non-human primate) and a second unlabeled antibody that is being tested for its ability to compete with the first antibody for binding to MS4A4A. The second antibody may be present in a hybridoma supernatant. As a control, immobilized MS4A4A or cells expressing MS4A4A is incubated in a solution comprising the first labeled antibody but not the second unlabeled antibody. After incubation under conditions permissive for binding of the first antibody to MS4A4A, excess unbound antibody is removed, and the amount of label associated with immobilized MS4A4A or cells expressing MS4A4A is measured. If the amount of label associated with immobilized MS4A4A or cells expressing MS4A4A is substantially reduced in the test sample relative to the control sample, then that indicates that the second antibody is competing with the first antibody for binding to MS4A4A. See, Harlow and Lane (1988) Antibodies: A Laboratory Manual ch.14 (Cold Spring Harbor Laboratory, Cold Spring Harbor, NY).

Further provided herein are anti-MS4A4A antibodies which competitively inhibit binding of and/or compete for binding with an anti-MS4A4A antibody comprising (a) a $V_H$ domain comprising (i) HVR-H1 comprising the amino acid sequence selected from the group consisting of SEQ ID NO: 94 and 308, (ii) HVR-H2 comprising an amino acid sequence selected from the group consisting of SEQ ID NOs: 96, 97, 98, 99, and 309, and (iii) HVR-H3 comprising an amino acid sequence selected from the group consisting of SEQ ID NOs: 100, 101, 102, and 310, and (b) a $V_L$ domain comprising (i) HVR-L1 comprising an amino acid sequence selected from the group consisting of SEQ ID NOs: 103, 104, and 314, (ii) HVR-L2 comprising an amino acid sequence selected from the group consisting of SEQ ID NOs: 105, 106, and 315, and (iii) HVR-L3 comprising the amino acid sequence selected from the group consisting of SEQ ID NOs: 107 and 316. In some embodiments, the antibody comprises the $V_H$ and $V_L$ sequences in SEQ ID NOs: 5-15 and 304, and SEQ ID NOs: 17-22 and 305, respectively.

Provided herein are anti-MS4A4A antibodies which bind to an epitope of human MS4A4A that is the same as or overlaps with the epitope bound by an anti-MS4A4A antibody comprising (a) a $V_H$ domain comprising (i) HVR-H1 comprising the amino acid sequence selected from the group consisting of SEQ ID NO: 94 and 308, (ii) HVR-H2 comprising an amino acid sequence selected from the group consisting of SEQ ID NOs: 96, 97, 98, 99, and 309, and (iii) HVR-H3 comprising an amino acid sequence selected from the group consisting of SEQ ID NOs: 100, 101, 102, and 310, and (b) a $V_L$ domain comprising (i) HVR-L1 comprising an amino acid sequence selected from the group consisting of SEQ ID NOs: 103, 104, and 314, (ii) HVR-L2 comprising an amino acid sequence selected from the group consisting of SEQ ID NOs: 105, 106, and 315, and (iii) HVR-L3 comprising the amino acid sequence selected from the group consisting of SEQ ID NO: 107 and 316. In some embodiments, the antibody comprises the $V_H$ and $V_L$ sequences in SEQ ID NOs: 5-15 and 304, and SEQ ID NOs: 17-22 and 305, respectively. In some embodiments, the epitope of human MS4A4A is the same epitope as bound by an anti-MS4A4A antibody.

Further provided herein are anti-MS4A4A antibodies which competitively inhibit binding of and/or compete for binding with an anti-MS4A4A antibody comprising (a) a $V_H$ domain comprising (i) HVR-H1 comprising the amino acid sequence of SEQ ID NO: 108, (ii) HVR-H2 comprising an amino acid sequence selected from the group consisting of SEQ ID NOs: 110 and 111, and (iii) HVR-H3 comprising the amino acid sequence of SEQ ID NO: 112, and (b) a $V_L$ domain comprising (i) HVR-L1 comprising the amino acid sequence of SEQ ID NO: 113, (ii) HVR-L2 comprising the amino acid sequence of SEQ ID NO: 114, and (iii) HVR-L3 comprising the amino acid sequence of SEQ ID NO: 115. In some embodiments, the antibody comprises the $V_H$ and $V_L$ sequences in SEQ ID NOs: 24-30 and SEQ ID NOs: 32-36, respectively.

Provided herein are anti-MS4A4A antibodies which bind to an epitope of human MS4A4A that is the same as or overlaps with the epitope bound by an anti-MS4A4A antibody comprising (a) a $V_H$ domain comprising (i) HVR-H1 comprising the amino acid sequence of SEQ ID NO: 108, (ii) HVR-H2 comprising an amino acid sequence selected from the group consisting of SEQ ID NOs: 110 and 111, and (iii) HVR-H3 comprising the amino acid sequence of SEQ ID NO: 112, and (b) a $V_L$ domain comprising (i) HVR-L1 comprising the amino acid sequence of SEQ ID NO: 113, (ii) HVR-L2 comprising the amino acid sequence of SEQ ID NO: 114, and (iii) HVR-L3 comprising the amino acid sequence of SEQ ID NO: 115. In some embodiments, the antibody comprises the $V_H$ and $V_L$ sequences in SEQ ID NOs: 24-30 and SEQ ID NOs: 32-36, respectively. In some embodiments, the epitope of human MS4A4A is the same epitope as bound by an anti-MS4A4A antibody.

Further provided herein are anti-MS4A4A antibodies which competitively inhibit binding of and/or compete for binding with an anti-MS4A4A antibody comprising (a) a $V_H$ domain comprising (i) HVR-H1 comprising the amino acid sequence of SEQ ID NO: 116, (ii) HVR-H2 comprising an amino acid sequence selected from the group consisting of SEQ ID NOs: 118, 119, 120, 121, and 122, and (iii) HVR-H3 comprising an amino acid sequence selected from the group consisting of SEQ ID NOs: 123, 124, 125, 126, 127, 128, and 129, and (b) a $V_L$ domain comprising (i) HVR-L1 comprising an amino acid sequence selected from the group consisting of SEQ ID NOs: 130, 131, 132, 133, 134, 135, 136, 137, and 138, (ii) HVR-L2 comprising an amino acid sequence selected from the group consisting of SEQ ID NOs: 139, 140, 141, 142, and 143, and (iii) HVR-L3 comprising an amino acid sequence selected from the group consisting of SEQ ID NOs: 144 and 145. In some embodiments, the antibody comprises the $V_H$ and $V_L$ sequences in SEQ ID NOs: 40-53 and SEQ ID NOs: 55-74, respectively.

Provided herein are anti-MS4A4A antibodies which bind to an epitope of human MS4A4A that is the same as or overlaps with the epitope bound by an anti-MS4A4A antibody comprising (a) a $V_H$ domain comprising (i) HVR-H1 comprising the amino acid sequence of SEQ ID NO: 116, (ii) HVR-H2 comprising an amino acid sequence selected from the group consisting of SEQ ID NOs: 118, 119, 120, 121, and 122, and (iii) HVR-H3 comprising an amino acid sequence selected from the group consisting of SEQ ID NOs: 123, 124, 125, 126, 127, 128, and 129, and (b) a $V_L$ domain comprising (i) HVR-L 1 comprising an amino acid sequence selected from the group consisting of SEQ ID NOs: 130, 131, 132, 133, 134, 135, 136, 137, and 138, (ii) HVR-L2 comprising an amino acid sequence selected from the group consisting of SEQ ID NOs: 139, 140, 141, 142, and 143, and (iii) HVR-L3 comprising an amino acid sequence selected from the group consisting of SEQ ID NOs: 144 and 145. In some embodiments, the antibody comprises the $V_H$ and $V_L$ sequences in SEQ ID NOs: 40-53 and SEQ ID NOs: 55-74, respectively. In some embodiments, the epitope of human MS4A4A is the same epitope as bound by an anti-MS4A4A antibody.

Further provided herein are anti-MS4A4A antibodies which competitively inhibit binding of and/or compete for binding with an anti-MS4A4A antibody comprising (a) a $V_H$ domain comprising (i) HVR-H1 comprising an amino acid sequence selected from the group consisting of SEQ ID NOs: 146 and 147, (ii) HVR-H2 comprising an amino acid sequence selected from the group consisting of SEQ ID NOs: 149, 150, 151, 152, and 153, and (iii) HVR-H3 comprising the amino acid sequence of SEQ ID NO: 154, and (b) a $V_L$ domain comprising (i) HVR-L1 comprising an amino acid sequence selected from the group consisting of SEQ ID NOs: 156, 157, and 158, (ii) HVR-L2 comprising an amino acid sequence selected from the group consisting of SEQ ID NOs: 160 and 161, and (iii) HVR-L3 comprising the amino acid sequence of SEQ ID NO: 163. In some embodiments, the antibody comprises the $V_H$ and $V_L$ sequences in SEQ ID NOs: 76-84 and SEQ ID NOs: 86-93, respectively.

Provided herein are anti-MS4A4A antibodies which bind to an epitope of human MS4A4A that is the same as or overlaps with the epitope bound by an anti-MS4A4A antibody comprising (a) a $V_H$ domain comprising (i) HVR-H1 comprising an amino acid sequence selected from the group consisting of SEQ ID NOs: 146 and 147, (ii) HVR-H2 comprising an amino acid sequence selected from the group consisting of SEQ ID NOs: 149, 150, 151, 152, and 153, and (iii) HVR-H3 comprising the amino acid sequence of SEQ ID NO: 154, and (b) a $V_L$ domain comprising (i) HVR-L1 comprising an amino acid sequence selected from the group consisting of SEQ ID NOs: 156, 157 and 158, (ii) HVR-L2 comprising an amino acid sequence selected from the group consisting of SEQ ID NOs: 160 and 161, and (iii) HVR-L3 comprising the amino acid sequence of SEQ ID NO: 163. In some embodiments, the antibody comprises the $V_H$ and $V_L$ sequences in SEQ ID NOs: 76-84 and SEQ ID Nos:86-93, respectively. In some embodiments, the epitope of human MS4A4A is the same epitope as bound by an anti-MS4A4A antibody.

In some embodiments, the anti-MS4A4A antibody according to any of the above embodiments is a monoclonal antibody, including a humanized and/or human antibody. In some embodiments, the anti-MS4A4A antibody is an antibody fragment, e.g., a Fv, Fab, Fab', scFv, diabody, or F(ab')2 fragment. In some embodiments, the anti-MS4A4A antibody is a substantially full-length antibody, e.g., an IgG1 antibody, IgG2a antibody or other antibody class or isotype as defined herein.

In some embodiments, an anti-MS4A4A antibody according to any of the above embodiments may incorporate any of the features, singly or in combination, as described in Sections 1-7 below:

(1) Anti-MS4A4A Antibody Binding Affinity

In some embodiments of any of the antibodies provided herein, the antibody has a dissociation constant (Kd) of <1 μM, <100 nM, <10 nM, <1 nM, <0.1 nM, <0.01 nM, or <0.001 nM (e.g., 10-8 M or less, e.g., from $10^{-8}$ M to $10^{-13}$ M, e.g., from $10^{-9}$ M to $10^{-13}$ M). Dissociation constants may be determined through any analytical technique, including any biochemical or biophysical technique such as ELISA, surface plasmon resonance (SPR), bio-layer interferometry (see, e.g., Octet System by ForteBio), isothermal titration calorimetry (ITC), differential scanning calorimetry (DSC), circular dichroism (CD), stopped-flow analysis, and colorimetric or fluorescent protein melting analyses. In one embodiment, Kd is measured by a radiolabeled antigen binding assay (RIA). In some embodiment, an RIA is performed with the Fab version of an antibody of interest and its antigen, for example as described in Chen et al. *J. Mol. Biol.* 293:865-881(1999)). In some embodiments, Kd is measured using a BIACORE surface plasmon resonance assay, for example, an assay using a BIACORE-2000 or a BIACORE-3000 (BIAcore, Inc., Piscataway, NJ) is performed at 25° C. with immobilized antigen CMS chips at −10 response units (RU). In some embodiments, the KD is determined using a monovalent antibody (e.g., a Fab) or a full-length antibody. In some embodiments, the KD is determined using a full-length antibody in a monovalent form.

(2) Antibody Fragments

In some embodiments of any of the antibodies provided herein, the antibody is an antibody fragment. Antibody fragments include, but are not limited to, Fab, Fab', Fab'-SH, F(ab')2, Fv, and scFv fragments, and other fragments described below. For a review of certain antibody fragments, see Hudson et al. *Nat. Med.* 9:129-134 (2003). For a review of scFv fragments, see, e.g., WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP404097; WO 1993/01161; Hudson et al. *Nat. Med.* 9:129-134 (2003). Triabodies and tetrabodies are also described in Hudson et al. *Nat. Med.* 9:129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (see, e.g., U.S. Pat. No. 6,248,516).

Antibody fragments can be made by various techniques, including but not limited to proteolytic digestion of an intact antibody as well as production by recombinant host cells (e.g., *E. coli* or phage), as described herein.

(3) Chimeric and Humanized Antibodies

In some embodiments of any of the antibodies provided herein, the antibody is a chimeric antibody. Certain chimeric antibodies are described, e.g., in U.S. Pat. No. 4,816,567. In one example, a chimeric antibody comprises a non-human variable region (e.g., a variable region derived from a mouse, rat, hamster, rabbit, or non-human primate, such as a monkey) and a human constant region. In a further example, a chimeric antibody is a “class switched” antibody in which the class or subclass has been changed from that of the parent antibody. Chimeric antibodies include antigen-binding fragments thereof.

In some embodiments of any of the antibodies provided herein, the antibody is a humanized antibody. Typically, a non-human antibody is humanized to reduce immunogenicity to humans, while retaining the specificity and affinity of the parental non-human antibody. In certain embodiments, a humanized antibody is substantially non-immunogenic in humans. In certain embodiments, a humanized antibody has substantially the same affinity for a target as an antibody from another species from which the humanized antibody is derived. See, e.g., U.S. Pat. Nos. 5,530,101, 5,693,761; 5,693,762; and 5,585,089. In certain embodiments, amino acids of an antibody variable domain that can be modified without diminishing the native affinity of the antigen binding domain while reducing its immunogenicity are identified. See, e.g., U.S. Pat. Nos. 5,766,886 and 5,869,619. Generally, a humanized antibody comprises one or more variable domains in which HVRs (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), for example, to restore or improve antibody specificity or affinity.

Humanized antibodies and methods of making them are reviewed, for example, in Almagro et al. *Front. Biosci.* 13:161 9-1633 (2008), and are further described, e.g., in U.S. Pat. Nos. 5,821,337, 7,527,791, 6,982,321, and 7,087,409. Human framework regions that may be used for humanization include but are not limited to: framework regions selected using the “best-fit” method (see, e.g., Sims et al. *J. Immunol.* 151:2296 (1993)); framework regions derived from the consensus sequence of human antibodies of a particular subgroup of light or heavy chain variable regions (see, e.g., Carter et al. Proc. *Natl. Acad. Sci. USA* 89:4285 (1992); and Presta et al., *J. Immunol.* 151:2623 (1993)); human mature (somatically mutated) framework regions or human germline framework regions (see, e.g., Almagro and Fransson *Front. Biosci.* 13:1619-1633 (2008)); and framework regions derived from screening FR libraries (see, e.g., Baca et al. *J. Biol. Chem.* 272:10678-10684 (1997) and Rosok et al. *J. Biol. Chem.* 271:22611-22618 (1996)).

(4) Human Antibodies

In some embodiments of any of the antibodies provided herein, the antibody is a human antibody. Human antibodies can be produced using various techniques known in the art. Human antibodies are described generally in van Dijk et al. *Curr. Opin. Pharmacol.* 5:368-74 (2001) and Lonberg *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. One can engineer mouse strains deficient in mouse antibody production with large fragments of the human Ig loci in anticipation that such mice would produce human antibodies in the absence of mouse antibodies. Large human Ig fragments can preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains can yield high affinity fully human antibodies against any antigen of interest, including human antigens. Using the hybridoma technology, antigen-specific human MAbs with the desired specificity can be produced and selected. Certain exemplary methods are described in U.S. Pat. No. 5,545,807, EP 546073, and EP 546073. See also, for example, U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology. Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol. 133:3001 (1984) and Boerner et al. J. Immunol. 147:86 (1991)). Human antibodies generated via human B-cell hybridoma technology are also described in Li et al. Proc. Natl. Acad. Sci. USA, 1 03:3557-3562 (2006). Additional methods include those described, for example, in U.S. Pat. No. 7,189,826 (describing production of monoclonal human IgM antibodies from hybridoma cell lines). Human hybridoma technology (Trioma technology) is also described in Vollmers et al. Histology and Histopathology 20(3):927-937 (2005) and Vollmers et al. Methods and Findings in Experimental and Clinical Pharmacology 27(3): 185-91 (2005). Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

In some embodiments of any of the antibodies provided herein, the antibody is a human antibody isolated by in vitro methods and/or screening combinatorial libraries for antibodies with the desired activity or activities. Suitable examples include but are not limited to phage display (CAT, Morphosys, Dyax, Biosite/Medarex, Xoma, Symphogen, Alexion (formerly Proliferon), Affimed) ribosome display (CAT), yeast display (Adimab), and the like. In certain phage display methods, repertoires of $V_H$ and $V_L$ genes are separately cloned by polymerase chain reaction (PCR) and recombined randomly in phage libraries, which can then be screened for antigen-binding phage as described in Winter et al. *Ann. Rev. Immunol.* 12: 433-455 (1994). For example, a variety of methods are known in the art for generating phage display libraries and screening such libraries for antibodies possessing the desired binding characteristics. See also Sidhu et al. *J. Mol. Biol.* 338(2): 299-310, 2004; Lee et al. *J. Mol. Biol.* 340(5): 1073-1093, 2004; Fellouse *Proc. Natl. Acad. Sci. USA* 101(34):12467-12472 (2004); and Lee et al. *J. Immunol. Methods* 284(–2):1 19-132 (2004). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naïve repertoire can be cloned (e.g., from human) to provide a single source of antibodies to a wide range of non-self and also self-antigens without any immunization as described by Griffiths et al. EMBO J. 12: 725-734 (1993). Finally, naïve libraries can also be made synthetically by cloning unrearranged V-gene segments from stem cells, and using PCR primers comprising random sequence to encode the highly variable HVR3 regions and to accomplish rearrangement in vitro, as described by Hoogenboom et al. *J. Mol. Biol.,* 227: 381-388, 1992. Patent publications describing human antibody phage libraries include, for example: U.S. Pat. No. 5,750,373, and US Patent Publication Nos. 2007/0292936 and 2009/0002360. Antibodies isolated from human antibody libraries are considered human antibodies or human antibody fragments herein.

(5) Constant Regions Including Fc Regions

In some embodiments of any of the antibodies provided herein, the antibody comprises an Fc. In some embodiments, the Fc is a human IgG1, IgG2, IgG3, and/or IgG4 isotype. In some embodiments, the antibody is of the IgG class, the IgM class, or the IgA class.

In certain embodiments of any of the antibodies provided herein, the antibody has an IgG2 isotype. In some embodiments, the antibody contains a human IgG2 constant region. In some embodiments, the human IgG2 constant region includes an Fc region. In some embodiments, the antibody induces the one or more MS4A4A activities or independently of binding to an Fc receptor. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has an IgG1 isotype. In some embodiments, the antibody contains a mouse IgG1 constant region. In some embodiments, the antibody contains a human IgG1 constant region. In some embodiments, the human IgG1 constant region includes an Fc region. In some embodiments, a human IgG1 light chain constant region comprises the amino acid sequence of SEQ ID NO: 344. In some embodiments, the antibody binds an inhibitory Fc receptor. In certain embodiments, the inhibitory Fc receptor is inhibitory Fc-gamma receptor IIB (FcyIIB).

In certain embodiments of any of the antibodies provided herein, the antibody has an IgG4 isotype. In some embodiments, the antibody contains a human IgG4 constant region. In some embodiments, the human IgG4 constant region includes an Fc region. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has a hybrid IgG2/4 isotype. In some embodiments, the antibody includes an amino acid sequence comprising amino acids 118 to 260 according to EU numbering of human IgG2 and amino acids 261-447 according to EU numbering of human IgG4 (WO 1997/11971; WO 2007/106585).

In some embodiments, the Fc region increases clustering without activating complement as compared to a corresponding antibody comprising an Fc region that does not comprise the amino acid substitutions. In some embodiments, the antibody induces one or more activities of a target specifically bound by the antibody. In some embodiments, the antibody binds to MS4A4A.

It may also be desirable to modify an anti-MS4A4A antibody of the present disclosure to modify effector function and/or to increase serum half-life of the antibody. For example, the Fc receptor binding site on the constant region may be modified or mutated to remove or reduce binding affinity to certain Fc receptors, such as FcγRI, FcγRII, and/or FcγRIII to reduce Antibody-dependent cell-mediated cytotoxicity. In some embodiments, the effector function is impaired by removing N-glycosylation of the Fc region (e.g., in the $C_H2$ domain of IgG) of the antibody. In some embodiments, the effector function is impaired by modifying regions such as 233-236, 297, and/or 327-331 of human IgG as described in WO 99/58572 and Armour et al. *Molecular Immunology* 40: 585-593 (2003); Reddy et al. *J. Immunology* 164:1925-1933 (2000). In other embodiments, it may also be desirable to modify an anti-MS4A4A antibody of the present disclosure to modify effector function to increase finding selectivity toward the ITIM-containing FcgRIIb (CD32b) to increase clustering of MS4A4A antibodies on adjacent cells without activating humoral responses including Antibody-dependent cell-mediated cytotoxicity and antibody-dependent cellular phagocytosis.

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule. Other amino acid sequence modifications.

(6) Multispecific Antibodies

Multispecific are antibodies that have binding specificities for at least two different epitopes, including those on the same or another polypeptide (e.g., one or more MS4A4A polypeptides of the present disclosure). In some embodiments, the multispecific antibody can be a bispecific antibody. In some embodiments, the multispecific antibody can be a trispecific antibody. In some embodiments, the multispecific antibody can be a tetraspecific antibody. Such antibodies can be derived from full-length antibodies or antibody fragments (e.g., F(ab') 2 bispecific antibodies). In some embodiments, the multispecific antibody comprises a first antigen binding region which binds to first site on MS4A4A and comprises a second antigen binding region which binds to a second site on MS4A4A. In some embodiment, the multispecific antibodies comprises a first antigen binding region which binds to MS4A4A and a second antigen binding region that binds to a second polypeptide.

Provided herein are multispecific antibodies comprises a first antigen binding region, wherein the first antigen binding region comprises the six HVRs of an antibody described herein, which binds to MS4A4A and a second antigen binding region that binds to a second polypeptide. In some embodiments, the first antigen binding region comprises the $V_H$ or $V_L$ of an antibody described herein.

In some embodiments of any of the multispecific antibodies, the second polypeptide is a) an antigen facilitating transport across the blood-brain-barrier; (b) an antigen facilitating transport across the blood-brain-barrier selected from transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, and ANG1005; (c) a disease-causing protein selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; (d) ligands and/or proteins expressed on immune cells, wherein the ligands and/or proteins selected from CD40, OX40, ICOS, CD28, CD137/4-1BB, CD27, GITR, PD-L1, CTLA-4, PD-L2, PD-1, B7-H3, B7-H4, HVEM, BTLA, KIR, GALS, TIM3, A2AR, LAG-3, and phosphatidylserine; and/or (e) a protein, lipid, polysaccharide, or glycolipid expressed on one or more tumor cells and any combination thereof.

Numerous antigens are known in the art that facilitate transport across the blood-brain barrier (see, e.g., Gabathuler R. *Neurobiol. Dis.* 37:48-57 (2010)). Such second antigens include, without limitation, transferrin receptor (TR), insulin receptor (HIR), Insulin-like growth factor receptor (IGFR), low-density lipoprotein receptor related proteins 1 and 2 (LPR-1 and 2), diphtheria toxin receptor, including CRM197 (a non-toxic mutant of diphtheria toxin), llama single domain antibodies such as TMEM 30(A) (Flippase), protein transduction domains such as TAT, Syn-B, or penetratin, poly-arginine or generally positively charged peptides, Angiopep peptides such as ANG1005 (see, e.g., Gabathuler, 2010), and other cell surface proteins that are enriched on blood-brain barrier endothelial cells (see, e.g., Daneman et al. *PLoS One* 5(10):e13741 (2010)).

The multivalent antibodies may recognize the MS4A4A antigen as well as without limitation additional antigens AP peptide, antigen or an α-synuclein protein antigen or, Tau protein antigen or, TDP-43 protein antigen or, prion protein antigen or, huntingtin protein antigen, or RAN, translation Products antigen, including the DiPeptide Repeats, (DPRs peptides) composed of glycine-alanine (GA), glycine-proline (GP), glycine-arginine (GR), proline-alanine (PA), or proline-arginine (PR), Insulin receptor, insulin like growth factor receptor. Transferrin receptor or any other antigen that facilitate antibody transfer across the blood brain barrier. In some embodiments, the second polypeptide is transferrin. In some embodiments, the second polypeptide is Tau. In some embodiments, the second polypeptide is AP. In some embodiments, the second polypeptide is TREM2. In some embodiments, the second polypeptide is α-synuclein.

The multivalent antibody contains at least one polypeptide chain (and preferably two polypeptide chains), wherein the polypeptide chain or chains comprise two or more variable domains. For instance, the polypeptide chain or chains may comprise VD1-$(X1)_n$-VD2-$(X2)_n$-Fc, wherein VD1 is a first variable domain, VD2 is a second variable domain, Fc is one polypeptide chain of an Fc region, X1 and X2 represent an amino acid or polypeptide, and n is 0 or 1. Similarly, the polypeptide chain or chains may comprise $V_H$-$C_H1$-flexible linker-$V_H$-$C_H1$-Fc region chain; or $V_H$-$C_H1$-$V_H$-$C_H1$-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Techniques for making multispecific antibodies include, but are not limited to, recombinant co-expression of two immunoglobulin heavy chain-light chain pairs having different specificities (see Milstein and Cuello *Nature* 305: 537 (1983), WO 93/08829, and Traunecker et al. *EMBO J.* 10:3655 (1991)), and "knob-in-hole" engineering (see, e.g., U.S. Pat. No. 5,731,168). See also WO 2013/026833 (CrossMab). Multi-specific antibodies may also be made by engineering electrostatic steering effects for making antibody Fc-heterodimeric molecules (WO 2009/089004A1); cross-linking two or more antibodies (see, e.g., U.S. Pat. No. 4,676,980); using leucine; using "diabody" technology for making bispecific antibody fragments (see, e.g., Hollinger et al. *Proc. Natl. Acad. Sci. USA* 90:6444-6448 (1993)); and using single-chain Fv (scFv) dimers (see, e.g., Gruber et al. *J. Immunol.* 152:5368 (1994)); and preparing trispecific antibodies as described, e.g., in Tutt et al. *J. Immunol.* 147: 60 (1991).

Engineered antibodies with three or more functional antigen binding sites, including “Octopus antibodies,” are also included herein (see, e.g., US 2006/0025576). The antibody herein also includes a “Dual Acting FAb” or “DAF” comprising an antigen binding site that binds to multiple MS4A4A (see, US 2008/0069820, for example).

(7) Antibody Variants

In some embodiments of any of the antibodies provided herein, amino acid sequence variants of the antibodies are contemplated. For example, it may be desirable to improve the binding affinity and/or other biological properties of the antibody.

(i) Substitution, Insertion, and Deletion Variants

In some embodiments of any of the antibodies provided herein, antibody variants having one or more amino acid substitutions are provided. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody.

TABLE A

Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Agr; Gln; Asn | Arg |
| Met (M) | Leu; Phe; Ile | Leu |
| Phe (F) | Leu; Val; Ile; Ala; Tyr | Tyr |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro; and
(6) aromatic: Trp, Tyr, Phe.

For example, non-conservative substitutions can involve the exchange of a member of one of these classes for a member from another class. Such substituted residues can be introduced, for example, into regions of a human antibody that are homologous with non-human antibodies, or into the non-homologous regions of the molecule.

In making changes to the polypeptide or antibody described herein, according to certain embodiments, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al. *J. Mol. Biol.,* 157:105-131 (1982). It is known that certain amino acids can be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0±1); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One can also identify epitopes from primary amino acid sequences on the basis of hydrophilicity. These regions are also referred to as “epitopic core regions”.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant $V_H$ and $V_L$ sequences provided above, each HVR either is unaltered, or contains no more than one, two or three amino acid substitutions.

Amino acid sequence insertions include amino- and/or carboxyl-terminal fusions ranging in length from one residue to polypeptides comprising a hundred or more residues, as well as intrasequence insertions of single or multiple amino acid residues. Examples of terminal insertions include an antibody with an N-terminal methionyl residue.

Other insertional variants of the antibody molecule include the fusion to the N- or C-terminus of the antibody to an enzyme (e.g., for ADEPT) or a polypeptide which increases the serum half-life of the antibody.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment, such as an Fv fragment).

(ii) Glycosylation Variants

In some embodiments of any of the antibodies provided herein, the antibody is altered to increase or decrease the extent to which the antibody is glycosylated. Addition or deletion of glycosylation sites to an antibody may be conveniently accomplished by altering the amino acid sequence such that one or more glycosylation sites is created or removed.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. Native antibodies produced by mammalian cells typically comprise a branched, biantennary oligosaccharide that is generally attached by an N-linkage to Asn297 according to Kabat numbering of the $C_H2$ domain of the Fc region. The oligosaccharide may include various carbohydrates, for example, mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the disclosure may be made in order to create antibody variants with certain improved properties.

In one embodiment, antibody variants are provided having a carbohydrate structure that lacks fucose attached (directly or indirectly) to an Fc region. See, e.g., US Patent Publication Nos. 2003/0157108 and 2004/0093621. Examples of publications related to "defucosylated" or "fucose-deficient" antibody variants include: US 2003/0157108; US 2003/0115614; US 2002/0164328; US 2004/0093621; US 2004/0132140; US 2004/0110704; US 2004/0110282; US 2004/0109865; Okazaki et al. *J. Mol. Biol.* 336:1239-1249 (2004); Yamane-Ohnuki et al. *Biotech. Bioeng.* 87:614 (2004). Examples of cell lines capable of producing defucosylated antibodies include Led 3 CHO cells deficient in protein fucosylation (Ripka et al. *Arch. Biochem. Biophys.* 249:533-545 (1986); US 2003/0157108), and knockout cell lines, such as alpha-1,6-fucosyltransferase gene, FUT8, knockout CHO cells (see, e.g., Yamane-Ohnuki et al. *Biotech. Bioeng.* 87: 614 (2004) and Kanda et al. *Biotechnol. Bioeng.* 94(4):680-688 (2006)).

(iii) Modified Constant Regions

In some embodiments of any of the antibodies provided herein, the antibody Fc is an antibody Fc isotypes and/or modification. In some embodiments, the antibody Fc isotype and/or modification is capable of binding to Fc gamma receptor.

In some embodiments of any of the antibodies provided herein, the modified antibody Fc is an IgG1 modified Fc. In some embodiments, the IgG1 modified Fc comprises one or more modifications. For example, in some embodiments, the IgG1 modified Fc comprises one or more amino acid substitutions (e.g., relative to a wild-type Fc region of the same isotype). In some embodiments, the one or more amino acid substitutions are selected from N297A (Bolt S et al. (1993) *Eur J Immunol* 23:403-411), D265A (Shields et al. (2001) *R. J. Biol. Chem.* 276, 6591-6604), L234A, L235A (Hutchins et al. (1995) *Proc Natl Acad Sci USA,* 92:11980-11984; Alegre et al., (1994) *Transplantation* 57:1537-1543. 31; Xu et al., (2000) *Cell Immunol,* 200:16-26), G237A (Alegre et al. (1994) *Transplantation* 57:1537-1543. 31; Xu et al. (2000) *Cell Immunol,* 200:16-26), C226S, C229S, E233P, L234V, L234F, L235E (McEarchern et al., (2007) *Blood,* 109:1185-1192), P331S (Sazinsky et al., (2008) *Proc Natl Acad Sci USA* 2008, 105:20167-20172), S267E, L328F, A330L, M252Y, S254T, and/or T256E, where the amino acid position is according to the EU numbering convention.

In some embodiments of any of the IgG1 modified Fc, the Fc comprises N297A mutation according to EU numbering. In some embodiments of any of the IgG1 modified Fc, the Fc comprises D265A and N297A mutations according to EU numbering. In some embodiments of any of the IgG1 modified Fc, the Fc comprises N297A mutation according to EU numbering. In some embodiments of any of the IgG1 modified Fc, the Fc comprises K322A mutation according to EU numbering. In some embodiments of any of the IgG1 modified Fc, the Fc comprises N297A mutation according to EU numbering. In some embodiments of any of the IgG1 modified Fc, the Fc comprises P331S mutation according to EU numbering. In some embodiments of any of the IgG1 modified Fc, the Fc comprises D270A mutations according to EU numbering. In some embodiments, the IgG1 modified Fc comprises L234A and L235A mutations according to EU numbering. In some embodiments of any of the IgG1 modified Fc, the Fc comprises L234A and G237A mutations according to EU numbering. In some embodiments of any of the IgG1 modified Fc, the Fc comprises L234A, L235A and G237A mutations according to EU numbering. In some embodiments of any of the IgG1 modified Fc, the Fc comprises one or more (including all) of P238D, L328E, E233, G237D, H268D, P271G and A330R mutations according to EU numbering. In some embodiments of any of the IgG1 modified Fc, the Fc comprises one or more of S267E/L328F mutations according to EU numbering. In some embodiments of any of the IgG1 modified Fc, the Fc comprises the N325S and L328F mutations according to EU numbering (N325S/L328F). In some embodiments of any of the IgG1 modified Fc, the Fc comprises P238D, L328E, E233D, G237D, H268D, P271G and A330R mutations according to EU numbering. In some embodiments of any of the IgG1 modified Fc, the Fc comprises P238D, L328E, G237D, H268D, P271G and A330R mutations according to EU numbering. In some embodiments of any of the IgG1 modified Fc, the Fc comprises P238D, S267E, L328E, E233D, G237D, H268D, P271G and A330R mutations according to EU numbering. In some embodiments of any of the IgG1 modified Fc, the Fc comprises P238D, S267E, L328E, G237D, H268D, P271G and A330R mutations according to EU numbering. In some embodiments of any of the IgG1 modified Fc, the Fc comprises C226S, C229S, E233P, L234V, and L235A mutations according to EU numbering. In some embodiments of any of the IgG1 modified Fc, the Fc comprises L234F, L235E, and P331S mutations according to EU numbering. In some embodiments of any of the IgG1 modified Fc, the Fc comprises S267E and L328F mutations according to EU numbering. In some embodiments of any of the IgG1 modified Fc, the Fc comprises S267E mutations according to EU numbering. In some embodiments of any of the IgG1 modified Fc, the Fc comprises a substitute of the constant heavy 1 ($C_H1$) and hinge region of IgG1 with $C_H1$ and hinge region of IgG2 (amino acids 118-230 of IgG2 according to EU numbering) with a Kappa light chain.

In some embodiments of any of the IgG1 modified Fc, the Fc includes two or more amino acid substitutions that increase antibody clustering without activating complement as compared to a corresponding antibody having an Fc region that does not include the two or more amino acid substitutions. Accordingly, in some embodiments of any of the IgG1 modified Fc, the IgG1 modified Fc is an antibody comprising an Fc region, where the antibody comprises an amino acid substitution at position E430G and one or more amino acid substitutions in the Fc region at a residue position selected from: L234F, L235A, L235E, S267E, K322A, L328F, A330S, P331S, and any combination thereof according to EU numbering. In some embodiments, the IgG1 modified Fc comprises an amino acid substitution at positions E430G, L234A, L235A, and P331S according to EU numbering. In some embodiments, the IgG1 modified Fc comprises an amino acid substitution at positions L234A, L235A, and P331S according to EU numbering. In some embodiments, the IgG1 modified Fc comprises an amino acid substitution at positions E430G and P331S according to EU numbering. In some embodiments, the IgG1 modified Fc comprises an amino acid substitution at positions E430G and K322A according to EU numbering. In some embodiments, the IgG1 modified Fc comprises an amino acid substitution at positions E430G, A330S, and P331S according to EU numbering. In some embodiments, the IgG1 modified Fc comprises an amino acid substitution at positions E430G, K322A, A330S, and P331S according to EU numbering. In some embodiments, the IgG1 modified Fc comprises an amino acid substitution at positions E430G, K322A, and A330S according to EU numbering. In some embodiments, the IgG1 modified Fc comprises an amino acid substitution at positions E430G, K322A, and P331S according to EU numbering.

In some embodiments of any of the IgG1 modified Fc, the IgG1 modified Fc may further comprise herein may be combined with an A330L mutation (Lazar et al. Proc Natl Acad Sci USA, 103:4005-4010 (2006)), or one or more of L234F, L235E, and/or P331S mutations (Sazinsky et al. Proc Natl Acad Sci USA, 105:20167-20172 (2008)), according to the EU numbering convention, to eliminate complement activation. In some embodiments of any of the IgG1 modified Fc, the IgG1 modified Fc may further comprise one or more of A330L, A330S, L234F, L235E, and/or P331S according to EU numbering. In some embodiments of any of the IgG1 modified Fc, the IgG1 modified Fc may further comprise one or more mutations to enhance the antibody half-life in human serum (e.g., one or more (including all) of M252Y, S254T, and T256E mutations according to the EU numbering convention). In some embodiments of any of the IgG1 modified Fc, the IgG1 modified Fc may further comprise one or more of E430G, E430S, E430F, E430T, E345K, E345Q, E345R, E345Y, S440Y, and/or S440W according to EU numbering.

Other aspects of the present disclosure relate to antibodies having modified constant regions (i.e., Fc regions). An antibody dependent on binding to FcgR receptor to activate targeted receptors may lose its agonist activity if engineered to eliminate FcgR binding (see, e.g., Wilson et al. *Cancer Cell* 19:101-113 (2011); Armour at al. *Immunology* 40:585-593 (2003); and White et al. *Cancer Cell* 27:138-148 (2015)). As such, it is thought that an anti-MS4A4A antibody of the present disclosure with the correct epitope specificity can activate the target antigen, with minimal adverse effects, when the antibody has an Fc domain from a human IgG2 isotype (CHI and hinge region) or another type of Fc domain that is capable of preferentially binding the inhibitory FcgRIIB r receptors, or a variation thereof.

In some embodiments of any of the antibodies provided herein, the modified antibody Fc is an IgG2 modified Fc. In some embodiments, the IgG2 modified Fc comprises one or more modifications. For example, in some embodiments, the IgG2 modified Fc comprises one or more amino acid substitutions (e.g., relative to a wild-type Fc region of the same isotype). In some embodiments of any of the IgG2 modified Fc, the one or more amino acid substitutions are selected from V234A (Alegre et al. *Transplantation* 57:1537-1543 (1994); Xu et al. *Cell Immunol,* 200:16-26 (2000)); G237A (Cole et al. *Transplantation,* 68:563-571 (1999)); H268Q, V309L, A330S, P331S (US 2007/0148167; Armour et al. *Eur J Immunol* 29: 2613-2624 (1999); Armour et al. *The Haematology Journal* 1(Suppl.1):27 (2000); Armour et al. *The Haematology Journal* 1(Suppl.1):27 (2000)), C219S, and/or C220S (White et al. *Cancer Cell* 27, 138-148 (2015)); S267E, L328F (Chu et al. *Mol Immunol,* 45:3926-3933 (2008)); and M252Y, S254T, and/or T256E according to the EU numbering convention. In some embodiments of any of the IgG2 modified Fc, the Fc comprises an amino acid substitution at positions V234A and G237A according to EU numbering. In some embodiments of any of the IgG2 modified Fc, the Fc comprises an amino acid substitution at positions C219S or C220S according to EU numbering. In some embodiments of any of the IgG2 modified Fc, the Fc comprises an amino acid substitution at positions A330S and P331S according to EU numbering. In some embodiments of any of the IgG2 modified Fc, the Fc comprises an amino acid substitution at positions S267E and L328F according to EU numbering.

In some embodiments of any of the IgG2 modified Fc, the Fc comprises a C127S amino acid substitution according to the EU numbering convention (White et al., (2015) *Cancer Cell* 27, 138-148; Lightle et al. *Protein Sci.* 19:753-762 (2010); and WO 2008/079246). In some embodiments of any of the IgG2 modified Fc, the antibody has an IgG2 isotype with a Kappa light chain constant domain that comprises a C214S amino acid substitution according to the EU numbering convention (White et al. *Cancer Cell* 27:138-148 (2015); Lightle et al. *Protein Sci.* 19:753-762 (2010); and WO 2008/079246).

In some embodiments of any of the IgG2 modified Fc, the Fc comprises a C220S amino acid substitution according to the EU numbering convention. In some embodiments of any of the IgG2 modified Fc, the antibody has an IgG2 isotype with a Kappa light chain constant domain that comprises a C214S amino acid substitution according to the EU numbering convention.

In some embodiments of any of the IgG2 modified Fc, the Fc comprises a C219S amino acid substitution according to the EU numbering convention. In some embodiments of any of the IgG2 modified Fc, the antibody has an IgG2 isotype with a Kappa light chain constant domain that comprises a C214S amino acid substitution according to the EU numbering convention.

In some embodiments of any of the IgG2 modified Fc, the Fc includes an IgG2 isotype heavy chain constant domain 1($C_H1$) and hinge region (White et al. *Cancer Cell* 27:138-148 (2015)). In certain embodiments of any of the IgG2 modified Fc, the IgG2 isotype $C_H1$ and hinge region comprise the amino acid sequence of 118-230 according to EU numbering. In some embodiments of any of the IgG2 modified Fc, the antibody Fc region comprises a S267E amino acid substitution, a L328F amino acid substitution, or both, and/or a N297A or N297Q amino acid substitution according to the EU numbering convention.

In some embodiments of any of the IgG2 modified Fc, the Fc further comprises one or more amino acid substitution at positions E430G, E430S, E430F, E430T, E345K, E345Q, E345R, E345Y, S440Y, and S440W according to EU numbering. In some embodiments of any of the IgG2 modified Fc, the Fc may further comprise one or more mutations to enhance the antibody half-life in human serum (e.g., one or more (including all) of M252Y, S254T, and T256E mutations according to the EU numbering convention). In some embodiments of any of the IgG2 modified Fc, the Fc may further comprise A330S and P331S.

In some embodiments of any of the IgG2 modified Fc, the Fc is an IgG2/4 hybrid Fc. In some embodiments, the IgG2/4 hybrid Fc comprises IgG2 aa 118 to 260 and IgG4 aa 261 to 447. In some embodiments of any IgG2 modified Fc, the Fc comprises one or more amino acid substitutions at positions H268Q, V309L, A330S, and P331S according to EU numbering.

In some embodiments of any of the IgG1 and/or IgG2 modified Fc, the Fc comprises one or more additional amino acid substitutions selected from A330L, L234F; L235E, or P331S according to EU numbering; and any combination thereof.

In certain embodiments of any of the IgG1 and/or IgG2 modified Fc, the Fc comprises one or more amino acid substitutions at a residue position selected from C127S, L234A, L234F, L235A, L235E, S267E, K322A, L328F, A330S, P331S, E345R, E430G, S440Y, and any combination thereof according to EU numbering. In some embodiments of any of the IgG1 and/or IgG2 modified Fc, the Fc comprises an amino acid substitution at positions E430G, L243A, L235A, and P331S according to EU numbering. In some embodiments of any of the IgG1 and/or IgG2 modified Fc, the Fc comprises an amino acid substitution at positions E430G and P331S according to EU numbering. In some embodiments of any of the IgG1 and/or IgG2 modified Fc, the Fc comprises an amino acid substitution at positions E430G and K322A according to EU numbering. In some embodiments of any of the IgG1 and/or IgG2 modified Fc, the Fc comprises an amino acid substitution at positions E430G, A330S, and P331S according to EU numbering. In some embodiments of any of the IgG1 and/or IgG2 modified Fc, the Fc comprises an amino acid substitution at positions E430G, K322A, A330S, and P331S according to EU numbering. In some embodiments of any of the IgG1 and/or IgG2 modified Fc, the Fc comprises an amino acid substitution at positions E430G, K322A, and A330S according to EU numbering. In some embodiments of any of the IgG1 and/or IgG2 modified Fc, the Fc comprises an amino acid substitution at positions E430G, K322A, and P331S according to EU numbering. In some embodiments of any of the IgG1 and/or IgG2 modified Fc, the Fc comprises an amino acid substitution at positions S267E and L328F according to EU numbering. In some embodiments of any of the IgG1 and/or IgG2 modified Fc, the Fc comprises an amino acid substitution at position C127S according to EU numbering. In some embodiments of any of the IgG1 and/or IgG2 modified Fc, the Fc comprises an amino acid substitution at positions E345R, E430G and S440Y according to EU numbering.

In some embodiments of any of the antibodies provided herein, the modified antibody Fc is an IgG4 modified Fc. In some embodiments, the IgG4 modified Fc comprises one or more modifications. For example, in some embodiments, the IgG4 modified Fc comprises one or more amino acid substitutions (e.g., relative to a wild-type Fc region of the same isotype). In some embodiments of any of the IgG4 modified Fc, the one or more amino acid substitutions are selected from L235A, G237A, S229P, L236E (Reddy et al. *J Immunol* 164:1925-1933(2000)), S267E, E318A, L328F, M252Y, S254T, and/or T256E according to the EU numbering convention. In some embodiments of any of the IgG4 modified Fc, the Fc may further comprise L235A, G237A, and E318A according to the EU numbering convention. In some embodiments of any of the IgG4 modified Fc, the Fc may further comprise S228P and L235E according to the EU numbering convention. In some embodiments of any of the IgG4 modified Fc, the IgG4 modified Fc may further comprise S267E and L328F according to the EU numbering convention.

In some embodiments of any of the IgG4 modified Fc, the IgG4 modified Fc comprises may be combined with an S228P mutation according to the EU numbering convention (Angal et al. *Mol Immunol.* 30:105-108 (1993)) and/or with one or more mutations described in (Peters et al. *J Blot Chem.* 287(29):24525-33 (2012)) to enhance antibody stabilization.

In some embodiments of any of the IgG4 modified Fc, the IgG4 modified Fc may further comprise one or more mutations to enhance the antibody half-life in human serum (e.g., one or more (including all) of M252Y, S254T, and T256E mutations according to the EU numbering convention).

In some embodiments of any of the IgG4 modified Fc, the Fc comprises L235E according to EU numbering. In some embodiments of any of the IgG4 modified Fc, the Fc comprises S228P mutation according to EU numbering. In some embodiments of any of the IgG4 modified Fc, the Fc comprises S267E and L328F mutations according to EU numbering. In certain embodiments of any of the IgG4 modified Fc, the Fc comprises one or more amino acid substitutions at a residue position selected from C127S, F234A, L235A, L235E, S267E, K322A, L328F, E345R, E430G, S440Y, and any combination thereof, according to EU numbering. In some embodiments of any of the IgG4 modified Fc, the Fc comprises an amino acid substitution at positions E430G, L243A, L235A, and P331S according to EU numbering. In some embodiments of any of the IgG4 modified Fc, the Fc comprises an amino acid substitution at positions E430G and P331S according to EU numbering. In some embodiments of any of the IgG4 modified Fc, the Fc comprises an amino acid substitution at positions E430G and K322A according to EU numbering. In some embodiments of any of the IgG4 modified Fc, the Fc comprises an amino acid substitution at position E430 according to EU numbering. In some embodiments of any of the IgG4 modified Fc, the Fc region comprises an amino acid substitution at positions E430G and K322A according to EU numbering. In some embodiments of any of the IgG4 modified Fc, the Fc comprises an amino acid substitution at positions S267E and L328F according to EU numbering. In some embodiments of any of the IgG4 modified Fc, the Fc comprises an amino acid substitution at position C127S according to EU numbering. In some embodiments of any of the IgG4 modified Fc, the Fc comprises an amino acid substitution at positions E345R, E430G and S440Y according to EU numbering.

In some embodiments, an antibody comprises a heavy chain comprising the amino acid sequence of SEQ ID NO: 336. In some embodiments, an antibody comprises a heavy chain comprising the amino acid sequence of SEQ ID NO: 328. In some embodiments, an antibody comprises a heavy chain comprising the amino acid sequence of SEQ ID NO: 320.

In some embodiments, an antibody has a human IgG1 heavy chain without a C-terminal lysine. In some embodiments, an antibody has a human IgG1 heavy chain with a P331S mutation. In some embodiments, an antibody has a human IgG1 heavy chain with a P331S mutation and without a C-terminal lysine. In some embodiments, an antibody has a human IgG1 heavy chain with N325S and L328F mutations (N325S/L328F). In some embodiments, an antibody has a human IgG1 heavy chain with a N325S/L328F mutation and without a C-terminal lysine. In some embodiments, an antibody has a human IgG1 heavy chain with a K322A mutation. In some embodiments, an antibody has a human IgG1 heavy chain with a K322A mutation and without a C-terminal lysine. In the foregoing embodiments, mutations are indicated according to EU numbering.

In some embodiments, an antibody comprises a heavy chain amino comprising the amino acid sequence of SEQ ID NO: 337. In some embodiments, an antibody comprises a heavy chain comprising the amino acid sequence of SEQ ID NO: 338. In some embodiments, an antibody comprises a heavy chain comprising the amino acid sequence of SEQ ID NO: 339. In some embodiments, an antibody comprises a heavy chain comprising the amino acid sequence of SEQ ID NO: 340. In some embodiments, an antibody comprises a heavy chain comprising the amino acid sequence of SEQ ID NO: 341. In some embodiments, an antibody comprises a heavy chain comprising the amino acid sequence of SEQ ID NO: 342. In some embodiments, an antibody comprises a heavy chain comprising the amino acid sequence of SEQ ID NO: 343.

In some embodiments, an antibody comprises a heavy chain amino comprising the amino acid sequence of SEQ ID NO: 329. In some embodiments, an antibody comprises a heavy chain comprising the amino acid sequence of SEQ ID NO: 330. In some embodiments, an antibody comprises a heavy chain comprising the amino acid sequence of SEQ ID NO: 331. In some embodiments, an antibody comprises a heavy chain comprising the amino acid sequence of SEQ ID NO: 332. In some embodiments, an antibody comprises a heavy chain comprising the amino acid sequence of SEQ ID NO: 333. In some embodiments, an antibody comprises a heavy chain comprising the amino acid sequence of SEQ ID NO: 334. In some embodiments, an antibody comprises a heavy chain comprising the amino acid sequence of SEQ ID NO: 335.

In some embodiments, an antibody comprises a heavy chain amino comprising the amino acid sequence of SEQ ID NO: 321. In some embodiments, an antibody comprises a heavy chain comprising the amino acid sequence of SEQ ID NO: 322. In some embodiments, an antibody comprises a heavy chain comprising the amino acid sequence of SEQ ID NO: 323. In some embodiments, an antibody comprises a heavy chain comprising the amino acid sequence of SEQ ID NO: 324. In some embodiments, an antibody comprises a heavy chain comprising the amino acid sequence of SEQ ID NO: 325. In some embodiments, an antibody comprises a heavy chain comprising the amino acid sequence of SEQ ID NO: 326. In some embodiments, an antibody comprises a heavy chain comprising the amino acid sequence of SEQ ID NO: 327.

(8) Other Antibody Modifications

In some embodiments of any of the antibodies, the antibody is a derivative. The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen binding protein can have a greater circulating half-life than an antigen binding protein that is not chemically modified. In certain embodiments, a chemically modified antigen binding protein can have improved targeting capacity for desired cells, tissues, and/or organs. In some embodiments, a derivative antigen binding protein is covalently modified to include one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative antigen binding protein comprises one or more polymer, including, but not limited to, monomethoxy-polyethylene glycol, dextran, cellulose, copolymers of ethylene glycol/propylene glycol, carboxymethylcellulose, polyvinyl pyrrolidone, poly-1, 3-dioxolane, poly-1,3,6-trioxane, ethylene/maleic anhydride copolymer, polyaminoacids (either homopolymers or random copolymers), poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers.

In certain embodiments, a derivative is covalently modified with polyethylene glycol (PEG) subunits. In certain embodiments, one or more water-soluble polymer is bonded at one or more specific position, for example at the amino terminus, of a derivative. In certain embodiments, one or more water-soluble polymer is randomly attached to one or more side chains of a derivative. In certain embodiments, PEG is used to improve the therapeutic capacity for an antigen binding protein. In certain embodiments, PEG is used to improve the therapeutic capacity for a humanized antibody. Certain such methods are discussed, for example, in U.S. Pat. No. 6,133,426, which is hereby incorporated by reference for any purpose.

Peptide analogs are commonly used in the pharmaceutical industry as non-peptide drugs with properties analogous to those of the template peptide. These types of non-peptide compound are termed "peptide mimetics" or "peptidomimetics." Fauchere, *J. Adv. Drug Res.,* 15:29 (1986); and Evans et al. *J. Med. Chem.,* 30:1229 (1987), which are incorporated herein by reference for any purpose. Such compounds are often developed with the aid of computerized molecular modeling. Peptide mimetics that are structurally similar to therapeutically useful peptides can be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: —$CH_2NH$—, —$CH_2S$—, —$CH_2$—$CH_2$—, —CH=CH- (cis and trans), —$COCH_2$—, —$CH(OH)CH_2$—, and —$CH_2SO$—, by methods well known in the art. Systematic substitution of one or more amino acids of a consensus sequence with a D-amino acid of the same type (e.g., D-lysine in place of L-lysine) can be used in certain embodiments to generate more stable peptides. In addition, constrained peptides comprising a consensus sequence or a substantially identical consensus sequence variation can be generated by methods known in the art (Rizo and Gierasch *Ann. Rev. Biochem.,* 61:387 (1992), incorporated herein by reference for any purpose); for example, by adding internal cysteine residues capable of forming intramolecular disulfide bridges which cyclize the peptide.

Drug conjugation involves coupling of a biological active cytotoxic (anticancer) payload or drug to an antibody that specifically targets a certain tumor marker (e.g. a polypeptide that, ideally, is only to be found in or on tumor cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cancer. Due to this targeting, ideally the drug has lower side effects and gives a wider therapeutic window than other chemotherapeutic agents. Technics to conjugate antibodies are disclosed are known in the art (see, e.g., Jane de Lartigue OncLive Jul. 5, 2012; ADC Review on antibody-drug conjugates; and Ducry et al. *Biocontugate Chemistry* 21 (1):5-13 (2010).

II. Nucleic Acids, Vectors, and Host Cells

Anti-MS4A4A antibodies of the present disclosure may be produced using recombinant methods and compositions, e.g., as described in U.S. Pat. No. 4,816,567. In some embodiments, isolated nucleic acids having a nucleotide sequence encoding any of the anti-MS4A4A antibodies of the present disclosure are provided. Such nucleic acids may encode an amino acid sequence comprising the $V_L$ and/or an amino acid sequence comprising the $V_H$ of the anti-MS4A4A antibody (e.g., the light and/or heavy chains of the antibody). In some embodiments, one or more vectors (e.g., expression vectors) comprising such nucleic acids are provided. In some embodiments, a host cell comprising such nucleic acid is also provided. In some embodiments, the host cell comprises (e.g., has been transduced with): (1) a vector comprising a nucleic acid that encodes an amino acid sequence comprising the $V_L$ of the antibody and an amino acid sequence comprising the $V_H$ of the antibody, or (2) a first vector comprising a nucleic acid that encodes an amino acid sequence comprising the $V_L$ of the antibody and a second vector comprising a nucleic acid that encodes an amino acid sequence comprising the $V_H$ of the antibody. In some embodiments, the host cell is eukaryotic, e.g., a Chinese Hamster Ovary (CHO) cell or lymphoid cell (e.g., Y0, NS0, Sp20 cell). Host cells of the present disclosure also include, without limitation, isolated cells, in vitro cultured cells, and ex vivo cultured cells.

Methods of making an anti-MS4A4A antibody of the present disclosure are provided. In some embodiments, the method includes culturing a host cell of the present disclosure comprising a nucleic acid encoding the anti-MS4A4A antibody, under conditions suitable for expression of the antibody. In some embodiments, the antibody is subsequently recovered from the host cell (or host cell culture medium).

For recombinant production of an anti-MS4A4A antibody of the present disclosure, a nucleic acid encoding the anti-MS4A4A antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable vectors comprising a nucleic acid sequence encoding any of the anti-MS4A4A antibodies of the present disclosure, or cell-surface expressed fragments or polypeptides thereof polypeptides (including antibodies) described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones comprising the vector. Suitable examples include plasmids and bacterial viruses, e.g., pUC18, pUC19, Bluescript (e.g., pBS SK+) and its derivatives, mp18, mp19, pBR322, pMB9, ColEl, pCR1, RP4, phage DNAs, and shuttle vectors such as pSA3 and pAT28. These and many other cloning vectors are available from commercial vendors such as BioRad, Strategene, and Invitrogen.

Suitable host cells for cloning or expression of antibody-encoding vectors include prokaryotic or eukaryotic cells. For example, anti-MS4A4A antibodies of the present disclosure may be produced in bacteria, in particular when glycosylation and Fc effector function are not needed. For expression of antibody fragments and polypeptides in bacteria (e.g., U.S. Pat. Nos. 5,648,237, 5,789,199, and 5,840,523. After expression, the antibody may be isolated from the bacterial cell paste in a soluble fraction and can be further purified.

In addition to prokaryotes, eukaryotic microorganisms, such as filamentous fungi or yeast, are also suitable cloning or expression hosts for antibody-encoding vectors, including fungi and yeast strains whose glycosylation pathways have been "humanized," resulting in the production of an antibody with a partially or fully human glycosylation pattern (e.g., Gerngross *Nat. Biotech.* 22:1409-1414 (2004); and Li et al. *Nat. Biotech.* 24:210-215 (2006)).

Suitable host cells for the expression of glycosylated antibody can also be derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts (e.g., U.S. Pat. Nos. 5,959,177, 6,040,498, 6,420,548, 7,125,978, and 6,417,429, describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV line transformed by SV40 (COS-7); human embryonic kidney line (293 or 293 cells as described, e.g., in Graham et al. *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al. *Annals N.Y. Acad. Sci.* 383:44-68 (1982); MRC 5 cells; and FS4 cells. Other useful mammalian host cell lines include Chinese hamster ovary (CHO) cells, including DHFR-CHO cells (Urlaub et al. *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B.K.C. Lo, ed., Humana Press, Totowa, NJ), pp. 255-268 (2003).

III. Pharmaceutical Compositions/Formulations

Provided herein are pharmaceutical compositions and/or pharmaceutical formulations comprising the anti-MS4A4A antibodies of the present disclosure and a pharmaceutically acceptable carrier.

In some embodiments, pharmaceutically acceptable carrier preferably are nontoxic to recipients at the dosages and concentrations employed. The antibodies described herein may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols. Pharmaceutically acceptable carriers can include, depending on the formulation desired, pharmaceutically acceptable, non-toxic carriers of diluents, which are vehicles commonly used to formulate pharmaceutical compositions for animal or human administration. In certain embodiments, the pharmaceutical composition can comprise formulation materials for modifying, maintaining or preserving, for example, the pH, osmolarity, viscosity, clarity, color, isotonicity, odor, sterility, stability, rate of dissolution or release, adsorption or penetration of the composition.

In certain embodiments, pharmaceutically acceptable carriers include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. Further examples of formulations that are suitable for various types of administration can be found in *Remington: The Science and Practice of Pharmacy*, Pharmaceutical Press 22nd ed. (2013). For a brief review of methods for drug delivery, see, Langer, *Science* 249:1527-1533 (1990).

Formulations suitable for parenteral administration include aqueous and non-aqueous, isotonic sterile injection solutions, which can comprise antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Formulations may be optimized for retention and stabilization in the brain or central nervous system. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the antibody, such as an anti-MS4A4A antibody of the present disclosure, in a biodegradable or bioerodible implant. The rate of release of the therapeutically active agent is controlled by the rate of transport through the polymeric matrix, and the biodegradation of the implant. Implants may be particles, sheets, patches, plaques, fibers, microcapsules and the like and may be of any size or shape compatible with the selected site of insertion. Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the present disclosure. Hydrogels are typically a copolymer material, characterized by the ability to imbibe a liquid.

IV. Therapeutic Uses

As disclosed herein, anti-MS4A4A antibodies of the present disclosure may be used for preventing, reducing risk, or treating diseases and disorders. In some embodiments, an anti-MS4A4A antibody of the present disclosure is effective at preventing, reducing risk, or treating Alzheimer's disease, late onset Alzheimer's disease, and cognitive impairment.

MS4A4A as a Disease Target

Genome wide association studies have identified various members of the MS4A family are associated with Alzheimer's disease. These are MS4A2, MS4A3, MS4A4A, MS4A4E, MS4A6A, and MS4A6E. The associated SNPs are found in the 3' UTR of MS4A6A (rs610932) and the intergenic region between MS4A4E and MS4A6A (rs670139). There are three SNPs in the MS4A gene cluster that have been associated with an increased risk of late-onset Alzheimer's disease. These include rs4938933 in MS4A4A, rs670139 in MS4A4E, and rs610932 in MS4A6A (Hollingworth et al, 2011, Nat Genetics, 43:429-435; Naj et al, 2011, Nature Genetics, 43:436-441; Antunez et al, 2011, Genome Medicine, 3, article 33). Additionally, MS4A4A locus SNPs (rs2304933 and rs2304935) associated with higher levels of MS4A4A and increased Alzheimer's disease risk, including late-onset Alzheimer's disease (LOAD) (Allen et al, 2012, Neurology, 79:221-228).

The methods provided herein find use in preventing, reducing risk, or treating an individual having a neurodegenerative disease, disorder, or condition. In some embodiments, the present disclosure provides a method for preventing, reducing risk, or treating an individual having a neurodegenerative disorder, the method comprising administering to the individual in need thereof a therapeutically effective amount of an anti-MS4A4A antibody.

In some embodiments, the present disclosure provides a method for preventing, reducing the risk, or treating an individual having Alzheimer's disease, the method comprising administering to the individual in need thereof a therapeutically effective amount of an anti-MS4A4A antibody.

In some embodiments, the present disclosure provides a method for preventing, reducing the risk, or treating an individual having late onset Alzheimer's disease, the method comprising administering to the individual in need thereof a therapeutically effective amount of an anti-MS4A4A antibody.

In some embodiments, the present disclosure provides a method for preventing, reducing the risk, or treating an individual having mild cognitive impairment, the method comprising administering to the individual in need thereof a therapeutically effective amount of an anti-MS4A4A antibody.

In some embodiments, the present disclosure provides a method for preventing, reducing risk, or treating an individual having a disease, disorder, or condition associated with over expression or increased activity of MS4A4A, the method comprising administering to an individual in need thereof a therapeutically effective amount of an anti-MS4A4A antibody.

In some embodiments, the present disclosure provides a method for preventing, reducing the risk, or treating an individual having a CSF1R-deficient disease or disorder, the method comprising administering to an individual in need thereof a therapeutically effective amount of an anti-MS4A4A antibody. In some embodiments, the CSF1R-deficient disease or disorder is adult-onset leukoencephalopathy with axonal spheroids and pigmented glia (ALSP) or hereditary diffuse leukoencephalopathy with spheroids (HDLS).

Other aspects of the present disclosure relate to a method of preventing, reducing risk, or treating an individual having a disease, disorder, or injury selected from the group consisting of frontotemporal dementia, Alzheimer's disease, mild cognitive impairment, vascular dementia, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotrophic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, degenerative disc disease, Shy-Drager syndrome, progressive supranuclear palsy, cortical basal ganglionic degeneration, acute disseminated encephalomyelitis, granulomatous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arthritis, multiple sclerosis, metabolic disorder, obesity, insulin resistance, type 2 diabetes, tissue or vascular damage, an injury, inflammatory cell debris or protein aggregates, abnormal circulating myeloid cells, unhealthy aging, age-related cognitive impairment, age-related brain atrophy, age-associated traits, including without limitation inflammation, neuronal loss, and cognitive deficits, such as cognitive deficits in the absence of known brain disease, including cognitive deficits of the frontal cerebral cortex of an older individual and, one or more undesirable symptoms of normal aging, comprising administering to the individual a therapeutically effective amount of the anti-MS4A4A antibody of any of the preceding embodiments. Other aspects of the present disclosure relate to an anti-MS4A4A antibody of any of the preceding embodiments for use in preventing, reducing risk, or treating an individual having a disease, disorder, or injury selected from the group consisting of frontotemporal dementia, Alzheimer's disease, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotrophic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, degenerative disc disease, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arthritis, multiple sclerosis, metabolic disorder, obesity, insulin resistance, type 2 diabetes, tissue or vascular damage, an injury, inflammatory cell debris or protein aggregates, abnormal circulating myeloid cells, unhealthy aging, age-related cognitive impairment, age-related brain atrophy, age-associated traits, including without limitation inflammation, neuronal loss, and cognitive deficits, such as cognitive deficits in the absence of known brain disease, including cognitive deficits of the frontal cerebral cortex of older individual, and one or more undesirable symptoms of normal aging. Other aspects of the present disclosure relate to an anti-MS4A4A antibody of any of the preceding embodiments for use in preventing or reducing metastasis. Other aspects of the present disclosure relate to an anti-MS4A4A antibody of any of the preceding embodiments for use in preventing, reducing risk, or treating an individual having cancer.

Other aspects of the present disclosure relate to use of an anti-MS4A4A antibody of any of the preceding embodiments in the manufacture of a medicament for preventing, reducing risk, or treating an individual having a disease, disorder, or injury selected from the group consisting of frontotemporal dementia, Alzheimer's disease, late-onset Alzheimer's disease, mild cognitive impairment, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotrophic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, degenerative disc disease, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arthritis, multiple sclerosis, metabolic disorder, obesity, insulin resistance, type 2 diabetes, tissue or vascular damage, an injury, inflammatory cell debris or protein aggregates, abnormal circulating myeloid cells, unhealthy aging, age-related cognitive impairment, age-related brain atrophy, age-associated traits, including without limitations inflammation, neuronal loss, and cognitive deficits, such as cognitive deficits in the absence of known brain disease, including cognitive deficits of the frontal cerebral cortex of older individual and one or more undesirable symptoms of normal aging. Other aspects of the present disclosure relate to a method of preventing, reducing risk, or treating an individual having a disease, disorder, or injury selected from the group consisting of frontotemporal dementia, progressive supranuclear palsy, Alzheimer's disease, late-onset Alzheimer's disease, mild cognitive impairment, vascular dementia, seizures, retinal dystrophy, amyotrophic lateral sclerosis, traumatic brain injury, a spinal cord injury, dementia, stroke, Parkinson's disease, acute disseminated encephalomyelitis, retinal degeneration, age related macular degeneration, glaucoma, multiple sclerosis, septic shock, bacterial infection, arthritis, and osteoarthritis, comprising administering to the individual a therapeutically effective amount of the anti-MS4A4A antibody of any of the preceding embodiments. Other aspects of the present disclosure relate to an anti-MS4A4A antibody of any of the preceding embodiments for use in preventing, reducing risk, or treating an individual having a disease, disorder, or injury selected from the group consisting of frontotemporal dementia, progressive supranticlear paisy. Alzheimer's disease, late-onset Alzheimer's disease, mild cognitive impairment, vascular dementia, seizures, retinal dystrophy, amyotrophic lateral sclerosis, traumatic brain injury, a spinal cord injury, dementia, stroke, Parkinson's disease, acute disseminated encephalomyelitis, retinal degeneration, age related macular degeneration, glaucoma, multiple sclerosis, septic shock, bacterial infection, arthritis, and osteoarthritis. Other aspects of the present disclosure relate to use of an anti-MS4A4A antibody of any of the preceding embodiments in the manufacture of a medicament for preventing, reducing risk, or treating an individual having a disease, disorder, or injury selected from the group consisting of frontotemporal dementia, progressive supranticlear palsy, Alzheimer's disease, vascular dementia, seizures, retinal dystrophy, amyotrophic lateral sclerosis, traumatic brain injury, a spinal cord injury, dementia, stroke, Parkinson's disease, acute disseminated encephalomyelitis, retinal degeneration, age related macular degeneration, glaucoma, multiple sclerosis, septic shock, bacterial infection, arthritis, and osteoarthritis.

In some embodiments, a subject or individual is a mammal. Mammals include, without limitation, domesticated animals (e.g., cows, sheep, cats, dogs, and horses), primates (e.g., humans and non-human primates such as monkeys), rabbits, and rodents (e.g., mice and rats). In some embodiments, the subject or individual is a human.

An antibody provided herein (and any additional therapeutic agent) can be administered by any suitable means, including parenteral, intrapulmonary, intranasal, intralesional administration, intracerobrospinal, intracranial, intraspinal, intrasynovial, intrathecal, oral, topical, or inhalation routes. Parenteral infusions include intramuscular, intravenous administration as a bolus or by continuous infusion over a period of time, intraarterial, intra-articular, intraperitoneal, or subcutaneous administration. In some embodiments, the administration is intravenous administration. In some embodiments, the administration is subcutaneous. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies provided herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the disclosure (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 μg/kg to 100 mg/kg of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 150 mg/kg, which may be administered to the patient intermittently, e.g., every week or every three weeks (e.g., such that the patient receives from about two to about twenty, or e.g., about six doses of the antibody). In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. An initial higher loading dose followed by one or more lower doses may be administered. However, other dosage regimens may be useful. The progress of this therapy is easily monitored by conventional techniques and assays.

V. Diagnostic Uses

In some embodiments of any of the antibodies, any of the anti-MS4A4A antibodies provided herein is useful for detecting the presence of MS4A4A in a sample or an individual. The term "detecting" as used herein encompasses quantitative or qualitative detection. Provided herein are methods of using the antibodies of this disclosure for diagnostic purposes, such as the detection of MS4A4A in an individual or in tissue samples derived from an individual. In some embodiments, the individual is a human.

The detection method may involve quantification of the antigen-bound antibody. Antibody detection in biological samples may occur with any method known in the art, including immunofluorescence microscopy, immunocytochemistry, immunohistochemistry, ELISA, FACS analysis, immunoprecipitation, or micro-positron emission tomography. In certain embodiments, the antibody is radiolabeled, for example with 18 F and subsequently detected utilizing micro-positron emission tomography analysis. Antibody-binding may also be quantified in a patient by non-invasive techniques such as positron emission tomography (PET), X-ray computed tomography, single-photon emission computed tomography (SPECT), computed tomography (CT), and computed axial tomography (CAT).

VI, Articles of Manufacture

Provided herein are articles of manufacture (e.g., kit) comprising an anti-MS4A4A antibody described herein. Article of manufacture may include one or more containers comprising an antibody described herein. Containers may be any suitable packaging including, but is not limited to, vials, bottles, jars, flexible packaging (e.g., sealed Mylar or plastic bags), and the like. The containers may be unit doses, bulk packages (e.g., multi-dose packages) or sub-unit doses.

In some embodiments, the kits may further include a second agent. In some embodiments, the second agent is a pharmaceutically acceptable buffer or diluting agent including, but not limited to, such as bacteriostatic water for injection (BWFI), phosphate-buffered saline, Ringer's solution and dextrose solution. In some embodiments, the second agent is a pharmaceutically active agent.

In some embodiments of any of the articles of manufacture, the article of manufactures further include instructions for use in accordance with the methods of this disclosure. The instructions generally include information as to dosage, dosing schedule, and route of administration for the intended treatment. In some embodiments, these instructions comprise a description of administration of the isolated antibody of the present disclosure (e.g., an anti-MS4A4A antibody described herein) to prevent, reduce risk, or treat an individual having a disease, disorder, or injury selected from of frontotemporal dementia, Alzheimer's disease, late onset Alzheimer's disease, cognitive decline or impairment, mild cognitive impairment, vascular dementia, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotrophic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, degenerative disc disease, Shy-Drager syndrome, progressive supranuclear palsy, cortical basal ganglionic degeneration, acute disseminated encephalomyelitis, granulomatous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arthritis, multiple sclerosis, metabolic disorder, obesity, insulin resistance, type 2 diabetes, tissue or vascular damage, an injury, inflammatory cell debris or protein aggregates, abnormal circulating myeloid cells, unhealthy aging, age-related cognitive impairment, age-related brain atrophy, age-associated traits, including without limitation inflammation, neuronal loss, and cognitive deficits, such as cognitive deficits in the absence of known brain disease, including cognitive deficits of the frontal cerebral cortex of an older individual and, one or more undesirable symptoms of normal aging, comprising administering to the individual a therapeutically effective amount of the anti-MS4A4A antibody of any of the preceding embodiments.

In some embodiments, the instructions include instructions for use of the anti-MS4A4A antibody and the second agent (e.g., second pharmaceutically active agent).

The present disclosure will be more fully understood by reference to the following Examples. They should not, however, be construed as limiting the scope of the present disclosure. All citations throughout the disclosure are hereby expressly incorporated by reference.

EXAMPLES

Example 1: Humanization of Murine Anti-MS4A4A Mouse Antibodies

The purpose of this example was to generate humanized variants of certain parental mouse anti-MS4A4A antibodies disclosed in international patent application serial number PCT/US2019/016156.

The parental mouse anti-MS4A4A antibody 4A-202 contains a heavy chain variable region comprising the amino acid sequence of: QVQLQQSGAELARPGASVKLSCKASGYTFTNYWMQWVKQRPGQGLEWIGATHPGHGDTRYTQ KFKGKATLSADKSSSTAYMQLSNLASEDSAVYYCAREEVYYGFRSYWYFDVWGRGTLVTVSS (SEQ ID NO: 164), and a light chain variable region comprising the amino acid sequence of: DIVLTQSPASLAVSLGQRATISCRASESVDNYGVSFMNWFQQKPGQPPKWYGASNQGSGVPARF SGSGSGTDFSLNIHPMEEDDTAMYFCQQSKEVPPTFGGGTKLEIK (SEQ ID NO: 165).

The parental mouse anti-MS4A4A 4A-18 contains a heavy chain variable region comprising the amino acid sequence of: QVQLQQPGTELVKPGASVKLSCKASGYTFTSYWIHWVKQRPGQGLEWIGNINPTNGGTNYNERF KSKATLTVDKSSSTAYMQLSSLTSEDSAVYYCARAYYYGSSLFAYWGQGTLVTVSS (SEQ ID NO: 166), and a light chain variable region comprising the amino acid sequence of: DIVMTQSQKFMSTTVGDRVSITCKASQNVGTAVAWSQQKPGQSPKWYSASYRHTGVPDRFTGSGSGTDFTLTITNMQSEDLADYFCQQYSTYPWTFGGGTKLEIK (SEQ ID NO: 167).

The parental mouse anti-MS4A4A antibody 4A-21 contains a heavy chain variable region comprising the amino acid sequence of: QIQLVQSGPELKKPGETVKISCKASGYIFTSYGLSWVKQTPGKGLKWMGWINTYSGVPTYANDFKGRFAFSLETSASTTYLRINNLKNDDTATYFCARSLVDYWGQGTPLTVSS (SEQ ID NO: 168), and a light chain variable region comprising the amino acid sequence of: DVVMTQTPFTLSVTIGQSASISCKSSQSLLYSDGKTYLSWLLQRPGQSPKRLIYLVSKLDSGVPDRFTGSGSGTDFTLKISRVEAEDLGVYYCWQGIDFHQTFGGGTKLEIK (SEQ ID NO: 169).

The parent mouse anti-MS4A4A antibody 4A-25 contains a heavy chain variable region comprising the amino acid sequence of: QVTLKESGPGILQPSQTLSLTCSFSGFSLRTSDMGVGWVRQPSGEGLEWLADIWWDDNKYYNPSLKSRLTISKDTSSNQVFLKITSVDTADTATYYCARRANYGNLFDYWGQGTAVTVSS (SEQ ID NO: 170), and a light chain variable region comprising the amino acid sequence of: DIVMTQSLKFMSTSVGDRVSITCKASQNVRSAVAWYQQKPGQSPKVLIYWASNRHTGVPDRFTGSGSGTDFTLTISNVQSEDLADYFCLQHWNYLTFGSGTKLEIK (SEQ ID NO: 171).

One method of humanizing non-human antibodies is to transplant the CDRs from a non-human (e.g., murine) antibody onto a human antibody acceptor framework. Such CDR transplantation may result in attenuation or complete loss of affinity of the humanized antibody to its target due to perturbation in its framework. As a result, certain amino acid residues in the human framework may need to be replaced by amino acid residues from the corresponding positions of the murine antibody framework (back mutations) in order to restore attenuated or lost affinity. Therefore, the amino acid residues to be replaced in the context of the selected human antibody germline acceptor framework must be determined so that the humanized antibody substantially retains functions and paratopes. In addition, retained or improved thermal stability and solubility are desired for good manufacturability and downstream development.

Accordingly, structure-based antibody modeling was applied in the process of humanizing mouse anti-MS4A4A monoclonal antibodies 4A-202, 4A-18, 4A-21, and 4A-25 utilizing the BioMOE module of MOE (Molecular Operating Environment, Chemical Computing Group, Montreal, Canada). Briefly, $V_H$ and $V_L$ amino acid sequences of the mouse monoclonal antibodies to be humanized were compared to human $V_L$, $V_H$, LJ, HJ functional germline amino acid sequences taken from IMGT. Pseudo-genes and ORFs were excluded from analysis. Per one mouse monoclonal antibody (query), five most similar $V_L$ and five most similar $V_H$ germline amino acid sequences were selected and combined with the most similar VJ and HJ genes, producing 25 humanized amino acid sequences. The CDRs to be transplanted onto the human framework were defined according to the AbM definition.

The query and the 25 humanized amino acid sequences were used to create Fv homology models using BioMOE module or the Antibody Modeler module of MOE (Molecular Operating Environment, Chemical Computing Group, Montreal, Canada). AMBER10:EHT force field analysis was used for energy minimization through the entire antibody homology modeling process. Based on the Fv homology models obtained, molecular descriptors such as interaction energy between $V_L$ and $V_H$, coordinate-based isoelctric point (3D pI), hydrophobic patch, and charged surface area were calculated, analyzed, and sorted by scoring metrics provided by MOE. These molecular descriptors were utilized to prioritize the humanized monoclonal antibodies for downstream experimental procedures, including protein expression, purification, binding affinity studies, and functional assays.

The BioMOE module of MOE provides a tool, Mutation Site Properties, to visualize and classify potential residues for back-mutation. In this context, back-mutation is defined as amino acid substitution which is reverted to the original query amino acid sequence replacing the humanized amino acid sequence. Using this tool, the original query (reference) was compared individually to the selected humanized variants for both the primary amino acid sequence and the 3D structure of the 3D Fv homology model.

Changes between the reference (i.e., parental) antibody and the humanized variant were classified based on amino acid type difference, interaction potential with CDR residues, impact potential for VL/V H pairing, and potential change in hydrophobic and charged surface area in and near the CDRs.

Mutations near the CDRs or the VL/VH interface having a significant charge difference or containing strong H-bond interactions were individually evaluated and the significantly disrupting mutations were reverted to the original query residues. As a result, humanized amino acid sequences may contain up to five back mutations. Amino acid sequences for the variable heavy chain and variable light chain query mouse monoclonal antibodies (mouse anti-MS4A4A antibody 4A-202, mouse anti-MS4A4A antibody 4A-18, mouse anti-MS4A4A antibody 4A-21, and mouse anti-MS4A4A antibody 4A-25) and the humanized monoclonal antibodies with or without back mutations are provided in Tables 1~4 below. In Tables 1-4, the CDR sequences (Kabat) are underlined.

TABLE 1

| Antibody | Heavy Chain Variable | SEQ ID NO: | Light Chain Variable | SEQ ID NO: |
|---|---|---|---|---|
| 4A-202 | QVQLQQSGAELARPGASVKLSCKASGYTFTNYWMQWVKQRPGQGLEWIGATHPGHGDTRYTQKFKGKATLSADKSSSTAYMQLSNLASEDSAVYYCAREEVYYGFRSYWYFDVWGRGTLVTVSS | 4 | DIVLTQSPASLAVSLGQRATISCRASESVDNYGVSFMNWFQQKPGQPPKLLIYGASNQGSGVPARFSGSGSGTDFSLNIHPMEEDDTAMYFCQQSKEVPPTFGGGTKLEIK | 16 |

TABLE 1-continued

| Antibody | Heavy Chain Variable | SEQ ID NO: | Light Chain Variable | SEQ ID NO: |
|---|---|---|---|---|
| 4A-301 | QVQLVQSGAEVKKPGASVKVSCKASGYTFTNYWMQWVRQAPGQGLEWMGATHPGHGDTRYAQKFQGRVTMTRDTSTSTVYMELSSLRSEDTAVYYCAREEVYYGFRSYWYFDVWGRGTLVTVSS | 5 | DIVMTQSPDSLAVSLGERATINCRASESVDNYGVSFMNWYQQKPGQPPKLLIYGASNQGSGVPDRFSGSGSGTDFTLTISSLQAEDVAVYYCQQSKEVPPTFGGGTKVEIK | 17 |
| 4A-302 | QVQLVQSGAEVKKPGASVKVSCKASGYTFTNYWMQWVRQAPGQGLEWMGATHPGHGDTRYAQKFQGRVTMTRDTSTSTVYMELSSLRSEDTAVYYCAREEVYYGFRSYWYFDVWGRGTLVTVSS | 5 | EIVLTQSPATLSLSPGERATLSCRASESVDNYGVSFMNWYQQKPGQAPRLLIYGASNQGSGIPARFSGSGSGTDFTLTISSLEPEDFAVYYCQQSKEVPPTFGGGTKVEIK | 18 |
| 4A-303 | EVQLVQSGAEVKKPGESLKISCKGSGYTFTNYWMQWVRQMPGKGLEWMGATHPGHGDTRYSPSFQGQVTISADKSISTAYLQWSSLKASDTAMYYCAREEVYYGFRSYWYFDVWGRGTLVTVSS | 6 | DIVMTQSPDSLAVSLGERATINCRASESVDNYGVSFMNWYQQKPGQPPKLLIYGASNQGSGVPDRFSGSGSGTDFTLTISSLQAEDVAVYYCQQSKEVPPTFGGGTKVEIK | 17 |
| 4A-304 | QVQLVQSGAEVKKPGASVKVSCKASGYTFTNYWMQWVRQAPGQGLEWMGATHPGHGDTRYAQKFQGRVTMTRDTSTSTVYMELSSLRSEDTAVYYCAREEVYYGFRSYWYFDVWGRGTLVTVSS | 5 | EIVLTQSPGTLSLSPGERATLSCRASESVDNYGVSFMNWYQQKPGQAPRLLIYGASNQGSGIPDRFSGSGSGTDFTLTISRLEPEDFAVYYCQQSKEVPPTFGGGTKVEIK | 19 |
| 4A-305 | EVQLVQSGAEVKKPGATVKISCKVSGYTFTNYWMQWVQQAPGKGLEWMGATHPGHGDTRYAEKFQGRVTITADTSTDTAYMELSSLRSEDTAVYYCAREEVYYGFRSYWYFDVWGRGTLVTVSS | 7 | DIVMTQSPDSLAVSLGERATINCRASESVDNYGVSFMNWYQQKPGQPPKLLIYGASNQGSGVPDRFSGSGSGTDFTLTISSLQAEDVAVYYCQQSKEVPPTFGGGTKVEIK | 17 |
| 4A-306 | QVQLVQSGAEVKKPGASVKVSCKASGYTFTNYWMQWVRQAPGQGLEWMGATHPGHGDTRYAQKFQGRVTMTRDTSTSTVYMELSSLRSEDTAVYYCAREEVYYGFRSYWYFDVWGRGTLVTVSS | 5 | DIQMTQSPSSLSASVGDRVTITCRASESVDNYGVSFMNWYQQKPGKAPKLLIYGASNQGSGVPSRFSGSGSGTDFTLTISSLQPEDFATYYCQQSKEVPPTFGGGTKVEIK | 20 |
| 4A-307 | QVQLVQSGAEVKKPGASVKVSCKASGYTFTNYWMQWVRQAPGQGLEWMGATHPGHGDTRYAQKFQGRVTMTADKSTSTVYMELSSLRSEDTAVYYCAREEVYYGFRSYWYFDVWGRGTLVTVSS | 8 | DIVMTQSPDSLAVSLGERATINCRASESVDNYGVSFMNWYQQKPGQPPKLLIYGASNQGSGVPDRFSGSGSGTDFTLTISSLQAEDVAVYYCQQSKEVPPTFGGGTKVEIK | 17 |
| 4A-308 | QVQLVQSGAEVKKPGASVKVSCKASGYTFTNYWMQWVRQAPGQGLEWMGATHPGHGDTRYAQKFQGRVTMTADKSTSTAYMELSSLRSEDTAVYYCAREEVYYGFRSYWYFDVWGRGTLVTVSS | 9 | DIVMTQSPDSLAVSLGERATINCRASESVDNYGVSFMNWYQQKPGQPPKLLIYGASNQGSGVPDRFSGSGSGTDFTLTISSLQAEDVAVYYCQQSKEVPPTFGGGTKVEIK | 17 |
| 4A-309 | QVQLVQSGAEVKKPGASVKVSCKASGYTFTNYWMQWVRQAPGQGLEWMGATHPGHGDTRYAQKFQGRVTLTADKSISTAYMELSRLRSDDTVVYYCAREEVYYGFRSYWYFDVWGRGTLVTVSS | 10 | EIVLTQSPATLSLSPGERATLSCRASESVDNYGVSFMNWYQQKPGQAPRLLIYGASNQGSGIPARFSGSGSGTDFTLTISSLEPEDFAVYYCQQSKEVPPTFGGGTKVEIK | 18 |
| 4A-310 | EVQLVQSGAEVKKPGESLKISCKGSGYTFTNYWMQWVRQMPGKGLEWMGATHPGHGDTRYSPSFQGQVTISADKSSSTAYLQ | 11 | DIVMTQSPDSLAVSLGERATINCRASESVDNYGVSFMNWYQQKPGQPPKLLIYGASNQGSGVPDRFSGSGSGTDFTLTISSLQAEDVAVYYCQQ | 17 |

TABLE 1-continued

| Antibody | Heavy Chain Variable | SEQ ID NO: | Light Chain Variable | SEQ ID NO: |
|---|---|---|---|---|
| | WSSLKASDTAMYYCAREEVY YGFRSYWYFDVWGRGTLVTV SS | | SKEVPPTFGGGTKVEIK | |
| 4A-311 | EVQLVQSGAEVKKPGATVKIS CKVSGYTFTNYWMQWVQQA PGKGLEWMGATHPGHGDTRY AEKFQGRVTITADKSTSTAYM ELSSLRSEDTAVYYCAREEVY YGFRSYWYFDVWGRGTLVTV SS | 12 | DIVMTQSPDSLAVSLGERATINCR ASESVDNYGVSFMNWYQQKPGQ PPKLLIYGASNQGSGVPDRFSGSG SGTDFTLTISSLQAEDVAVYYCQQ SKEVPPTFGGGTKVEIK | 17 |
| 4A-312 | QVQLVQSGAEVKKPGASVKV SCKASGYTFTNYWMQWVRQ APGQGLEWMGATHPGHGDTR YAQKFQGRVTMTRDTSTSTV YMELSSLRSEDTAVYYCAREE VDYGFRSYWYFDVWGRGTLV TVSS | 13 | EIVLTQSPATLSLSPGERATLSCRA SESVDNYGVSFMNWYQQKPGQA PRLLIYGASNQQSGIPARFSGSGSG TDFTLTISSLEPEDFAVYYCQQSK EVPPTFGGGTKVEIK | 21 |
| 4A-313 | QVQLVQSGAEVKKPGASVKV SCKASGYTFTNYWMQWVRQ APGQGLEWMGATHPGHGDTR YAQKFQGRVTMTRDTSTSTV YMELSSLRSEDTAVYYCAREE VYYGFRSYWYFDLWGRGTLV TVSS | 14 | EIVLTQSPATLSLSPGERATLSCRA SESVDNYGVSRMNWYQQKPGQA PRLLIYGASNQGSGIPARFSGSGSG TDFTLTISSLEPEDFAVYYCQQSK EVPPTFGGGTKVEIK | 22 |
| 4A-314 | QVQLVQSGAEVKKPGASVKV SCKASGYTFTNYWMQWVRQ APGQGLEWMGTTLPGHGDTR YAQKFQGRVTMTRDTSTSTV YMELSSLRSEDTAVYYCAREE VYYGFRSYWYFDVWGRGTLV TVSS | 15 | EIVLTQSPATLSLSPGERATLSCRA SESVDNYGVSRMNWYQQKPGQA PRLLIYGASNQGSGIPARFSGSGSG TDFTLTISSLEPEDFAVYYCQQSK EVPPTFGGGTKVEIK | 22 |

TABLE 2

| Antibody | Heavy Chain Variable | SEQ ID NO: | Light Chain Variable | SEQ ID NO: |
|---|---|---|---|---|
| 4A-18 | QVQLQQPGTELVKPGASVKLS CKASGYTFTSYWIHWVKQRP GQGLEWIGNINPTNGGTNYNE RFKSKATLTVDKSSSTAYMQL SSLTSEDSAVYYCARAYYYGS SLFAYWGQGTLVTVSS | 23 | DIVMTQSQKFMSTTVGDRVSITC KASQNVGTAVAWSQQKPGQSP KLLIYSASYRHTGVPDRFTGSGS GTDFTLTITNMQSEDLADYFCQ QYSTYPWTFGGGTKLEIK | 31 |
| 4A-315 | QVQLVQSGAEVKKPGASVKV SCKASGYTFTSYWIHWVRQAP GQGLEWMGNINPTNGGTNYA QKFQGRVTMTRDTSTSTVYM ELSSLRSEDTAVYYCARAYYY GSSLFAYWGQGTLVTVSS | 24 | DIVMTQSPSFLSASVGDRVTITC KASQNVGTAVAWYQQKPGKAP KLLIYSASYRHTGVPSRFSGSGS GTEFTLTISSLQPEDFATYYCQQ YSTYPWTFGGGTKVEIK | 32 |
| 4A-316 | QVQLVQSGAEVKKPGASVKV SCKASGYTFTSYWIHWVRQAP GQGLEWMGNINPTNGGTNYA QKFQGRVTMTVDKSTSTVYM ELSSLRSEDTAVYYCARAYYY GSSLFAYWGQGTLVTVSS | 25 | DIQLTQSPSFLSASVGDRVTITCK ASQNVGTAVAWYQQKPGKAPK LLIYSASYRHTGVPSRFSGSGSG TEFTLTISSLQPEDFATYYCQQY STYPWTFGGGTKVEIKR | 33 |
| 4A-317 | QVQLVQSGAEVKKPGASVKV SCKASGYTFTSYWIHWVRQAP GQGLEWMGNINPTNGGTNYA QKFQGRVTMTVDKSTSTVYM ELSSLRSEDTAVYYCARAYYY GSSLFAYWGQGTLVTVSS | 25 | DIVMTQSPSFLSASVGDRVTITC KASQNVGTAVAWYQQKPGKAP KLLIYSASYRHTGVPSRFSGSGS GTEFTLTISSLQPEDFATYYCQQ YSTYPWTFGGGTKVEIK | 32 |
| 4A-318 | QVQLVQSGAEVKKPGASVKV SCKASGYTFTSYWIHWVRQAP GQGLEWMGNINPTNGGTNYA | 26 | DIQLTQSPSFLSASVGDRVTITCK ASQNVGTAVAWYQQKPGKAPK LLIYSASYRHTGVPSRFSGSGSG | 33 |

TABLE 2-continued

| Antibody | Heavy Chain Variable | SEQ ID NO: | Light Chain Variable | SEQ ID NO: |
|---|---|---|---|---|
| | QKFQGRVTMTVDKSTSTAYM ELSSLRSEDTAVYYCARAYYY GSSLFAYWGQGTLVTVSS | | TEFTLTISSLQPEDFATYYCQQY STYPWTFGGGTKVEIKR | |
| 4A-319 | QVQLVQSGAEVKKPGASVKV SCKASGYTFTSYWIHWVRQAP GQGLEWMGNINPTNGGTNYA QKFQGRVTMTVDKSTSTAYM ELSSLRSEDTAVYYCARAYYY GSSLFAYWGQGTLVTVSS | 26 | DIVMTQSPSFLSASVGDRVTITC KASQNVGTAVAWYQQKPGKAP KLLIYSASYRHTGVPSRFSGSGS GTEFTLTISSLQPEDFATYYCQQ YSTYPWTFGGGTKVEIK | 32 |
| 4A-320 | QVQLVQSGAEVKKPGASVKV SCKASGYTFTSYWIHWVRQAP GQGLEWMGNINPTNGGTNYA QKFQGRVTSTRDTSISTAYME LSRLRSDDTVVYYCARAYYY GSSLFAYWGQGTLVTVSS | 27 | DIVMTQSPSFLSASVGDRVTITC KASQNVGTAVAWYQQKPGKAP KLLIYSASYRHTGVPSRFSGSGS GTEFTLTISSLQPEDFATYYCQQ YSTYPWTFGGGTKVEIK | 32 |
| 4A-321 | QVQLVQSGAEVKKPGASVKV SCKASGYTFTSYWIHWVRQAP GQGLEWMGNINPTNGGTNYA QKFQGRVTSTRDTSISTAYME LSRLRSDDTVVYYCARAYYY GSSLFAYWGQGTLVTVSS | 27 | DIVMTQSPSSLSASVGDRVTITC KASQNVGTAVAWYQQKPEKAP KSLIYSASYRHTGVPSRFSGSGS GTDFTLTISSLQPEDFATYYCQQ YSTYPWTFGGGTKVEIK | 34 |
| 4A-322 | QVQLVQSGAEVKKPGASVKV SCKASGYTFTSYWIHWVRQAP GQGLEWMGNINPTNGGTNYA QKFQGRVTSTVDKSISTAYME LSRLRSDDTVVYYCARAYYY GSSLFAYWGQGTLVTVSS | 28 | DIQLTQSPSFLSASVGDRVTITCK ASQNVGTAVAWYQQKPGKAPK LLIYSASYRHTGVPSRFSGSGSG TEFTLTISSLQPEDFATYYCQQY STYPWTFGGGTKVEIKR | 33 |
| 4A-323 | QVQLVQSGAEVKKPGASVKV SCKASGYTFTSYWIHWVRQAP GQGLEWMGNINPTNGGTNYA QKFQGRVTSTVDKSISTAYME LSRLRSDDTVVYYCARAYYY GSSLFAYWGQGTLVTVSS | 28 | DIVMTQSPSFLSASVGDRVTITC KASQNVGTAVAWYQQKPGKAP KLLIYSASYRHTGVPSRFSGSGS GTEFTLTISSLQPEDFATYYCQQ YSTYPWTFGGGTKVEIK | 32 |
| 4A-324 | QVQLVQSGAEVKKPGASVKV SCKASGYTFTSYWIHWVRQAP GQGLEWMGNINPTNGGTNYA QKFQGRVTSTVDKSISTAYME LSRLRSDDTVVYYCARAYYY GSSLFAYWGQGTLVTVSS | 28 | DIQMTQSPSSLSASVGDRVTITC KASQNVGTAVAWYQQKPEKAP KSLIYSASYRHTGVPSRFSGSGS GTDFTLTISSLQPEDFATYYCQQ YSTYPWTFGGGTKVEIK | 35 |
| 4A-325 | QVQLVQSGAEVKKPGASVKV SCKASGYTFTSYWIHWVRQAP GQGLEWMGNINPTNGGTNYA QKFQGRVTSTVDKSISTAYME LSRLRSDDTVVYYCARAYYY GSSLFAYWGQGTLVTVSS | 28 | DIVMTQSPSSLSASVGDRVTITC KASQNVGTAVAWYQQKPEKAP KSLIYSASYRHTGVPSRFSGSGS GTDFTLTISSLQPEDFATYYCQQ YSTYPWTFGGGTKVEIK | 34 |
| 4A-326 | QVQLVQSGAEVKKPGASVKV SCKASGYTFTSYWIHWVRQAP GQRLEWMGNINPTNGGTNYS QKFQGRVTITRDTSASTAYME LSSLRSEDTAVYYCARAYYYG SSLFAYWGQGTLVTVSS | 29 | DIVMTQSPSFLSASVGDRVTITC KASQNVGTAVAWYQQKPGKAP KLLIYSASYRHTGVPSRFSGSGS GTEFTLTISSLQPEDFATYYCQQ YSTYPWTFGGGTKVEIK | 32 |
| 4A-327 | QVQLVQSGAEVKKPGASVKV SCKASGYTFTSYWIHWVRQAP GQRLEWMGNINPTNGGTNYS QKFQGRVTITRDTSASTAYME LSSLRSEDTAVYYCARAYYYG SSLFAYWGQGTLVTVSS | 29 | AIQMTQSPSSLSASVGDRVTITC KASQNVGTAVAWYQQKPGKAP KLLIYSASYRHTGVPSRFSGSGS GTDFTLTISSLQPEDFATYYCQQ YSTYPWTFGGGTKVEIK | 36 |
| 4A-328 | QVQLVQSGAEVKKPGASVKV SCKASGYTFTSYWIHWVRQAP GQRLEWMGNINPTNGGTNYS QKFQGRVTITVDKSASTAYME LSSLRSEDTAVYYCARAYYYG SSLFAYWGQGTLVTVSS | 30 | DIQLTQSPSFLSASVGDRVTITCK ASQNVGTAVAWYQQKPGKAPK LLIYSASYRHTGVPSRFSGSGSG TEFTLTISSLQPEDFATYYCQQY STYPWTFGGGTKVEIK | 37 |
| 4A-329 | QVQLVQSGAEVKKPGASVKV SCKASGYTFTSYWIHWVRQAP | 30 | DIVMTQSPSFLSASVGDRVTITC KASQNVGTAVAWYQQKPGKAP | 32 |

TABLE 2-continued

| Antibody | Heavy Chain Variable | SEQ ID NO: | Light Chain Variable | SEQ ID NO: |
|---|---|---|---|---|
| | GQRLEWMGNINPTNGGTNYS QKFQGRVTITVDKSASTAYME LSSLRSEDTAVYYCARAYYYG SSLFAYWGQGTLVTVSS | | KLLIYSASYRHTGVPSRFSGSGS GTEFTLTISSLQPEDFATYYCQQ YSTYPWTFGGGTKVEIK | |
| 4A-330 | QVQLVQSGAEVKKPGASVKV SCKASGYTFTSYWIHWVRQAP GQRLEWMGNINPTNGGTNYS QKFQGRVTITVDKSASTAYME LSSLRSEDTAVYYCARAYYYG SSLFAYWGQGTLVTVSS | 30 | AIQLTQSPSSLSASVGDRVTITCK ASQNVGTAVAWYQQKPGKAPK LLIYSASYRHTGVPSRFSGSGSG TDFTLTISSLQPEDFATYYCQQY STYPWTFGGGTKVEIK | 38 |
| 4A-331 | QVQLVQSGAEVKKPGASVKV SCKASGYTFTSYWIHWVRQAP GQRLEWMGNINPTNGGTNYS QKFQGRVTITVDKSASTAYME LSSLRSEDTAVYYCARAYYYG SSLFAYWGQGTLVTVSS | 30 | AIQMTQSPSSLSASVGDRVTITC KASQNVGTAVAWYQQKPGKAP KLLIYSASYRHTGVPSRFSGSGS GTDFTLTISSLQPEDFATYYCQQ YSTYPWTFGGGTKVEIK | 36 |

TABLE 3

| Antibody | Heavy Chain Variable | SEQ ID NO: | Light Chain Variable | SEQ ID NO: |
|---|---|---|---|---|
| 4A-21 | QIQLVQSGPELKKPGETVKI SCKASGYIFTSYGLSWVKQ TPGKGLKWMGWINTYSGV PTYANDFKGRFAFSLETSAS TTYLRINNLKNDDTATYFC ARSLVDYWGQGTPLTVSS | 39 | DVVMTQTPFTLSVTIGQSASIS CKSSQSLLYSDGKTYLSWLLQ RPGQSPKRLIYLVSKLDSGVPD RFTGSGSGTDFTLKISRVEAED LGVYYCWQGIDFHQTFGGGT KLEIK | 54 |
| 4A-332 | QVQLVQSGSELKKPGASVK VSCKASGYIFTSYGLSWVR QAPGQGLEWMGWINTYSG VPTYAQGFTGRFVFSLDTS VSTAYLQISSLKAEDTAVY YCARSLVDYWGQGTLVTV SS | 40 | DVVMTQSPLSLPVTLGQPASIS CKSSQSLLYSDGKTYLSWFQQ RPGQSPRRLIYLVSKLDSGVPD RFSGSGSGTDFTLKISRVEAED VGVYYCWQGIDFHQTFGGGT KVEIK | 55 |
| 4A-333 | QVQLVQSGSELKKPGASVK VSCKASGYIFTSYGLSWVR QAPGQGLEWMGWINTYSG VPTYAQGFTGRFVFSLDTS VSTTYLQISSLKAEDTAVY YCARSLVDYWGQGTLVTV SS | 41 | DVVMTQSPLSLPVTLGQPASIS CKSSQSLLYSDGKTYLSWFQQ RPGQSPRRLIYLVSKLDSGVPD RFSGSGSGTDFTLKISRVEAED VGVYYCWQGIDFHQTFGGGT KVEIK | 55 |
| 4A-334 | QVQLVQSGSELKKPGASVK VSCKASGYIFTSYGLSWVR QAPGQGLEWMGWINTYSG VPTYAQGFTGRFVFSLDTS VSTAYLQISSLKAEDTAVY YCARSLVDYWGQGTLVTV SS | 40 | DIVMTQTPLSSPVTLGQPASIS CKSSQSLLYSDGKTYLSWLQQ RPGQPPRLLIYLVSKLDSGVPD RFSGSGAGTDFTLKISRVEAED VGVYYCWQGIDFHQTFGGGT KVEIK | 56 |
| 4A-335 | QVQLVQSGSELKKPGASVK VSCKASGYIFTSYGLSWVR QAPGQGLEWMGWINTYSG VPTYAQGFTGRFVFSLDTS VSTAYLQISSLKAEDTAVY YCARSLVDYWGQGTLVTV SS | 40 | DVVMTQTPLSSPVTLGQPASIS CKSSQSLLYSDGKTYLSWLQQ RPGQPPRLLIYLVSKLDSGVPD RFSGSGAGTDFTLKISRVEAED VGVYYCWQGIDFHQTFGGGT KVEIK | 57 |
| 4A-336 | QVQLVQSGSELKKPGASVK VSCKASGYIFTSYGLSWVR QAPGQGLEWMGWINTYSG VPTYAQGFTGRFVFSLDTS VSTAYLQISSLKAEDTAVY YCARSLVDYWGQGTLVTV SS | 40 | DVVMTQTPLSSPVTLGQPASIS CKSSQSLLYSDGKTYLSWLQQ RPGQPPRRLIYLVSKLDSGVPD RFSGSGAGTDFTLKISRVEAED VGVYYCWQGIDFHQTFGGGT KVEIK | 58 |

TABLE 3-continued

| Antibody | Heavy Chain Variable | SEQ ID NO: | Light Chain Variable | SEQ ID NO: |
|---|---|---|---|---|
| 4A-337 | QVQLVQSGSELKKPGASVKVSCKASGYIFTSYGLSWVRQAPGQGLEWMGWINTYSGVPTYAQGFTGRFVFSLDTSVSTTYLQISSLKAEDTAVYYCARSLVDYWGQGTLVTVSS | 41 | DIVMTQTPLSSPVTLGQPASISCKSSQSLLYSDGKTYLSWLQQRPGQPPRLLIYLVSKLDSGVPDRFSGSGAGTDFTLKISRVEAEDVGVYYCWQGIDFHQTFGGGTKVEIK | 56 |
| 4A-338 | QVQLVQSGSELKKPGASVKVSCKASGYIFTSYGLSWVRQAPGQGLEWMGWINTYSGVPTYAQGFTGRFVFSLDTSVSTTYLQISSLKAEDTAVYYCARSLVDYWGQGTLVTVSS | 41 | DVVMTQTPLSSPVTLGQPASISCKSSQSLLYSDGKTYLSWLQQRPGQPPRLLIYLVSKLDSGVPDRFSGSGAGTDFTLKISRVEAEDVGVYYCWQGIDFHQTFGGGTKVEIK | 57 |
| 4A-339 | QVQLVQSGSELKKPGASVKVSCKASGYIFTSYGLSWVRQAPGQGLEWMGWINTYSGVPTYAQGFTGRFVFSLDTSVSTTYLQISSLKAEDTAVYYCARSLVDYWGQGTLVTVSS | 41 | DVVMTQTPLSSPVTLGQPASISCKSSQSLLYSDGKTYLSWLQQRPGQPPRRLIYLVSKLDSGVPDRFSGSGAGTDFTLKISRVEAEDVGVYYCWQGIDFHQTFGGGTKVEIK | 58 |
| 4A-340 | QVQLVQSGAEVKKPGASVKVSCKASGYIFTSYGLSWVRQAPGQRLEWMGWINTYSGVPTYSQKFQGRVTITLDTSASTTYMELSSLRSEDTAVYYCARSLVDYWGQGTLVTVSS | 42 | DVVMTQTPLSLSVTPGQPASISCKSSQSLLYSDGKTYLSWYLQKPGQPPQLLIYLVSKLDSGVPDRFSGSGSGTDFTLKISRVEAEDVGVYYCWQGIDFHQTFGGGTKVEIK | 59 |
| 4A-341 | QVQLVQSGAEVKKPGASVKVSCKASGYIFTSYGLSWVRQAPGQRLEWMGWINTYSGVPTYSQKFQGRVTITRDTSASTAYMELSSLRSEDTAVYYCARSLVDYWGQGTLVTVSS | 43 | DVVMTQTPLSLSVTPGQPASISCKSSQSLLYSDGKTYLSWYLQKPGQPPQLLIYLVSKLDSGVPDRFSGSGSGTDFTLKISRVEAEDVGVYYCWQGIDFHQTFGGGTKVEIK | 59 |
| 4A-342 | QIQLVQSGAEVKKPGASVKVSCKASGYIFTSYGLSWVRQAPGQGLEWMGWINTYSGVPTYAQKFQGRVTMTRDTSTSTVYMELSSLRSEDTAVYYCARSLVDYWGQGTLVTVSS | 44 | DVVMTQTPLSLSVTPGQPASISCKSSQSLLYSDGKTYLSWYLQKPGQPPQRLIYLVSKLDSGVPDRFSGSGSGTDFTLKISRVEAEDVGVYYCWQGIDFHQTFGGGTKVEIK | 60 |
| 4A-343 | QIQLVQSGAEVKKPGASVKVSCKASGYIFTSYGLSWVRQAPGQGLEWMGWINTYSGVPTYAQKFQGRVTMTLDTSTSTTYMELSSLRSEDTAVYYCARSLVDYWGQGTLVTVSS | 45 | DVVMTQTPLSLSVTPGQPASISCKSSQSLLYSDGKTYLSWYLQKPGQPPQRLIYLVSKLDSGVPDRFSGSGSGTDFTLKISRVEAEDVGVYYCWQGIDFHQTFGGGTKVEIK | 60 |
| 4A-344 | QVQLVQSGAEVKKPGASVKVSCKASGYIFTSYGLSWVRQAPGQGLEWMGWINTYSGVPTYAQKFQGRVTMTRDTSTSTVYMELSSLRSEDTAVYYCARSLVDYWGQGTLVTVSS | 46 | DVVMTQTPLSLSVTPGQPASISCKSSQSLLYSDGKTYLSWYLQKPGQPPQRLIYLVSKLDSGVPDRFSGSGSGTDFTLKISRVEAEDVGVYYCWQGIDFHQTFGGGTKVEIK | 60 |
| 4A-345 | QVQLVQSGAEVKKPGASVKVSCKASGYIFTSYGLSWVRQAPGQRLEWMGWINTYSGVPTYSQKFQGRVTITRDTSASTAYMELSSLRSEDTAVYYCARSLVDYWGQGTLVTVSS | 43 | DIVMTQTPLSLSVTPGQPASISCKSSQSLLYSDGKTYLSWYLQKPGQPPQLLIYLVSKLDSGVPDRFSGSGSGTDFTLKISRVEAEDVGVYYCWQGIDFHQTFGGGTKVEIK | 61 |
| 4A-346 | QVQLVQSGAEVKKPGASVKVSCKASGYIFTSYGLSWVRQAPGQGLEWMGWINTYS | 46 | DIVMTQTPLSLSVTPGQPASISCKSSQSLLYSDGKTYLSWYLQKPGQPPQLLIYLVSKLDSGVPD | 61 |

TABLE 3-continued

| Antibody | Heavy Chain Variable | SEQ ID NO: | Light Chain Variable | SEQ ID NO: |
|---|---|---|---|---|
| | GVPTYAQKFQGRVTMTRD TSTSTVYMELSSLRSEDTAV YYCARSLVDYWGQGTLVT VSS | | RFSGSGSGTDFTLKISRVEAED VGVYYCWQGIDFHQTFGGGT KVEIK | |
| 4A-347 | QVQLVQSGAEVKKPGASV KVSCKASGYIFTSYGLSWV RQAPGQRLEWMGWINTYS GVPTYSQKFQGRVTITLDTS ASTTYMELSSLRSEDTAVY YCARSLVDYWGQGTLVTV SS | 42 | DIVMTQTPLSLSVTPGQPASIS CKSSQSLLYSDGKTYLSWYLQ KPGQPPQLLIYLVSKLDSGVPD RFSGSGSGTDFTLKISRVEAED VGVYYCWQGIDFHQTFGGGT KVEIK | 61 |
| 4A-348 | QIQLVQSGAEVKKPGASVK VSCKASGYIFTSYGLSWVR QAPGQGLEWMGWINTYSG VPTYAQKFQGRVTMTRDTS TSTVYMELSSLRSEDTAVY YCARSLVDYWGQGTLVTV SS | 44 | DIVMTQTPLSLSVTPGQPASIS CKSSQSLLYSDGKTYLSWYLQ KPGQPPQLLIYLVSKLDSGVPD RFSGSGSGTDFTLKISRVEAED VGVYYCWQGIDFHQTFGGGT KVEIK | 61 |
| 4A-349 | QIQLVQSGAEVKKPGASVK VSCKASGYIFTSYGLSWVR QAPGQGLEWMGWINTYSG VPTYAQKFQGRVTMTLDTS TSTTYMELSSLRSEDTAVY YCARSLVDYWGQGTLVTV SS | 45 | DIVMTQTPLSLSVTPGQPASIS CKSSQSLLYSDGKTYLSWYLQ KPGQPPQLLIYLVSKLDSGVPD RFSGSGSGTDFTLKISRVEAED VGVYYCWQGIDFHQTFGGGT KVEIK | 61 |
| 4A-350 | QVQLVQSGSELKKPGASVK VSCKASGYIFTSYGLSWVR QAPGQGLEWMGWINTYSG VPTYAQGFTGRFVFSLDTS VSTAYLQISSLKAEDTAVY YCARTLADYWGQGTLVTV SS | 47 | DVVMTQSPLSLPVTLGQPASIS CKSSQSLLYSDGKTYLSWFQQ RPGQSPRRLIYLVSKLDSGVPD RFSGSGSGTDFTLKISRVEAED VGVYYCWQGIDFHQTFGGGT KVEIK | 55 |
| 4A-351 | QVQLVQSGSELKKPGASVK VSCKASGYIFTSYGLSWVR QAPGQGLEWMGWINTYSG VPTYAQGFTGRFVFSLDTS VSTAYLQISSLKAEDTAVY YCARTLADYWGQGTLVTV SS | 47 | DVVMTQSPLSLPVTLGQPASIS CKSSRSLLYSDGKTYLSWFQQ RPGQSPRRLIYLVSKLDSGVPD RFSGSGSGTDFTLKISRVEAED VGVYYCWQGIDFHQTFGGGT KVEIK | 62 |
| 4A-352 | QVQLVQSGSELKKPGASVK VSCKASGYIFTSYGLSWVR QAPGQGLEWMGWINTYSG VPTYAQGFTGRFVFSLDTS VSTAYLQISSLKAEDTAVY YCARTLADYWGQGTLVTV SS | 47 | DVVMTQSPLSLPVTLGQPASIS CKSSRSLLYSGGKTYLSWFQQ RPGQSPRRLIYLVSKLDSGVPD RFSGSGSGTDFTLKISRVEAED VGVYYCWQGIDFHQTFGGGT KVEIK | 63 |
| 4A-353 | QVQLVQSGSELKKPGASVK VSCKASGYIFTSYGLSWVR QAPGQGLEWMGWINTYSG VPTYAQGFTGRFVFSLDTS VSTAYLQISSLKAEDTAVY YCARTLADYWGQGTLVTV SS | 47 | DVVMTQSPLSLPVTLGQPASIS CKSSRSLLYSEGKTYLSWFQQ RPGQSPRRLIYLVSKLDSGVPD RFSGSGSGTDFTLKISRVEAED VGVYYCWQGIDFHQTFGGGT KVEIK | 64 |
| 4A-354 | QVQLVQSGSELKKPGASVK VSCKASGYIFTSYGLSWVR QAPGQGLEWMGWINTYSG VPTYAQGFTGRFVFSLDTS VSTAYLQISSLKAEDTAVY YCARTLADYWGQGTLVTV SS | 47 | DVVMTQSPLSLPVTLGQPASIS CKSSRSLLYSAGKTYLSWFQQ RPGQSPRRLIYLVSKLDSGVPD RFSGSGSGTDFTLKISRVEAED VGVYYCWQGIDFHQTFGGGT KVEIK | 65 |
| 4A-355 | QVQLVQSGSELKKPGASVK VSCKASGYIFTSYGLSWVR QAPGQGLEWMGWINTYSG VPTYAQGFTGRFVFSLDTS VSTAYLQISSLKAEDTAVY YCARTLADYWGQGTLVTV SS | 47 | DVVMTQSPLSLPVTLGQPASIS CKSSRSLLYSSGKTYLSWFQQ RPGQSPRRLIYLVSKLDSGVPD RFSGSGSGTDFTLKISRVEAED VGVYYCWQGIDFHQTFGGGT KVEIK | 66 |

TABLE 3-continued

| Antibody | Heavy Chain Variable | SEQ ID NO: | Light Chain Variable | SEQ ID NO: |
|---|---|---|---|---|
| 4A-356 | QVQLVQSGSELKKPGASVKVSCKASGYIFTSYGLSWVRQAPGQGLEWMGWINTYSGVPTYAQGFTGRFVFSLDTSVSTAYLQISSLKAEDTAVYYCARTLADYWGQGTLVTVSS | 47 | DVVMTQSPLSLPVTLGQPASISCKSSRSLLYSQGKTYLSWFQQRPGQSPRRLIYLVSKLDSGVPDRFSGSGSGTDFTLKISRVEAEDVGVYYCWQGIDFHQTFGGGTKVEIK | 67 |
| 4A-357 | QVQLVQSGSELKKPGASVKVSCKASGYIFTSYGLSWVRQAPGQGLEWMGWINTYSGVPTYAQGFTGRFVFSLDTSVSTAYLQISSLKAEDTAVYYCARTLADYWGQGTLVTVSS | 47 | DVVMTQSPLSLPVTLGQPASISCKSSQSLLYSDGKTYLSWFQQRPGQSPRRLIYEVSKLDSGVPDRFSGSGSGTDFTLKISRVEAEDVGVYYCWQGIDFHQTFGGGTKVEIK | 68 |
| 4A-358 | QVQLVQSGSELKKPGASVKVSCKASGYIFTSYGLSWVRQAPGQGLEWMGWINTYSGVPTYAQGFTGRFVFSLDTSVSTAYLQISSLKAEDTAVYYCARTLADYWGQGTLVTVSS | 47 | DVVMTQSPLSLPVTLGQPASISCKSSQSLLYSDGKTYLSWFQQRPGQSPRRLIYLVSKLDSGVPDRFSGSGSGTDFTLKISRVEAEDVGVYYCWQGIRFHQTFGGGTKVEIK | 69 |
| 4A-359 | QVQLVQSGSELKKPGASVKVSCKASGYIFTSYGLSWVRQAPGQGLEWMGWINTYSGVPTYAQGFTGRFVFSLDTSVSTAYLQISSLKAEDTAVYYCARTLADYWGQGTLVTVSS | 47 | DVVMTQSPLSLPVTLGQPASISCKASQSLLYSDGKTYLSWFQQRPGQSPRRLIYLVSKLDSGVPDRFSGSGSGADFTLKISRVEAEDVGVYYCWQGIDFHQTFGGGTKVEIK | 70 |
| 4A-360 | QVQLVQSGSELKKPGASVKVSCKASGYIFTSYGLSWVRQAPGQGLEWMGWINTYSGVPTYAQGFTGRFVFSLDTSVSTAYLQISSLKAEDTAVYYCARTLADYWGQGTLVTVSS | 47 | DVVMTQSPLSLPVTLGQPASISCKSGQSLLYSDGKTYLSWFQQRPGQSPRRLIYLVSRLDSGVPDRFSGSGSGTDFTLKISRVEAEDVGVYYCWQGIDFHQTFGGGTKVEIK | 71 |
| 4A-361 | QVQLVQSGSELKKPGASVKVSCKASGYIFTSYGLSWVRQAPGQGLEWMGWINTYSGVPTYAQGFTGRFVFSLDTSVSTAYLQISSLKAEDTAVYYCARTLADYWGQGTLVTVSS | 47 | DVVMTQSPLSLPVTLGQPASISCKSSQSLLYSDGKTYLSWFQQRPGQSPRRLIYLVSKLESGVPDRFSGSGSGTDFTLKISRVEAEDVGVYYCWQGIDFHQTFGGGTKVEIK | 72 |
| 4A-362 | QVQLVQSGSELKKPGASVKVSCKASGYIFTSYGLSWVRQAPGQGLEWMGWINTYSGVPTYAQGFTGRFVFSLDTSVSTAYLQISSLKAEDTAVYYCARTLADYWGQGTLVTVSS | 47 | DVVMTQSPLSLPVTLGQPASISCKSSQSLLYSDGKTYLSWFQQRPGQSPRRLIYLVSRLDSGVPDRFSGSGSGTDFTLKISRVEAEDVGVYYCWQGIDFHQTFGGGTKVEIK | 73 |
| 4A-363 | QVQLVQSGSELKKPGASVKVSCKASGYIFTSYGLSWVRQAPGQGLEWMGWINTYSGVPTYAQGFTGRFVFSLDTSVSTAYLQISSLKAEDTAVYYCARTLADYWGQGTLVTVSS | 47 | DVVMTQSPLSLPVTLGQPASISCKSSQSLLYSDGKTYLSWFQQRPGQSPRRLIYLVSKLSSGVPDRFSGSGSGTDFTLKISRVEAEDVGVYYCWQGIDFHQTFGGGTKVEIK | 74 |
| 4A-364 | QVQLVQSGSELKKPGASVKVSCKASGYTFTSYGLSWIRQAPGQGLEWMGWINTYSGVPTYAQGFTGRFVFSLDTSVSTAYLQISSLKAEDTAVYYCARTMVDYWGQGTLVTVSS | 48 | DVVMTQSPLSLPVTLGQPASISCKASQSLLYSDGKTYLSWFQQRPGQSPRRLIYLVSKLDSGVPDRFSGSGSGADFTLKISRVEAEDVGVYYCWQGIDFHQTFGGGTKVEIK | 70 |
| 4A-365 | QVQLVQSGSELKKPGASVKVSCKASGYTFTSYGLSWIRQAPGQGLEWMGWINTYSG | 48 | DVVMTQSPLSLPVTLGQPASISCKSSQSLLYSDGKTYLSWFQQRPGQSPRRLIYLVSKLSSGVPD | 74 |

TABLE 3-continued

| Antibody | Heavy Chain Variable | SEQ ID NO: | Light Chain Variable | SEQ ID NO: |
|---|---|---|---|---|
| | VPTYAQGFTGRFVFSLDTS<br>VSTAYLQISSLKAEDTAVY<br>YCARTMVDYWGQGTLVTV<br>SS | | RFSGSGSGTDFTLKISRVEAED<br>VGVYYCWQGIDFHQTFGGGT<br>KVEIK | |
| 4A-366 | QVQLVQSGSELKKPGASVK<br>VSCKASGYTFTSYGLSWIR<br>QAPGQGLEWMGWINTYSG<br>VPTYAQGFTGRFVFSLDTS<br>VSTAYLQISSLKAEDTAVY<br>YCARTMVDYWGQGTLVTV<br>SS | 48 | DVVMTQSPLSLPVTLGQPASIS<br>CKSSRSLLYSDGKTYLSWFQQ<br>RPGQSPRRLIYLVSKLDSGVPD<br>RFSGSGSGTDFTLKISRVEAED<br>VGVYYCWQGIDFHQTFGGGT<br>KVEIK | 62 |
| 4A-367 | QVQLVQSGSELKKPGASVK<br>VSCKASGYTFTSYGLSWIR<br>QAPGQGLEWMGWINTYSG<br>VPTYAQGFTGRFVFSLDTS<br>VSTAYLQISSLKAEDTAVY<br>YCARTMVDYWGQGTLVTV<br>SS | 48 | DVVMTQSPLSLPVTLGQPASIS<br>CKSSQSLLYSDGKTYLSWFQQ<br>RPGQSPRRLIYLVSKLDSGVPD<br>RFSGSGSGTDFTLKISRVEAED<br>VGVYYCWQGIDFHQTFGGGT<br>KVEIK | 55 |
| 4A-368 | QVQLVQSGSELKKPGASVK<br>VSCKASGYTFTSYGLSWIR<br>QAPGQGLEWMGWINTYSG<br>VPTYAQGFTGRFVFSLDTS<br>VSTAYLQISSLKAEDTAVY<br>YCARTMVDYWGQGTLVTV<br>SS | 48 | DVVMTQSPLSLPVTLGQPASIS<br>CKSSQSLLYSDGKTYLSWFQQ<br>RPGQSPRRLIYLVSKLESGVPD<br>RFSGSGSGTDFTLKISRVEAED<br>VGVYYCWQGIDFHQTFGGGT<br>KVEIK | 72 |
| 4A-369 | QVQLVQSGSELKKPGASVK<br>VSCKASGYTFTSYGLSWIR<br>QAPGQGLEWMGWINTYSG<br>VPTYAQGFTGRFVFSLDTS<br>VSTAYLQISSLKAEDTAVY<br>YCARTMVDYWGQGTLVTV<br>SS | 48 | DVVMTQSPLSLPVTLGQPASIS<br>CKSSQSLLYSDGKTYLSWFQQ<br>RPGQSPRRLIYLVSKLDSGVPD<br>RFSGSGSGTDFTLKISRVEAED<br>VGVYYCWQGIRFHQTFGGGT<br>KVEIK | 69 |
| 4A-370 | QVQLVQSGSELKKPGASVK<br>VSCKASGYIFTSYGLSWVR<br>QAPGQGLEWMGWINTYSG<br>VPTYAQGFTGRFVFSLDTS<br>VSTAYLQISSLKAEDTAVY<br>YCARTLGDYWGQGTLVTV<br>SS | 49 | DVVMTQSPLSLPVTLGQPASIS<br>CKSGQSLLYSDGKTYLSWFQQ<br>RPGQSPRRLIYLVSRLDSGVPD<br>RFSGSGSGTDFTLKISRVEAED<br>VGVYYCWQGIDFHQTFGGGT<br>KVEIK | 71 |
| 4A-371 | QVQLVQSGSELKKPGASVK<br>VSCKASGYIFTSYGLSWVR<br>QAPGQGLEWMGWINTYSG<br>VPTYAQGFTGRFVFSLDTS<br>VSTAYLQISSLKAEDTAVY<br>YCARTLGDYWGQGTLVTV<br>SS | 49 | DVVMTQSPLSLPVTLGQPASIS<br>CKSSQSLLYSDGKTYLSWFQQ<br>RPGQSPRRLIYLVSKLDSGVPD<br>RFSGSGSGTDFTLKISRVEAED<br>VGVYYCWQGIDFHQTFGGGT<br>KVEIK | 55 |
| 4A-372 | QVQLVQSGSELKKPGASVK<br>VSCKASGYIFTSYGLSWVR<br>QAPGQGLEWMGWINTYSG<br>VPTYAQGFTGRFVFSLDTS<br>VSTAYLQISSLKAEDTAVY<br>YCARTLGDYWGQGTLVTV<br>SS | 49 | DVVMTQSPLSLPVTLGQPASIS<br>CKSSQSLLYSDGKTYLSWFQQ<br>RPGQSPRRLIYLVSRLDSGVPD<br>RFSGSGSGTDFTLKISRVEAED<br>VGVYYCWQGIDFHQTFGGGT<br>KVEIK | 73 |
| 4A-373 | QVQLVQSGSELKKPGASVK<br>VSCKASGYIFTSYGLSWVR<br>QAPGQGLEWMGWINTYSG<br>VPTYAQGFTGRFVFSLDTS<br>VSTAYLQISSLKAEDTAVY<br>YCARTLVDYWGQGTLVTV<br>SS | 50 | DVVMTQSPLSLPVTLGQPASIS<br>CKSSRSLLYSDGKTYLSWFQQ<br>RPGQSPRRLIYLVSKLDSGVPD<br>RFSGSGSGTDFTLKISRVEAED<br>VGVYYCWQGIDFHQTFGGGT<br>KVEIK | 62 |
| 4A-374 | QVQLVQSGSELKKPGASVK<br>VSCKASGYIFTSYGLSWVR<br>QAPGQGLEWMGWINTYSG<br>VPTYAQGFAGRFVFSLDTS<br>VSTAYLQISSLKAEDTAVY<br>YCARTLVDYWGQGTLVTV<br>SS | 51 | DVVMTQSPLSLPVTLGQPASIS<br>CKSSRSLLYSDGKTYLSWFQQ<br>RPGQSPRRLIYLVSKLDSGVPD<br>RFSGSGSGTDFTLKISRVEAED<br>VGVYYCWQGIDFHQTFGGGT<br>KVEIK | 62 |

TABLE 3-continued

| Antibody | Heavy Chain Variable | SEQ ID NO: | Light Chain Variable | SEQ ID NO: |
|---|---|---|---|---|
| 4A-375 | QVQLVQSGSELKKPGASVK<br>VSCKASGYIFTSYGLSWVR<br>QAPGQGLEWMGWINTYSG<br>VPTYAQGFTGRFVFSLDTS<br>VSTAYLQISSLKAEDTAVY<br>YCARSLADYWGQGTLVTV<br>SS | 52 | DVVMTQSPLSLPVTLGQPASIS<br>CKSSRSLLYSDGKTYLSWFQQ<br>RPGQSPRRLIYLVSKLDSGVPD<br>RFSGSGSGTDFTLKISRVEAED<br>VGVYYCWQGIDFHQTFGGGT<br>KVEIK | 62 |
| 4A-376 | QVQLVQSGSELKKPGASVK<br>VSCKASGYIFTSYGLSWVR<br>QAPGQGLEWMGWINTYSG<br>VPTYAQGFTGRFVFSLDTS<br>VSTAYLQISSLKAEDTAVY<br>YCARSMADYWGQGTLVTV<br>SS | 53 | DVVMTQSPLSLPVTLGQPASIS<br>CKSSRSLLYSDGKTYLSWFQQ<br>RPGQSPRRLIYLVSKLDSGVPD<br>RFSGSGSGTDFTLKISRVEAED<br>VGVYYCWQGIDFHQTFGGGT<br>KVEIK | 62 |
| 4A-377 | QVQLVQSGSELKKPGASVK<br>VSCKASGYIFTSYGLSWVR<br>QAPGQGLEWMGWINTYSG<br>VPTYAQGFTGRFVFSLDTS<br>VSTAYLQISSLKAEDTAVY<br>YCARSMADYWGQGTLVTV<br>SS | 53 | DVVMTQSPLSLPVTLGQPASIS<br>CKSSRSLLYSGGKTYLSWFQQ<br>RPGQSPRRLIYLVSKLDSGVPD<br>RFSGSGSGTDFTLKISRVEAED<br>VGVYYCWQGIDFHQTFGGGT<br>KVEIK | 63 |
| 4A-378 | QVQLVQSGSELKKPGASVK<br>VSCKASGYIFTSYGLSWVR<br>QAPGQGLEWMGWINTYSG<br>VPTYAQGFTGRFVFSLDTS<br>VSTAYLQISSLKAEDTAVY<br>YCARSMADYWGQGTLVTV<br>SS | 53 | DVVMTQSPLSLPVTLGQPASIS<br>CKSSRSLLYSGGKTYLSWFQQ<br>RPGQSPRRLIYLVSKLDSGVPD<br>RFSGSGSGTDFTLKISRVEAED<br>VGVYYCWQGIDFHQTFGGGT<br>KVEIK | 64 |
| 4A-379 | QVQLVQSGSELKKPGASVK<br>VSCKASGYIFTSYGLSWVR<br>QAPGQGLEWMGWINTYSG<br>VPTYAQGFTGRFVFSLDTS<br>VSTAYLQISSLKAEDTAVY<br>YCARSMADYWGQGTLVTV<br>SS | 53 | DVVMTQSPLSLPVTLGQPASIS<br>CKSSRSLLYSGGKTYLSWFQQ<br>RPGQSPRRLIYLVSKLDSGVPD<br>RFSGSGSGTDFTLKISRVEAED<br>VGVYYCWQGIDFHQTFGGGT<br>KVEIK | 65 |
| 4A-380 | QVQLVQSGSELKKPGASVK<br>VSCKASGYIFTSYGLSWVR<br>QAPGQGLEWMGWINTYSG<br>VPTYAQGFTGRFVFSLDTS<br>VSTAYLQISSLKAEDTAVY<br>YCARSMADYWGQGTLVTV<br>SS | 53 | DVVMTQSPLSLPVTLGQPASIS<br>CKSSRSLLYSGGKTYLSWFQQ<br>RPGQSPRRLIYLVSKLDSGVPD<br>RFSGSGSGTDFTLKISRVEAED<br>VGVYYCWQGIDFHQTFGGGT<br>KVEIK | 66 |
| 4A-381 | QVQLVQSGSELKKPGASVK<br>VSCKASGYIFTSYGLSWVR<br>QAPGQGLEWMGWINTYSG<br>VPTYAQGFTGRFVFSLDTS<br>VSTAYLQISSLKAEDTAVY<br>YCARSMADYWGQGTLVTV<br>SS | 53 | DVVMTQSPLSLPVTLGQPASIS<br>CKSSRSLLYSGGKTYLSWFQQ<br>RPGQSPRRLIYLVSKLDSGVPD<br>RFSGSGSGTDFTLKISRVEAED<br>VGVYYCWQGIDFHQTFGGGT<br>KVEIK | 67 |

TABLE 4

| Antibody | Heavy Chain Variable | SEQ ID NO: | Light Chain Variable | SEQ ID NO: |
|---|---|---|---|---|
| 4A-25 | QVTLKESGPGILQPSQTLSLTC<br>SFSGFSLRTSDMGVGWVRQPS<br>GEGLEWLADIWWDDNKYYNP<br>SLKSRLTISKDTSSNQVFLKITS<br>VDTADTATYYCARRANYGNL<br>FDYWGQGTAVTVSS | 75 | DIVMTQSLKFMSTSVGDRVSIT<br>CKASQNVRSAVAWYQQKPGQ<br>SPKVLIYWASNRHTGVPDRFT<br>GSGSGTDFTLTISNVQSEDLAD<br>YFCLQHWNYLTFGSGTKLEIK | 85 |
| 4A-382 | QVTLKESGPALVQPTQTLTLT<br>CTFSGFSLRTSDMGVSWIRQPP<br>GEALEWLALIWWDDNKYYST | 76 | DIVLTQSPSSLSASVGDRVTIT<br>CRASQNVRSALAWYQQKPGQ<br>APKVLIYWASNRHSGVPSRFS | 86 |

TABLE 4-continued

| Antibody | Heavy Chain Variable | SEQ ID NO: | Light Chain Variable | SEQ ID NO: |
|---|---|---|---|---|
| | SLKTRLTISKDTSSNQVVLTMT<br>NMDPVDTATYYCARRANYGN<br>LFDYWGQGTAVTVSS | | GSGSGTDFTLTISSLQPEDFAT<br>YYCQQHWNYLTFGGGTKVEI<br>K | |
| 4A-383 | QVTLKESGPTLVQPTQTLTLTC<br>TFSGFSLRTSDMGVGWIRQPP<br>GKALEWLALIWWDDNKYYSP<br>SLKSRLTISKDTSSNQVVLTMT<br>NMDPVDTATYYCARRANYGN<br>LFDYWGQGTLVTVSS | 77 | DIVLTQSPSSLSASVGDRVTIT<br>CRASQNVRSALAWYQQKPGQ<br>APKLLIYWASNRHSGVPSRFS<br>GSGSGTDFTLTISSLQPEDFAT<br>YYCQQHWNYLTFGGGTKVEI<br>K | 87 |
| 4A-384 | QVTLRESGPALVQPTQTLTLT<br>CTFSGFSLRTSDMGVSWIRQPP<br>GEALEWLALIWWDDNKYYST<br>SLKTRLTISKDTSSNQVVLTMT<br>NMDPVDTATYYCARRANYGN<br>LFDYWGQGTLVTVSS | 78 | DIVMTQSPSSMSASVGDRVTIT<br>CQASQNVRSAVAWYQQKPGK<br>APKLLIYWASNRHTGVPSRFS<br>GSGSGTDFTFTISSLQPEDIATY<br>YCQQHWNYLTFGGGTKVEIK | 88 |
| 4A-385 | QVTLKESGPTLVKPTQTLTLTC<br>TFSGFSLRTSDMGVGWIRQPP<br>GKALEWLALIWWDDNKYYSP<br>SLKSRLTITKDTSSNQVVLTMT<br>NMDPVDTATYYCARRANYGN<br>LFDYWGQGTLVTVSS | 79 | DIVMTQSPSSLSTSVGDRVTIT<br>CRASQNVRSALAWYQQKPEK<br>APKSLIYWASNRHSGVPSRFS<br>GSGSGTDFTLTISSLQPEDFAT<br>YYCQQHWNYLTFGGGTKVEI<br>K | 89 |
| 4A-386 | QVTLKESGPGLVQPTETLTLTC<br>TFSGFSLRTSDMGVSWIRQPPG<br>KALEWLAHIWWDDNKSYSTS<br>LKSRLTISKDTSSNQVVLTMT<br>NMDPVDTATYYCARRANYGN<br>LFDYWGQGTLVTVSS | 80 | DIVMTQSPSSLSASVGDRVTIT<br>CRASQNVRSALAWYQQKPEQ<br>APKSLIYWASNRHSGVPSRFS<br>GSGSGTDFTLTISSLQPEDFAT<br>YYCQQHWNYLTFGGGTKVEI<br>K | 90 |
| 4A-387 | QVTLKESGPVLVKPTETLTLTC<br>TFSGFSLRTSDMGVSWIRQPSG<br>KALEWLAHIWWDDNKSYSTS<br>LKSRLTISKDTSKNQVVLTMT<br>NMDPVDTATYYCARRANYGN<br>LFDYWGQGTLVTVSS | 81 | DIVMTQSPSSLSASVGDRVTIT<br>CQASQNVRSALNWYQQKPGK<br>APKLLIYWASNRHTGVPSRFS<br>GSGSGTDFTFTISSLQSEDIATY<br>YCQQHWNYLTFGGGTKVEIK | 91 |
| 4A-388 | QVTLKESGPVLVKPTETLTLTC<br>TFSGFSLRTSDMGVSWIRQPSG<br>EGLEWLAHIWWDDNKSYSTS<br>LKSRLTISKDTSKNQVVLTMT<br>NMDPVDTATYYCARRANYGN<br>LFDYWGQGTLVTVSS | 82 | DIVMTQSPSSLSASVGDRVTIT<br>CQASQNVRSALNWYQQKPGK<br>APKLLIYWASNRHTGVPSRFS<br>GSGSGTDFTFTISSLQSEDIATY<br>YCQQHWNYLTFGGGTKVEIK | 91 |
| 4A-389 | QVTLQESGPGLVKPSETLSLTC<br>AVSGFSLRTSDMGVGWIRQPP<br>GEGLEWIGSIWWDDNKYYNP<br>SLKSRVTISKDTSKNQVSLKLS<br>SVDAADTAVYYCARRANYGN<br>LFDYWGQGTLVTVSS | 83 | DIQMTQSPSSLSASVGDRVTIT<br>CRASQNVRSALAWYQQKPEQ<br>APKSLIYWASSLQSGVPSRFSG<br>SGSGTDFTLTISNRHPEDFATY<br>YCQQHWNYLTFGGGTKVEIK | 92 |
| 4A-390 | QVQLQESGPGLVQPSETLSLTC<br>AVSGFSLRTSDMGVGWIRQPP<br>GKGLEWIGSIWYDDNKYYNPS<br>LKSRVTISKDTSSNQFSLKLSS<br>VTAADTAVYYCARRANYGNL<br>FDYWGQGTLVTVSS | 84 | DIQMTQSPSSLSTSVGDRVTIT<br>CQASQNVRSALNWYQQKPGK<br>APKLLIYWASNRHTGVPSRFS<br>GSGSGTDFTFTISSLQSEDIATY<br>YCQQHWNYLTFGGGTKVEIK | 93 |

The CDR sequences according to Kabat for the anti-MS4A4A antibodies of the present disclosure are provided below in Tables 5-8.

TABLE 5

| Antibody | CDR-H1 | SEQ ID NO: | CDR-H2 | SEQ ID NO: | CDR-H3 | SEQ ID NO: | CDR-L1 | SEQ ID NO: | CDR-L2 | SEQ ID NO: | CDR-L3 | SEQ ID NO: |
|---|---|---|---|---|---|---|---|---|---|---|---|---|
| 4A-202 | NYWMQ | 94 | ATHPGHG<br>DTRYTQK<br>FKG | 95 | EEVYYGFR<br>SYWYFDV | 100 | RASESVDN<br>YGVSFMN | 103 | GASNQGS | 105 | QQSKEVP<br>PT | 107 |

TABLE 5-continued

| Antibody | CDR-H1 | SEQ ID NO: | CDR-H2 | SEQ ID NO: | CDR-H3 | SEQ ID NO: | CDR-L1 | SEQ ID NO: | CDR-L2 | SEQ ID NO: | CDR-L3 | SEQ ID NO: |
|---|---|---|---|---|---|---|---|---|---|---|---|---|
| 4A-301 | NYWMQ | 94 | ATHPGHG DTRYAQK FQG | 96 | EEVYYGFR SYWYFDV | 100 | RASESVDN YGVSFMN | 103 | GASNQGS | 105 | QQSKEVP PT | 107 |
| 4A-302 | NYWMQ | 94 | ATHPGHG DTRYAQK FQG | 96 | EEVYYGFR SYWYFDV | 100 | RASESVDN YGVSFMN | 103 | GASNQGS | 105 | QQSKEVP PT | 107 |
| 4A-303 | NYWMQ | 94 | ATHPGHG DTRYSPS FQG | 97 | EEVYYGFR SYWYFDV | 100 | RASESVDN YGVSFMN | 103 | GASNQGS | 105 | QQSKEVP PT | 107 |
| 4A-304 | NYWMQ | 94 | ATHPGHG DTRYAQK FQG | 96 | EEVYYGFR SYWYFDV | 100 | RASESVDN YGVSFMN | 103 | GASNQGS | 105 | QQSKEVP PT | 107 |
| 4A-305 | NYWMQ | 94 | ATHPGHG DTRYAEK FQG | 98 | EEVYYGFR SYWYFDV | 100 | RASESVDN YGVSFMN | 103 | GASNQGS | 105 | QQSKEVP PT | 107 |
| 4A-306 | NYWMQ | 94 | ATHPGHG DTRYAQK FQG | 96 | EEVYYGFR SYWYFDV | 100 | RASESVDN YGVSFMN | 103 | GASNQGS | 105 | QQSKEVP PT | 107 |
| 4A-307 | NYWMQ | 94 | ATHPGHG DTRYAQK FQG | 96 | EEVYYGFR SYWYFDV | 100 | RASESVDN YGVSFMN | 103 | GASNQGS | 105 | QQSKEVP PT | 107 |
| 4A-308 | NYWMQ | 94 | ATHPGHG DTRYAQK FQG | 96 | EEVYYGFR SYWYFDV | 100 | RASESVDN YGVSFMN | 103 | GASNQGS | 105 | QQSKEVP PT | 107 |
| 4A-309 | NYWMQ | 94 | ATHPGHG DTRYAQK FQG | 96 | EEVYYGFR SYWYFDV | 100 | RASESVDN YGVSFMN | 103 | GASNQGS | 105 | QQSKEVP PT | 107 |
| 4A-310 | NYWMQ | 94 | ATHPGHG DTRYSPS FQG | 97 | EEVYYGFR SYWYFDV | 100 | RASESVDN YGVSFMN | 103 | GASNQGS | 105 | QQSKEVP PT | 107 |
| 4A-311 | NYWMQ | 94 | ATHPGHG DTRYAEK FQG | 98 | EEVYYGFR SYWYFDV | 100 | RASESVDN YGVSFMN | 103 | GASNQGS | 105 | QQSKEVP PT | 107 |
| 4A-312 | NYWMQ | 94 | ATHPGHG DTRYAQK FQG | 96 | EEVDYGFR SYWYFDV | 101 | RASESVDN YGVSFMN | 103 | GASNQQS | 106 | QQSKEVP PT | 107 |
| 4A-313 | NYWMQ | 94 | ATHPGHG DTRYAQK FQG | 96 | EEVYYGFR SYWYFDL | 102 | RASESVDN YGVSRMN | 104 | GASNQGS | 105 | QQSKEVP PT | 107 |
| 4A-314 | NYWMQ | 94 | TTLPGHG DTRYAQK FQG | 99 | EEVYYGFR SYWYFDV | 100 | RASESVDN YGVSRMN | 104 | GASNQGS | 105 | QQSKEVP PT | 107 |

TABLE 6

| Antibody | CDR-H1 | SEQ ID NO: | CDR-H2 | SEQ ID NO: | CDR-H3 | SEQ ID NO: | CDR-L1 | SEQ ID NO: | CDR-L2 | SEQ ID NO: | CDR-L3 | SEQ ID NO: |
|---|---|---|---|---|---|---|---|---|---|---|---|---|
| 4A-18 | SYWIH | 108 | NINPTN GGTNYN ERFKS | 109 | AYYYGS SLFAY | 112 | KASQNV GTAVA | 113 | SASYRH T | 114 | QQYSTY PWT | 115 |
| 4A-315 | SYWIH | 108 | NINPTN GGTNYA QKFQG | 110 | AYYYGS SLFAY | 112 | KASQNV GTAVA | 113 | SASYRH T | 114 | QQYSTY PWT | 115 |

TABLE 6-continued

| Antibody | CDR-H1 | SEQ ID NO: | CDR-H2 | SEQ ID NO: | CDR-H3 | SEQ ID NO: | CDR-L1 | SEQ ID NO: | CDR-L2 | SEQ ID NO: | CDR-L3 | SEQ ID NO: |
|---|---|---|---|---|---|---|---|---|---|---|---|---|
| 4A-316 | SYWIH | 108 | NINPTN GGTNYA QKFQG | 110 | AYYYGS SLFAY | 112 | KASQNV GTAVA | 113 | SASYRH T | 114 | QQYSTY PWT | 115 |
| 4A-317 | SYWIH | 108 | NINPTN GGTNYA QKFQG | 110 | AYYYGS SLFAY | 112 | KASQNV GTAVA | 113 | SASYRH T | 114 | QQYSTY PWT | 115 |
| 4A-318 | SYWIH | 108 | NINPTN GGTNYA QKFQG | 110 | AYYYGS SLFAY | 112 | KASQNV GTAVA | 113 | SASYRH T | 114 | QQYSTY PWT | 115 |
| 4A-319 | SYWIH | 108 | NINPTN GGTNYA QKFQG | 110 | AYYYGS SLFAY | 112 | KASQNV GTAVA | 113 | SASYRH T | 114 | QQYSTY PWT | 115 |
| 4A-320 | SYWIH | 108 | NINPTN GGTNYA QKFQG | 110 | AYYYGS SLFAY | 112 | KASQNV GTAVA | 113 | SASYRH T | 114 | QQYSTY PWT | 115 |
| 4A-321 | SYWIH | 108 | NINPTN GGTNYA QKFQG | 110 | AYYYGS SLFAY | 112 | KASQNV GTAVA | 113 | SASYRH T | 114 | QQYSTY PWT | 115 |
| 4A-322 | SYWIH | 108 | NINPTN GGTNYA QKFQG | 110 | AYYYGS SLFAY | 112 | KASQNV GTAVA | 113 | SASYRH T | 114 | QQYSTY PWT | 115 |
| 4A-323 | SYWIH | 108 | NINPTN GGTNYA QKFQG | 110 | AYYYGS SLFAY | 112 | KASQNV GTAVA | 113 | SASYRH T | 114 | QQYSTY PWT | 115 |
| 4A-324 | SYWIH | 108 | NINPTN GGTNYA QKFQG | 110 | AYYYGS SLFAY | 112 | KASQNV GTAVA | 113 | SASYRH T | 114 | QQYSTY PWT | 115 |
| 4A-325 | SYWIH | 108 | NINPTN GGTNYA QKFQG | 110 | AYYYGS SLFAY | 112 | KASQNV GTAVA | 113 | SASYRH T | 114 | QQYSTY PWT | 115 |
| 4A-326 | SYWIH | 108 | NINPTN GGTNYS QKFQG | 111 | AYYYGS SLFAY | 112 | KASQNV GTAVA | 113 | SASYRH T | 114 | QQYSTY PWT | 115 |
| 4A-327 | SYWIH | 108 | NINPTN GGTNYS QKFQG | 111 | AYYYGS SLFAY | 112 | KASQNV GTAVA | 113 | SASYRH T | 114 | QQYSTY PWT | 115 |
| 4A-328 | SYWIH | 108 | NINPTN GGTNYS QKFQG | 111 | AYYYGS SLFAY | 112 | KASQNV GTAVA | 113 | SASYRH T | 114 | QQYSTY PWT | 115 |
| 4A-329 | SYWIH | 108 | NINPTN GGTNYS QKFQG | 111 | AYYYGS SLFAY | 112 | KASQNV GTAVA | 113 | SASYRH T | 114 | QQYSTY PWT | 115 |
| 4A-330 | SYWIH | 108 | NINPTN GGTNYS QKFQG | 111 | AYYYGS SLFAY | 112 | KASQNV GTAVA | 113 | SASYRH T | 114 | QQYSTY PWT | 115 |
| 4A-331 | SYWIH | 108 | NINPTN GGTNYS QKFQG | 111 | AYYYGS SLFAY | 112 | KASQNV GTAVA | 113 | SASYRH T | 114 | QQYSTY PWT | 115 |

TABLE 7

| Antibody | CDR-H1 | SEQ ID NO: | CDR-H2 | SEQ ID NO: | CDR-H3 | SEQ ID NO: | CDR-L1 | SEQ ID NO: | CDR-L2 | SEQ ID NO: | CDR-L3 | SEQ ID NO: |
|---|---|---|---|---|---|---|---|---|---|---|---|---|
| 4A-21 | SYGLS | 116 | WINTYS GVPTYA NDFKG | 117 | SLVDY | 123 | KSSQSL LYSDGK TYLS | 130 | LVSKLDS | 139 | WQGIDFHQT | 144 |
| 4A-332 | SYGLS | 116 | WINTYS GVPTYA QGFTG | 118 | SLVDY | 123 | KSSQSL LYSDGK TYLS | 130 | LVSKLDS | 139 | WQGIDFHQT | 144 |
| 4A-333 | SYGLS | 116 | WINTYS GVPTYA QGFTG | 118 | SLVDY | 123 | KSSQSL LYSDGK TYLS | 130 | LVSKLDS | 139 | WQGIDFHQT | 144 |
| 4A-334 | SYGLS | 116 | WINTYS GVPTYA QGFTG | 118 | SLVDY | 123 | KSSQSL LYSDGK TYLS | 130 | LVSKLDS | 139 | WQGIDFHQT | 144 |
| 4A-335 | SYGLS | 116 | WINTYS GVPTYA QGFTG | 118 | SLVDY | 123 | KSSQSL LYSDGK TYLS | 130 | LVSKLDS | 139 | WQGIDFHQT | 144 |
| 4A-336 | SYGLS | 116 | WINTYS GVPTYA QGFTG | 118 | SLVDY | 123 | KSSQSL LYSDGK TYLS | 130 | LVSKLDS | 139 | WQGIDFHQT | 144 |
| 4A-337 | SYGLS | 116 | WINTYS GVPTYA QGFTG | 118 | SLVDY | 123 | KSSQSL LYSDGK TYLS | 130 | LVSKLDS | 139 | WQGIDFHQT | 144 |
| 4A-338 | SYGLS | 116 | WINTYS GVPTYA QGFTG | 118 | SLVDY | 123 | KSSQSL LYSDGK TYLS | 130 | LVSKLDS | 139 | WQGIDFHQT | 144 |
| 4A-339 | SYGLS | 116 | WINTYS GVPTYA QGFTG | 118 | SLVDY | 123 | KSSQSL LYSDGK TYLS | 130 | LVSKLDS | 139 | WQGIDFHQT | 144 |
| 4A-340 | SYGLS | 116 | WINTYS GVPTYS QKFQG | 119 | SLVDY | 123 | KSSQSL LYSDGK TYLS | 130 | LVSKLDS | 139 | WQGIDFHQT | 144 |
| 4A-341 | SYGLS | 116 | WINTYS GVPTYS QKFQG | 119 | SLVDY | 123 | KSSQSL LYSDGK TYLS | 130 | LVSKLDS | 139 | WQGIDFHQT | 144 |
| 4A-342 | SYGLS | 116 | INTYSG VPTYAQ KFQG | 120 | SLVDY | 123 | KSSQSL LYSDGK TYLS | 130 | LVSKLDS | 139 | WQGIDFHQT | 144 |
| 4A-343 | SYGLS | 116 | WINTYS GVPTYA QKFQG | 121 | SLVDY | 123 | KSSQSL LYSDGK TYLS | 130 | LVSKLDS | 139 | WQGIDFHQT | 144 |
| 4A-344 | SYGLS | 116 | WINTYS GVPTYA QKFQG | 121 | SLVDY | 123 | KSSQSL LYSDGK TYLS | 130 | LVSKLDS | 139 | WQGIDFHQT | 144 |
| 4A-345 | SYGLS | 116 | WINTYS GVPTYS QKFQG | 119 | SLVDY | 123 | KSSQSL LYSDGK TYLS | 130 | LVSKLDS | 139 | WQGIDFHQT | 144 |
| 4A-346 | SYGLS | 116 | WINTYS GVPTYA QKFQG | 121 | SLVDY | 123 | KSSQSL LYSDGK TYLS | 130 | LVSKLDS | 139 | WQGIDFHQT | 144 |
| 4A-347 | SYGLS | 116 | WINTYS GVPTYS QKFQG | 119 | SLVDY | 123 | KSSQSL LYSDGK TYLS | 130 | LVSKLDS | 139 | WQGIDFHQT | 144 |
| 4A-348 | SYGLS | 116 | WINTYS GVPTYA QKFQG | 121 | SLVDY | 123 | KSSQSL LYSDGK TYLS | 130 | LVSKLDS | 139 | WQGIDFHQT | 144 |
| 4A-349 | SYGLS | 116 | WINTYS GVPTYA QKFQG | 121 | SLVDY | 123 | KSSQSL LYSDGK TYLS | 130 | LVSKLDS | 139 | WQGIDFHQT | 144 |

TABLE 7-continued

| Antibody | CDR-H1 | SEQ ID NO: | CDR-H2 | SEQ ID NO: | CDR-H3 | SEQ ID NO: | CDR-L1 | SEQ ID NO: | CDR-L2 | SEQ ID NO: | CDR-L3 | SEQ ID NO: |
|---|---|---|---|---|---|---|---|---|---|---|---|---|
| 4A-350 | SYGLS | 116 | WINTYS GVPTYA QGFTG | 118 | TLADY | 124 | KSSQSL LYSDGK TYLS | 130 | LVSKLDS | 139 | WQGIDFHQT | 144 |
| 4A-351 | SYGLS | 116 | WINTYS GVPTYA QGFTG | 118 | TLADY | 124 | KSSRSL LYSDGK TYLS | 131 | LVSKLDS | 139 | WQGIDFHQT | 144 |
| 4A-352 | SYGLS | 116 | WINTYS GVPTYA QGFTG | 118 | TLADY | 124 | KSSRSL LYSGGK TYLS | 132 | LVSKLDS | 139 | WQGIDFHQT | 144 |
| 4A-353 | SYGLS | 116 | WINTYS GVPTYA QGFTG | 118 | TLADY | 124 | KSSRSL LYSEGK TYLS | 133 | LVSKLDS | 139 | WQGIDFHQT | 144 |
| 4A-354 | SYGLS | 116 | WINTYS GVPTYA QGFTG | 118 | TLADY | 124 | KSSRSL LYSAGK TYLS | 134 | LVSKLDS | 139 | WQGIDFHQT | 144 |
| 4A-355 | SYGLS | 116 | WINTYS GVPTYA QGFTG | 118 | TLADY | 124 | KSSRSL LYSSGK TYLS | 135 | LVSKLDS | 139 | WQGIDFHQT | 144 |
| 4A-356 | SYGLS | 116 | WINTYS GVPTYA QGFTG | 118 | TLADY | 124 | KSSRSL LYSQGK TYLS | 136 | LVSKLDS | 139 | WQGIDFHQT | 144 |
| 4A-357 | SYGLS | 116 | WINTYS GVPTYA QGFTG | 118 | TLADY | 124 | KSSQSL LYSDGK TYLS | 130 | EVSKLDS | 140 | WQGIDFHQT | 144 |
| 4A-358 | SYGLS | 116 | WINTYS GVPTYA QGFTG | 118 | TLADY | 124 | KSSQSL LYSDGK TYLS | 130 | LVSKLDS | 139 | WQGIRFHQT | 145 |
| 4A-359 | SYGLS | 116 | WINTYS GVPTYA QGFTG | 118 | TLADY | 124 | KASQSL LYSDGK TYLS | 137 | LVSKLDS | 139 | WQGIDFHQT | 144 |
| 4A-360 | SYGLS | 116 | WINTYS GVPTYA QGFTG | 118 | TLADY | 124 | KSGQSL LYSDGK TYLS | 138 | LVSRLDS | 141 | WQGIDFHQT | 144 |
| 4A-361 | SYGLS | 116 | WINTYS GVPTYA QGFTG | 118 | TLADY | 124 | KSSQSL LYSDGK TYLS | 130 | LVSKLES | 142 | WQGIDFHQT | 144 |
| 4A-362 | SYGLS | 116 | WINTYS GVPTYA QGFTG | 118 | TLADY | 124 | KSSQSL LYSDGK TYLS | 130 | LVSRLDS | 141 | WQGIDFHQT | 144 |
| 4A-363 | SYGLS | 116 | WINTYS GVPTYA QGFTG | 118 | TLADY | 124 | KSSQSL LYSDGK TYLS | 130 | LVSKLSS | 143 | WQGIDFHQT | 144 |
| 4A-364 | SYGLS | 116 | WINTYS GVPTYA QGFTG | 118 | TMVDY | 125 | KASQSL LYSDGK TYLS | 137 | LVSKLDS | 139 | WQGIDFHQT | 144 |
| 4A-365 | SYGLS | 116 | WINTYS GVPTYA QGFTG | 118 | TMVDY | 125 | KSSQSL LYSDGK TYLS | 130 | LVSKLSS | 143 | WQGIDFHQT | 144 |
| 4A-366 | SYGLS | 116 | WINTYS GVPTYA QGFTG | 118 | TMVDY | 125 | KSSRSL LYSDGK TYLS | 131 | LVSKLDS | 139 | WQGIDFHQT | 144 |
| 4A-367 | SYGLS | 116 | WINTYS GVPTYA QGFTG | 118 | TMVDY | 125 | KSSQSL LYSDGK TYLS | 130 | LVSKLDS | 139 | WQGIDFHQT | 144 |
| 4A-368 | SYGLS | 116 | WINTYS GVPTYA QGFTG | 118 | TMVDY | 125 | KSSQSL LYSDGK TYLS | 130 | LVSKLES | 142 | WQGIDFHQT | 144 |

TABLE 7-continued

| Antibody | CDR-H1 | SEQ ID NO: | CDR-H2 | SEQ ID NO: | CDR-H3 | SEQ ID NO: | CDR-L1 | SEQ ID NO: | CDR-L2 | SEQ ID NO: | CDR-L3 | SEQ ID NO: |
|---|---|---|---|---|---|---|---|---|---|---|---|---|
| 4A-369 | SYGLS | 116 | WINTYSGVPTYAQGFTG | 118 | TMVDY | 125 | KSSQSLLYSDGKTYLS | 130 | LVSKLDS | 139 | WQGIRFHQT | 145 |
| 4A-370 | SYGLS | 116 | WINTYSGVPTYAQGFTG | 118 | TLGDY | 126 | KSGQSLLYSDGKTYLS | 138 | LVSRLDS | 141 | WQGIDFHQT | 144 |
| 4A-371 | SYGLS | 116 | WINTYSGVPTYAQGFTG | 118 | TLGDY | 126 | KSSQSLLYSDGKTYLS | 130 | LVSKLDS | 139 | WQGIDFHQT | 144 |
| 4A-372 | SYGLS | 116 | WINTYSGVPTYAQGFTG | 118 | TLGDY | 126 | KSSQSLLYSDGKTYLS | 130 | LVSRLDS | 141 | WQGIDFHQT | 144 |
| 4A-373 | SYGLS | 116 | WINTYSGVPTYAQGFTG | 118 | TLVDY | 127 | KSSRSLLYSDGKTYLS | 131 | LVSKLDS | 139 | WQGIDFHQT | 144 |
| 4A-374 | SYGLS | 116 | WINTYSGVPTYAQGFAG | 122 | TLVDY | 127 | KSSRSLLYSDGKTYLS | 131 | LVSKLDS | 139 | WQGIDFHQT | 144 |
| 4A-375 | SYGLS | 116 | WINTYSGVPTYAQGFTG | 118 | SLADY | 128 | KSSRSLLYSDGKTYLS | 131 | LVSKLDS | 139 | WQGIDFHQT | 144 |
| 4A-376 | SYGLS | 116 | WINTYSGVPTYAQGFTG | 118 | SMADY | 129 | KSSRSLLYSDGKTYLS | 131 | LVSKLDS | 139 | WQGIDFHQT | 144 |
| 4A-377 | SYGLS | 116 | WINTYSGVPTYAQGFTG | 118 | SMADY | 129 | KSSRSLLYSGGKTYLS | 132 | LVSKLDS | 139 | WQGIDFHQT | 144 |
| 4A-378 | SYGLS | 116 | WINTYSGVPTYAQGFTG | 118 | SMADY | 129 | KSSRSLLYS EGKTYLS | 133 | LVSKLDS | 139 | WQGIDFHQT | 144 |
| 4A-379 | SYGLS | 116 | WINTYSGVPTYAQGFTG | 118 | SMADY | 129 | KSSRSLLYSAGKTYLS | 134 | LVSKLDS | 139 | WQGIDFHQT | 144 |
| 4A-380 | SYGLS | 116 | WINTYSGVPTYAQGFTG | 118 | SMADY | 129 | KSSRSLLYSSGKTYLS | 135 | LVSKLDS | 139 | WQGIDFHQT | 144 |
| 4A-381 | SYGLS | 116 | WINTYSGVPTYAQGFTG | 118 | SMADY | 129 | KSSRSLLYSQGKTYLS | 136 | LVSKLDS | 139 | WQGIDFHQT | 144 |

TABLE 8

| Antibody | CDR-H1 | SEQ ID NO: | CDR-H2 | SEQ ID NO: | CDR-H3 | SEQ ID NO: | CDR-L1 | SEQ ID NO: | CDR-L2 | SEQ ID NO: | CDR-L3 | SEQ ID NO: |
|---|---|---|---|---|---|---|---|---|---|---|---|---|
| 4A-25 | TSDMGVG | 146 | DIWWDDNKYYNPSLKS | 148 | RANYGNLFDY | 154 | KASQNVRSAVA | 155 | WASNRHT | 159 | QHWNYLT | 162 |
| 4A-382 | TSDMGVS | 147 | LIWWDDNKYYSTSLKT | 149 | RANYGNLFDY | 154 | RASQNVRSALA | 156 | WASNRHS | 160 | QQHWNYLT | 163 |
| 4A-383 | TSDMGVG | 146 | LIWWDDNKYYSPSLKS | 150 | RANYGNLFDY | 154 | RASQNVRSALA | 156 | WASNRHS | 160 | QQHWNYLT | 163 |

TABLE 8-continued

| Antibody | CDR-H1 | SEQ ID NO: | CDR-H2 | SEQ ID NO: | CDR-H3 | SEQ ID NO: | CDR-L1 | SEQ ID NO: | CDR-L2 | SEQ ID NO: | CDR-L3 | SEQ ID NO: |
|---|---|---|---|---|---|---|---|---|---|---|---|---|
| 4A-384 | TSDMGVS | 147 | LIWWDDNKYYSTSLKT | 149 | RANYGNLFDY | 154 | QASQNVRSAVA | 157 | WASNRHT | 159 | QQHWNYLT | 163 |
| 4A-385 | TSDMGVG | 146 | LIWWDDNKYYSPSLKS | 150 | RANYGNLFDY | 154 | RASQNVRSALA | 156 | WASNRHS | 160 | QQHWNYLT | 163 |
| 4A-386 | TSDMGVS | 147 | HIWWDDNKSYSTSLKS | 151 | RANYGNLFDY | 154 | RASQNVRSALA | 156 | WASNRHS | 160 | QQHWNYLT | 163 |
| 4A-387 | TSDMGVS | 147 | HIWWDDNKSYSTSLKS | 151 | RANYGNLFDY | 154 | QASQNVRSALN | 158 | WASNRHT | 159 | QQHWNYLT | 163 |
| 4A-388 | TSDMGVS | 147 | HIWWDDNKSYSTSLKS | 151 | RANYGNLFDY | 154 | QASQNVRSALN | 158 | WASNRHT | 159 | QQHWNYLT | 163 |
| 4A-389 | TSDMGVG | 146 | SIWWDDNKYYNPSLKS | 152 | RANYGNLFDY | 154 | RASQNVRSALA | 156 | WASSLQS | 161 | QQHWNYLT | 163 |
| 4A-390 | TSDMGVG | 146 | SIWYDDNKYYNPSLKS | 153 | RANYGNLFDY | 154 | QASQNVRSALN | 158 | WASNRHT | 159 | QQHWNYLT | 163 |

Example 2: Preparation of Recombinant MS4A4A Soluble Polypeptides

The primary amino acid sequence of human MS4A4A (SEQ ID NO: 1) was analyzed to provide information about its secondary and tertiary structure. Human MS4A4A protein has four transmembrane domains (TMDs) and each TMD is composed of 21 amino acids. Predicted from the amino acid composition, residue numbers, and the thickness of the lipid bilayer, MS4A4A is predicted to comprise a four helix bundle (4HB) with two extra cellular loops (ECLs), connecting TMD1 and TMD2, and TMD3 and TMD4 from the N-terminus to the C-terminus, respectively (see FIG. 1). FIG. 1 shows the primary amino acid sequence of human MS4A4A; intracellular domains are italicized, transmembrane domains are underlined, and the two extracellular loops are bold-italicized.

Two template structures of soluble 4HB scaffold proteins (which are predicted to mimic the geometry and configuration of MS4A4A) were identified using the RCSB Protein Data Bank. The PDB ID of these protein scaffolds are 1P68 and 1M6T. FIG. 2A, FIG. 2B, and FIG. 2C show the structure and primary amino acid sequence of two soluble four-helix bundle scaffolds (PDB_ID: 1P68 and PDB ID: 1M6T). In FIG. 2A, the transmembrane domains are rendered as helical in the structure; in FIG. 2B and FIG. 2C, the transmembrane domains are underlined in the corresponding amino acid sequences of 1P68 and 1M6T.

The amino acid sequences of the two ECLs of human MS4A4A were recombinantly placed into 1P68, resulting in polypeptide JS1 and polypeptide JS4 (negative control for polypeptide JS1) and into 1M6T, resulting in polypeptide JS5, polypeptide JS6; and polypeptide JS10 (which serve as negative controls for polypeptide JS5 and polypeptide JS6). (See FIG. 3.) FIG. 3A shows the amino acid sequences of polypeptide JS1, polypeptide JS5, and polypeptide JS6. FIG. 3B shows the amino acid sequences of negative control polypeptide JS4 and negative control polypeptide JS10. Nucleic acid encoding these protein/polypeptide scaffolds were inserted into pcDNA3.4 expression vector with a 3' his-tag and Avi-tag, respectively. The resulting clones were expressed in Expi293 cells and purified by Ni-NTA agarose (QIAGEN cat #30230) using the manufacturer's protocol. These recombinant MS4A4A soluble polypeptides (also referred to as loop grafted antigens) were produced in order to obtain soluble proteins that mimic the structure and function of the two ECLs of MS4A4A for use as soluble reagents for antibody binding characterizations.

Example 3: Epitope Determination of Anti-MS4A4A Antibodies by Peptide Binding Epitope binding characteristics of anti-MS4A4A antibody 4A-21 were determined as follows. A panel of overlapping peptides derived from the extracellular loops (ECLs) of human MS4A4A (SEQ ID NO: 1) were synthesized by JPT peptides (Berlin, Germany). These peptides were 15 amino acids in length, each offset by 2 amino acids. The peptides were biotinylated on the N-terminus. Peptides 4A.1 through 4A.4 were derived from human MS4A4A ECL1 and surrounding regions. Peptides 4A.5 through 4A.12 were derived from human MS4A4A ECL2 and surrounding regions.

The peptide library was printed onto a streptavidin-coated chip (Xantec SAD50M, Dusseldorf, Germany) using the Continuous Flow Microspotter (CFM). First, the chip was activated with 100 mM MES, pH 5.5, 100 μL EDC (133 mM final), 1004 of S-NHS (33.3 mM final). The peptide library was immobilized onto the chip at 250 nM per peptide diluted into HBS-EP+buffer (Teknova Cat #H8022) with 1 mg/ml BSA and 1 μg/ml mouse IgG-Biotin. Following immobilization, the chip surface was deactivated with 1M ethanolamine at pH 8.5 for 10 minutes. Hybridoma supernatants and purified anti-MS4A4A antibodies were diluted in HBS- EP+buffer with 1 mg/ml BSA and injected onto the chip. Duplicate measurements for each anti-MS4A4A antibody were taken to ensure reproducibility. Binding characteristics were determined for each peptide-antibody combination, allowing the mapping of the linear peptide region each antibody interacts with.

Anti-MS4A4A antibody 4A-21 and commercially available anti-MS4A4A antibody 5C12 displayed robust binding to peptides corresponding to regions in human MS4A4A ECL2, as indicated in bold in Table 9 below. Anti-MS4A4A antibody 4A-21 binds peptides 4A.5 through 4A.9, spanning amino acid residues 155 to 177 of human MS4A4A. Anti-MS4A4A antibody 5C12 binds peptides 4A.6 through 4A.9, spanning amino acid residues 157 to 177 of human MS4A4A. The binding regions of these two antibodies are overlapping but not identical, indicating that they interact with different residues within ECL2 of human MS4A4A. Neither of these two antibodies showed binding to human MS4A4A ECL1 using the methodology described above.

TABLE 9

| Peptide | Sequence | 4A-21 | 5C12 |
|---|---|---|---|
| 4A.1 | ITMMCMASNTYGSNP (SEQ ID NO: 292) | -11.16 | -1.49 |
| 4A.2 | MMCMASNTYGSNPIS (SEQ ID NO: 293) | -11.53 | -0.19 |
| 4A.3 | CMASNTYGSNPISVY (SEQ ID NO: 294) | -10.55 | -1.54 |
| 4A.4 | ASNTYGSNPISVYIG (SEQ ID NO: 295) | -7.90 | -0.46 |
| 4A.5 | LAFYSFHHPYCNYYG (SEQ ID NO: 296) | **382.80** | 1.60 |
| 4A.6 | FYSFHHPYCNYYGNS (SEQ ID NO: 297) | **485.67** | **44.38** |
| 4A.7 | SFHHPYCNYYGNSNN (SEQ ID NO: 298) | **446.10** | **17.75** |
| 4A.8 | HHPYCNYYGNSNNCH (SEQ ID NO: 299) | **308.63** | **22.30** |
| 4A.9 | PYCNYYGNSNNCHGT (SEQ ID NO: 300) | **225.21** | **30.86** |
| 4A.10 | CNYYGNSNNCHGTMS (SEQ ID NO: 301) | -4.50 | 1.13 |
| 4A.11 | YYGNSNNCHGTMSIL (SEQ ID NO: 302) | -6.50 | -2.73 |
| 4A.12 | GNSNNCHGTMSILMG (SEQ ID NO: 303) | -5.20 | -4.08 |

Example 4: Anti-MS4A4A Antibody Binding to Peptides Corresponding to Human MS4A4A Extracellular Domains Anti-MS4A4A hybridoma supernatants (neat) or as purified mIgG (5 μg/ml) were tested for binding to human MS4A4A peptides corresponding to ECL1 (amino acid residues 86-98 of human MS4A4A of SEQ ID NO: 1) and ECL2 (amino acid residues 159-179 of human MS4A4A of SEQ ID NO: 1) using an enzyme-linked immunosorbent assay (ELISA). Briefly, 96-well polystyrene plates were coated with 2 or 10 μg/ml of synthetic free or BSA-conjugated peptides in coating buffer (0.05M carbonate buffer, pH9.6, Millipore Sigma Cat #C3041) overnight at 4° C. Coated plates were then blocked with ELISA diluent (PBS+0.5% BSA+0.05% Tween20) for 1-hour, washed 3×300 μL in PBST (PBS+Tween20, Thermo Cat #28352), and then the antibodies were added to the plate (50 μl/well). After 30 mins incubation (room temperature, with shaking), the plates were washed 3×300 μL in PBST. A secondary anti-mouse HRP antibody (Jackson Immunoresearch Cat #115-035-003) was added at a 1:1000 dilution in ELISA diluent (50 μl/well) and incubated for 30 minutes at room temperature with shaking. After a final set of washes (3×300 μL in PBST), 50 μL of TMB substrate (BioFx Cat #TMBW-1000-01) was added and the reaction was then quenched after 5-10 mins with 504 of stop solution (BioFx Cat #BSTP-1000-01). The quenched reaction wells were detected for absorbance at 650 nm with a BioTek Synergy Microplate Reader using GENS 2.04 software.

Purified anti-MS4A4A murine antibodies and 3 commercially available murine anti-MS4A4A antibodies (5C12, 3F2, and 4H2) were tested. Murine anti-MS4A4A antibodies (4A-21, 4A-25, 4A-202, and 4A-214) displayed strong binding to the huMS4A4A-ELC2 free-peptide compared to that observed for BSA mouse DAP12, an irrelevant negative peptide control. The three commercially available anti-MS4A4A antibodies did not display binding to human MS4A4A ECL1 and ECL2 peptides.

Example 5: Epitope Determination of Anti-MS4A4A Antibodies

The primary amino acid sequence of MS4A4A provides important information about its secondary and tertiary structure. The MS4A4A protein has four transmembrane domains (TMDs) and each TMD is composed of 21 amino acids. A typical TMD is composed of a phosphodiester lipid bilayer with approximately 40 Å in thickness. The phosphate head moiety creates a hydrophilic layer that interacts with the hydrophilic environment either in the extracellular or cytosolic space and the lipid tail creates an internal lipid bilayer that interacts with the lipophilic residues of the TMDs. The thickness of the TMD lipid bilayer is approximately 32 to 34 Å. Predicted from the amino acid composition, residue numbers, and the thickness of the lipid bilayer, MS4A4A is predicted to comprise a four-helix bundle (4HB) with two extra cellular loops (ECLs), connecting TMD1 and TMD2, and TMD3 and TMD4 from the N-terminus to the C-terminus, respectively. The 4-helix bundle stabilizes the MS4A4A in the membrane by a significant enthalpy gain obtained from the helix-lipid bilayer interactions and helix-helix interactions.

The primary amino acid sequence and composition of the MS4A4A ECLs indicate important features associated with epitopes and dynamic properties. ECL1 is composed of 13 amino acids including one cysteine, one methionine, one alanine, three serine, one threonine, two asparagine, one tyrosine, one proline, one isoleucine, and only one glycine residue(s). ECL2 is composed of 21 amino acids including two cysteine residues which are separated by 8 amino acids, three serine, one threonine, one phenylalanine, three histidine, one proline, three tyrosine, four asparagine, one methionine, and only two glycine residues. Very few glycine residues but several large beta-branched amino acid residues and a proline residue are found in ECL1 and ECL2. Moreover, ECL2 contains two cysteine residues that are predicted to create an intra-loop disulfide bond, which further reduces conformational entropy. As a result, ECL1 and ECL2 tend to employ a significantly reduced number of conformational isomers interacting with each other in rigid-body type internal movements.

An expression plasmid encoding human MS4A4A (NM 024021) containing a C-terminal GFP tag was purchased from Origene (cat #RG223557) and used as template to generate single alanine scanning mutations in the coding region of extracellular loop 1 (ECL1) of human MS4A4A (4A.Ala1-A1a13 in Table 10 below; C67 to S79 of SEQ ID NO: 1 corresponding to ECL1; CMASNTYGSNPIS; in the coding region of extracellular loop 2 (ECL2) of human MS4A4A (4A.A1a14-A1a34 in Table 10 below; S140 to S160 of SEQ ID NO: 1 corresponding to ECL2; SFHHPYCNYYGNSNNCHGTMS; and ECL2 deletion mutations (4A.A1a35 (deletion of amino acid residues 150-152 of SEQ ID NO: 1 within ECL2) and 4A.A1a36 (deletion of amino acid residues 148-152 of SEQ ID NO: 1 within ECL2) in Table 11 below). The mutations were performed using overlap polymerase chain reaction techniques standard in the art. Each polymerase chain reaction polynucleic acid fragment was purified and subcloned back into the expression vector using MluI and AsiSI restriction sites.

Prior to performing epitope determination using alanine-scanning techniques, relative EC50s of the anti-MS4A4A antibodies were determined as follows using transient transfections of the above-described expression constructs in HEK293T cells. HEK293T cells were seeded in 6 well plates and grown overnight. The next day, cells were transfected with Fugene HD (Promega) or Lipofectamine 3000 (Thermo Fisher Scientific) with a 4:1 ratio of Fugene to DNA or a 3:1 ratio of Lipofectamine to DNA, following the manufacturer's protocols. Approximately 24 hours after transfection, cells were harvested using Trypsin-EDTA and processed for FACS staining.

For FACS staining, 150,000 cells were added to each well of 96 well plates and a titration of anti-MS4A4A antibodies was added in FACS buffer (PBS+2% FBS) and incubated on ice for 60 minutes. Plates were centrifuged (1,400 rpm, 3 minutes), supernatant decanted, and the cells were washed thrice with 200 μl FACS buffer, each followed by a spin and decant step. Antibodies were tested as msIgG1 or huIgG1 chimera and either goat anti-human PE (Southern Biotech, Cat #2040-09, 1:200) or goat anti-mouse APC (BD Biosciences, Cat #550826, 1:100) were added in FACS buffer on ice for 30 minutes. Cells were subsequently washed twice with 200 μl FACS buffer and imaged on an iQue cytometer. Median fluorescence intensity (MFI) was measured on the GFP positive population, representing cells expressing MS4A4A.

Six of the initially tested anti-MS4A4A antibodies bind to HEK293T cells expressing wild-type (WT) MS4A4A-GFP: these included anti-MS4A4A antibodies 4A-18, 4A-21, 4A-202, as well as published murine monoclonal anti-MS4A4A antibodies 4H2 (Kerafast), 5C12 (Biolegend), 3F2 (Millipore). Titration curves for each antibody were determined to establish the optimal anti-MS4A4A antibody concentrations for subsequent epitope mapping studies.

For epitope mapping experiments, HEK293T cells were transfected with the different human MS4A4A expression constructs (as described above; see Table 10 below), and antibody binding was determined using six different anti-MS4A4A antibodies: 4A-21, 4A-18, 4A-202, 4H2, 5C12, and 3F5. Anti-MS4A4A antibody binding was calculated as the % of the MFI from binding to cells transfected with wildtype human MS4A4A expression construct. If an amino acid mutation in the MS4A4A polypeptide resulted in decreased antibody binding to below 20% of that of binding to wildtype MS4A4A, the mutated amino acid was considered a critical amino acid necessary for anti-MS4A4A antibody binding to the MS4A4A protein. Some amino acid mutations in the MS4A4A protein resulted in a decrease in anti-MS4A4A antibody binding to below 51% but above 20% (compared to the binding to wildtype MS4A4A); such amino acids were defined as amino acids contributing to binding of the anti-MS4A4A antibody to the MS4A4A protein.

Some amino acids in MS4A4A affected binding of all tested antibodies, such as the two cysteines, C165 and C174, that are thought to form a cysteine bridge in MS4-type proteins. Such amino acids were considered structural amino acids.

The results of these experiments are provided in Table 10 below. As stated above, A1a.1 to A1a.13 refer to MS4A4A mutations in ECL1; A1a.14 to A1a.36 refer to MS4A4A mutations in ECL2. Data is shown as % binding of the anti-MS4A4A antibodies to the various alanine-scanning mutations compared to the binding of the anti-MS4A4A antibodies to wildtype MS4A4A protein. The mapping experiments were independently repeated twice with very similar results. One difference was that anti-MS4A4A antibodies 4A-21 and 4A-18 were tested once as huIgG1 and second as msIgG1 at two concentrations. Table 11 below shows results from the msIgG1 test for these antibodies. For all other antibodies, Table 10 shows average antibody binding across both experiments. Values showing anti-MS4A4A antibody binding to MS4A4A protein below 20% of that measured for binding to wildtype MS4A4A are in bold in Table 10 below.

All mutations showed equivalent transfection efficiencies of between approximately 22-33% (data not shown). No correlation between average antibody binding and GFP levels in the cells was observed, suggesting that GFP levels cannot be used as a predictor for MS4A4A cell surface expression.

TABLE 10

| Construct | Loop sequence | 4A-21 | 4A-18 | 4A-202* | 4H2 | 5C12 | 3F2 |
|---|---|---|---|---|---|---|---|
| WT ECL1 | CMASNTYGSNPIS (SEQ ID NO: 289) | | | | 100 | | |
| 4A.Ala.1 | SMASNTYGSNPIS (SEQ ID NO: 255) | 84.1 | 96.6 | 86.99 | 72.80 | 82.36 | 79.58 |
| 4A.Ala.2 | CAASNTYGSNPIS (SEQ ID NO: 256) | **12.5** | **19.1** | **9.93** | **7.42** | **11.04** | **7.33** |
| 4A.Ala.3 | CMSSNTYGSNPIS (SEQ ID NO: 257) | 90.7 | 116.6 | 99.12 | 87.76 | 94.47 | 87.46 |

TABLE 10-continued

| Construct | Loop sequence | 4A-21 | 4A-18 | 4A-202* | 4H2 | 5C12 | 3F2 |
|---|---|---|---|---|---|---|---|
| 4A.Ala.4 | CMA**A**NTYGSNPIS (SEQ ID NO: 258) | 91.2 | 85.8 | 92.48 | 77.90 | 88.62 | 82.49 |
| 4A.Ala.5 | CMAS**A**TYGSNPIS (SEQ ID NO: 259) | 93.1 | 65.6 | 81.64 | 75.95 | 80.92 | 83.89 |
| 4A.Ala.6 | CMASN**A**YGSNPIS (SEQ ID NO: 260) | 100.4 | 87.5 | 83.22 | 77.29 | 78.57 | 78.38 |
| 4A.Ala.7 | CMASNT**A**GSNPIS (SEQ ID NO: 261) | 114.5 | **15.8** | 98.41 | 93.36 | 94.96 | 92.91 |
| 4A.Ala.8 | CMASNTY**A**SNPIS (SEQ ID NO: 262) | 94.6 | 70.4 | 83.82 | 74.41 | **17.39** | 84.41 |
| 4A.Ala.9 | CMASNTYG**A**NPIS (SEQ ID NO: 263) | 99.6 | 106.0 | 102.06 | 85.83 | 89.83 | 94.67 |
| 4A.Ala.10 | CMASNTYGS**A**PIS (SEQ ID NO: 264) | 102.3 | 103.2 | 124.27 | 91.27 | 93.95 | 89.57 |
| 4A.Ala.11 | CMASNTYGSN**A**IS (SEQ ID NO: 265) | 28.7 | **14.8** | 35.06 | 20.53 | 32.79 | 25.29 |
| 4A.Ala.12 | CMASNTYGSNP**A**S (SEQ ID NO: 266) | 66.4 | 91.4 | 57.21 | 48.93 | 56.33 | 49.19 |
| 4A.Ala.13 | CMASNTYGSNPI**A** (SEQ ID NO: 267) | 38.4 | 41.8 | 32.34 | 27.38 | 36.36 | 28.92 |
| WT ECL2 | SFHHPYCNYYGNSNNCHGTMS (SEQ ID NO: 290) | | | | 100 | | |
| 4A.Ala.14 | **A**FHHPYCNYYGNSNNCHGTMS (SEQ ID NO: 268) | 94.3 | 87.8 | 78.14 | 83.99 | 81.28 | 85.27 |
| 4A.Ala.15 | S**A**HHPYCNYYGNSNNCHGTMS (SEQ ID NO: 269) | 118.7 | 116.9 | 111.77 | 84.71 | 98.51 | 87.20 |
| 4A.Ala.16 | SF**A**HPYCNYYGNSNNCHGTMS (SEQ ID NO: 270) | 71.0 | 48.1 | 76.87 | 58.00 | 71.46 | 64.58 |
| 4A.Ala.17 | SFH**A**PYCNYYGNSNNCHGTMS (SEQ ID NO: 271) | 102.8 | 99.4 | 125.37 | 77.01 | 82.95 | 85.21 |
| 4A.Ala.18 | SFHH**A**YCNYYGNSNNCHGTMS (SEQ ID NO:) | 101.4 | 103.7 | 89.39 | 36.92 | 46.13 | 42.33 |
| 4A.Ala.19 | SFHHP**A**CNYYGNSNNCHGTMS (SEQ ID NO: 272) | 83.8 | **16.3** | 26.68 | **1.66** | 42.27 | **1.08** |
| 4A.Ala.20 | SFHHPY**S**NYYGNSNNCHGTMS (SEQ ID NO: 273) | **5.0** | **2.8** | **8.66** | **1.94** | **1.74** | **1.60** |
| 4A.Ala.21 | SFHHPYC**A**YYGNSNNCHGTMS (SEQ ID NO: 274) | **1.8** | 73.3 | 93.33 | 70.08 | 73.76 | 80.30 |
| 4A.Ala.22 | SFHHPYCN**A**YGNSNNCHGTMS (SEQ ID NO: 275) | **1.8** | **3.0** | 31.23 | **1.10** | **0.99** | **0.88** |
| 4A.Ala.23 | SFHHPYCNY**A**GNSNNCHGTMS (SEQ ID NO: 276) | **1.4** | **2.7** | 50.05 | **1.19** | **0.96** | **0.95** |
| 4A.Ala.24 | SFHHPYCNYY**A**NSNNCHGTMS (SEQ ID NO: 277) | 57.5 | 63.0 | 75.76 | 27.67 | **18.20** | 33.76 |
| 4A.Ala.25 | SFHHPYCNYYG**A**SNNCHGTMS (SEQ ID NO: 278) | 69.2 | 40.0 | 100.54 | 37.09 | 25.55 | 45.60 |
| 4A.Ala.26 | SFHHPYCNYYGN**A**NNCHGTMS (SEQ ID NO: 279) | 89.3 | 96.5 | 90.84 | 68.48 | 81.73 | 68.38 |
| 4A.Ala.27 | SFHHPYCNYYGNS**A**NCHGTMS (SEQ ID NO:) | 98.3 | 118.6 | 98.39 | 99.46 | 91.60 | 94.25 |

TABLE 10-continued

| Construct | Loop sequence | 4A-21 | 4A-18 | 4A-202* | 4H2 | 5C12 | 3F2 |
|---|---|---|---|---|---|---|---|
| 4A.Ala.28 | SFHHPYCNYYGNSNACHGTMS (SEQ ID NO: 280) | 87.3 | 116.4 | 98.61 | 86.22 | 85.94 | 83.37 |
| 4A.Ala.29 | SFHHPYCNYYGNSNNSHGTMS (SEQ ID NO: 281) | **8.4** | **2.7** | **4.54** | **1.09** | **1.01** | **0.91** |
| 4A.Ala.30 | SFHHPYCNYYGNSNNCAGTMS (SEQ ID NO: 282) | 87.5 | 62.6 | 92.83 | 72.87 | 80.56 | 82.45 |
| 4A.Ala.31 | SFHHPYCNYYGNSNNCHATMS (SEQ ID NO: 283) | 147.8 | 158.6 | 142.81 | 123.13 | 124.19 | 135.58 |
| 4A.Ala.32 | SFHHPYCNYYGNSNNCHGAMS (SEQ ID NO: 284) | 61.6 | 42.9 | 63.28 | 44.61 | 56.19 | 45.14 |
| 4A.Ala.33 | SFHHPYCNYYGNSNNCHGTAS (SEQ ID NO: 285) | 81.8 | 36.1 | 73.09 | 62.83 | 59.85 | 60.45 |
| 4A.Ala.34 | SFHHPYCNYYGNSNNCHGTMA (SEQ ID NO: 286) | 113.4 | 91.0 | 117.02 | 102.44 | 99.15 | 103.80 |
| 4A.Ala.35 | SFHHPYCNYY---NNCHGTMS (SEQ ID NO: 287) | 107.3 | **2.7** | 73.14 | **1.08** | **1.00** | **0.88** |
| 4A.Ala.36 | SFHHPYCN-----NNCHGTMS (SEQ ID NO: 288) | **1.3** | **2.6** | **0.07** | **0.99** | **0.93** | **0.83** |

*antibody tested as huIgG1 chimera

Results shown above suggest that anti-MS4A4A antibodies of the present disclosure recognize distinct linear and/or 3D structural epitopes within MS4A4A.

Based on the anti-MS4A4A antibody binding data obtained from these experiments, the following loop amino acid residues within human MS4A4A were considered structural amino acids within the MS4A4A protein as mutating each of them affected binding of anti-MS4A4A antibodies tested: M87, C165, Y167, Y168, C174 (Based on human MS4A4A protein; SEQ ID NO: 1). Amino acid residues C165 and C174 are predicted to establish a cysteine bridge forming a loop in ECL2. In the absence of this cysteine bridge, anti-MS4A4A antibodies did not bind MS4A4A protein, suggesting that the loop structure within ECL2 of MS4A4A is important for antibody binding. More evidence for loop structure being important comes from the two loop deletion mutants (A1a.35 and A1a.36) which also strongly affect binding of the antibodies.

The results further showed that amino acid residues Y167 and Y168 strongly affected binding of anti-MS4A4A antibodies 4A-21, 4A-18, 4H2, 5C12, and 3F2. These amino acid residues also affected binding of anti-MS4A4A antibody 4A-202 to a lesser degree. Additionally, amino acid residues P96, 197, and S98 in ECL1 reduced binding to some degree of all anti-MS4A4A antibodies tested. These results suggested either that mutations in any of these five amino acid residues altered the structure of the extracellular domains important for antibody recognition and binding, or that these amino acid residues are important for the interaction and binding of each of the six anti-MS4A4A antibodies listed. Proline is the most restrained amino acid residue, which is critical to the secondary and tertiary structure of a polypeptide. For example, proline acts as a disrupter in the middle of regular secondary structure elements, including that of alpha helices and beta sheets; however, proline is commonly found as the first amino acid residue of an alpha helix and in the edge stands of beta sheets. Tyrosine, isoleucine, and serine residues provide multiple antigen-antibody interactions, including, for example, Van der Waals interaction(s), pi-pi stacking and pi-facial hydrogen bonding interactions, and/or hydrogen bonds. Accordingly, either tyrosine, proline, isoleucine, or serine residues can create well-defined structural epitopes. Any subtle changes in these four amino acid residues have the potential to significantly disrupt antibody binding affinity.

The mutation at amino acid residue M87A in MS4A4A greatly reduced or abolished binding of all anti-MS4A4A antibodies tested. Based on the prediction that ECL1 and ECL2 employ well-defined rigid body structures and may interact with each other, the M87A binding result shown indicated that the M87 amino acid residue is predicted to be one of the most critical residues in maintaining the rigid loop structure of MS4A4A, as the side chain of M87 can interact with one or more beta-branched amino acids in ECL1 and/or ECL2 by Van de Waals contacts and hydrogen bonds through backbone-side chain and/or backbone-backbone interactions.

Table 11 below lists the unique binding amino acid residues for anti-MS4A4A antibodies disclosed herein. Anti-MS4A4A antibody 4A-21 requires N166 in ECL2 for binding to human MS4A4A. The data showed that anti-MS4A4A antibodies 4A-18 and 5C12 bind ECL1 as well as ECL2 of human MS4A4A. Anti-MS4A4A antibody 4A-202 had some binding contribution by amino acid residue Y164.

All three commercial anti-MS4A4A antibodies bind P163, whereas none of the anti-MS4A4A antibodies disclosed herein and tested in this study did. This proline P163 of human MS4A4A is replaced by arginine in the cynomolgous MS4A4A protein. Such observation suggests that this proline to arginine change is important for determining cyno cross-reactivity, or the lack thereof, as displayed by the binding characteristics of the commercial MS4A4A antibodies. Proline is the most structurally restrained amino acid residue and arginine (in cyno MS4A4A) is a positively charged amino acid at physiological pH. The proline to arginine difference in human vs cyno MS4A4A may profoundly affect the conformation of the MS4A4A protein, therefore preventing the commercial MS4A4A antibodies from binding. Anti-MS4A4A antibodies 4A-18, 4A-21, and 4A-202 appeared not to be dependent on this amino acid for binding, and thus their binding to the cynomolgous protein was not affected.

In summary, anti-MS4A4A antibodies 4A-21, 4A-18, and 4A-202 bound epitopes on MS4A4A which are distinct from that of commercially available anti-MS4A4A antibodies (Table 11 below). The commercial anti-MS4A4A antibodies 4H2 and 3F2 exhibited identical epitopes, which overlapped significantly with that of anti-MS4A4A antibody 5C12. In contrast, anti-MS4A4A antibodies 4A-18, 4A-21, and 4A-202 each exhibited unique epitope binding characteristics distinct from each other and distinct from that of the commercial anti-MS4A4A antibodies. These differences in binding properties are shown in Table 10. Additionally, the results showed that no two anti-MS4A4A antibodies tested bound identical epitopes within human MS4A4A; however, there are shared amino acid binding residues across some or all antibodies (e.g., amino acid residues Y167 and Y168, Y164, N170, T177).

TABLE 11

| Antibody | ECL1 residues | ECL2 residues |
|---|---|---|
| 4A-21 | | N166 (critical) |
| 4A-18 | Y92 (critical) | Y164 (critical) |
| | | H161, N170, T177, M178 (contribute) |
| 4A-202 | | Y164 (contributes) |
| 4H2 | | Y164 (critical) |
| | | P163, G169, N170, T177 (contribute) |
| 5C12 | G93 (critical) | G169 (critical) |
| | | P163, Y164, N170 (contribute) |
| 3F2 | | Y164 (critical) |
| | | P163, G169, N170, T177 (contribute) |

#PI15120) for 1 hour. Plates were washed 3 times, followed by the addition of antibodies (1 μg/ml, 0.33 μg/ml, and 0.11 μg/ml antibodies. Plates were incubated at room temperature with shaking for 1 hr, washed 3 times, then 1/2500 dilution of HRP conjugates goat anti human kappa antibodies added (SigmaAldrich cat #. A7164-1ML).

Figure 4:
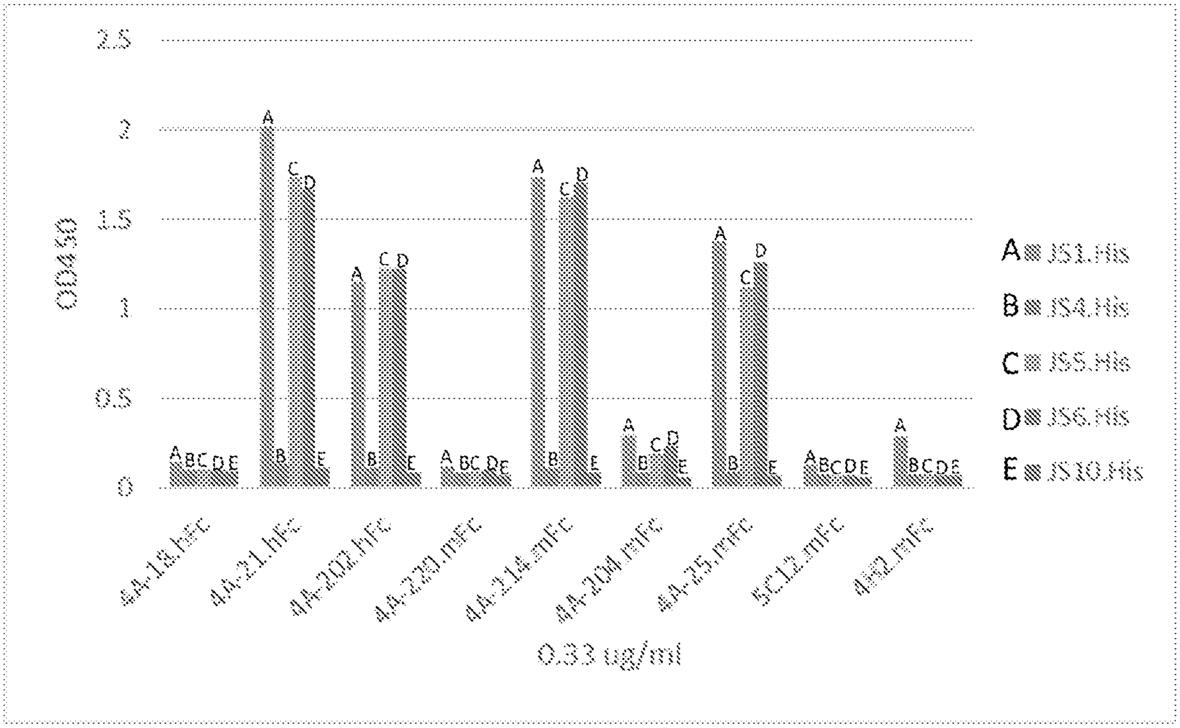
FIG. 4 shows certain anti-MS4A4A antibodies of the present disclosure binding to recombinant MS4A4A soluble looped grafted polypeptides JS1, JS4, JS5, JS6, and JS10 by ELISA.

FIG. 4 shows ELISA binding results of certain humanized anti-MS4A4A antibodies binding to recombinant MS4A4A soluble polypeptides JS1, JS4, JS5, JS6, and JS10. As shown in FIG. 4, certain anti-MS4A4A antibodies (4A-18.hFc, 4A-21.hFc, 4A-202.hFc, 4A-220.mFc, 4A-214.mFc, 4A-204.mFc' hFc refers to human Fc; mFc refers to murine Fc)) showed binding by ELISA to recombinant MS4A4A soluble polypeptides JS1, JS5, and JS6, which contain the two ECLs of human MS4A4A. Anti-MS4A4A antibodies of the present invention did not bind to recombinant soluble polypeptides JS4 and JS10, which are negative control polypeptides and do not contain MS4A4A ECL region sequence. Two commercially available anti-MS4A4A antibodies, 5C12 and 4H2, did not show binding to any of the recombinant MS4A4A soluble polypeptides (see FIG. 4). In FIG. 4, anti-MS4A4A antibody 4A-214 was previously disclosed in international patent application no PCT/US2019/016156, and has a heavy chain variable region amino acid sequence of EVKLEESGGGLVQPGRSMKLSCVASGFTFSNYWMNWVRQSPEKGLEWVAEIRLKSNNYATHY AESVKGRFTISRDDSKSSVYLQMNNLRAEDTGIYYCSSMIIVDYWGQGTT VTVSS (SEQ ID NO: 179) and a light chain variable region amino acid sequence of DIVLTQSPASLTVSLGQRATISCRASQSVSSSTYSYLHWYQQRPGQPPKLLIKYASNLESGVPARF SGSGSGTVFTLNIHPVEEEDTATYYCQHSWEIPLTFGAGTKLEMK (SEQ ID NO: 180).

Results presented in FIG. 4 were derived from data shown below in Table 12:

TABLE 12

| | 4A-18.hFc | 4A-21.hFc | 4A-202.hFc | 4A-220.mFc | 4A-214.mFc | 4A-204.mFc | 4A-25.mFc | 5C12.mFc | 4H2.mFc |
|---|---|---|---|---|---|---|---|---|---|
| JS1.His | 0.146 | 2.019 | 1.157 | 0.123 | 1.737 | 0.29 | 1.381 | 0.129 | 0.285 |
| JS4.His | 0.098 | 0.138 | 0.111 | 0.087 | 0.11 | 0.08 | 0.091 | 0.076 | 0.077 |
| JS5.His | 0.099 | 1.731 | 1.219 | 0.091 | 1.624 | 0.188 | 1.117 | 0.068 | 0.072 |
| JS6.His | 0.105 | 1.668 | 1.225 | 0.1 | 1.706 | 0.229 | 1.26 | 0.066 | 0.069 |
| JS10.His | 0.092 | 0.112 | 0.084 | 0.064 | 0.086 | 0.058 | 0.063 | 0.061 | 0.064 |

Figure 5:
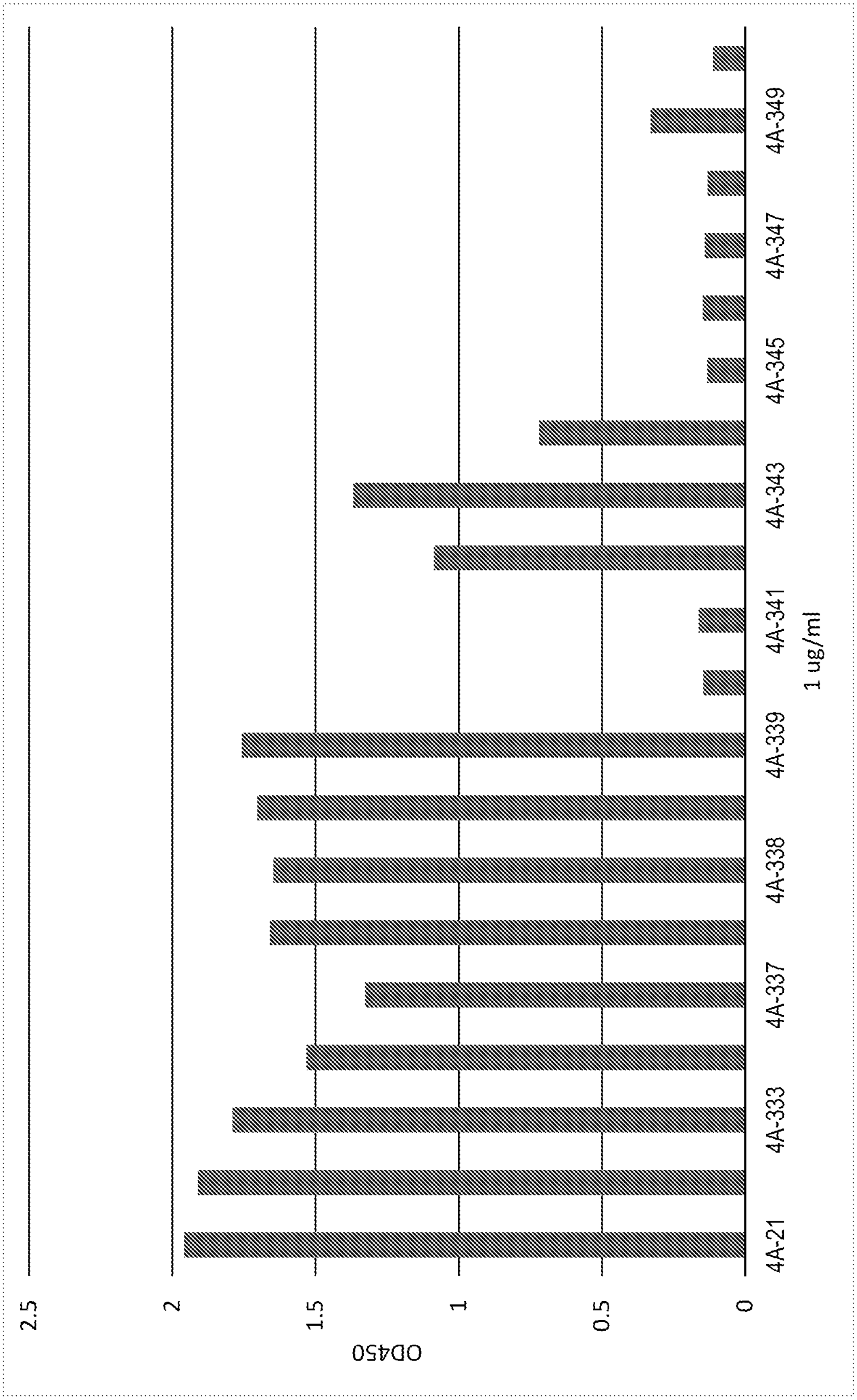
FIG. 5 shows certain humanized anti-MS4A4A antibody variants of murine anti-MS4A4A antibody 4A-21 binding to recombinant MS4A4A soluble looped grafted polypeptide JS1.

Example 6: Binding of Anti-MS4A4A Antibodies to Recombinant MS4A4A Soluble Polypeptides Anti-MS4A4A antibodies of the present disclosure were tested for their ability to bind to the different recombinant MS4A4A soluble polypeptides, as described in Example 2, as follows. Nucleic acid encoding the $V_H$ and $V_L$ domains of humanized anti-MS4A4A antibodies of the present disclosure were cloned into pcDNA3.4 vector which contains either the human IgG1 heavy chain constant domain or human kappa constant domain. The humanized anti-MS4A4A antibodies were expressed in Expi293 cells and were purified by Mab select antibody purification resin (GE Healthcare Life Science, cat #17519902) following the manufacture's protocol. ELISA was performed to measure binding of anti-MS4A4A antibodies of the present disclosure the recombinant MS4A4A soluble polypeptides. 1 μg/ml biotinylated antigens were preincubated on the streptavidin-coated ELISA plates (Thermo Scientific, cat FIG. 5 shows ELISA binding results of humanized versions of murine anti-MS4A4A antibody 4A-21 to recombinant MS4A4A soluble polypeptide JS1. The antibodies were used at a concentration of 1 μg/ml. As shown in FIG. 5, many of the humanized versions of anti-MS4A4A antibody 4A-21 retained their ability to bind to this recombinant polypeptide. Certain humanized versions of anti-MS4A4A antibody 4A-21 showed reduced binding to recombinant MS4A4A soluble polypeptide JS1.

Results presented in FIG. 5 were derived from data shown below in Table 13:

TABLE 13

| Antibody | OD450 |
|---|---|
| 4A-21 | 1.958 |
| 4A-332 | 1.91 |
| 4A-333 | 1.79 |
| 4A-334 | 1.531 |

TABLE 13-continued

| Antibody | OD450 |
|---|---|
| 4A-337 | 1.326 |
| 4A-335 | 1.659 |
| 4A-338 | 1.647 |
| 4A-336 | 1.703 |
| 4A-339 | 1.757 |
| 4A-340 | 0.146 |
| 4A-341 | 0.162 |
| 4A-342 | 1.086 |
| 4A-343 | 1.368 |
| 4A-344 | 0.719 |
| 4A-345 | 0.132 |
| 4A-346 | 0.148 |
| 4A-347 | 0.141 |
| 4A-348 | 0.131 |
| 4A-349 | 0.331 |
| Isotype | 0.113 |

Figure 6:
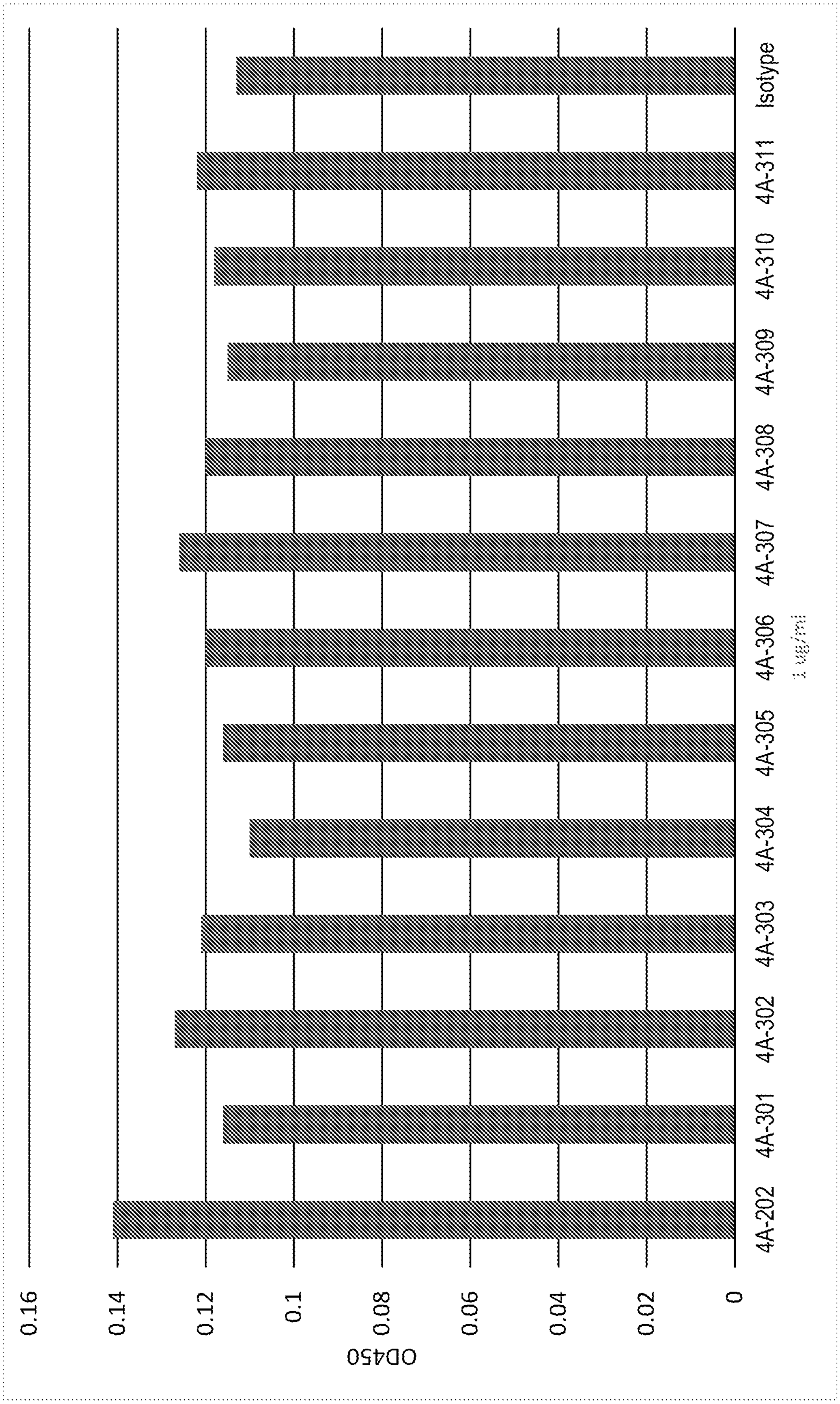
FIG. 6 shows certain humanized anti-MS4A4A antibody variants of murine anti-MS4A4A antibody 4A-202 binding to recombinant MS4A4A soluble looped grafted polypeptide JS1.

FIG. 6 shows ELISA binding results of humanized versions of murine anti-MS4A4A antibody 4A-202 to recombinant MS4A4A soluble polypeptide JS1. The antibodies were used at a concentration of 1 μg/ml. As shown in FIG. 6, humanized versions of anti-MS4A4A antibody 4A-202 were able to bind to this recombinant polypeptide.

Results presented in FIG. 6 were derived from data shown below in Table 14:

TABLE 14

| Antibody | OD450 |
|---|---|
| 4A-202 | 0.141 |
| 4A-301 | 0.116 |
| 4A-302 | 0.127 |
| 4A-303 | 0.121 |
| 4A-304 | 0.11 |
| 4A-305 | 0.116 |
| 4A-306 | 0.12 |
| 4A-307 | 0.126 |
| 4A-308 | 0.12 |
| 4A-309 | 0.115 |
| 4A-310 | 0.118 |
| 4A-311 | 0.122 |
| Isotype | 0.113 |

Various humanized versions of murine anti-MS4A4A antibody 4A-202 and murine anti-MS4A4A antibody 4A-21 were further tested for their ability to bind to recombinant MS4A4A soluble polypeptides. Humanized anti-MS4A4A antibody 4A-332 and humanized anti-MS4A4A antibody 4A-302 showed reasonable binding and were selected for further affinity improvement as follows. Random mutations in the 6 CDRs of anti-MS4A4A antibody 4A-322 and of anti-MS4A4A antibody 4A-302 were introduced using an overlapping PCR technique. Biotinylated recombinant MS4A4A soluble polypeptide JS5 was used for phage display panning of these antibody variants. After 3 rounds of panning, approximately 190 mutant anti-MS4A4A antibody variants were selected and expressed in TG1 cells, the lysates of which were screened by ELISA. Twenty-two humanized anti-MS4A4A antibody 4A-21 variants and fifteen humanized anti-MS4A4A antibody 4A-202 variants were selected, recombinantly converted to full human IgG, and expressed in Expi293 cells. The anti-MS4A4A antibodies were purified by MabSelect Antibody Purification Resin (GE Healthcare Life Science, cat #17519902) as indicated in the manufacturer's protocol. ELISA and Flow Cytometry experiments were subsequently repeated.

Humanized and affinity matured anti-MS4A4A antibodies 4A-312, 4A-313, and 4A-314 showed binding to recombinant MS4A4A soluble polypeptide JS5 by ELISA (see FIG. 7) at various antibody concentrations (1 μg/ml, 0.33 μg/ml, and 0.11 μg/ml), and were selected for further functional analysis.

Figure 7:
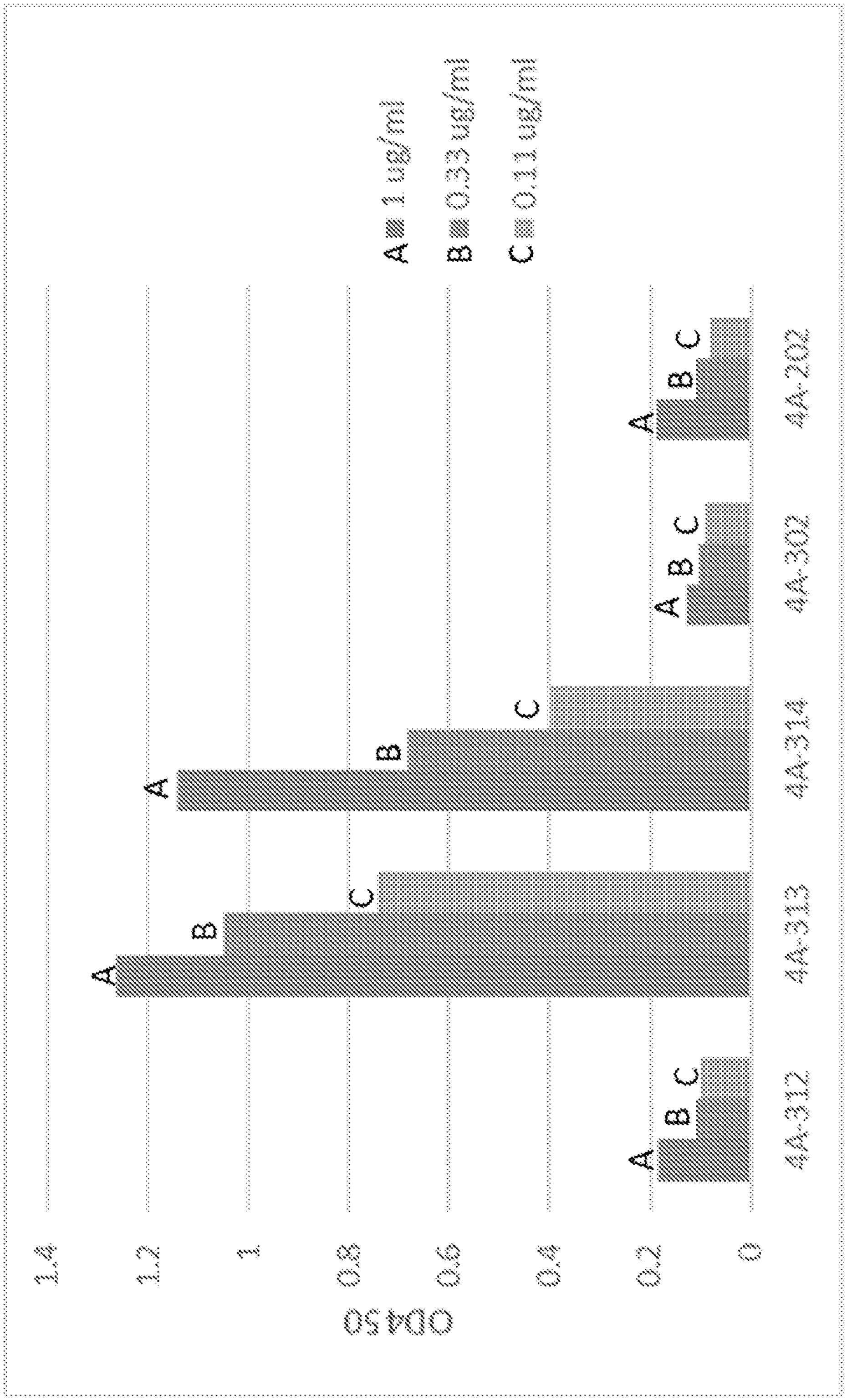
FIG. 7 shows certain humanized and affinity matured anti-MS4A4A antibody variants of murine anti-MS4A4A antibody 4A-202 binding to recombinant MS4A4A soluble looped grafted polypeptide JS5.

Results presented in FIG. 7 were derived from data shown below in Table 15:

TABLE 15

| Antibody | 1 ug/ml | 0.33 ug/ml | 0.11 ug/ml |
|---|---|---|---|
| 4A-312 | 0.184 | 0.11 | 0.097 |
| 4A-313 | 1.262 | 1.05 | 0.741 |
| 4A-314 | 1.142 | 0.682 | 0.399 |
| 4A-302 | 0.128 | 0.103 | 0.091 |
| 4A-202 | 0.188 | 0.111 | 0.079 |

Figure 8:
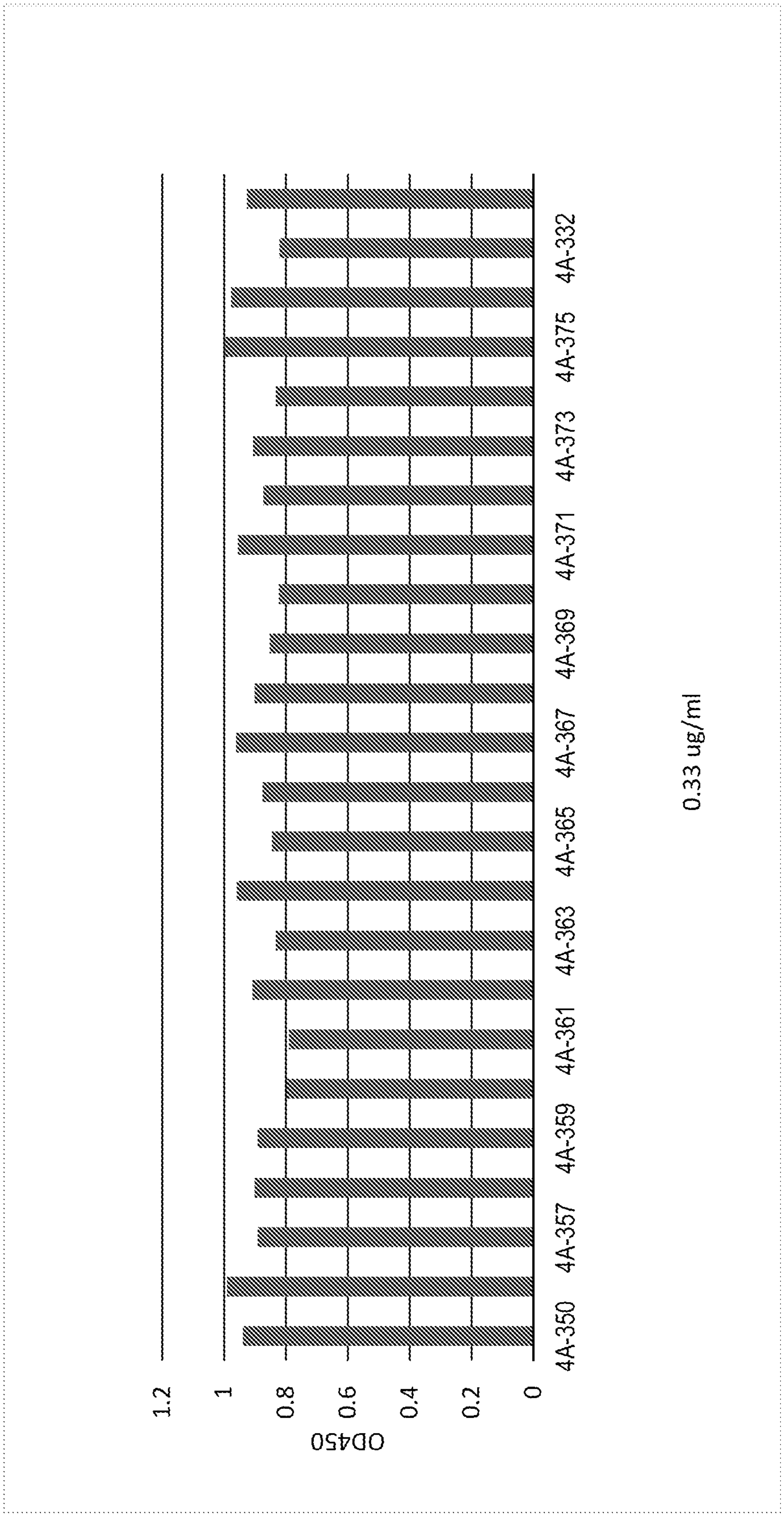
FIG. 8 shows certain humanized and affinity matured anti-MS4A4A antibody variants of murine anti-MS4A4A antibody 4A-21 binding to recombinant MS4A4A soluble looped grafted polypeptide JS5.

Humanized and affinity matured anti-MS4A4A antibodies 4A-351 and 4A-376 (0.4 μg/ml) showed good binding to recombinant MS4A4A soluble polypeptide JS5 by ELISA (see FIG. 8). These anti-MS4A4A antibodies were then selected for use as templates for which amino acid substitutions were made to amino acid D28 in CDR-L1; such amino acid substitutions included D28G, D28E, D28S, D28A, and D28Q.

Results presented in FIG. 8 were derived from data shown below in Table 16:

TABLE 16

| Antibody | OD450 |
|---|---|
| 4A-350 | 0.939 |
| 4A-351 | 0.99 |
| 4A-357 | 0.892 |
| 4A-358 | 0.901 |
| 4A-359 | 0.892 |
| 4A-360 | 0.797 |
| 4A-361 | 0.79 |
| 4A-362 | 0.908 |
| 4A-363 | 0.833 |
| 4A-364 | 0.959 |
| 4A-365 | 0.845 |
| 4A-366 | 0.875 |
| 4A-367 | 0.961 |
| 4A-368 | 0.901 |
| 4A-369 | 0.852 |
| 4A-370 | 0.822 |
| 4A-371 | 0.955 |
| 4A-372 | 0.873 |
| 4A-373 | 0.907 |
| 4A-374 | 0.833 |
| 4A-375 | 0.996 |
| 4A-376 | 0.977 |
| 4A-332 | 0.821 |
| 4A-21 | 0.925 |

Figure 9:
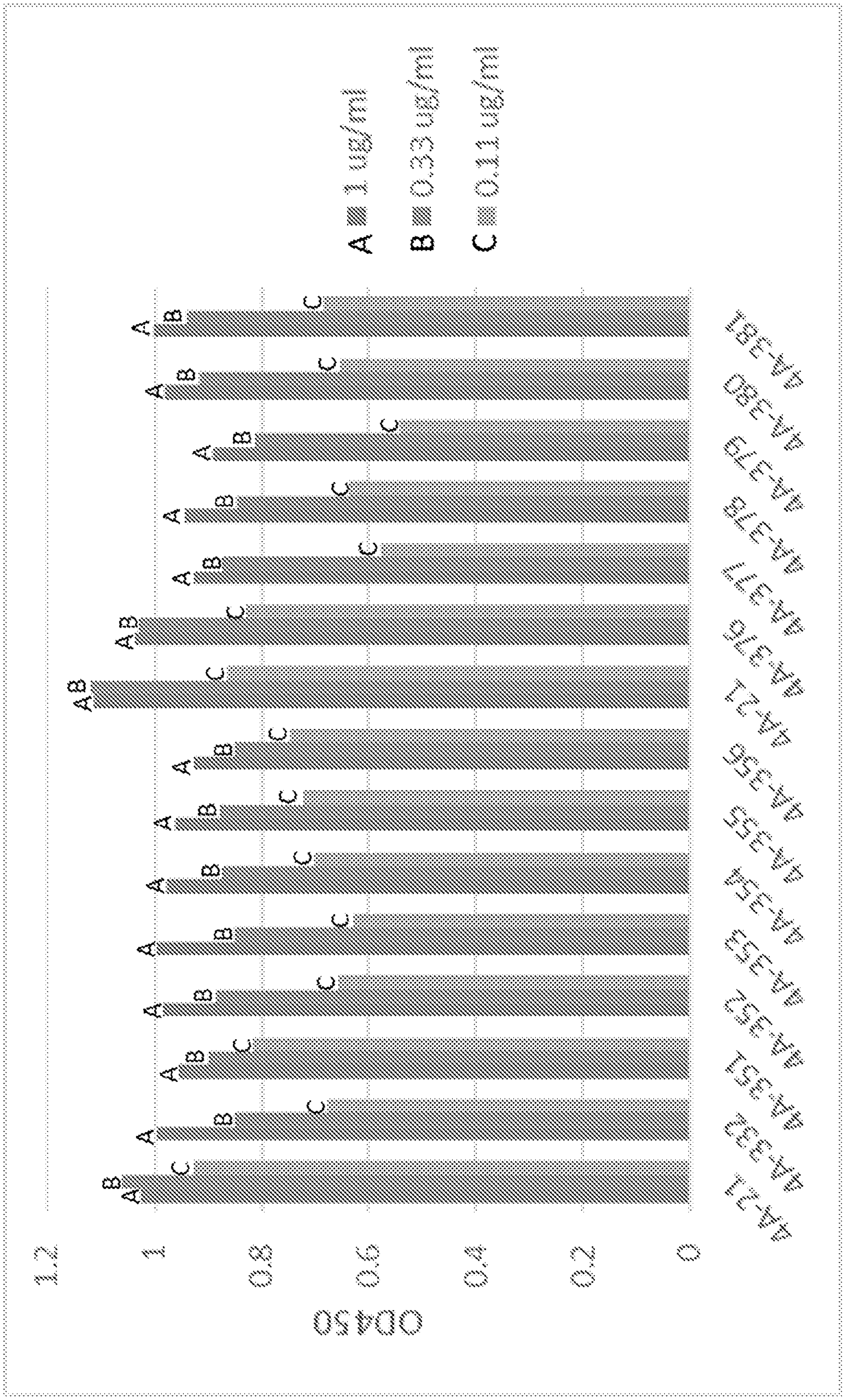
FIG. 9 shows certain humanized and affinity matured anti-MS4A4A antibody variants of murine anti-MS4A4A antibody 4A-21 binding to recombinant MS4A4A soluble looped grafted polypeptide JS5.

These additional anti-MS4A4A antibodies included anti-MS4A4A antibody 4A-352, 4A-353, 4A-354, 4A-355, 4A-356, 4A-377, 4A-378, 4A-379, 4A-380, and 4A-381, and were tested by ELISA for binding to recombinant MS4A4A soluble polypeptide JS5 at three different antibody concentrations (1 μg/ml, 0.33 μg/ml, and 0.11 μg/ml). The results of these studies are shown in FIG. 9. As shown in FIG. 9, these additional anti-MS4A4A antibodies showed binding to recombinant MS4A4A soluble polypeptide JS5.

Results presented in FIG. 9 were derived from data shown below in Table 17:

TABLE 17

| Antibody | 1 ug/ml | 0.33 ug/ml | 0.11 ug/ml |
|---|---|---|---|
| 4A-21 | 1.027 | 1.063 | 0.927 |
| 4A-332 | 0.997 | 0.851 | 0.677 |
| 4A-351 | 0.953 | 0.898 | 0.816 |
| 4A-352 | 0.985 | 0.885 | 0.655 |
| 4A-353 | 0.996 | 0.85 | 0.63 |
| 4A-354 | 0.98 | 0.874 | 0.701 |
| 4A-355 | 0.961 | 0.878 | 0.721 |
| 4A-356 | 0.927 | 0.85 | 0.746 |
| 4A-21 | 1.114 | 1.121 | 0.865 |
| 4A-376 | 1.037 | 1.031 | 0.83 |
| 4A-377 | 0.928 | 0.873 | 0.577 |
| 4A-378 | 0.944 | 0.848 | 0.636 |
| 4A-379 | 0.893 | 0.812 | 0.543 |
| 4A-380 | 0.981 | 0.916 | 0.654 |
| 4A-381 | 1.002 | 0.94 | 0.685 |

Example 7: Binding of Humanized and Affinity Matured Anti-MS4A4A Antibodies to U937 Cells Overexpressing Human MS4A4A Humanized and affinity matured versions of anti-MS4A4A antibodies of the present disclosure were evaluated for their binding to human MS4A4A-expressing U937 cells as follows.

Anti-MS4A4A antibodies tested were either mouse IgGs purified from hybridoma supernatant or human IgG1 Fc chimeras produced recombinantly in Expi293 cells. Affinity binding to cells was determined as follows. Briefly, cells were harvested, washed, and labeled with Aqua Live/Dead for viability discrimination. After a wash with PBS, 2×10^4 cells were aliquoted per well in 96-well U-bottom plates and incubated with 50 μL of purified anti-MS4A4A antibody at various concentrations (3× dilutions starting at 10 μg/mL) in FACS buffer (PBS+2% FBS+1 mM EDTA). After this primary incubation, the supernatant was removed via centrifugation, washed 2× with 1504, of ice-cold FACS buffer, and incubated with the appropriate secondary antibody on ice for 15 minutes. Following the secondary antibody incubation, the cells were again washed 2× with ice-cold FACS buffer and resuspended in a final volume of 200 μL of FACS buffer. Flow cytometry analysis was performed on a FACSCanto system (BD Biosciences). Binding data was expressed as Median Fluorescent Intensity (MFI).

The results of these binding experiments are shown in Table 18 and Table 19 below. Table 18 shows binding of certain anti-MS4A4A antibodies of the present disclosure to U937 cells overexpressing recombinant human MS4A4A. These experiments were performed using anti-MS4A4A antibodies at a concentration of 5 μg/ml and were assayed for cell binding by flow cytometry.

TABLE 18

| Antibody | MFI |
|---|---|
| 4A-18 | 382 |
| 4A-202 | 216 |
| 4A-21 | 670 |
| 4A-25 | 648 |
| 4A-301 | 89.7 |
| 4A-302 | 113 |
| 4A-303 | 94.7 |
| 4A-304 | 112 |
| 4A-305 | 69.6 |
| 4A-306 | 71.3 |
| 4A-307 | 68.8 |
| 4A-308 | 97.2 |
| 4A-309 | 131 |
| 4A-310 | 75.4 |
| 4A-311 | 68.8 |
| 4A-332 | 324 |
| 4A-333 | 350 |
| 4A-334 | 296 |
| 4A-335 | 286 |
| 4A-336 | 309 |
| 4A-337 | 218 |
| 4A-338 | 222 |
| 4A-339 | 284 |
| 4A-340 | 41.8 |
| 4A-341 | 65.3 |
| 4A-342 | 538 |
| 4A-343 | 513 |
| 4A-344 | 427 |
| 4A-345 | 54.4 |
| 4A-346 | 56.1 |
| 4A-347 | 50.2 |
| 4A-348 | 47.8 |
| 4A-349 | 142 |
| Isotype control | 33.4 |

Table 19 shows binding of certain anti-MS4A4A antibodies of the present disclosure to U937 cells over-expressing recombinant human MS4A4A. These experiments were performed using anti-MS4A4A antibodies at a concentration of 5 μg/ml and were assayed for cell binding by flow cytometry. In this assay, the MFI value of cells stained with secondary antibody alone was approximately 200.

TABLE 19

| Antibody | MFI |
|---|---|
| 4A-21 | 18779 |
| 4A-332 | 8821 |
| 4A-350 | 11581 |
| 4A-351 | 12175 |
| 4A-358 | 12107 |
| 4A-360 | 10277 |
| 4A-362 | 10023 |
| 4A-369 | 10079 |
| 4A-373 | 11874 |
| 4A-376 | 16664 |
| 4A-352 | 10955 |
| 4A-353 | 10363 |
| 4A-354 | 13682 |
| 4A-355 | 13418 |
| 4A-356 | 11974 |
| 4A-377 | 12243 |
| 4A-378 | 9913 |
| 4A-379 | 10567 |
| 4A-380 | 11809 |
| 4A-381 | 12588 |
| 4A-202 | 31745 |
| 4A-302 | 24450 |
| 4A-312 | 17715 |
| 4A-313 | 41794 |
| 4A-314 | 15289 |

Example 8: Anti-MS4A4A Antibodies Modulate TREM2 Protein in Primary Human Myeloid Cells It has been reported that SNPs in the MS4A locus affect soluble TREM2 (sTREM2) levels in humans, the TREM2 pathway generally, and Alzheimer's disease susceptibility. Alzheimer's disease protective MS4A4A alleles are linked to increased sTREM2 levels in the cerebrospinal fluids. Together these pathways may play a role in the prevention of Alzheimer's Disease or other neurodegenerative diseases. Additionally, treatment of human macrophages in culture with commercially available anti-MS4A4A antibodies reduced sTREM2 levels (Piccio et. al. Acta Neuropathol 2016, 131:925-933). To examine the effect of anti-MS4A4A antibodies of the present disclosure modulating sTREM2 and plasma-membrane/cell surface TREM2 (mTREM2) levels in macrophages, the following studies were performed.

Primary human macrophages were plated in 96-well plates and treated with the panel of anti-MS4A4A antibodies (10 μg/ml) in complete RPMI. After 48 hours of incubation, supernatants were collected and sTREM2 levels determined using Meso Scale Discovery (MSD). Briefly, wells of an MSD plate (Cat #L15XA-3) were incubated with capture antibody at 1m/ml, overnight on orbital shaker at 500 RPM at 4° C. The wells were washed and then blocked in binding buffer (1% heat-inactivated high-grade BSA) in PBS) for an hour on an orbital shaker at 500 RPM at 20° C. Standards (Recombinant Human Trem2 Fc 1828-T2 (R&D Systems)) and unknown samples at proper concentrations were prepared in binding buffer, added to the wells, then incubated for 1 hour on orbital shaker at 500 RPM at 20° C. The wells were washed and then incubated with secondary antibody (Biotinylated goat anti-human TREM2 (R&D Systems Cat #BAF1828)) at 100 ng/ml for 1 hour on an orbital shaker at 500 RPM at 20° C. The wells were washed and then incubated with a detection reagent (Sulfo Tag-Streptavidin; MSD Cat #R32AD) at 0.2 μg/ml in binding buffer. The wells were then washed, 150 μl read buffer (1×, MSD) was added to each well, and the plates read on a Sector Imager.

Separately, anti-MS4A4A antibody treated cells (above) were collected and subjected to flow cytometry to determine mTREM2 levels using an anti-TREM2 antibody (Alector) conjugated to allophycocyanin or similar fluorophores.

As shown in Table 20, anti-MS4A4A antibodies increased the level of sTREM2 in the supernatants of cultured human primary macrophages obtained from various donors. The results described herein showed that the anti-MS4A4A antibodies of the present disclosure increase or upregulate sTREM2 levels in the supernatants of human primary macrophages. Numbers reported in Table 20 are relative to those obtained using an isotype control antibody, which was set at 100.

TABLE 20

| | Donor | | |
|---|---|---|---|
| Antibody | 686 | 687 | 688 |
| 4A-202 | 249.7 | 208.9 | 431.2 |
| 4A-214 | 142.8 | 168.3 | 137.7 |
| 4A-18 | 151.2 | 152.4 | 181.0 |
| 4A-21 | 340.0 | 230.4 | 489.7 |
| huIgG1 | 100 | 100 | 100 |

As shown below in Table 21, anti-MS4A4A antibodies increased the level of plasma-membrane/cell surface TREM2 (mTREM2) on cultured human primary macrophages obtained from various donors. These results were consistent with the corresponding increase in sTREM2 observed in the supernatants of these cells, as shown above in Table 20. Numbers reported in Table 21 are relative to those obtained using an isotype control antibody, which was set at 100.

TABLE 21

| | Donor | | |
|---|---|---|---|
| Antibody | 695 | 696 | 697 |
| 4A-202 | 319.2 | 374.5 | 373.2 |
| 4A-214 | 178.3 | 124.6 | 65.7 |
| 4A-18 | 273.0 | 286.1 | 313.6 |
| 4A-21 | 209.1 | 356.4 | 546.1 |
| hIgG1 | 100.0 | 100.0 | 100.0 |

These data showed that treatment of human primary macrophages with anti-MS4A4A antibodies of the present invention increased both sTREM2 and mTREM2 levels in these cells of myeloid lineage. These results contrast with a prior report showing that the commercially available anti-MS4A4A antibody 5C12 reduced sTREM2 levels in supernatants of cultured human macrophages (Deming et al, supra).

The above experiments examining the effect of anti-MS4A4A antibodies on soluble and membrane TREM2 were repeated using anti-MS4A4A antibodies prepared to have low endotoxin levels. Levels of sTREM2 as measured in culture supernatants are shown in Table 22 below. Most of the anti-MS4A4A antibodies of the present disclosure, when highly purified and essentially free of endotoxin, induced increased sTREM2 levels to varying degrees. Commercially available anti-MS4A4A antibodies 3F2, 4H2, and 5C12 also increased sTREM2 levels, but to a lesser degree. These results are in contrast to previously published data, which showed that these commercially available anti-MS4A4A antibodies reduced sTREM2 levels in culture; this is likely due to contaminating endotoxin, impurities, and aggregates present in commercial preparations. Data in Table 22 shows levels of sTREM2 expressed in ng/ml and are normalized to that observed with isotype control antibody.

The increase in sTREM2 observed was paralleled by an increase in membrane bound TREM2 (mTREM2) levels after anti-MS4A4A antibody treatment (Table 23 below). Variation among donors' responsiveness notwithstanding, most of the anti-MS4A4A antibodies increased the level of mTREM2 in 2 or 3 of the three donors tested. When compared to commercially available anti-MS4A4A antibodies (3F2, 4H2 and 5C12), a number of antibodies in the present disclosure display equivalent or superior activity. Levels shown in Table 23 below are expressed as Mean Fluorescence Intensity as determined by flow cytometry and are normalized that observed using isotype control antibody.

TABLE 22

| | Donor | | |
|---|---|---|---|
| Antibody | 753 | 754 | 755 |
| 4A-202 | 50.5 | 15.1 | 16.1 |
| 4A-18 | 54.9 | −2.4 | −0.3 |
| 4A-21 | 108.3 | 36.5 | 65.5 |
| 4A-25 | 21.5 | 12.0 | 33.8 |
| 4A-214 | 43.9 | 15.1 | 28.5 |
| 3F2 | 14.1 | 5.0 | 17.4 |
| 4H2 | −1.0 | 7.5 | −5.1 |
| 5C12 | −0.4 | 5.5 | 35.2 |

TABLE 23

| | TREM2 MFI, delta over control | | |
|---|---|---|---|
| Antibody | Donor 753 | Donor 754 | Donor 755 |
| 4A-202 | 5258 | 1171 | 6591 |
| 4A-18 | 3531 | −76 | 4289 |
| 4A-21 | 5585 | 2097 | 6334 |
| 4A-25 | 687 | 888 | 2528 |
| 4A-214 | 6017 | 1774 | 6009 |
| 3F2 | 2176 | 103 | 2423 |
| 4H2 | 1625 | 207 | 2444 |
| 5C12 | 926 | 499 | 1803 |

As genetic studies have linked the Alzheimer's disease protective MS4A4A allele with increased levels of sTREM2 in Alzheimer's disease patients, these results suggested that anti-MS4A4A antibodies are an effective treatment for Alzheimer's disease and other neurodegenerative disorders by modulating (i.e., increasing) TREM2 activity and function.

The effect of humanized anti-MS4A4A antibodies of the present disclosure on sTREM2 and membrane bound TREM2 (mTREM2) were also determined. To examine this, human primary macrophages from two donors were treated with anti-MS4A4A antibodies of the present disclosure for 48 hours. Culture supernatants were collected and assayed for levels of soluble TREM2 using Mesoscale Discovery assays. Cell surface TREM2 was measured in separately treated cells by flow cytometry after staining with anti-TREM2 antibodies conjugated with fluorophores. Soluble TREM2 was measured in the culture supernatant of macrophages using the Mesoscale Discovery system (MSD, Rockville, MD, USA).

Table 24 below shows the results of the effect of anti-MS4A4A antibodies on changes in soluble TREM2 levels. In Table 24, soluble TREM2 levels are listed as ng/ml. As shown in Table 24, most of the anti-MS4A4A antibodies of the present disclosure increased soluble TREM2 levels in human primary macrophages. Commercially available anti-MS4A4A antibodies 5C12, 4H2, and 3F2 did not show an increase in soluble TREM2 levels to any significant degree compared to that observed with many of the anti-MS4A4A antibodies of the present disclosure, and the effects of 5C12, 4H2, and 3F2 were comparable to isotype control.

TABLE 24

| Antibody | Donor 888 | Donor 904 |
|---|---|---|
| hIgG1 isotype | 24.1 | 25.0 |
| 4A-202 | 46.5 | 38.4 |
| 4A-21 | 47.2 | 39.7 |
| 4A-25 | 41.3 | 41.2 |
| 4A-302 | 49.3 | 41.3 |
| 4A-312 | 41.4 | 36.2 |
| 4A-313 | 53.7 | 40.4 |
| 4A-314 | 47.9 | 37.2 |
| 4A-332 | 44.6 | 37.3 |
| 4A-350 | 51.4 | 44.0 |
| 4A-351 | 45.4 | 42.2 |
| 4A-352 | 41.2 | 41.0 |
| 4A-353 | 32.3 | 34.7 |
| 4A-354 | 41.4 | 38.0 |
| 4A-355 | 35.5 | 23.2 |
| 4A-356 | 40.4 | 38.0 |
| 4A-358 | 55.0 | 45.8 |
| 4A-360 | 45.3 | 38.4 |
| 4A-362 | 56.0 | 45.7 |
| 4A-369 | 54.4 | 41.6 |
| 4A-373 | 54.2 | 44.5 |
| 4A-376 | 54.2 | 51.1 |

TABLE 24-continued

| Antibody | Donor 888 | Donor 904 |
|---|---|---|
| 4A-377 | 34.4 | 37.0 |
| 4A-378 | 32.7 | 35.1 |
| 4A-379 | 31.9 | 31.2 |
| 4A-380 | 38.1 | 33.0 |
| 4A-381 | 33.7 | 33.1 |
| 4A-382 | 26.9 | 31.3 |
| 4A-383 | 29.0 | 30.5 |
| 4A-384 | 23.2 | 24.1 |
| 4A-385 | 27.4 | 27.2 |
| 4A-386 | 25.4 | 28.3 |
| 4A-387 | 26.0 | 30.6 |
| 4A-388 | 28.7 | 31.1 |
| 4A-390 | 26.8 | 31.5 |
| mIgG1 isotype | 25.9 | 28.8 |
| 5C12 | 29.7 | 30.0 |
| 4H2 | 28.9 | 30.6 |
| 3F2 | 29.4 | 28.8 |

Table 25 below shows the results of the effect of anti-MS4A4A antibodies on changes in cell surface (e.g., membrane) TREM2 levels. In Table 25, cell surface TREM2 levels are shown as mean fluorescence intensity (MFI) as measured in the flow cytometry procedure. As shown in Table 25, most of the anti-MS4A4A antibodies of the present invention increased cell surface TREM2 levels in human primary macrophages. Commercially available anti-MS4A4A antibodies 5C12, 4H2, and 3F2 did not show an increase in cell surface TREM2 levels to any significant degree compared to that observed with many of the anti-MS4A4A antibodies of the present disclosure, and the effects of 5C12, 4H2, and 3F2 were comparable to isotype control.

TABLE 25

| Antibody | Donor 888 | Donor 904 |
|---|---|---|
| hIgG1 isotype | 2566.5 | 2637.5 |
| 4A-202 | 4045.5 | 4100 |
| 4A-21 | 3329 | 3325 |
| 4A-25 | 2967.5 | 3191 |
| 4A-302 | 5336 | 4741.5 |
| 4A-312 | 5492 | 4672 |
| 4A-313 | 3645.5 | 3345.5 |
| 4A-314 | 4335 | 4070 |
| 4A-332 | 3257 | 3061 |
| 4A-350 | 3552 | 3192.5 |
| 4A-351 | 3464 | 3235.5 |
| 4A-352 | 3247.5 | 3227.5 |
| 4A-353 | 2835 | 3133 |
| 4A-354 | 2940 | 3092.5 |
| 4A-355 | 3319 | 3891.5 |
| 4A-356 | 2971.5 | 3328.5 |
| 4A-358 | 3659 | 3273.5 |
| 4A-360 | 3421.5 | 3154.5 |
| 4A-362 | 3759.5 | 3240 |
| 4A-369 | 3558.5 | 3256 |
| 4A-373 | 3430 | 3313 |
| 4A-376 | 3521 | 3398.5 |
| 4A-377 | 3376.5 | 3553.5 |
| 4A-378 | 3920.5 | 3804.5 |
| 4A-379 | 3847.5 | 3745 |
| 4A-380 | 4070 | 3754 |
| 4A-381 | 4070.5 | 3952.5 |
| 4A-382 | 2618.5 | 2621.5 |
| 4A-383 | 2611.5 | 2812.5 |
| 4A-384 | 2524.5 | 2601 |

TABLE 25-continued

| Antibody | Donor 888 | Donor 904 |
|---|---|---|
| 4A-385 | 2576.5 | 2560.5 |
| 4A-386 | 2546 | 2614 |
| 4A-387 | 2534 | 2601 |
| 4A-388 | 2589.5 | 2624.5 |
| 4A-390 | 2561 | 2639.5 |
| mIgG1 isotype | 2459.5 | 2690.5 |
| 5C12 | 2596 | 2683.5 |
| 4H2 | 2611.5 | 2780 |
| 3F2 | 2629 | 2629.5 |

As shown in Table 24 and Table 25, both membrane TREM2 levels and soluble TREM2 levels were upregulated upon treatment with anti-MS4A4A antibodies of the present disclosure. Commercially available anti-MS4A4A antibodies 5C12, 4H2, and 3F2 did not induce TREM2 expression to any significant degree.

EXAMPLE: 9: Effect of Anti-MS4A4A Antibodies on Macrophage Cell Surface Markers

The effect of anti-MS4A4A antibodies on various M1 and M2 macrophage cell surface markers was examined as follows. Human primary macrophages were treated with various anti-MS4A4A antibodies (10 μg/ml) in complete RPMI1640 for 48 hours. The cells were then harvested and subjected to flow cytometry, using antibodies specific for M1 markers (CD16, MHC Class II, CD86), M2 markers (CD200R, Dectin-1, CD163), and a pan-macrophage marker CD14.

The results of these studies are shown in Table 26 below. Cell surface marker expression levels were assayed by flow cytometry and were normalized to that obtained in cells treated with an isotype control antibody, which was set at 100%. The cell surface expression of certain M1 markers, including CD86 and were unaltered or only modestly affected by anti-MS4A4A antibody treatment. By contrast, the cell surface expression of certain M2 markers, including CD200R, CD163, and Dectin-1 was significantly reduced by anti-MS4A4A antibody treatment.

TABLE 26

| Antibody | CD200R (M2) | CD14 (Pan) | Dectin-1 (M2) | CD16 (M1) | CD163 (M2) | MHC-II (M1) | CD86 (M1) |
|---|---|---|---|---|---|---|---|
| huIgG1 | 100.0 | 100.0 | 100.0 | 100.0 | 100.0 | 100.0 | 100.0 |
| 4A-202 | 35.2 | 60.2 | 47.3 | 171.0 | 39.1 | 73.6 | 121.8 |
| 4A-214 | 89.5 | 98.1 | 108.3 | 106.5 | 112.8 | 144.2 | 131.6 |
| 4A-18 | 29.0 | 56.6 | 46.6 | 239.3 | 33.6 | 45.6 | 112.3 |
| 4A-21 | 67.9 | 39.4 | 22.9 | 75.5 | 65.0 | 81.3 | 177.0 |

Together, these results indicated that anti-MS4A4A antibodies of the present disclosure affect macrophage polarization, affecting cells away from an M2 phenotype. These results suggested that within the CNS, anti-MS4A4A antibody treatment may provide a beneficial enhancement of microglial activity by potentiating, increasing, or restoring their neuroprotective function in the context of neurodegenerative diseases and disorders. As homeostatic microglia in healthy conditions express more M2 markers, such as CD200R, CD163 and CD115, these results suggested that anti-MS4A4A antibodies of the present disclosure are affective at altering the physiological state of microglial cells to that of a more protective phenotype, including to a more proinflammatory or activated state. As disease associated microglia (DAM) in Alzheimer's disease mouse models and in human Alzheimer's disease are in a proinflammatory or activated state, which is considered beneficial in Alzheimer's disease, anti-MS4A4A antibodies of the present disclosure are useful in treating Alzheimer's disease and other neurodegenerative disorders.

Example 10: Anti-MS4A4A Antibodies Increase Expression of Osteopontin and Gelsolin Alzheimer's disease-associated genetic variants (SNPs) associated with the MS4A gene cluster have been identified. One of those variant alleles is rs1582763, which is associated with elevated CSF sTREM2 levels and with reduced Alzheimer's disease risk and delayed age-at-onset. (Deming et al, 2018, bioRxiv, doi: dx doi org/10.1101/352179). The rs1582763 allele decreases MS4A4A mRNA levels in blood. These findings suggest that the rs1582763 allele performs a protective role by reducing MS4A4A levels, potentially decreasing Alzheimer's disease risk or severity.

An RNA expression profile showing the effect of this protective allele in human macrophages was derived from published RNA expression data. The mRNA for SPP1 (osteopontin) and GSN (gelsolin) showed the most significant increase in expression, as indicated by fold change ("FC") and p-values (see columns under "rs1582763" in Table 27 and duplicated in Table 28 below), compared to other markers showing increased expression (not shown). The data indicated that SPP1 and GSN are pharmacodynamic markers for the protective biological activity associated with the rs158273 allele.

Parental MS4A4A antibodies were tested for their ability to phenocopy the protective allele. Human PBMC-derived macrophages were treated with anti-MS4A4A antibodies as indicated in Table 27 and Table 28 for 24 hours (up to three replicates). RNA was extracted and RNA libraries were prepared and sequenced, followed by genome mapping and quantification. The results indicated that all but one (4A-220) of the indicated parental anti-MS4A4A antibodies phenocopy the protective rs1582763 allele with respect to increasing expression of SPP1 and GSN (Table 27 and Table 28). These results suggested that MS4A4A antibodies of the present disclosure that are effective at increasing expression of SPP1 and GSN are biologically active in decreasing Alzheimer's disease risk and/or severity, similar to the protective allele.

TABLE 27

| | rs1582763 | | 4A-18 | | 4A-18 + 4A-21 | | 4A-25 | | 4A-214 | |
|---|---|---|---|---|---|---|---|---|---|---|
| Gene | FC | p | FC | p | FC | p | FC | p | FC | p |
| SPP1 | 0.82 | 4.E−06 | 0.73 | 1.E−08 | 0.25 | 4.E−02 | 0.37 | 3.E−03 | 0.29 | 1.E−02 |
| GSN | 0.34 | 6.E−06 | 1.28 | 1.E−17 | 0.85 | 2.E−09 | 0.65 | 3.E−06 | 0.56 | 8.E−06 |

TABLE 28

| | rs1582763 | | 4A-220 | | 4A-21 | | 4A-202 | |
|---|---|---|---|---|---|---|---|---|
| Gene | FC | p | FC | p | FC | p | FC | p |
| SPP1 | 0.82 | 4.E−06 | −0.13 | 3.E−01 | 0.56 | 7.E−06 | 0.49 | 2.E−03 |
| GSN | 0.34 | 6.E−06 | −0.11 | 4.E−01 | 0.94 | 5.E−11 | 0.82 | 2.E−06 |

Example 11: Derivation and Stimulation of iPSC-Derived Microglial Cells with Anti-MS4A4A Antibodies Adult cells of any tissue-origin can be converted into induced pluripotent stem cells (iPSCs) through the introduction of a mixture of transcriptional factors associated with stem cells. iPSCs can be maintained indefinitely, and when given appropriate growth factors, can be driven to differentiate into various mature cell types. Methods for deriving neurons from iPSC have long been established (Salimi et. al., Mol. Bio. Rep. 2014; 41: 1717-1721; Engle et. al., Neuron 2018; 100: 783-797). More recently, iPSCs have been used to derive astrocytes (*Julia* et. al., Stem Cell Report 2017; 9:600-614) and microglia (reviewed by Pocock and Piers, Nat. Rev. Neurosci. 2018; 19: 445-452). These culture systems allow investigation of the biology and function of these cell in controlled environments that may otherwise not be possible. Furthermore, iPSCs can be genetically manipulated by various methods, such as by CRISPR gene editing, to allow for further dissection of the functional relevance of genes of interest in these cell types.

After derivation from iPSCs, microglia are cultured alone in vitro, where they are subjected to stimulation with anti-MS4A4A antibodies in the present disclosure. After stimulation, cell viability is assessed by quantification of intracellular ATP levels. The effect on changes in cell surface TREM2 expression or on changes in soluble TREM2 levels is measured as described above. Supernatants from these cultures are analyzed for changes in expression or levels of various cytokines and chemokines as a result of anti-MS4A4A antibody treatment, using methods such as ELISA, Mesoscale Discovery assays (MSD, Rockville, MD, USA), Legendplex (BioLegend, San Diego, CA, USA), or CBA (BD Biosciences, San Jose, CA, USA). Changes in phagocytosis capacity, autophagy rate, surface marker expression, and gene expression profile in these iPSC-microglia resulting from anti-MS4A4A antibody treatment are measured and compared to that obtained from monocyte-derived macrophages treated with anti-MS4A4A antibodies, using various methods, including flow cytometry, western blotting, fixed- and real-time imaging, and RNAseq analysis.

Example 12: Effect of Anti-MS4A4A Antibodies on Macrophage Cell Surface Markers Myeloid cells in both the CNS and in peripheral organs are inherently plastic in their phenotype and function. This can be modeled by macrophages in vitro, which can be divided into M1 and M2 type macrophages, showing differing phagocytic and inflammatory potentials, phenotypes, and activities. In peripheral organs, macrophages associated with the M1 phenotype are thought to be more pro-inflammatory and anti-microbial, while M2-like macrophages are more homeostatic and anti-inflammatory. Within the CNS, microglia in homeostatic conditions also express M2 markers such as CD200R, CD163, suggesting regulatory functions in this cell type. MS4A4A expression is elevated in M2 macrophages in vitro.

The effect of anti-MS4A4A antibodies on various M1 and M2 macrophage cell surface markers is examined as follows. Human primary macrophages are treated with various anti-MS4A4A antibodies (e.g., 10 μg/ml) in complete RPMI1640 for 48 hours. The cells are then harvested and subjected to flow cytometry, using antibodies specific for M1 markers (such as CD16, MHC Class II, CD86), M2 markers (such as CD200R, Dectin-1, CD163), and a pan-macrophage marker including CD14 and others.

Example 13: Kinetic Characterization of Anti-MS4A4A Antibodies

Binding kinetic characterization of the purified antibodies to MS4A4A ECL1 and ECL2 peptides is performed by Carterra (South San Francisco, CA) using a proprietary array Surface Plasmon Resonance (SPR) instrument (MX-96) as follows. Antibodies are printed onto a CMD500D chip (Xantec #SPMX CMD500D lot #SC CMD500D0117.a Exp. 31.12.18) using the Continous Flow Microspotter (CFM). First, the chip is activated with 100 mM MES pH 5.5, 1004 EDC (133 mM final), 1004 of S-NHS (33.3 mM final), for 7 minutes. A lawn of anti-mouse IgG-Fc (Jackson ImmunoResearch cat #115-005-071) is injected for 15 minutes to establish a surface density of 10000-12000 RU, after which the chip surface is deactivated with 1M ethanolamine at pH 8.5 for 10 minutes. Anti-MS4A4A antibodies in question are diluted 2:1 with HBS-EP+buffer (Teknova Cat #H8022) and then printed as duplicates with a 20 minute and a 5-minute print from the same sample solution. Control antibodies are diluted to for printing.

To perform kinetic analysis, the peptides in question are prepared in HBS-EP+buffer with lmg/ml BSA at final assay concentrations of 2000 nM, 400 nM, 80 nM, 16 nm, and 3.2 nM. These are then injected on the chip for five minutes, followed by a seven-minute dissociation period at 8 uL per second in a non-regenerative kinetic series. Duplicate measurements for each anti-MS4A4A antibody are taken to ensure reproducibility.

Example 14: Affinity Measurement of MS4A4A Antibodies to Transiently and Natively Expressing Cell Lines Purified anti-MS4A4A antibodies are evaluated for their binding affinity to various MS4A4A-expressing cell lines. These include transfected cells as described above in Example 8, as well as myeloid cell lines and primary cells that endogenously express MS4A4A. Anti-MS4A4A antibodies tested are either mouse IgGs purified from hybridoma supernatant or human IgG1 Fc chimeras produced recombinantly in Expi293 cells. Affinity binding to cells is determined as follows. Briefly, cells are harvested, washed and labeled with Aqua Live/Dead for viability discrimination. After a wash with PBS, $2\times10^5$ cells are aliquoted per well in 96-well U-bottom plates and incubated with 504, of purified anti-MS4A4A antibody at various concentrations (3× dilutions starting at 10 μg/mL) in FACS buffer (PBS+2% FBS+1 mM EDTA). After primary incubation, the supernatant was removed via centrifugation, washed 2× with 1504 of ice-cold FACS buffer and incubated with the appropriate secondary antibody on ice for 30 minutes. Following the secondary incubation, the cells are again washed 2× with ice-cold FACS buffer and resuspended in a final volume of 2004 of FACS buffer. Flow cytometry analysis is performed on a FACSCanto system (BD Biosciences). Binding data was analyzed using Median fluorescent intensity and curves were fit in Prism (nonlinear regression: log inhibitor vs. dose response with four parameters) to determine EC50 values.

Example 15: Downregulation of MS4A4A Protein

The ability of anti-MS4A4A antibodies to reduce cell surface and total cellular protein levels of MS4A4A in various cell lines and primary cells is evaluated. Reduction in MS4A4A protein in either compartment indicates a reduction in MS4A4A activity in the cells.

Cells are incubated with anti-MS4A4A antibodies of the present disclosure for various time periods and then the levels of MS4A4A protein remaining associated with the cells is assayed by either FACS (cell surface) or western blot (total cell protein level). For FACS assays, detection of the remaining MS4A4A is carried out with direct-allophycocyanin (APC) conjugated, non-competing antibodies. For Western blot detection, cells are lysed by the addition of 504 lysis buffer (RIPA lysis buffer (ThermoFischerScientific Cat #89900)+1:100 HALT protease inhibitor cocktail (ThermoFischerScientific Cat #87786), and cleared for insoluble debris by centrifugation at 14,000×g for minutes. Soluble fraction is assayed with bicinchoninic acid (BCA) reagent for protein quantification. Equal amounts of proteins from each sample are loaded on a 4-12% Bis-Tris Plus polyacrylamide gel (ThermoFisher Scientific NW04120) and subjected to electrophoresis separation, after which proteins in the gel are transferred onto a polyvinylidene difluoride (PVDF) membrane using iBlot2 (ThermoFisher Scientific IM21001) and Transfer Stacks (ThermoFisher Scientific IB24002). The membrane is blocked with either 1% bovine serum albumin or 5% non-fat milk to prevent non-specific binding. It is then incubated with in-house or commercial detection antibodies, washed, and incubated with HRP-conjugated secondary antibody (rabbit, Abcam #205718; mouse, Abcam #205719). Binding is visualized by developing with SuperSignal West Pico Plus chemiluminescent substrate (ThermoFisher Scientific #34577) and recorded digitally with iBright FL1000 (ThermoFisher Scientific A32752) or other compatible systems.

Down-regulation of MS4A4A protein levels may also be accomplished by down-regulation of MS4A4A nucleic acid expression or levels, by, e.g., use of antisense methodologies, gene therapy, etc, using methods known and available to one of skill in the art.

Example 16: Characterization of the Activity of Anti-MS4A4A Antibodies Utilizing Animal Models for Aging, Seizures, Spinal Cord Injury, Retinal Dystrophy, Frontotemporal Dementia, and Alzheimer's Disease The therapeutic utility of anti-MS4A4A antibodies can also be tested in animal models for aging, seizures, spinal cord injury, retinal dystrophy, frontotemporal dementia, and Alzheimer disease, as previously described (e.g., Beattie, M S et al., (2002) Neuron 36, 375-386; Volosin, M et al., (2006) J. Neurosci. 26, 7756-7766; Nykjaer, A et al., (2005) Curr. Opin. Neurobiol. 15, 49-57; Jansen, P et al., (2007) Nat. Neurosci. 10, 1449-1457; Volosin, M et al., (2008) J. Neurosci. 28, 9870-9879; Fahnestock, M et al., (2001) Mol. Cell Neurosci. 18, 210-220; Nakamura, K et al., (2007) Cell Death. Differ. 14, 1552-1554; Yune, T et al., (2007) Brain Res. 1183, 32-42; Wei, Y et al., (2007) Neurosci. Lett. 429, 169-174; Provenzano, M J et al., (2008) Laryngoscope 118, 87-93; Nykjaer, A et al., (2004) Nature 427, 843-848; Harrington, A W et al., (2004) Proc. Natl. Acad. Sci. U.S.A. 101, 6226-6230; Teng, H K et al., (2005) J. Neurosci. 25, 5455-5463; Jansen, P et al., (2007) Nat. Neurosci. 10, 1449-1457; Volosin, M et al., (2008) J. Neurosci. 28, 9870-9879; Fan, Y J et al., (2008) Eur. J. Neurosci. 27, 2380-2390; Al-Shawi, R et al., (2008) Eur. J. Neurosci. 27, 2103-2114; and Yano, H et al., (2009) J. Neurosci. 29, 14790-14802).

Example 17: Characterization of the Effects of Anti-MS4A4A Antibodies Utilizing Animal Models for Oncology Myeloid cells represent a major component of the immune cells present in most solid tumors. Their role in tumor biology is context-dependent—while such cells have the potential to play a key role in the eradication of tumors, they are most often co-opted by the host tumor to assist in providing a pro-tumor phenotype. This is achieved mostly through the polarization of myeloid cells towards an M2-phenotype, which is typically immunosuppressive and thus blocks the immune system from eradicating the tumor. Anti-MS4A4A antibodies, through repolarization of myeloid cells, can reverse this immunosuppressive phenotype and promote an anti-tumor immune response.

Numerous animal tumor models exist. Examples of relevant animal models include humanized mouse models, where the mouse immune system is genetically deleted, as typified by the NSG mice (Jackson Laboratory, Bar Harbor, Maine). These mice act as receptive hosts for human immune cells, leading to the engraftment of human adaptive and innate immune cells. These animals are then inoculated with tumor cells, usually under the skin on the flanks. Tumor size over time represents the balance between the growth of tumor cells and their eradication by the host immune system. Throughout the time course the animals are treated with anti-MS4A4A antibodies, which modifies tumor progression when compared to isotype-treated animals. At the end of treatment period tumors are extracted and subjected to various analyses to determine the effect of anti-MS4A4A antibodies on the tumor cells and infiltrating immune cells. Tumors can be sectioned, mounted onto slides and analyzed under the microscope for histological changes. mRNA can be analyzed by RT-PCR, RNASeq or microarray to determine changes in gene expression. Single cell suspensions of tumor and infiltrating immune cells can be prepared, stained with antibodies against various cell surface markers and analyzed by flow cytometry, to delineate changes in cell surface phenotype, especially in immune cells such as macrophages and T cells. Changes observed as a result of anti-MS4A4A treatment in any of these analyses will indicate an immune-modulatory function for these antibodies.

Example 18: Effect of Anti-MS4A4A Antibodies on TREM2 Transcription and mRNA The effect of anti-MS4A4A antibodies on TREM2 transcriptional level and mRNA is evaluated as follows. Cultured cells are treated with various concentration of an anti-MS4A4A antibody of the present disclosure for various periods of time. Afterward, changes in TREM2 mRNA levels within the cells are then determined using standard methodologies for measuring and/or quantitating mRNA levels known to one of skill in the art.

Example 19: Effect of Anti-MS4A4A Antibodies on TREM2 Recycling and Degradation In order to better understand the effect of anti-MS4A4A antibodies on increased levels of sTREM2 and mTREM2, the following studies to examine TREM2 recycling and/or degradation are performed. In these studies, cycloheximide treatment of cells is used in order to prevent further new TREM2 synthesis in association with anti-MS4A4A antibody treatment. Various methods known in the art are available to examine the recycling and degradation of TREM2 in control cells compared to cells treated with anti-MS4A4A antibodies.

Example 20: Additional Anti-MS4A4A Antibodies

Two additional anti-MS4A4A antibodies were humanized and affinity matured from the parental antibody 4A-21, as described above in Example 1, resulting in anti-MS4A4A antibody 4A-450 and anti-MS4A4A antibody 4A-419. The variable heavy chain and variable light chain sequences of each of these antibodies are shown below in Table 29, with their corresponding CDRs (according to Kabat) underlined. The heavy chain CDR sequences are shown in Table 30; the light chain CDR sequences are shown in Table 31.

TABLE 29

| Antibody | Heavy Chain Variable | SEQ ID NO: | Light Chain Variable | SEQ ID NO: |
|---|---|---|---|---|
| 4A-450 | QVQLVQSGSELKKPGASVKVSCKASGYAFTSYGLSWVRQAPGQGLEWMGWINTYSGVPTYAQGFTGRFVFSLDTSVSTAYLQISSLKAEDTAVYYCARTMADYWGQGTLVTVSS | 304 | DVVMTQSPLSLPVTLGQPASISCKSSRSLLYSAGKTYLSWFQQRPGQSPRRLIYLVSKLDSGVPDRFSGSGSGTDFTLKISRVEAEDVGVYYCWQGIDFHQTFGGGTKVEIK | 305 |
| 4A-419 | QVQLVQSGSELKKPGASVKVSCKASGYRFTSYGLSWVRQAPGQGLEWMGWINTYSGVPTYAQGFKGRFVFSLDTSVSTAYLQISSLKAEDTAVYYCARTMADYWGQGTLVTVSS | 306 | DVVMTQSPLSLPVTLGQPASISCKSSRSLLYSAGKTYLSWFQQRPGQSPRRLIYLVSKLDSGVPDRFSGSGSGTDFTLKISRVEAEDVGVYYCWQGIDFHQTFGGGTKVEIK | 307 |

TABLE 30

| Antibody | CDR-H1 | SEQ ID NO: | CDR-H2 | SEQ ID NO: | CDR-H3 | SEQ ID NO: |
|---|---|---|---|---|---|---|
| 4A-450 | SYGLS | 308 | WINTYSGVPTYAQGFTG | 309 | TMADY | 310 |
| 4A-419 | SYGLS | 311 | WINTYSGVPTYAQGFKG | 312 | TMADY | 313 |

TABLE 31

| Antibody | CDR-L1 | SEQ ID NO: | CDR-L2 | SEQ ID NO: | CDR-L3 | SEQ ID NO: |
|---|---|---|---|---|---|---|
| 4A-450 | KSSRSLLYSAGKTYLS | 314 | LVSKLDS | 315 | WQGIDFHQT | 316 |
| 4A-419 | KSSRSLLYSAGKTYLS | 317 | LVSKLDS | 318 | WQGIDFHQT | 319 |

Example 21: Effect of Anti-MS4A4A Antibodies on sTREM Levels In Vivo

To examine the effect of anti-MS4A4A antibodies of the present disclosure on sTREM levels in serum and cerebrospinal fluid (CSF) in vivo, the following studies were performed.

Cynomolgus monkeys were administered anti-MS4A4A antibody 4A-202 or isotype control (huIgG1) at a single dose of 80 mg/ml by intravenous infusion. Serum samples were collected from the animals at pre-dose, 0.5, 4, 10, 24, 48, 96, 192, 312, 480, and 648 hours post administration of antibody; CSF samples were collected from the animals at pre-dose, 48, 96, 192, and 336 hours post administration of antibody.

sTREM levels in serum and CSF were measured as follows. Single spot Meso Scale Discovery (MSD) plates (Rockville, MD) were coated with a capture antibody in PBS at 4° C. overnight. Monkey serum and CSF samples (as well as monkey TREM2-Fc standards) were diluted in binding buffer and added to the wells for 1 hour at room temperature. Biotinylated goat anti-human TREM2 polyclonal antibody (R&D Systems) was added at a 1:2,000 dilution in binding buffer and incubated for 1 hour at room temperature, followed by detection with sulfo tag streptavidin (MSD). 150 μl of 1× Read Buffer was added to the plates, and the plates were then analyzed on a Sector Imager (MSD).

Figure 10A:
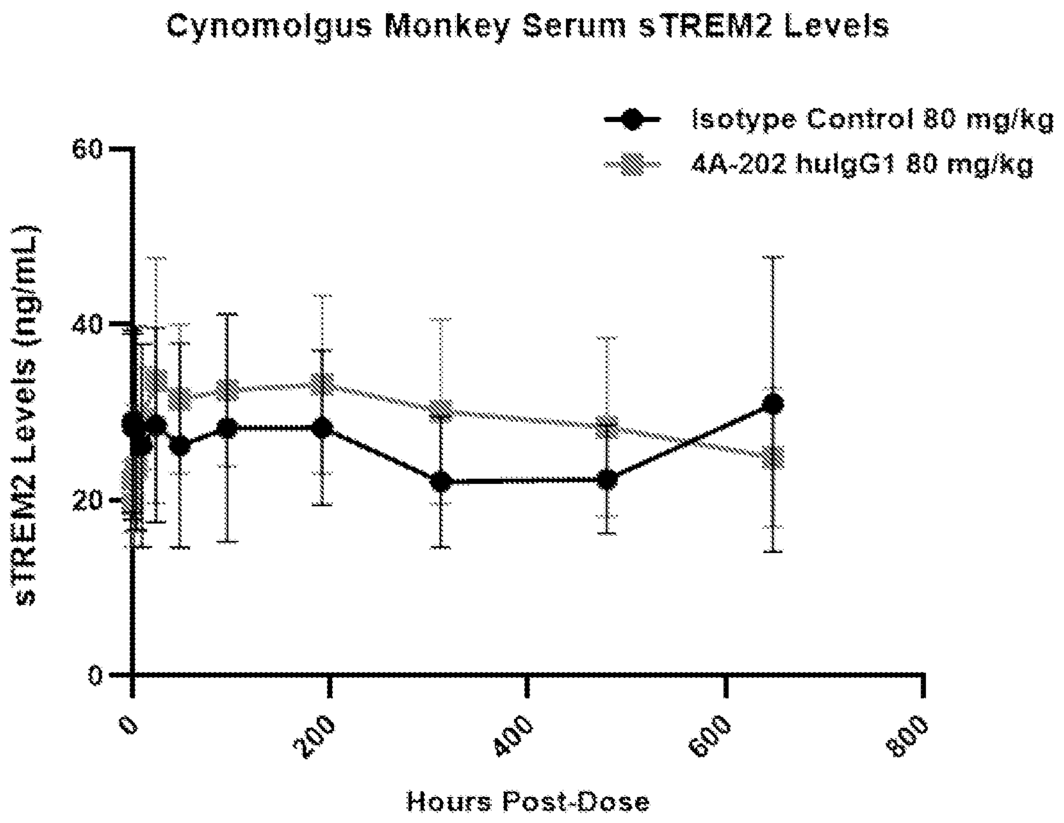
FIGS. 10A-10B show the effect of anti-MS4A4A antibody 4A-202 on the levels of sTREM2 in the serum of cynomolgus monkeys.
Figure 10B:
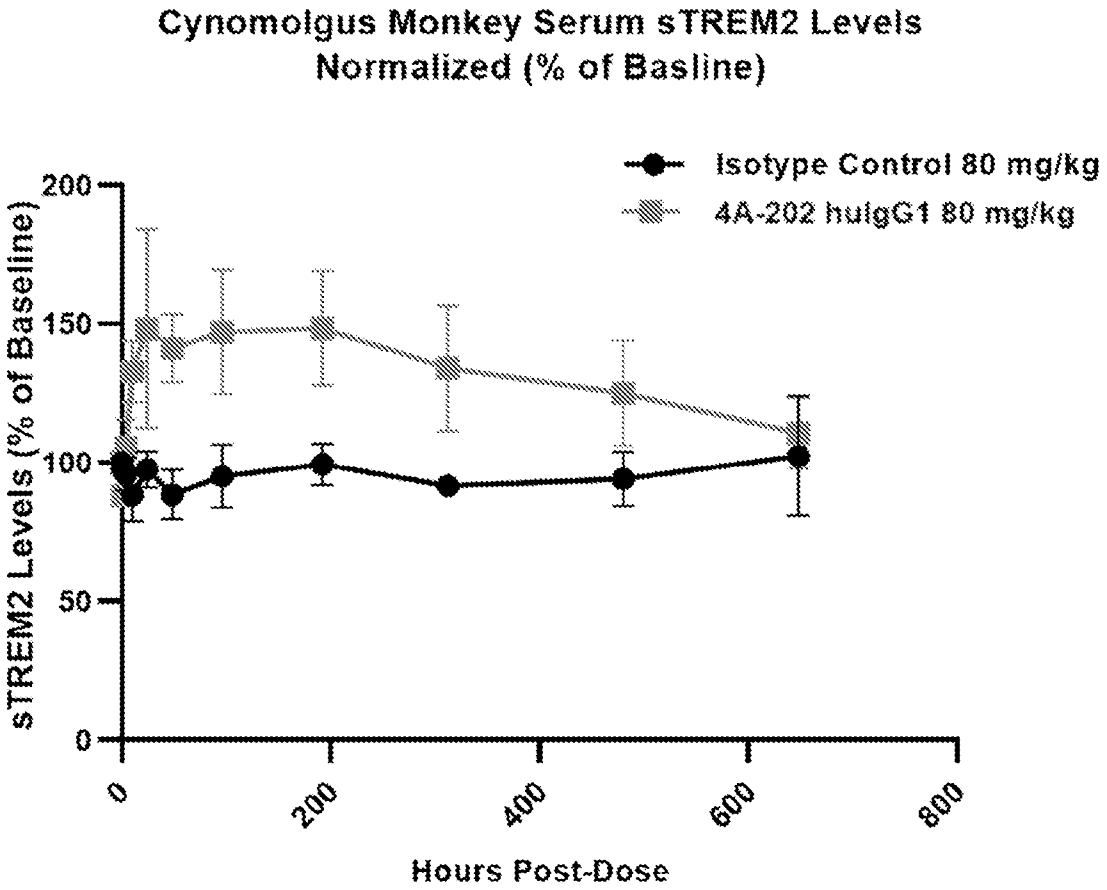

In serum, sTREM2 levels increased approximately 1.5-fold from baseline (approximately 50% increase from baseline) following administration of anti-MS4A4A antibody 4A-202 (FIGS. 10A-10B). Serum sTREM2 levels remained elevated (above baseline levels) for at least 480 hours (20 days) following a single dose of anti-MS4A4A antibody 4A-202 in cynomolgus monkeys.

Figure 11A:
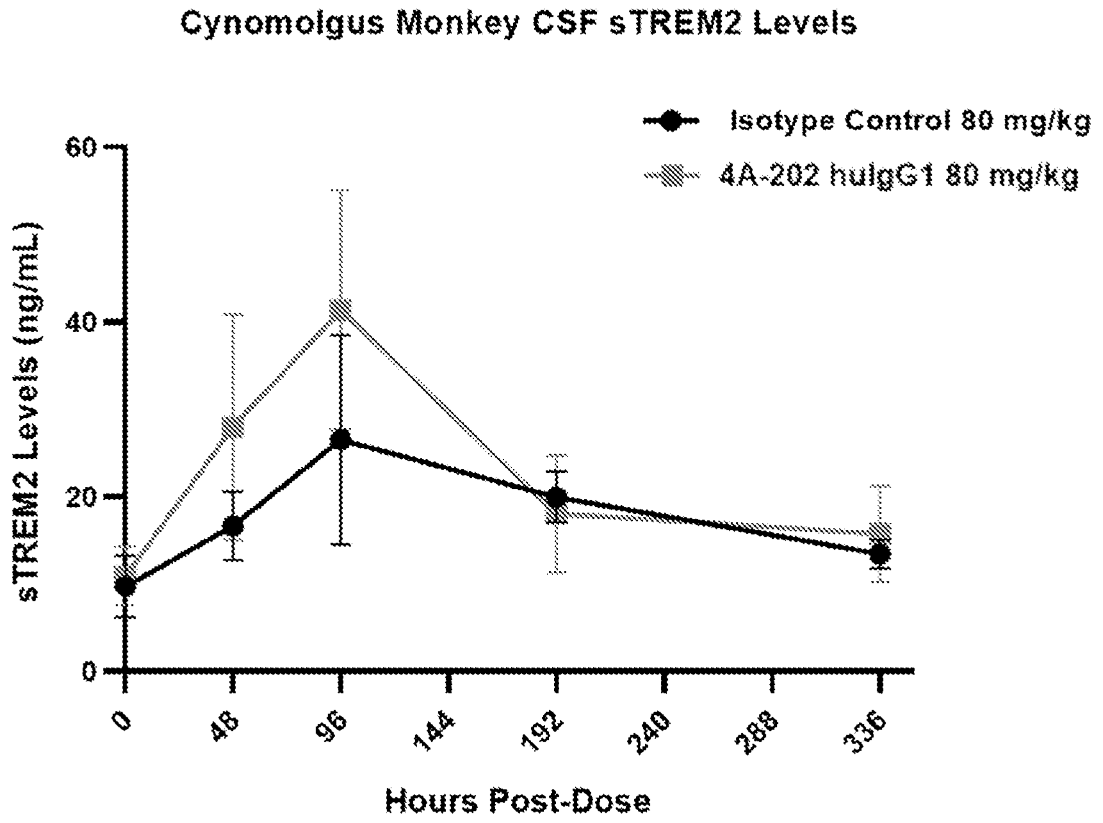
FIGS. 11A-11B show the effect of anti-MS4A4A antibody 4A-202 on the levels of sTREM2 in the cerebrospinal fluid (CSF) of cynomolgus monkeys.
Figure 11B:
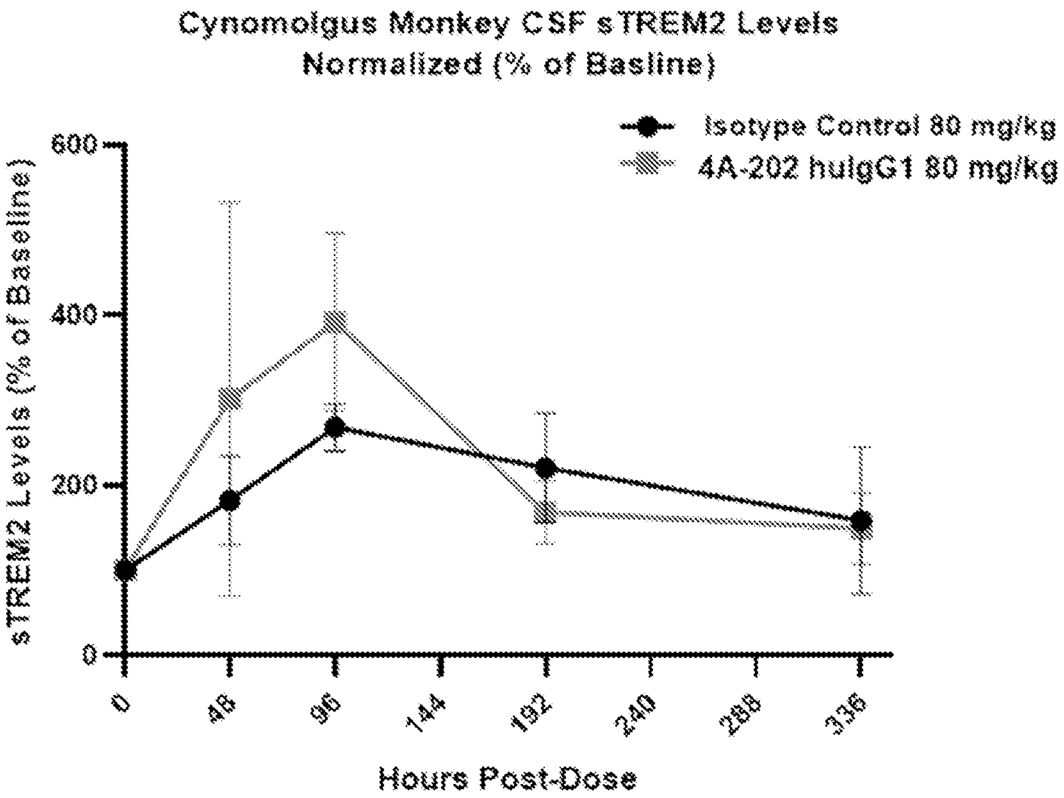

In CSF, sTREM2 levels increased approximately 2- to 4-fold above baseline (approximately 300% increase from baseline) following administration of anti-MS4A4A antibody 4A-202 (FIGS. 11A-11B). CSF sTREM2 levels remained elevated (above baseline levels) for at least 96 hours (4 days) following a single dose of anti-MS4A4A antibody 4A-202 in cynomolgus monkeys.

These results showed that anti-MS4A4A antibodies of the present disclosure are effective at increasing sTREM2 levels in serum and in CSF in vivo.

Example 22: Binding of Anti-MS4A4A Antibodies to U937 Cells Overexpressing Recombinant MS4A4A Anti-MS4A4A antibodies of the present disclosure were evaluated for their binding affinity to human recombinant MS4A4A-expressing U937 cells (the generation of these cells is described above). Binding affinity of anti-MS4A4A antibodies to the cells was determined as follows. Briefly, U937 cells expressing recombinant human MS4A4A were harvested, washed, and labeled with Aqua Live/Dead for viability discrimination. After washing the cells with PBS, 2×10^4 cells were aliquoted per well in 96-well U-bottom plates and incubated with 504 of purified anti-MS4A4A antibody at various concentrations in FACS buffer (PBS+2% FBS+1 mM EDTA). After this primary incubation, the supernatant was removed via centrifugation, the cells washed 2× with 1504 of ice-cold FACS buffer, and then incubated with the appropriate secondary antibody on ice for 15 minutes. Following the secondary antibody incubation, the cells were again washed 2× with ice-cold FACS buffer and resuspended in a final volume of 2004 of FACS buffer. Flow cytometry analysis was then performed using the FACSCanto system (BD Biosciences). Binding data was expressed as Mean Fluorescent Intensity (MFI). MFI values measured by the flow cytometer were analyzed on Prism (Graphpad) software, using the following equation (or one could use a similar 4-parameter fit) based on Kuek, et al, 2016, Immunology and Cell Biology. 94:11-23:

$$Y=((F\mathrm{max}-B)/(n*((C/6.02e23)/(V*le-6)))*[[(\mathrm{aptKD}+X+n*((C/6.02e23)/(V*le-6)))-\mathrm{SQRT}\{((\mathrm{aptKD}+X+n*((C/6.02e23)/(V*le-6)))\hat{}2)-4*(n*((C/6.02e23)/(V*le-6))*X)\}]/2]+B)$$

In these analyses, the following values were constrained according to experimental conditions: C=number of cells per well (20,000); V=total volume of staining in microliters; n=number of receptors on cell surface, estimated to be 100,000 receptors per cell. The results of these binding studies are shown in FIG. 12.

Figure 12:
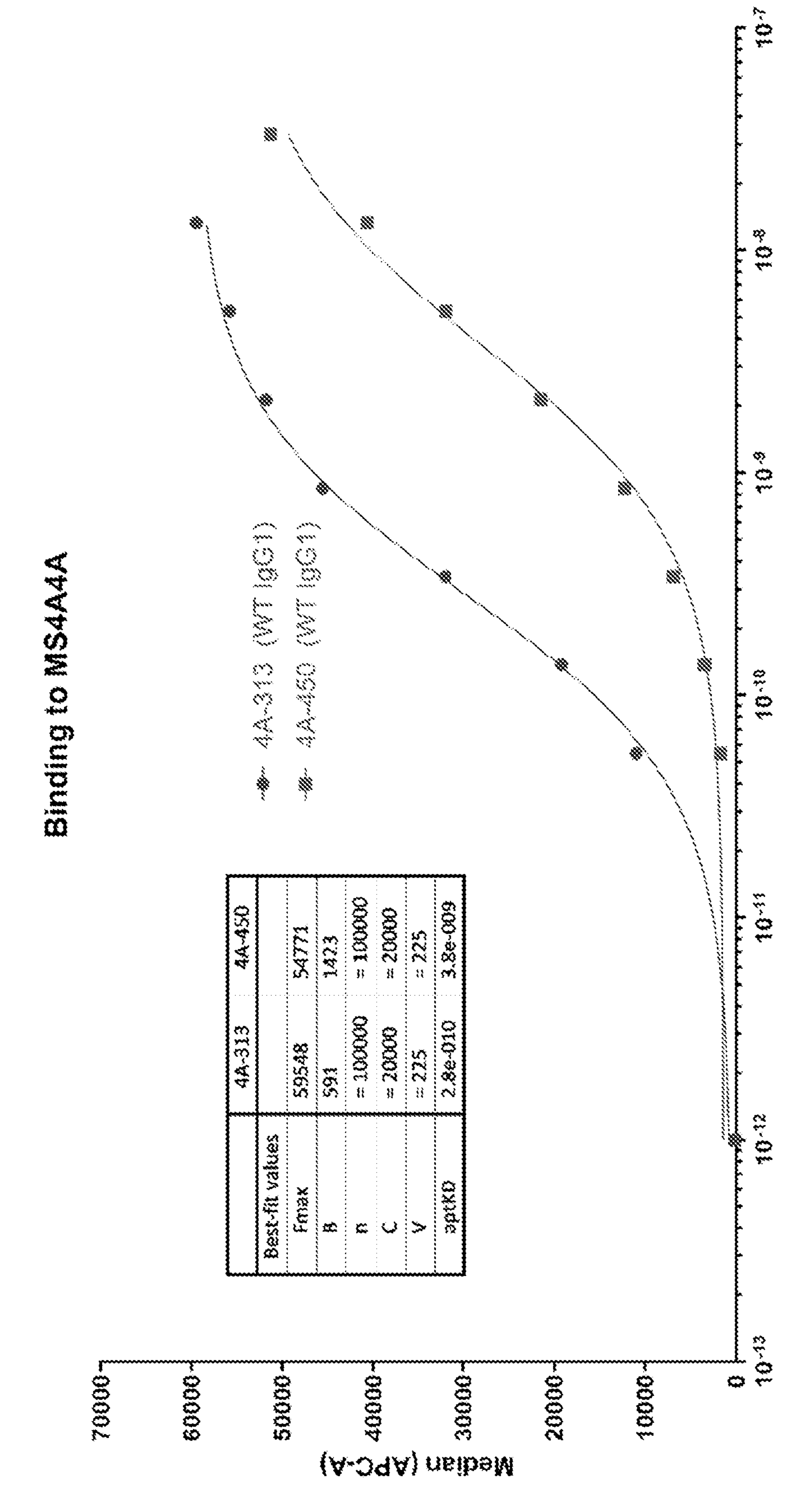
FIG. 12 sets forth data showing binding curves of anti-MS4A4A antibodies 4A-313 wildtype (WT) huIgG1 and 4A-450 WT huIgG1 to U937 cells expressing recombinant human MS4A4A.

As shown in FIG. 12, anti-MS4A4A antibody 4A-313 WT huIgG1 displayed a binding affinity to recombinant human MS4A4A expressed on U937 cells of approximately 2.8e-10, while anti-MS4A4A antibody 4A-450 WT huIgG1 displayed a binding affinity of 3.8e-09 in this assay.

Example 23: Generation of MS4A4A Overexpressing Cell Line

Given the difficulty for generating stably transfected HEK293 cell lines expressing recombinant human MS4A4A, other DNA vectors and cell lines were examined to determine if they would be more compatible for expression of recombinant human MS4A4A. For stable transfection, MS4A4A coding sequence was introduced into expression vectors pD2533-G418 or pD3539-puro (Atum, Newark, CA, USA).

MS4A4A is expressed natively in myeloid cells in vivo. Therefore, to overcome the toxicity observed using cells described above, several myeloid-derived cell lines were tested for their ability to express recombinant human MS4A4A with minimal or no observed toxicity. The panel of myeloid-derived cell lines used in these studies included THP-1 cells (ATCC TIB202), U937 cells (ATCC CRL-1593.2), K562 cells (ATCC CCL243), HL60 cells (ATCC CCL240), and Kasumi-1 cells (ATCC CRL-2724). 300.19 cells (Tufts University T000710), a mouse pre-B cell line, were also tested as these cells are commonly used for recombinant protein expression purposes. Each of these cell lines was screened for antibiotic susceptibility in order to determine a suitable dose of G418 or puromycin for selection and transfection efficiency. Transfectants from U937 cells, K562 cells, and 300.19 cells were found to be viable after recombinant human encoding MS4A4A expression plasmid transfection and antibiotic selection. After cloning these cells by limiting-dilution, individual clones were generated and subsequently screened for human MS4A4A protein cell surface expression using flow cytometry.

Example 24: Humanized and Affinity Matured Anti-MS4A4A Antibodies Modulate TREM2 Protein in Primary Human Myeloid Cells Data from human genetics studies have identified links between MS4A4A, the TREM2 pathway, and Alzheimer's disease (AD) susceptibility (Piccio et al., 2016, Acta Neuropathol, 131:925-933; doi: https://dx.doi.org/10.1101/352179). For example, AD-protective MS4A4A alleles are linked to increased sTREM2 levels in cerebrospinal fluid. To gain insight into these protective pathways, the following studies were performed. Human primary macrophages were treated with various concentrations of anti-MS4A4A antibodies of the present disclosure for 48 hours. In these studies, the following anti-MS4A4A antibodies were tested: 4A-450 with wildtype huIgG1 Fc (WT), 4A-450 with huIgG1 Fc N325S and L328F (NSLF), 4A-450 with huIgG1 Fc K322A, 4A-313 WT huIgG1, 4A-313 NSLF huIgG1, and 4A-313 K322A huIgG1. Cell surface (membrane bound) expression of TREM2 was then measured by flow cytometry after the cells were subsequently stained with an anti-TREM2 antibody conjugated with fluorophores. Soluble TREM2 levels were measured in the culture supernatant of the cells using Mesoscale Discovery system (MSD, Rockville, MD, USA).

Figure 13:
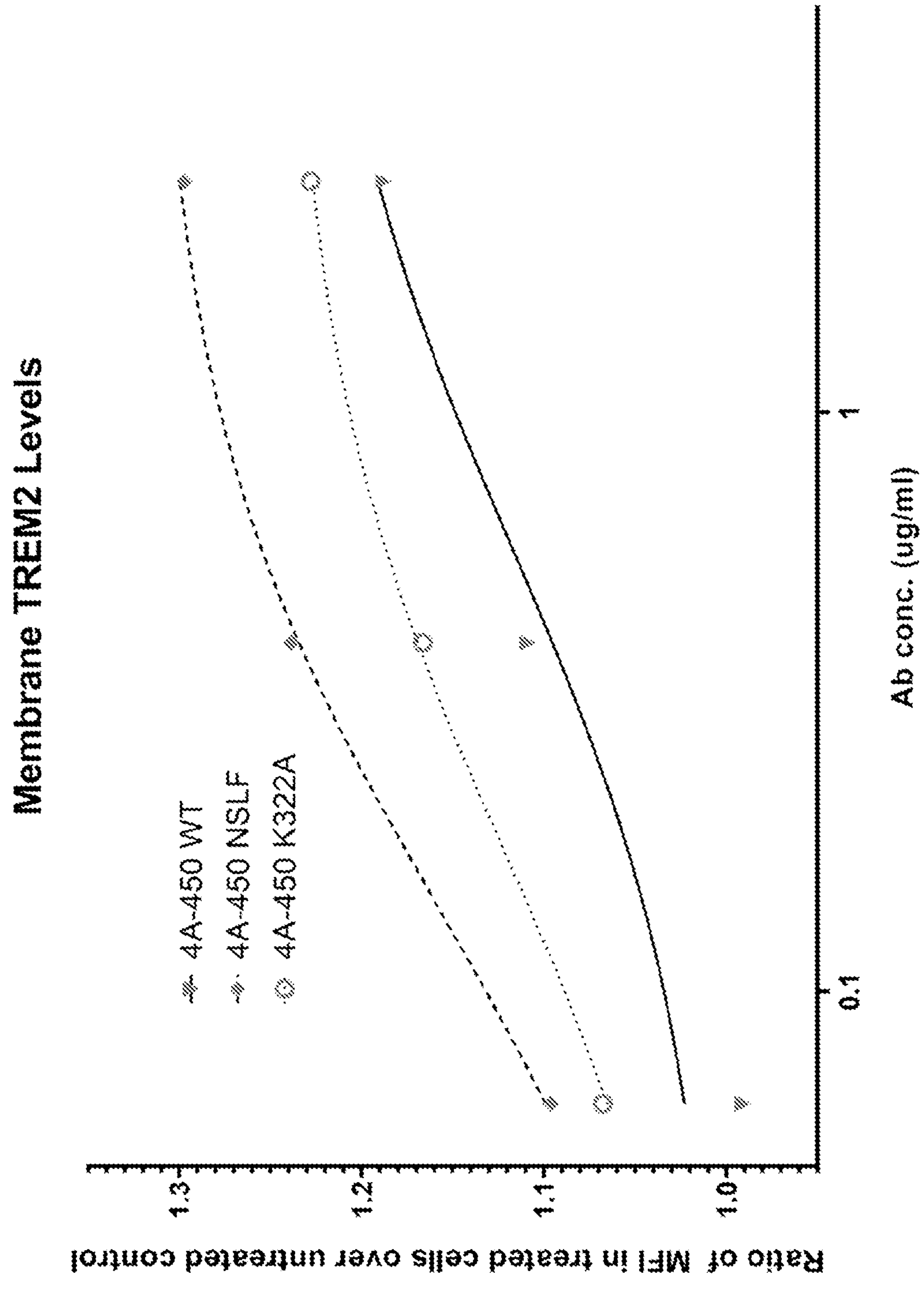
FIG. 13 sets forth data showing membrane TREM2 levels in primary human macrophages treated with anti-MS4A4A antibodies 4A-450 WT huIgG1, 4A-450 NSLF huIgG1, and 4A-450 K322A huIgG1.
Figure 14:
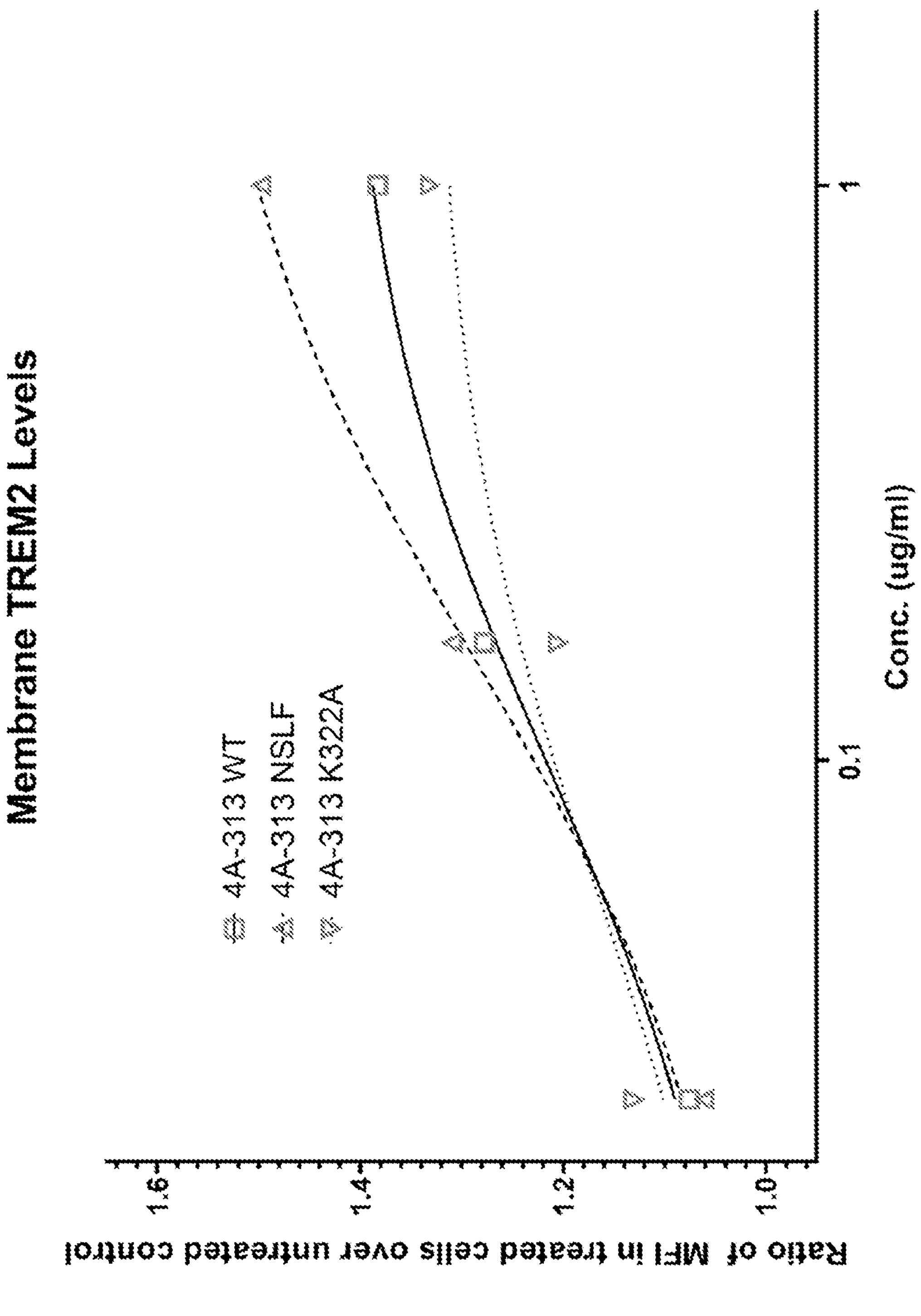
FIG. 14 sets forth data showing membrane TREM2 levels in primary human macrophages treated with anti-MS4A4A antibodies 4A-313 WT huIgG1, 4A-313 NSLF huIgG1, and 4A-313 K322A huIgG1.

As shown in FIGS. 13 and 14, membrane TREM2 levels were increased in human primary macrophages following addition to the cells of anti-MS4A4A antibodies in a dose-dependent manner. Anti-MS4A4A antibodies on different huIgG1 Fc sequences—wildtype huIgG1, N325S/L328F amino acid substitutions in huIgG1, and K322A amino acid substitution in huIgG1 were all capable of increasing membrane TREM2 expression levels. Tables 32 and 33 below present the numeric values for the ratio of MFI observed in anti-MS4A4A treated cells for changes in membrane bound TREM2 levels compared to that observed in untreated control cells obtained from FIGS. 13 and 14, respectively.

Figure 15:
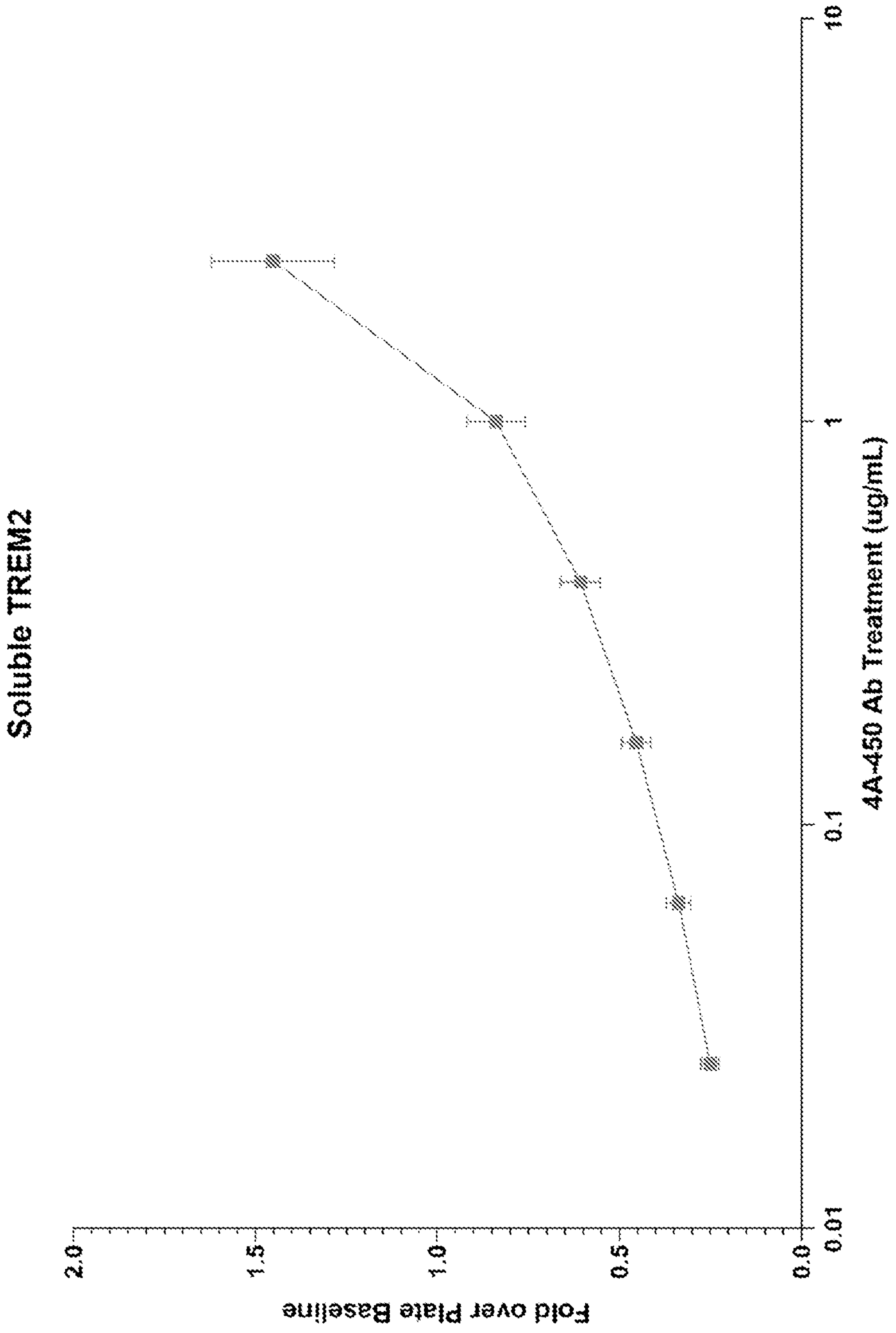
FIG. 15 sets forth data showing increased soluble TREM2 levels in the supernatant of primary human macrophages treated with anti-MS4A4A antibody 4A-450 huIgG1.
Figure 16:
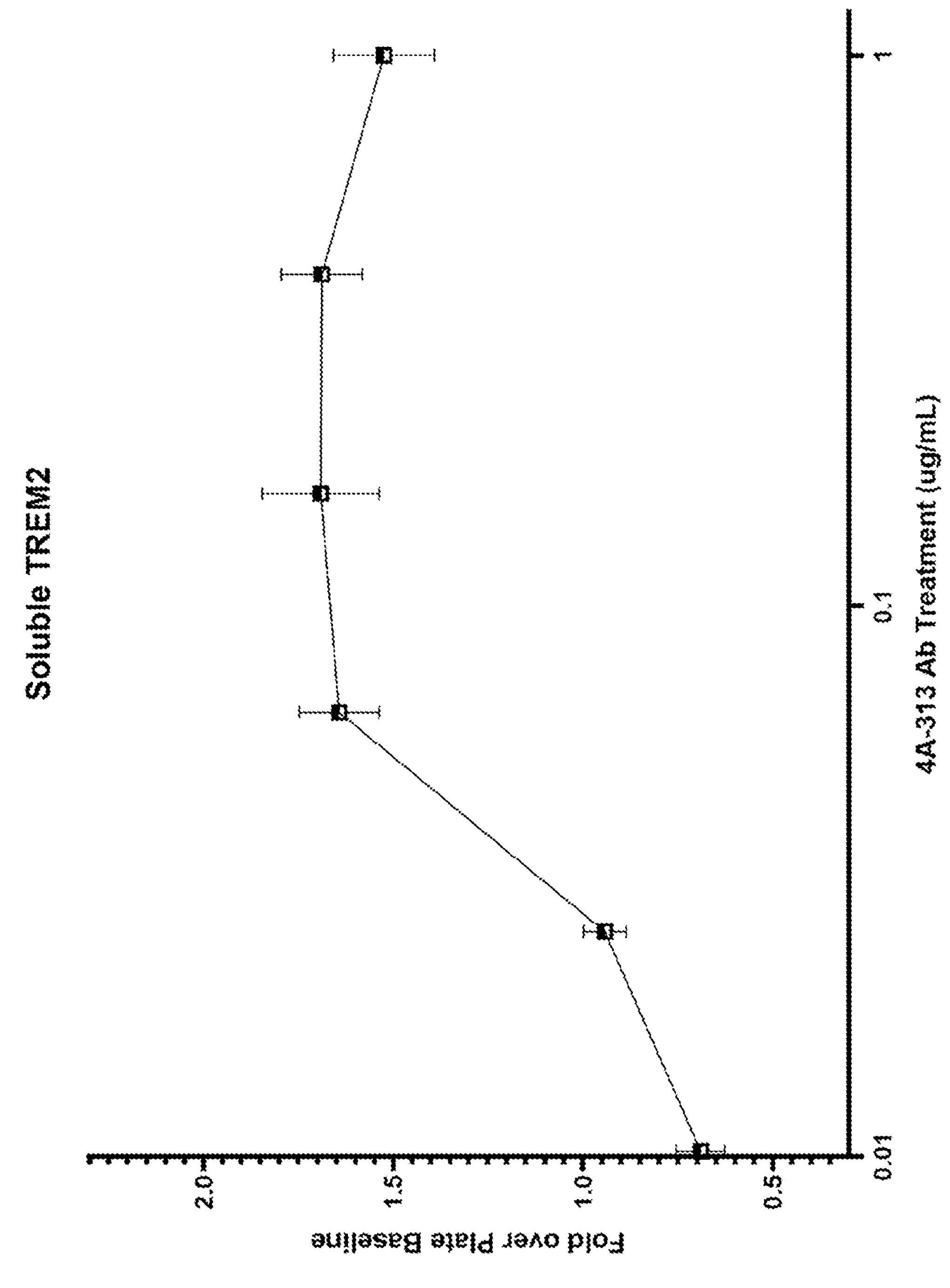
FIG. 16 sets forth data showing increased soluble TREM2 levels in the supernatant of primary human macrophages treated with anti-MS4A4A antibody 4A-313 huIgG1.

FIGS. 15 and 16 show anti-MS4A4A antibodies 4A-450 and 4A-313 on a wildtype huIgG1 Fc backbone (respectively) increased soluble TREM2 levels in the supernatants of primary human macrophages in a dose-dependent manner. Tables 34 and 35 below present the numeric values of the fold increase in soluble TREM2 observed in anti-MS4A4A treated cells over that measured as plate baseline levels obtained from FIGS. 15 and 16, respectively.

TABLE 32

| Antibody (μg/ml) | 4A-450 WT | | | 4A-450 NSLF | | | 4A-450 K322A | | |
|---|---|---|---|---|---|---|---|---|---|
| 2.5 | 1.184 | 1.174 | 1.205 | 1.297 | 1.176 | 1.418 | 1.176 | 1.180 | 1.327 |
| 0.4 | 1.236 | 1.063 | 1.028 | 1.276 | 1.270 | 1.168 | 1.163 | 1.173 | 1.163 |
| 0.064 | 1.043 | 1.033 | 0.897 | 1.169 | 1.026 | 1.093 | 1.002 | 1.178 | 1.023 |

TABLE 33

| Antibody (µg/ml) | 4A-313 WT | | | 4A-313 NSLF | | | 4A-313 K322A | | |
|---|---|---|---|---|---|---|---|---|---|
| 1 | 1.431 | 1.242 | 1.475 | 1.570 | 1.380 | 1.542 | 1.348 | 1.240 | 1.405 |
| 0.16 | 1.388 | 1.210 | 1.235 | 1.392 | 1.262 | 1.274 | 1.290 | 1.155 | 1.170 |
| 0.0256 | 1.194 | 1.056 | 0.978 | 1.106 | 1.103 | 0.974 | 1.163 | 1.161 | 1.068 |

TABLE 34

| 4A-450 WT IgG1 (µg/ml) | sTREM2 (fold over plate background) |
|---|---|
| 0.0256 | 0.250851509 |
| 0.064 | 0.337610359 |
| 0.16 | 0.453324666 |
| 0.4 | 0.60750507 |
| 1 | 0.838142928 |
| 2.5 | 1.452549482 |

TABLE 35

| 4A-313 WT IgG1 (µg/ml) | sTREM2 (fold over plate background) |
|---|---|
| 0.0256 | 0.690304672 |
| 0.064 | 0.942481014 |
| 0.16 | 1.64173901 |
| 0.4 | 1.690748748 |
| 1 | 1.687668894 |
| 2.5 | 1.52381547 |

These results showed that anti-MS4A4A antibody 4A-450 WT huIgG1 (2.5 µg/ml) increased sTREM levels in primary human macrophages by about 1.4-fold compared to untreated cells. These results also showed that anti-MS4A4A antibody 4A-313 WT huIgG1 increased sTREM levels in primary human macrophages by about 1.5-fold to about 1.7-fold compared to untreated cells. These results indicated that anti-MS4A4A antibodies of the present disclosure are effective at increasing sTREM levels in vitro and thus may provide an effective means of increasing sTREM levels in plasma and CSF in vivo, mimicking the effect of MS4A4A alleles protective to developing Alzheimer's disease.

Example 25: Effect of Anti-MS4A4A Antibodies on Cellular ATP Levels

Human monocytes were isolated from whole blood using RosetteSep Human monocyte enrichment cocktail (Stemcell technologies) and Ficoll centrifugation per manufacturer protocols. After lysing red blood cells with ACK lysing buffer, monocytes were resuspended in complete media (RPMI, 10% FBS, Pen/Strep, L-glutamine, HEPES, non-essential amino acid, Sodium pyruvate). To obtain macrophages from these isolated monocytes, 100 ng/ml human M-CSF and 8% v/v human serum were added to the cells for 5-7 days. Cells were then plated at 50,000 cells/well in complete RPMI-1640 and cultured for 2 days in the presence or absence of various concentrations of anti-MS4A4A antibodies (4A-313 NSLF, 4A-313 PS, 4A-450 NSLF, and 4A-450 PS) or isotype control antibody at various concentrations in solution for 48 hours. ATP content within the cells was then quantified using the CellTiter-Glo Luminescent cell viability kit (Promega, Cat #G7571) following the manufacturer's protocol.

Figure 17:
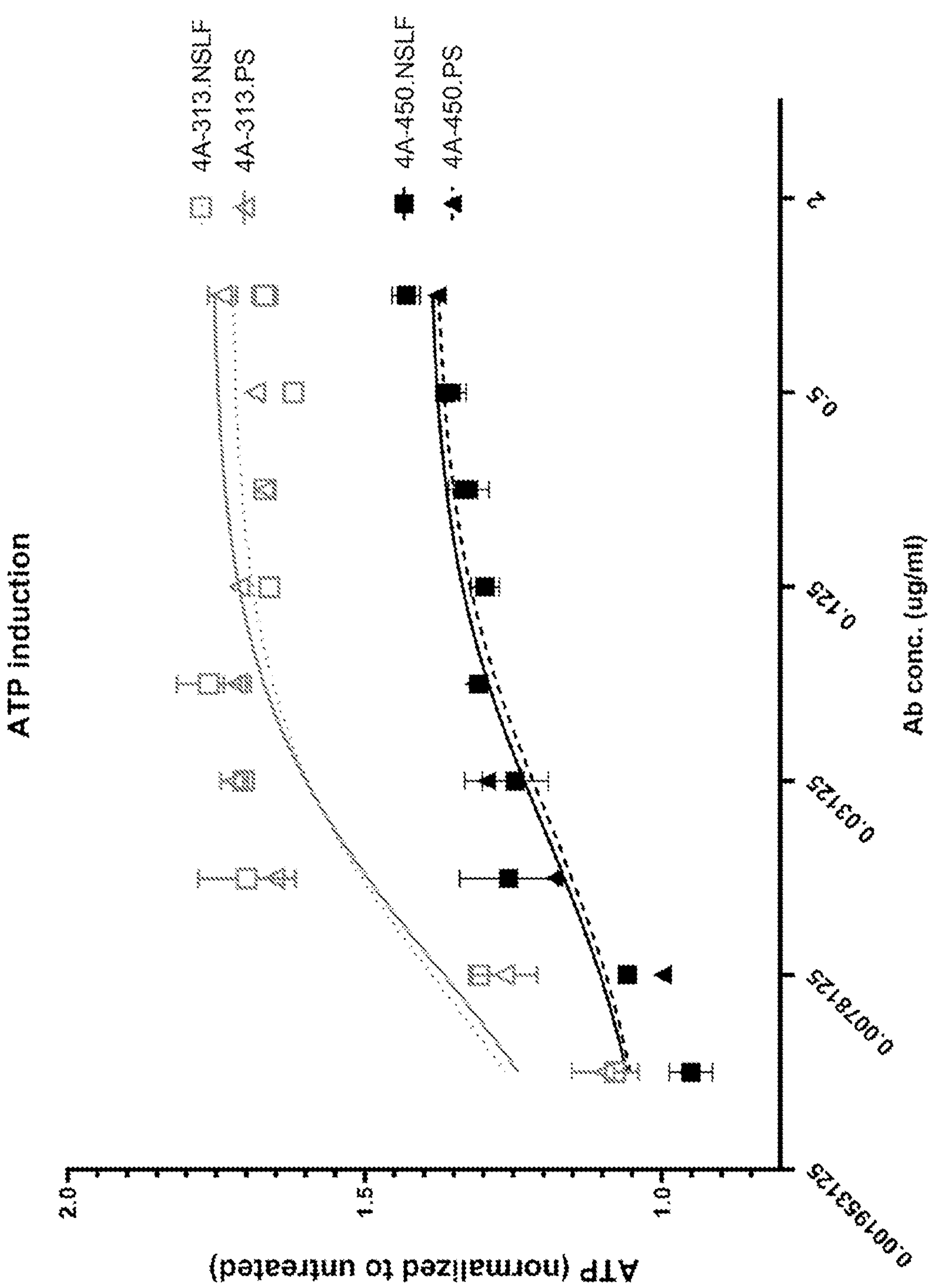
FIG. 17 sets forth data showing increased ATP levels in primary human macrophages treated with anti-MS4A4A antibodies 4S-313 NSLF huIgG1, 4A-313 PS huIgG1, 4A-450.NSLF huIgG1, and 4A-450.PS hu IgG1.

As shown in FIG. 17, anti-MS4A4A antibodies 4A-313 NSLF hulgG1, 4A-313 PS hulgG1, 4A-450 NSLF hulgG1, and 4A-450 PS hulgG1 increased ATP levels in primary human macrophages in a dose-dependent manner. Anti-MS4A4A antibodies having hulgG1 Fc containing N325S/L328F amino acid substitutions, which abolish FcγRIIIa binding (Journal of Biological Chemistry 2014, 289: 15309-15318), or having hulgG1 Fc containing P331S amino acid substitution, which abolishes Clq binding (Journal of Immunology 2000, 164: 4178-4184), were both effective at increasing ATP levels in human macrophages. The increase in ATP levels indicates increased viability of the human macrophages.

Table 36 below presents the numeric values of ATP levels determined in these studies (associated with FIG. 17), which were normalized to that observed in untreated macrophages. These results showed that anti-MS4A4A antibodies of the present disclosure were effective at increasing ATP levels in human macrophages in a dose-dependent manner. ATP levels increased by about 1.2-fold (with 0.016 µg/ml anti-MS4A4A antibody) to about 1.4-fold (with 1.0 µg/ml anti-MS4A4A antibody) above that observed in non-treated cells using anti-MS4A4A antibody 4A-450. ATP levels increased by about 1.3-fold (with anti-MS4A4A antibody) to about 1.7-fold (with 1.0 µg/ml anti-MS4A4A antibody) above that observed in non-treated ells using anti-MS4A4A antibody 4A-313.

TABLE 36

| Antibody (µg/ml) | 4A-450.NSLF | 4A-450.PS | 4A-313.NSLF | 4A-313.PS |
|---|---|---|---|---|
| 1.000 | 1.431 | 1.378 | 1.669 | 1.739 |
| 0.500 | 1.362 | 1.355 | 1.620 | 1.685 |
| 0.250 | 1.332 | 1.325 | 1.670 | 1.667 |
| 0.125 | 1.298 | 1.303 | 1.661 | 1.711 |
| 0.063 | 1.308 | 1.317 | 1.762 | 1.715 |
| 0.031 | 1.247 | 1.296 | 1.704 | 1.720 |
| 0.016 | 1.258 | 1.182 | 1.698 | 1.652 |
| 0.008 | 1.058 | 1.000 | 1.308 | 1.266 |
| 0.004 | 0.952 | 0.957 | 1.079 | 1.096 |

Example 26: Effect of Anti-MS4A4A Antibodies on Macrophage Cell Surface Markers Myeloid cells in both the CNS and peripheral organs are inherently plastic in their phenotype and function. In peripheral organs, macrophages having an M1-like phenotype are more pro-inflammatory and anti-microbial, while macrophages having an M2-like phenotype are more homeostatic and anti-inflammatory. Within the CNS, microglia in homeostatic conditions also express M2-like markers, such as, for example, CD200R and CD163. MS4A4A expression is elevated in M2-like macrophages in vitro, and it has been suggested that MS4A4A is a novel cell surface marker for M2-like macrophages (Immunology and Cell Biology 2017, 95: 611-619).

The effect of anti-MS4A4A antibodies of the present disclosure on various macrophage cell surface markers was examined as follows. Human primary macrophages were treated with various concentrations (10 µg/ml, 1.0 µg/ml, 0.1 µg/ml) of anti-MS4A4A antibodies 4A-313 NSLF huIgG1 or 4A-419 wildtype (WT) huIgG1 in complete RPMI1640 for 48 hours. The cells were then harvested and subjected to flow cytometry, using antibodies specific for M1-like markers (e.g., CD16, MHC Class II, CD86), M2-like markers (e.g., CD200R, Dectin-1, CD163), and a pan-macrophage marker CD14.

Figure 18A:
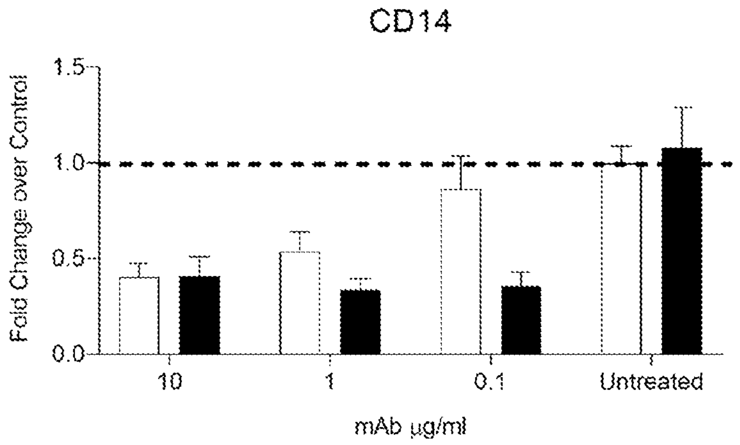
FIGS. 18A, 18B, and 18C set forth data showing changes in the levels of CD14, CD163, and CD200R (respectively) in primary human macrophages treated with anti-MS4A4A antibodies 4A-313 NSLF huIgG1 and 4A-419 WT huIgG1.
Figure 18B:
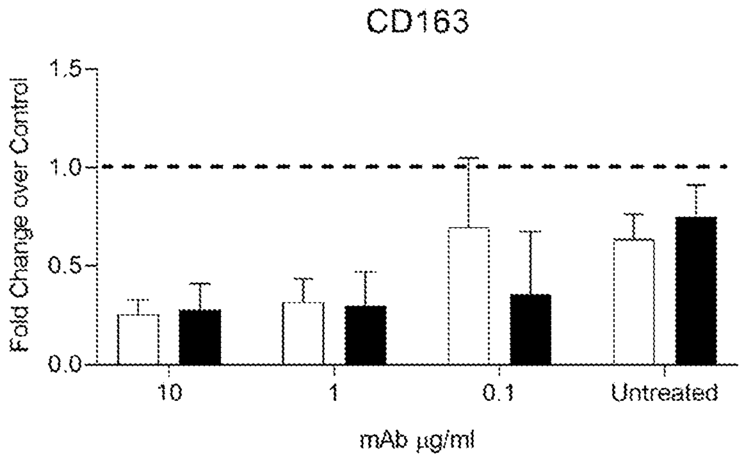
Figure 18C:
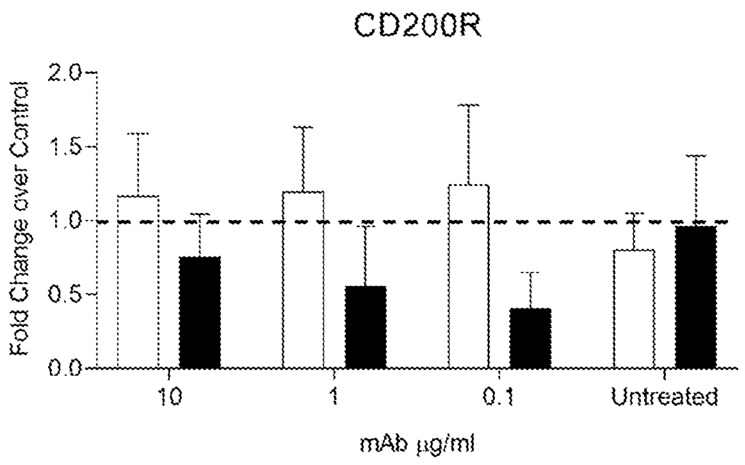

As shown in FIGS. 18A, 18B, and 18C, addition of anti-MS4A4A antibodies to primary human macrophages resulted in a decrease in CD14 and in CD163 cell surface markers in a dose-dependent manner compared to that observed in untreated cells (anti-MS4A4A antibody 4A-313 NSLF huIgG1 Fc (bars on the right in each pair), anti-MS4A4A antibody 4A-419 wildtype huIgG1 Fc (WT) (bars on the left in each pair). Addition of anti-MS4A4A antibody 4A-313 NSLF to primary human macrophages resulted in levels of CD200R cell surface marker that were below that observed in untreated cells. In contrast, addition of anti-MS4A4A antibody 4A-419 to primary human macrophages resulted in an increase in CD200R cell surface marker compared to that observed in untreated cells. This result is considered an anomaly to this specific experiment in view of the results obtained with anti-MS4A4A antibody 4A-313 NSLF, above, and in view of the results obtained with otheranti-MS4A4A antibodies of the present disclosure, which reduced M2-like cell surface markers such as CD200R (see Example 9 and Table 26 above). Table 37 below presents numeric values for the fold change (above untreated cells) in the cell surface makers obtained from the graphs in FIGS. 18A, 18B, and 18C. Data is averaged over triplicate wells from two donors.

TABLE 37

| Antibody (μg/ml) | 4A-419.WT | 4A-313.NSLF |
|---|---|---|
| | CD14 | |
| 10 | 0.40 | 0.41 |
| 1 | 0.54 | 0.34 |
| 0.1 | 0.86 | 0.36 |
| Untreated | 1.00 | 1.08 |
| | CD163 | |
| 10 | 0.25 | 0.28 |
| 1 | 0.32 | 0.30 |
| 0.1 | 0.70 | 0.36 |
| Untreated | 0.63 | 0.75 |
| | CD200R | |
| 10 | 1.17 | 0.75 |
| 1 | 1.20 | 0.56 |
| 0.1 | 1.24 | 0.41 |
| Untreated | 0.80 | 0.96 |

These results showed that anti-MS4A4A antibodies of the present disclosure are effective at decreasing M2-like macrophage cell surface makers.

Example 27: Human IgG1 Fc Variants in Complement Dependent Cytotoxicity (CDC) Assay The Fc domain of a human IgG1 antibody affects effector functions by its interaction with multiple downstream effector molecules, such as for example, Clq, Fc gamma receptors, and neonatal Fc receptors. The ability of anti-MS4A4A antibodies of the present disclosure having variant huIgG1 Fc regions to affect complement deposition was measured using a C3b deposition/cell killing assay as follows.

U937 cells overexpressing recombinant human MS4A4A, generated as described above, were used as target cells in these studies. Cells were harvested, washed 1× in PBS, and diluted to $2\times10^6$ cells/mL, an RPMI 1640 media. 504 of target cells were aliquoted per well ($1\times10^5$ cells per well) in round-bottom 96 well plates (Falcon #351177). To these cells was added 254 of anti-MS4A4A antibodies prepared in the same media at four times predetermined concentrations. Cell-antibody mixture was incubated at 37° C. for 15 min, then 254 of pooled complement human serum (Innovative Research, IPLA-CSER) was added per well as a complement source and the plates incubated for a further 2 h at 37° C. Afterwards, cells were washed 2× with FACS buffer (PBS+2% FBS+1 mM EDTA) and 1004 of 1:50 diluted anti-C3b-APC antibody (Biolegend 846106) was added per well and incubated on ice for 30 minutes. Cells were washed 2× with FACS buffer and resuspended in 804 of FACS buffer+0.254/well of propidium iodide (Fischer Scientific, BD 556463) prior to analysis on an iQue flow cytometer (IntelliCyt). Complement activity was measured in two ways, either by percentage of PI-high cells to identify the extent of CDC-mediated cell killing, or MFI of cells in the APC channel to measure C3b deposition.

Figure 19:
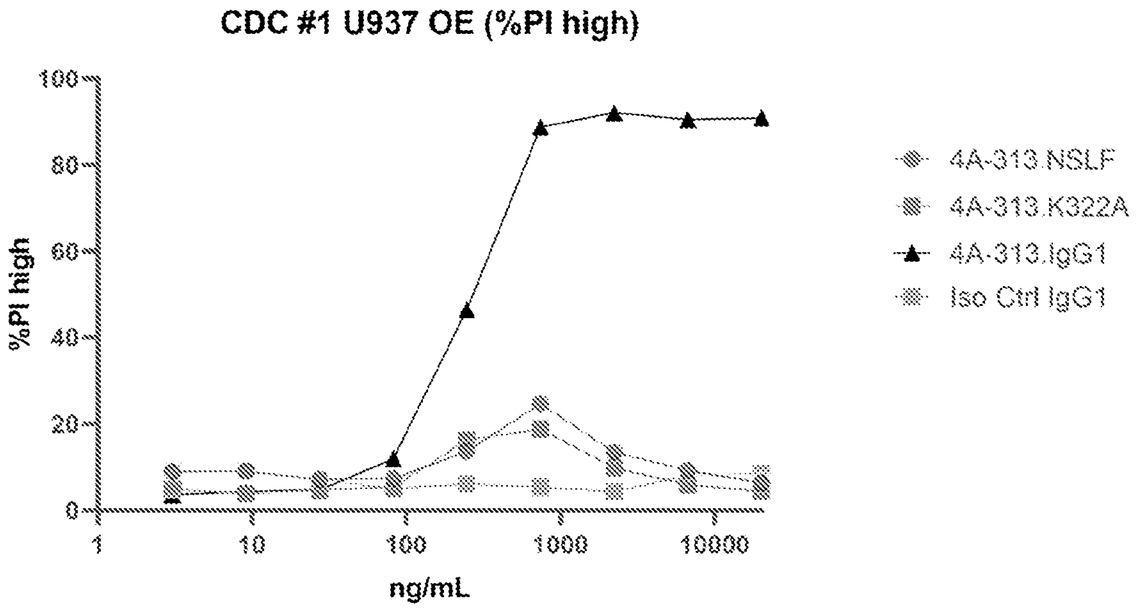
FIG. 19 sets forth data showing complement dependent cytotoxicity (CDC) activity of anti-MS4A4A antibodies 4A-313 NSLF huIgG1, 4A-313 K322A huIgG1 and 4A-313 WT huIgG1 in U937 cells expressing recombinant human MS4A4A as measured by propidium iodide uptake.

FIG. 19 shows the % PI (propidium iodide) uptake in U937 cells expressing recombinant human MS4A4A treated with anti-MS4A4A antibody 4A-313 with various hulgG1 Fc variants. As shown in FIG. 19, anti-MS4A4A antibody 4A-313 with a wildtype hulgG1 is highly capable of driving complement deposition and killing of target-expressing cells, observed as an increase in PI uptake by the cells. This effect was dose dependent. Anti-MS4A4A antibody 4A-313 with hulgG1 N325S/L328F amino acid substitutions in the Fc region (which significantly reduces Clq binding), CDC was almost completely abolished in this assay. Additionally, anti-MS4A4A antibody 4A-313 with hulgG1 K322A amino acid substitution in the Fc region had a similar effect of no CDC activity in this assay.

Table 38 below shows the numeric values associated with the graphs shown in FIG. 19.

TABLE 38

| Antibody (ng/mL) | 4A-313.NSLF | 4A-313.K322A | 4A-313.IgG1 | Isotype Ctrl IgG1 |
|---|---|---|---|---|
| 20,000.0 | 6.35 | 4.42 | 90.93 | 8.51 |
| 6,666.7 | 9.27 | 5.96 | 90.53 | 8.08 |
| 2,222.2 | 13.48 | 9.82 | 92.19 | 4.38 |
| 740.7 | 24.70 | 18.79 | 88.78 | 5.36 |
| 246.9 | 13.64 | 16.27 | 46.49 | 6.15 |
| 82.3 | 7.39 | 5.43 | 11.95 | 5.08 |
| 27.4 | 7.15 | 4.72 | 4.72 | 7.14 |
| 9.1 | 9.04 | 3.89 | 4.38 | 9.01 |
| 3.0 | 8.96 | 4.95 | 3.63 | 9.13 |
| 0.0 | 7.58 | 5.49 | 7.09 | 9.29 |

These results showed that anti-MS4A4A antibodies having a wildtype human IgG1 Fc region are effective at complement dependent cytotoxicity while anti-MS4A4A antibodies having a human IgG1 Fc variant of either N325S/L328F amino acid substitutions or K322A amino acid substitutions are not effective at complement dependent cytotoxicity.

Example 28: Human IgG1 Fc Variants in Antibody Dependent Cellular Phagocytosis (ADCP)

The ability of anti-MS4A4A antibodies of the present disclosure to mediate antibody-dependent cellular phagocytosis (ADCP) was evaluated using the ADCH Reporter Bioassay system (Promega #G9901). This system utilizes an engineered Jurkat T cell line stably expressing FcγRIIa receptor (H131 variant) and an NFAT response element driving expression of firefly luciferase. Activity in this assay correlates with ADCP activity by effector cells (in this case, myeloid cells). Target cells used here were either U937 cells over-expressing recombinant human MS4A4A or primary human macrophages derived from monocytes and polarized with hIL-4 (20 ng/ml) and dexamethasone (20 nM).

Cells were diluted in assay buffer (RPMI+4% low IgG Serum) at a concentration of $1.2\times10^6$ per mL, and 254 of cells (30,000 per well) were aliquoted to inner wells of a 96-well white assay plate (Costar 3922). The outer wells of the plate were filled with 754 of assay buffer with no cells or antibody. To wells containing cells, 254 of anti-MS4A4A antibody at a concentration 3 times the desired final concentration, also diluted in assay buffer, were added. Following addition of antibody to the target cells, the effector cells provided in the assay system (frozen at $2\times10^7$ per mL) were thawed at 37° C., and 6304 added to 3.6 mL of prewarmed (37° C.) assay buffer and gently mixed. Twenty-five μL of effector cells (75,000 per well, for an E:T ratio of 2.5) were immediately added to the wells containing target cells and antibody. The plate was then incubated at 37° C. and 5% $CO_2$ for six hours to allow for receptor cell activation and luciferase expression. After this incubation, the plate was equilibrated to room temperature (15 min), after which 754 of the Luciferase Assay Reagent were added to each well. The plate was then incubated for 20 min on a plate shaker and luminescence was measured on a BioTek plate reader.

Figure 20:
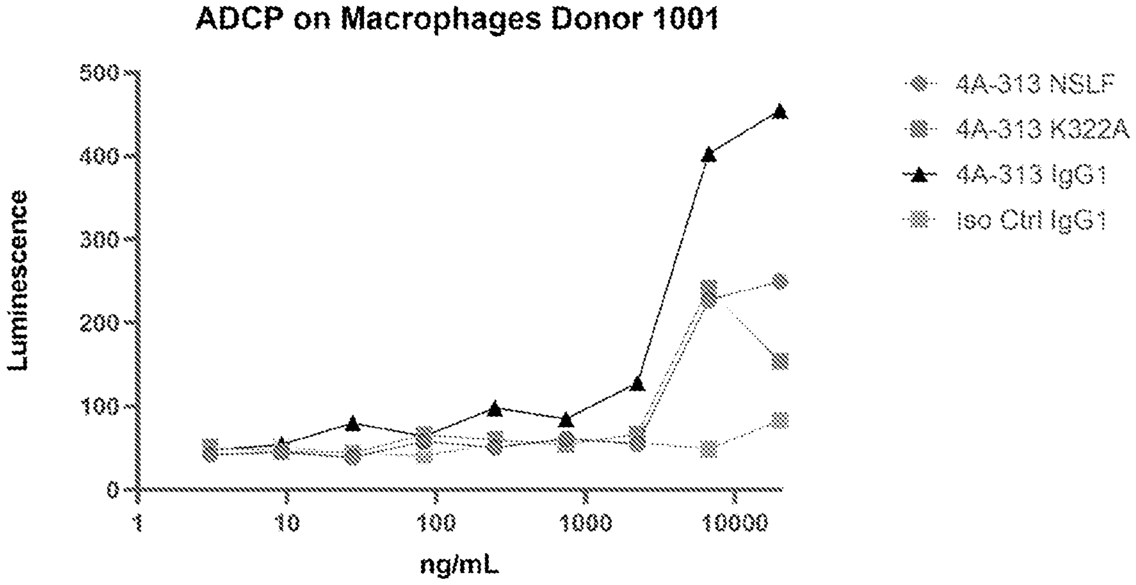
FIG. 20 sets forth data showing ADCP activity of anti-MS4A4A antibodies 4A-313 NSLF huIgG1, 4A-313 K322A huIgG1, and 4A-313 WT huIgG1 in primary human macrophages as measured by FcyRIIIa activation.

As shown in FIG. 20, wildtype huIgG1 (Iso Ctrl IgG1) was robust at driving luciferase activity in this assay, which is an indication of FcγRIIa-H131 activation. Anti-MS4A4A antibody 4A-313 having a huIgG1 Fc with N325S/L328F amino acid substitutions displayed a substantial loss of FcγRIIa-H131 activation compared to that observed with Iso Ctlr IgG1; anti-MS4A4A antibody 4A-313 having a huIgG1 Fc with K322A amino acid substitution had a similar effect in this assay.

Table 39 below provides the numeric values associated with the graphs presented in FIG. 20.

TABLE 39

| Antibody (ng/mL) | 4A-313.NSLF | 4A-313.K322A | 4A-313.IgG1 | Isotype Ctrl IgG1 |
|---|---|---|---|---|
| 20,000 | 250 | 154 | 455 | 83 |
| 6,666.667 | 227 | 242 | 403 | 49 |
| 2,222.222 | 55 | 67 | 128 | 57 |
| 740.7407 | 61 | 54 | 85 | 60 |
| 246.9136 | 51 | 60 | 98 | 54 |
| 82.30453 | 58 | 66 | 64 | 41 |
| 27.43484 | 39 | 44 | 80 | 42 |
| 9.144947 | 45 | 46 | 54 | 52 |
| 3.048316 | 42 | 51 | 48 | 45 |
| 0 | 50 | 50 | 49 | 64 |

These results showed that anti-MS4A4A antibodies having a wildtype human IgG1 Fc region are effective at antibody dependent cellular phagocytosis. Additionally, these results showed that anti-MS4A4A antibodies having a human IgG1 Fc variant of either N325S/L328F amino acid substitutions or K322A amino acid substitutions are also effective at antibody dependent cellular phagocytosis, albeit to a lesser degree.

Example 29: Human IgG1 Fc Variants in Antibody Dependent Cellular Cytotoxicity (ADCC)

Antibodies bound to their target cells can mediate ADCC, an activity thought to be primarily driven by FcyRIIIa activation on natural killer cells. The ability of anti-MS4A4A antibodies of the present disclosure to cause antibody-dependent cellular cytotoxicity (ADCC) was evaluated using an ADCC Reporter Bioassay system (Promega #G7010). This assay system utilizes an engineered Jurkat T cell line stably expressing the FcγRIIIa receptor (V158 variant) and an NFAT response element driving expression of firefly luciferase. Target cells used here were either U937 cells over-expressing recombinant human MS4A4A or primary human macrophages derived from monocytes and polarized with hIL-4 (20 ng/ml) and dexamethasone (20 nM). Target cells were diluted in assay buffer (RPMI+4% low IgG Serum) at a concentration of $1.2\times10^6$ per mL and 254 of cells (30,000 per well) were aliquoted to inner wells of a 96-well white assay plate (Costar 3922). The outer wells of the plate were filled with 754 of assay buffer without cells or antibody. To wells containing cells, 254 of antibody at a concentration of 3 times the desired final concentrations, also diluted in assay buffer, were added. Following addition of antibody to target cells, the provided effector cells (frozen at $2\times10^7$ per mL) were thawed at 37° C., and 6304 added to 3.6 mL of warmed (37° C.) assay buffer, gently mixed, and 254 of effector cells (75,000 per well, for an E:T ratio of 2.5) immediately added to the wells containing target cells and antibody. The plate was then incubated at 37° C. and 5% $CO_2$ for six hours to allow for receptor cell activation and luciferase expression. After this incubation, the plate was equilibrated to room temperature (15 min), after which 754 of the Luciferase Assay Reagent were added to each well. The plate then incubated for 20 min on a plate shaker and luminescence was measured on a BioTek plate reader.

Figure 21:
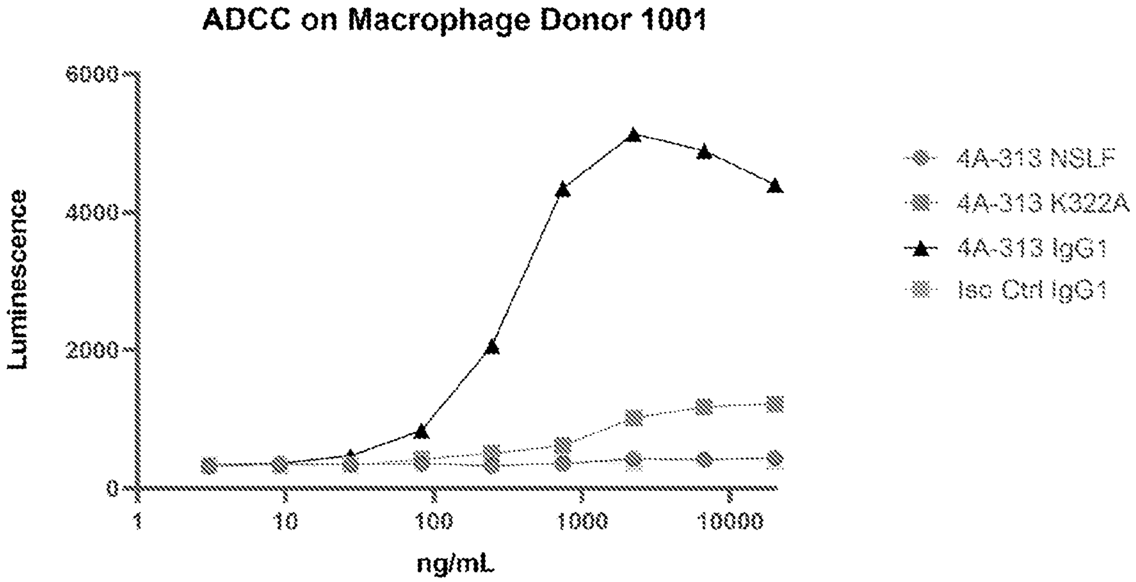
FIG. 21 sets forth data showing ADCC activity of anti-MS4A4A antibodies 4A-313 NSLF huIgG1, 4A-313 K322A huIgG1, and 4A-313 WT huIgG1 in primary human macrophages as measured by FcyRIIIa activation.

As shown in FIG. 21, wildtype hu IgG1 (Iso Ctrl IgG1) was robust at driving luciferase activity in this assay, an indication of FcγRIIIa-V158 activation. Anti-MS4A4A antibody 4A-313 having a huIgG1 Fc with N325S/L328F amino acid substitutions displayed a substantial loss of FcγRIIa-H131 activation compared to that observed with Iso Ctlr IgG1; anti-MS4A4A antibody 4A-313 having a huIgG1 Fc with K322A amino acid substitution had a similar effect in this assay.

Table 40 below provides the numeric values associated with the graphs presented in FIG. 21.

TABLE 40

| Antibody (ng/mL) | 4A-313.NSLF | 4A-313.K322A | 4A-313.IgG1 | Isotype Ctrl IgG1 |
|---|---|---|---|---|
| 20,000 | 442 | 1222 | 4397 | 399 |
| 6,666.667 | 415 | 1182 | 4891 | 431 |
| 2,222.222 | 431 | 1017 | 5133 | 373 |
| 740.7407 | 363 | 623 | 4346 | 379 |
| 246.9136 | 332 | 508 | 2063 | 381 |
| 82.30453 | 360 | 426 | 839 | 377 |
| 27.43484 | 347 | 341 | 473 | 340 |
| 9.144947 | 356 | 338 | 367 | 329 |
| 3.048316 | 324 | 338 | 346 | 314 |
| 0 | 328 | 343 | 348 | 368 |

These results showed that anti-MS4A4A antibodies having a wildtype hu IgG1 Fc region are effective at antibody dependent cellular cytotoxicity while anti-MS4A4A antibodies having a human IgG1 Fc variant of either N325S/L328F amino acid substitutions or K322A amino acid substitutions are not effective at antibody dependent cellular cytotoxicity.

Example 30: Effect of MS4A4A Knockout on Membrane and Soluble TREM2 Levels in Primary Human Macrophages The effect of MS4A4A knockout on membrane and soluble TREM2 levels in macrophages was examined as follows. CRISPR technology was used to knockout expression of MS4A4A in primary human macrophages. In brief, knockout macrophages were generated by electroporation with Cas9 protein (IDT), which was complexed with non-targeting (NT) or MS4A4A-specific gRNAs consisting of locus-specific crRNAs (IDT; NT1, IDT negative control crRNA #1 and #2; NT2, GTAGGCGCGCCGCTCTCTAC (SEQ ID NO: 345) and AACCCCTGATTGTATCCGCA (SEQ ID NO: 346); MS4A4A #1, AATTGTGTACCCGATATACA (SEQ ID NO: 347); MS4A4A #2, AACCATGCAAGGAATGGAAC (SEQ ID NO: 348); MS4A4A #3, TATTCATTCCTAGACTACCT (SEQ ID NO: 349); MS4A4A #4, GCTCTGTACTGGCTGCATCA (SEQ ID NO: 350)) annealed to a tracrRNA (IDT). MS4A4A knockout efficiency was evaluated by flow cytometric analysis and was greater than 90% (data not shown).

Figure 22A:
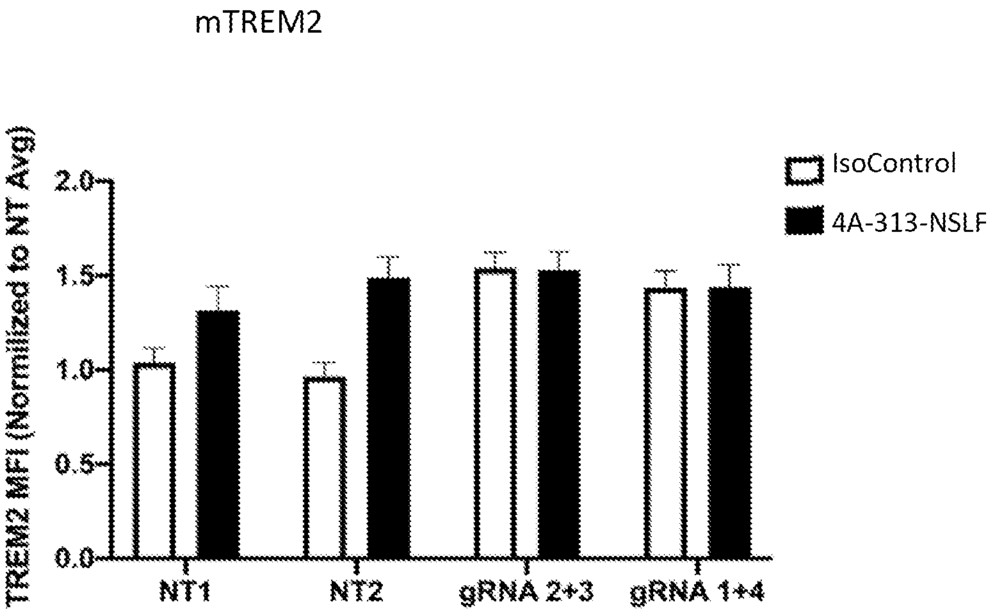
FIGS. 22A and 22B set forth data showing the effect of MS4A4A knockout on membrane TREM2 (FIG. 22A) and soluble TREM2 (FIG. 22B) in primary human macrophages.
Figure 22B:
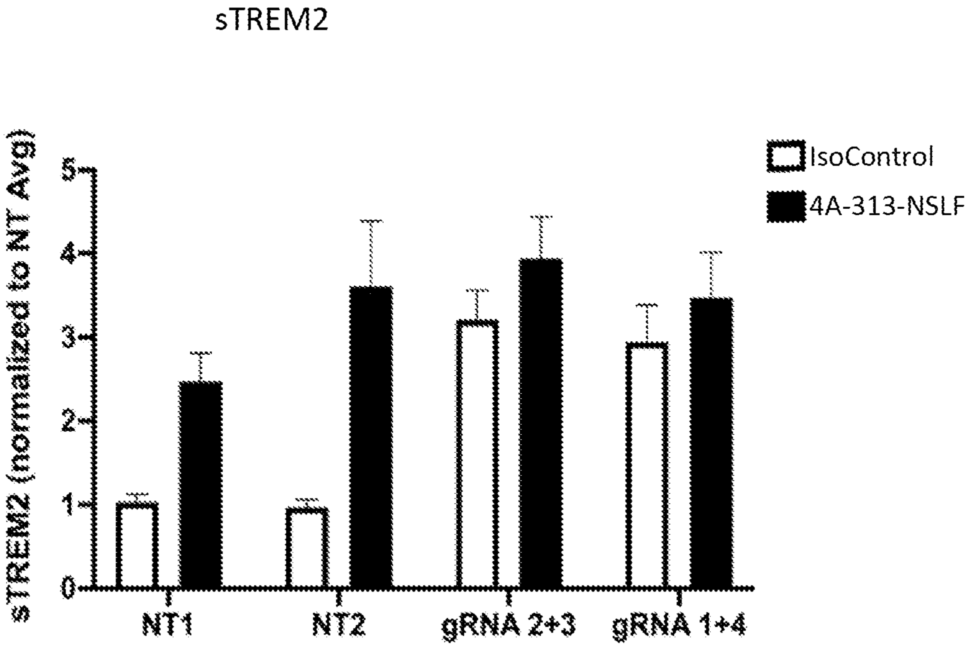

FIGS. 22A and 22B show the effect of MS4A4A knockout on membrane TREM2 (mTREM2) levels and soluble TREM2 (sTREM2) levels. In FIGS. 22A and 22B, NT1 and NT2 are non-targeting CRISPR controls; gRNA 2+3 and gRNA 1+4 refer to different guides used for knocking out MS4A4A.

As shown in FIGS. 22A and 22B, knockout of MS4A4A in primary human macrophages resulted in an increase in mTREM2 and sTREM2 levels. The increased levels of mTREM2 and sTREM2 observed upon MS4A4A knockout were comparable to the increase in mTREM2 and sTREM2 levels upon addition of anti-MS4A4A antibody 4A-313 to the NT1 and NT2 control cells. Upon anti-MS4A4A antibody treatment of the MS4A4A knockout primary human macrophages, no further increase in mTREM2 or sTREM2 levels was observed, suggesting that the increase in mTREM2 and sTREM2 levels observed upon addition of anti-MS4A4A antibody of the present disclosure to human macrophages is a result of anti-MS4A4A antibody binding to MS4A4A on the cells.

Example 31: Kinetics of Membrane and Soluble TREM2 Modulation by Anti-MS4A4A Antibodies Cell surface expression of TREM2 protein is regulated by endocytosis/exocytosis of TREM2 to and from the plasma membrane and by regulated cleavage of TREM2 by membrane bound proteases (Thornton et al., 2017, EMBO Mol. Med. 9: 1366-1378; doi: 10.15252/emmm.201707673). As described in Examples above, treatment of human macrophages with anti-MS4A4A antibodies of the present disclosure increased both membrane and soluble TREM2 levels. The following studies were performed to further understand the kinetics of the changes in levels of membrane and soluble TREM2.

To assess changes in soluble TREM2 (sTREM2) levels, primary human macrophages were plated in either 24-well or 96-well plates followed by the addition of anti-MS4A4A antibodies 4A-313.NSLF, 4A-450.NSLF, or isotype control antibody (all at 1 μg/ml). After 0.5, 1, 4, 24, and 48 hours of cell culture in the presence of the antibodies, supernatants were collected and sTREM2 levels determined using Meso Scale Discovery.

The kinetics of the increase in membrane TREM2 (mTREM2) levels in primary human macrophages following addition of anti-MS4A4A antibodies of the present disclosure were assessed as follows. Primary human macrophages were plated at 100,000 cells/well in 96-well U-bottom plates 3 days before analysis (T minus 72 hrs). At various time points (T minus 48 hrs, T minus 24 hrs, T minus 4 hrs, T minus 1 hr), antibodies were added to the plated cells, which included an isotype control antibody (IsoControl.NSLF) and anti-MS4A4A antibody 4A-313.NSLF. 72-hrs post-plating, cell surface (membrane bound) expression levels of TREM2 was measured by flow cytometry after staining the cells with a fluorophore-conjugated anti-TREM2 antibody.

Figure 23A:
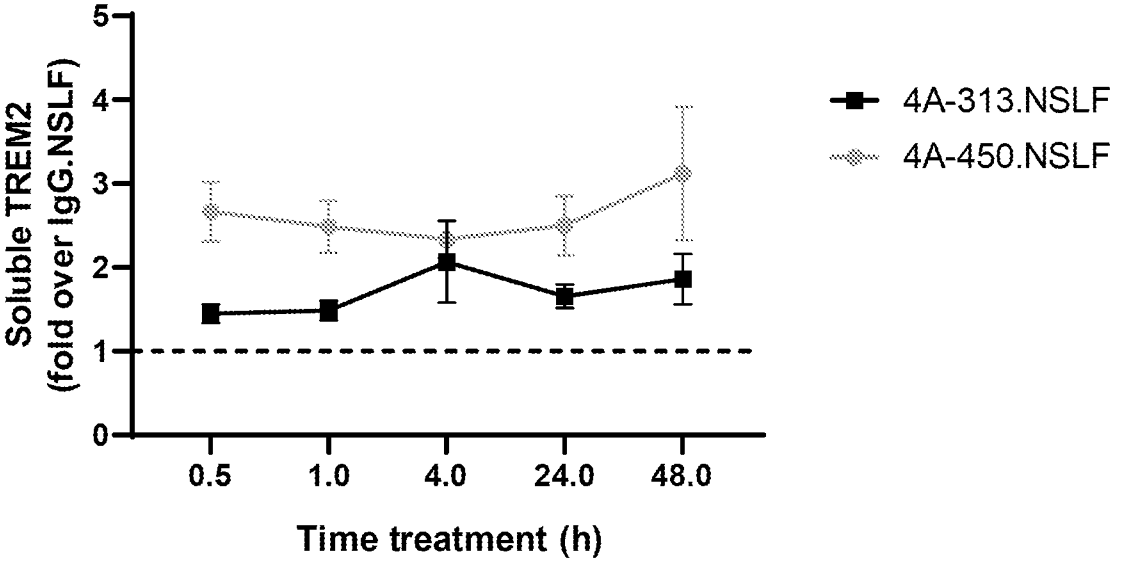
FIGS. 23A, 23B, and 23C set forth data showing the kinetics of changes in soluble TREM2 protein levels, membrane TREM2 protein levels, and TREM2 mRNA levels, respectively, in human macrophages treated with anti-MS4A4A antibodies of the present disclosure.

As shown in FIG. 23A, anti-MS4A4A antibodies of the present disclosure rapidly increased the levels of sTREM2 in the supernatants of cultured primary human macrophages obtained from various donors. Anti-MS4A4A antibody 4A-313.NSLF increased sTREM2 levels approximately 0.5-fold above that observed in cells treated with isotype control antibody (approximately 50% increase). Anti-MS4A4A antibody 4A-450.NSLF increased sTREM2 levels approximately 2.5-fold above that observed in cells treated with isotype control antibody (approximately 250% increase).

Figure 23B:
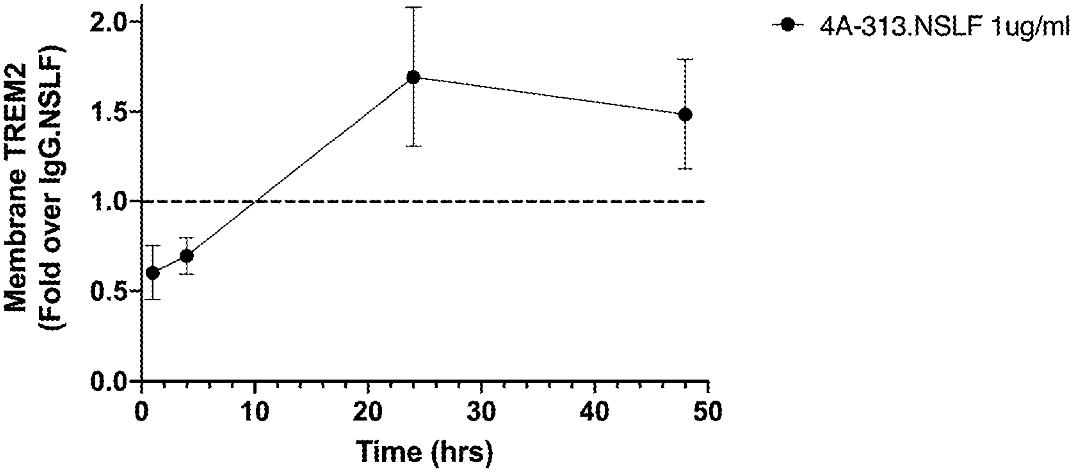

As shown in FIG. 23B, at 1 hour and 4 hours following addition of anti-MS4A4A antibody 4A-313.NSLF to primary human macrophages, membrane TREM2 levels decreased compared to that observed following the addition of an isotype control antibody. In FIG. 23B, the dotted line represents the level of mTREM2 in isotype control antibody treated cells. At 24-hour and 48-hour timepoints following addition of anti-MS4A4A antibody 4A-313.NSLF, levels of mTREM2 increased above that observed in cells treated with isotype control antibody. The early decrease in membrane TREM2 is consistent with increases in TREM2 shedding at all time points examined, as shown in FIG. 23A.

As anti-MS4A4A antibodies of the present disclosure increased TREM2 protein levels in primary human macrophages, the following experiments were performed to examine the effects on TREM2 mRNA levels following anti-MS4A4A antibody addition. Primary human macrophages were plated either in 24 or in 96-well plates and treated with anti-MS4A4A antibody 4A-313.NSLF and isotype (1 μg/ml) in complete RPMI. After 0.5, 1, 4, 24, and 48 hours of incubation, cell pellets were collected, and TREM2 mRNA levels determined using quantitative PCR analysis (qPCR). Briefly, RNA was extracted using the RNeasy Mini Kit (Qiagen), cDNA was prepared from the total RNA using QuantiNova Reverse Transcription Kit (Qiagen). Gene expression levels were analyzed by real-time PCR using TaqMan assays for TREM2 (Hs00219132_ml) and GAPDH (Hs027886624_gl). CT values for each sample were normalized to CT values for the housekeeping gene GAPDH.

Figure 23C:
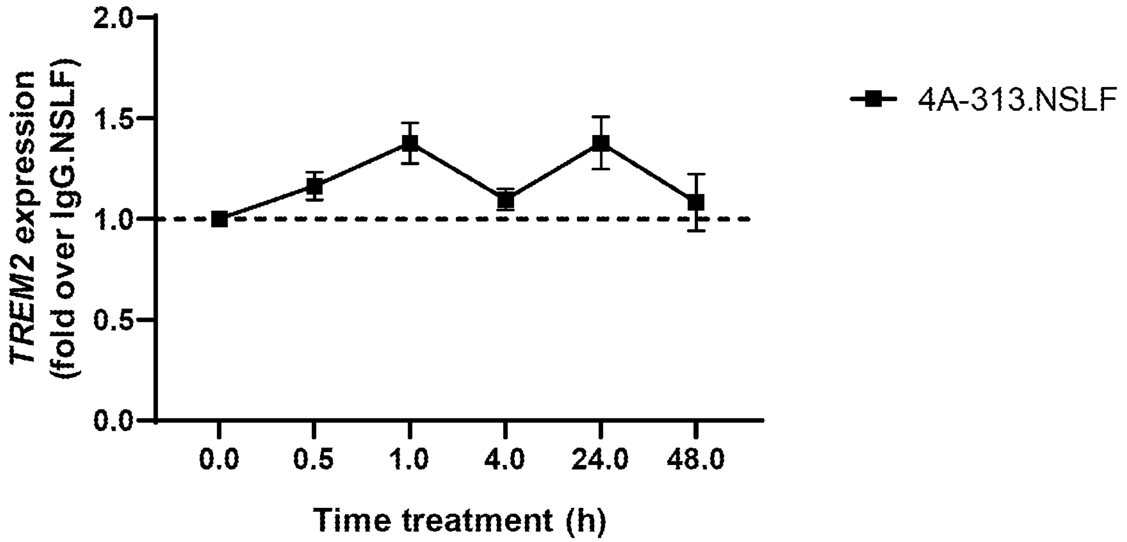

As shown in FIG. 23C, anti-MS4A4A antibody 4A-313.NSLF did not affect TREM2 mRNA levels in cultured human primary macrophages obtained from various donors; some minor fluctuations in mRNA levels were observed (less than 0.5-fold above that observed in isotype control). These results indicated that anti-MS4A4A antibodies of the present disclosure increased TREM2 protein levels without affecting TREM2 mRNA levels in cultured human primary macrophages.

Example 32: Anti-MS4A4A Antibodies Increase SPP1 and IL1RN Secretion in Primary Human Macrophages The effect of anti-MS4A4A antibodies of the present disclosure on secreted levels of osteopontin (SSP1) and interleukin-1 receptor antagonist (IL1RN) in primary human macrophages was examined and compared to that observed in primary human macrophages genetically modified to knockout MS4A4A expression as follows.

MS4A4A genetic knockout in primary human macrophages was generated by electroporation with Cas9 protein, which was complexed with guide RNAs (gRNAs) in the form of either single gRNA molecules or gRNA duplexes consisting of crRNAs annealed to a tracrRNA: non-targeting NT1 (IDT negative control RNA #1 and #2); NT2 (GTAGGCGCGCCGCTCTCTAC [SEQ ID NO: 345] and AACCCCTGATTGTATCCGCA [SEQ ID NO: 346]); MS4A4A #1 (AATTGTGTACCCGATATACA [SEQ ID NO: 347]); MS4A4A #2 (AACCATGCAAGGAATGGAAC [SEQ ID NO: 348]); MS4A4A #3 (TATTCATTCCTAGACTACCT [SEQ ID NO: 349]); MS4A4A #4, GCTCTGTACTGGCTGCATCA [SEQ ID NO: 350]) (all from IDT, Coralville, Iowa, USA) using standard procedures. Cells were then plated at 50,000 cells/well in complete RPMI-1640 and cultured for 48 hours in the presence of anti-MS4A4A antibody 4A-313.NSLF (0.1 μg/ml), anti-MS4A4A antibody 4A-450.NSLF (0.1 μg/ml), or isotype control antibody. Supernatants from the cells were collected, and levels of IL1RN and SPP1 were analyzed using R&D DuoSet ELISA kits (IL1RN Cat #DY280, SPP1 Cat #DY1433).

Treatment of NT control cells with either anti-MS4A4A antibody 4A-313.NSLF or 4A-450.NSLF resulted in an increase in the level of secreted SPP1. Genetic knockout of MS4A4A in these cells also resulted in an increase in secreted SPP1 levels comparable to that seen with MS4A4A antibody treatment. Levels of SPP1 in these studies were: approximately 100 ng/ml following addition of isotype control antibody in NT control cells; approximately 200 ng/ml following addition of anti-MS4A4A antibody 4A-313.NSLF in NT control cells; approximately 275 ng/ml following addition of anti-MS4A4A antibody 4A-450.NSLF in NT control cells; and approximately 225 ng/ml in MS4A4A knockout cells. The increase in secreted SPP1 levels following addition of either anti-MS4A4A antibody of the present disclosure was comparable to that observed in cells in which MS4A4A expression was genetically knocked-out.

Treatment of NT control cells with either anti-MS4A4A antibody 4A-313.NSLF or 4A-450.NSLF resulted in an increase in the level of secreted IL1RN. Genetic knockout of MS4A4A in these cells also resulted in an increase in secreted IL1RN levels comparable to that seen with MS4A4A antibody treatment. Levels of IL1RN in these studies were: approximately 8 ng/ml following addition of isotype control antibody in NT control cells; approximately 12 ng/ml following addition of anti-MS4A4A antibody 4A-313.NSLF in NT control cells; approximately 16 ng/ml following addition of anti-MS4A4A antibody 4A-450.NSLF in NT control cells; and approximately 14 ng/ml in MS4A4A knockout cells. The increase in secreted IL1RN levels following addition of either anti-MS4A4A antibody of the present disclosure was comparable to that observed in cells in which MS4A4A expression was genetically knocked-out.

Taken together, these results indicated that anti-MS4A4A antibodies of the present disclosure are effective at increasing secreted levels of SPP1 and of IL1RN in primary human macrophages. Additionally, these results showed that the effect of anti-MS4A4A antibodies of the present disclosure on increasing the level of secreted SPP1 and IL1RN was similar to that observed when expression of MS4A4A was genetically knocked-out, suggesting that anti-MS4A4A antibodies of the present disclosure reduced or blocked the activity of MS4A4A in these cells, resulting in the observed increases in SPP1 and IL1RN levels.

Example 33: Anti-MS4A4A Antibody-Induced Viability in Human Macrophages is TREM2-Independent As shown above, anti-MS4A4A antibodies of the present disclosure were effective at increasing the viability of primary human macrophages (as measured by increases in total cellular ATP) following anti-MS4A4A antibody addition. Additionally, as shown above, anti-MS4A4A antibodies of the present disclosure increased membrane TREM2 levels in cells. As anti-MS4A4A antibodies of the present disclosure increased membrane TREM2 levels, and as anti-MS4A4A antibodies increased cell viability, a series of experiments were performed to examine whether the increase in cell viability observed in response to anti-MS4A4A antibody addition was, at least in part, TREM2-dependent. To explore this, TREM2 was genetically knocked-out in human primary macrophages using CRISPR technology to examine the effects of anti-MS4A4A antibodies of the present disclosure on cell viability in primary human macrophages genetically lacking TREM2 expression.

TREM2 knockout macrophages were generated by electroporation with Cas9 protein, which was complexed with guide RNAs (gRNAs) in the form of either single gRNA molecules or gRNA duplexes consisting of crRNAs annealed to tracrRNA: non-targeting 1 (NT1) (1DT negative control crRNA #1 and #2); NT2 (GTAGGCGCGCCGCTCTCTAC [SEQ ID NO: 345] and AACCCCTGATTGTATCCGCA [SEQ ID NO: 346]); TREM2 #1 (GCCATCACAGACGATACCCT [SEQ ID NO: 351]); TREM2 #2 (ATAGGGGCAAGACACCTGCA [SEQ ID NO: 352]); TREM2 #3 (CAGCATCCCGGTGATCCAGG [SEQ ID NO: 353]); TREM2 #4, TGGAGATCTCTGGTTCCCCG [SEQ ID NO: 354]) (all from IDT, Coralville, Iowa, USA).

The cells were then plated at 50,000 cells/well in complete RPMI-1640 and cultured in the presence of anti-MS4A4A antibodies (4A-313 NSLF, 4A-450 NSLF), or isotype control antibody (all at 0.1 μg/ml) in solution for 48 hours. ATP content within the cells was then quantified using the CellTiter-Glo Luminescent cell viability kit (Promega, Cat #G7571) following the manufacturer's protocol.

Addition of anti-MS4A4A antibody 4A-313.NSLFor anti-MS4A4A antibody 4A-450.NSLF increased ATP levels in NT control cells by approximately 20% compared to that observed with the isotype control antibody. Additionally, anti-MS4A4A antibody addition to the TREM2 knockout cells resulted in increased ATP levels by approximately 15%-20% above that observed with the isotype control antibody. Taken together, these results showed that anti-MS4A4A antibodies of the present disclosure increase cellular ATP levels (and thus cell viability), at least in part, in a TREM2-independent manner.

Example 34: siRNA Knockdown of MS4A4A Increae Membrane and Soluble TREM2 Levels in Primary Human Macrophages As shown above, genetic ablation of MS4MA expression using CRISPR technology resulted in increased membrane and soluble TREM2 levels in human macrophages. To further support these findings, the effect of loss of expression of MS4A4A on TREM2 levels was assessed using an independent experimental approach. In these studies, siRNA knockdown of MS4A4A in primary human macrophages was performed and its effect on membrane and soluble TREM2 levels measured.

MS4A4A knock-down macrophages were generated by transfecting control (Millipore Sigma, SIC001) and MS4A4A-targeting siRNAs (Millipore Sigma. SASI_Hs01_00150955) using the N-TER Nanoparticle siRNA Transfection System (Millipore Sigma). MS4A4A knockout efficiency was evaluated by flow cytometric analysis (data not shown). Cell surface (membrane bound) expression of TREM2 was measured by flow cytometry after staining the cells with a fluorophore-conjugated anti-TREM2 antibody.

Figure 24A:
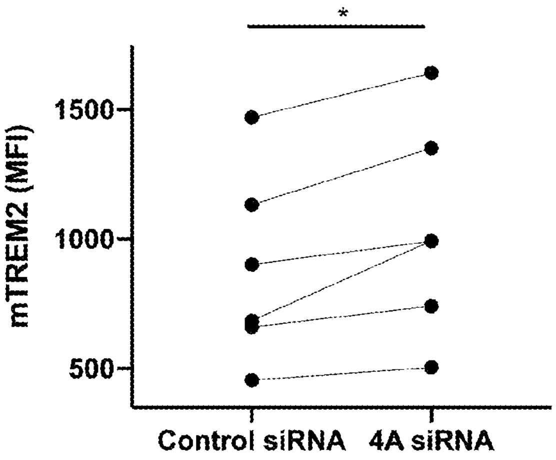
FIGS. 24A and 24B set forth data showing siRNA knockdown of MS4A4A increased membrane TREM2 and soluble TREM2 levels in human macrophages.
Figure 24B:
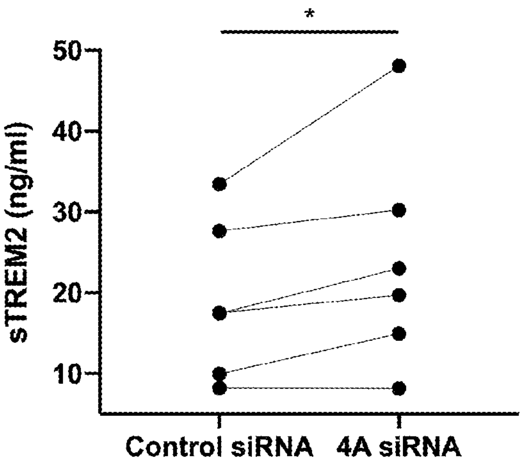

As shown in FIG. 24A and FIG. 24B, siRNA knockdown of MS4A4A expression led to an increase in membrane TREM2 levels and in soluble TREM2 levels, respectively. In FIG. 24A and FIG. 24B, each sett of connected dots represents the average result from one individual donor (for a total of 6 donors) with and without siRNA knockdown. These data are in alignment with similar results showing increased mTREM2 and sTREM2 levels in genetically engineered MS4A4A knockout cells described above, Taken together, these results indicated that loss of MS4A4A expression or activity increased both soluble TREM2 levels and membrane TREM2 levels in primary human macrophages.

Example 35: Anti-MS4A4A Antibody Potency at Increasing mTREM2, sTREM2, and ATP Levels In Vitro The effect of anti-MS4A4A antibodies of the present disclosure at increasing mTREM2, sTREM2, and ATP levels (as previously described above in Examples 24 and 25) was further examined in primary human macrophages obtained from three separate donors. Primary human macrophages were treated with various concentrations of anti-MS4A4A antibodies 4A-313.NSLF and 4A-450.NSLF for 48 hours. Changes in the levels of mTREM2, sTREM2, and ATP were then measured.

Figure 25A:
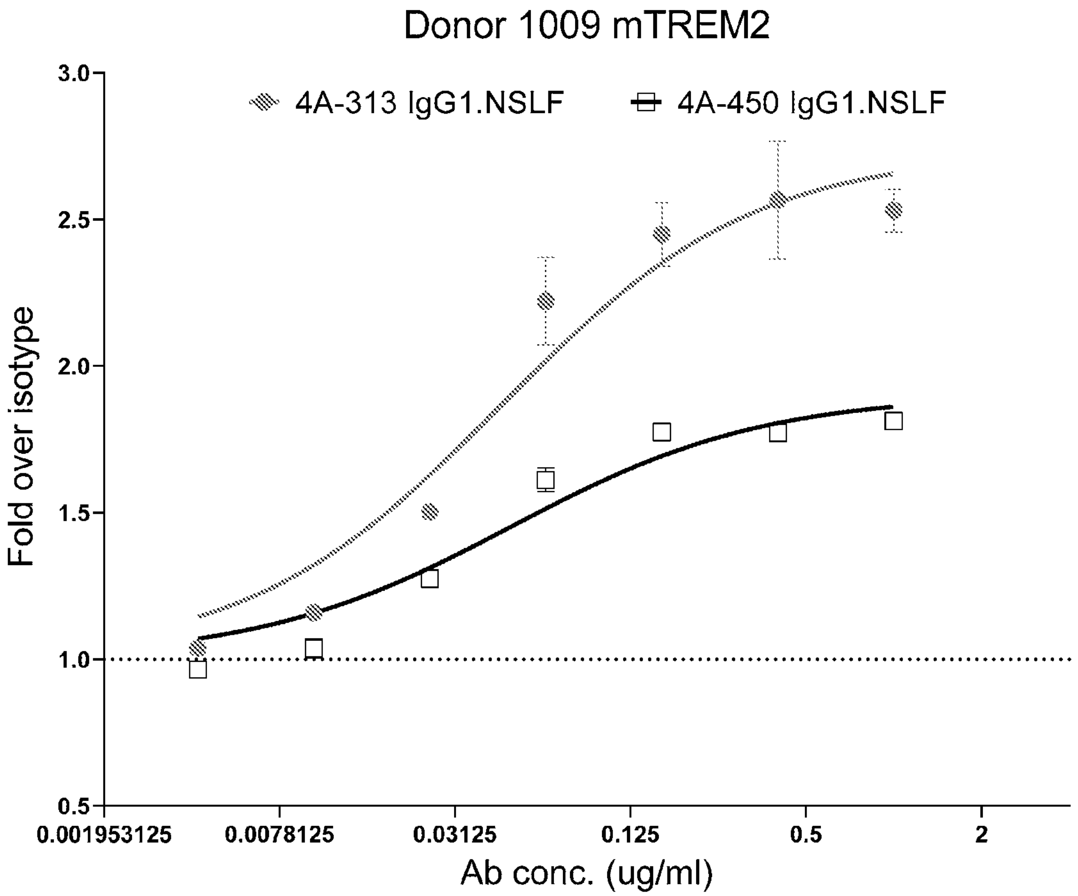
FIGS. 25A, 25B, and 25C set forth data showing a dose-dependent increase in membrane TREM2 levels in primary human macrophages from three different donors following addition of anti-MS4A4A antibodies of the present disclosure.
Figure 25B:
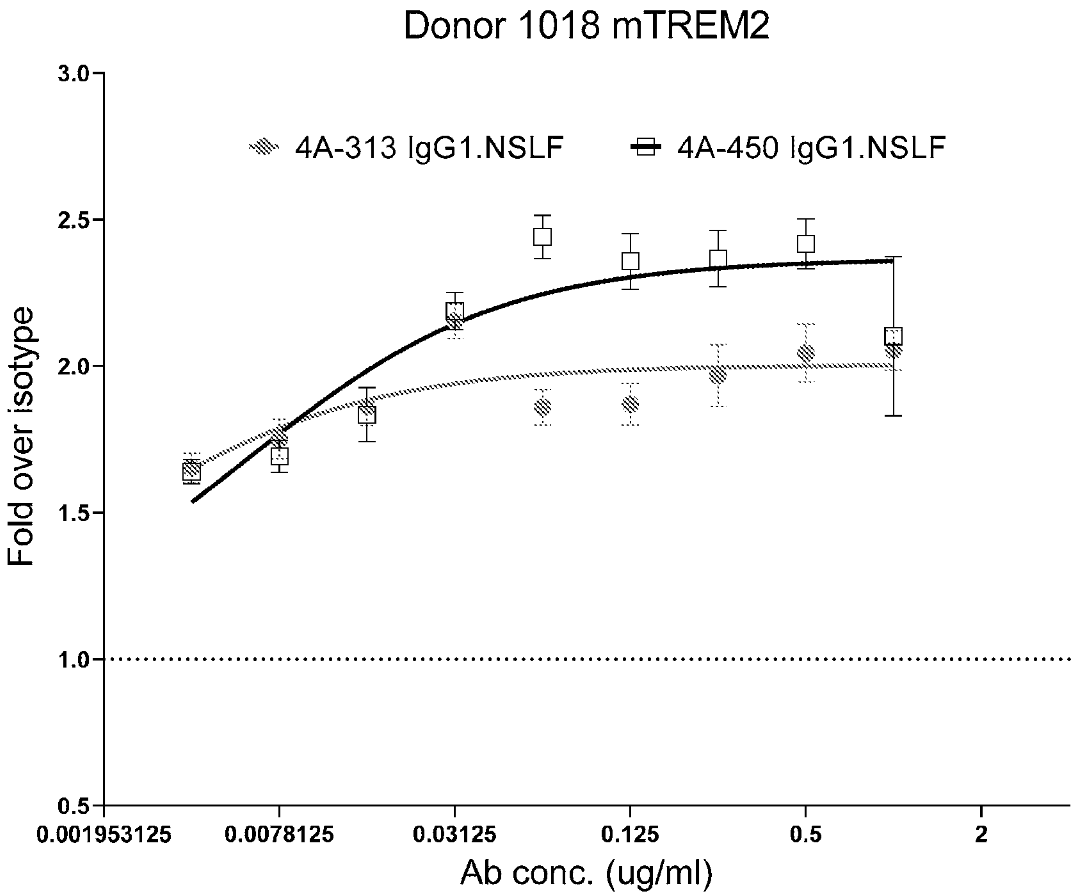
Figure 25C:
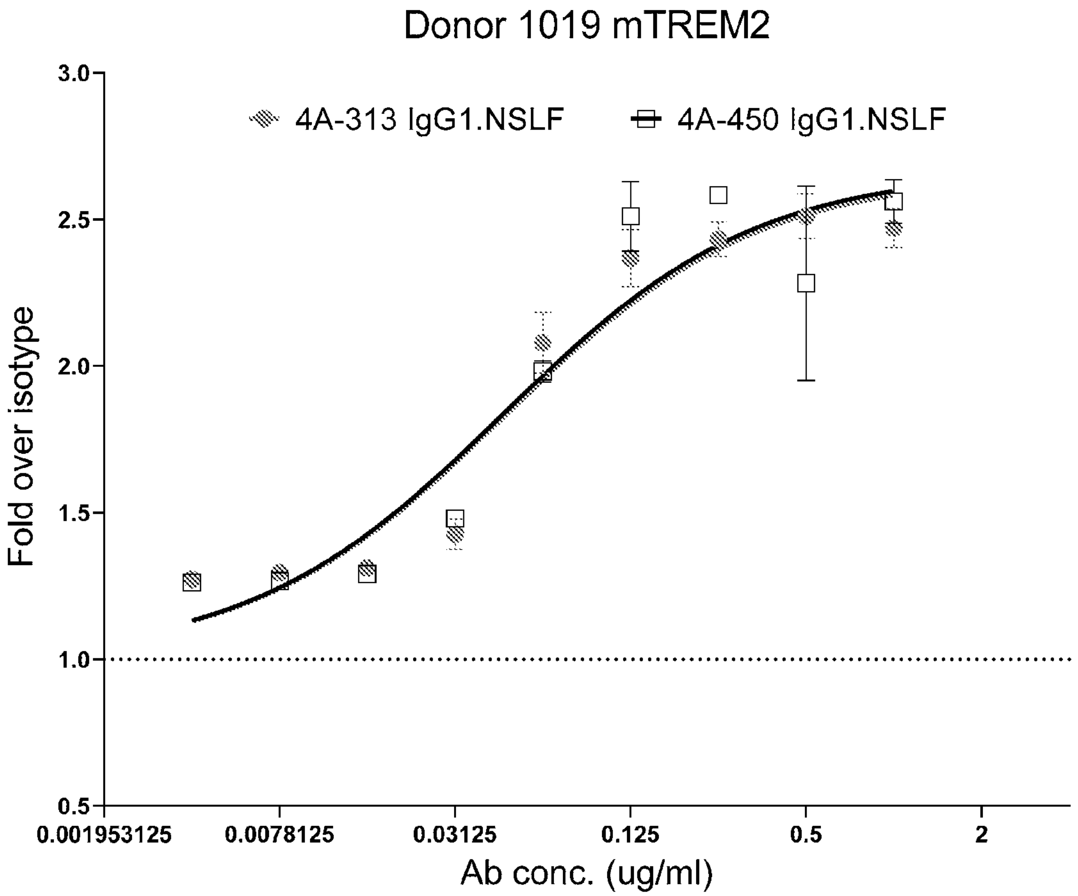

As shown in FIG. 25A, FIG. 25B, and FIG. 25C, anti-MS4A4A antibody 4A-313.NSLF and anti-MS4A4A antibody 4A-450.NSLF increased levels of mTREM2 in a dose-dependent manner in primary human macrophages obtained from three different donors, respectively. Data in FIG. 25A, FIG. 25B, and FIG. 25C is presented as fold-increase in the levels of mTREM2 over that observed using an isotype control antibody (the x-axis shows antibody concentrations Wimp and the y-axis shows fold-increase above control, which was set at 1.0). Data from these graphs were analyzed to determine EC50 values and maximum response; these results are shown below in Table 41 (shown as mean+/−SEM).

TABLE 41

| Antibody | EC50 (μg/ml) | Max mTREM2 Response (fold increase over isotype control) |
|---|---|---|
| 4A-313.NSLF | 0.028 +/− 0.013 | 2.45 +/− 0.23 |
| 4A-450.NSLF | 0.039 +/− 0.014 | 2.36 +/− 0.27 |

Figure 26A:
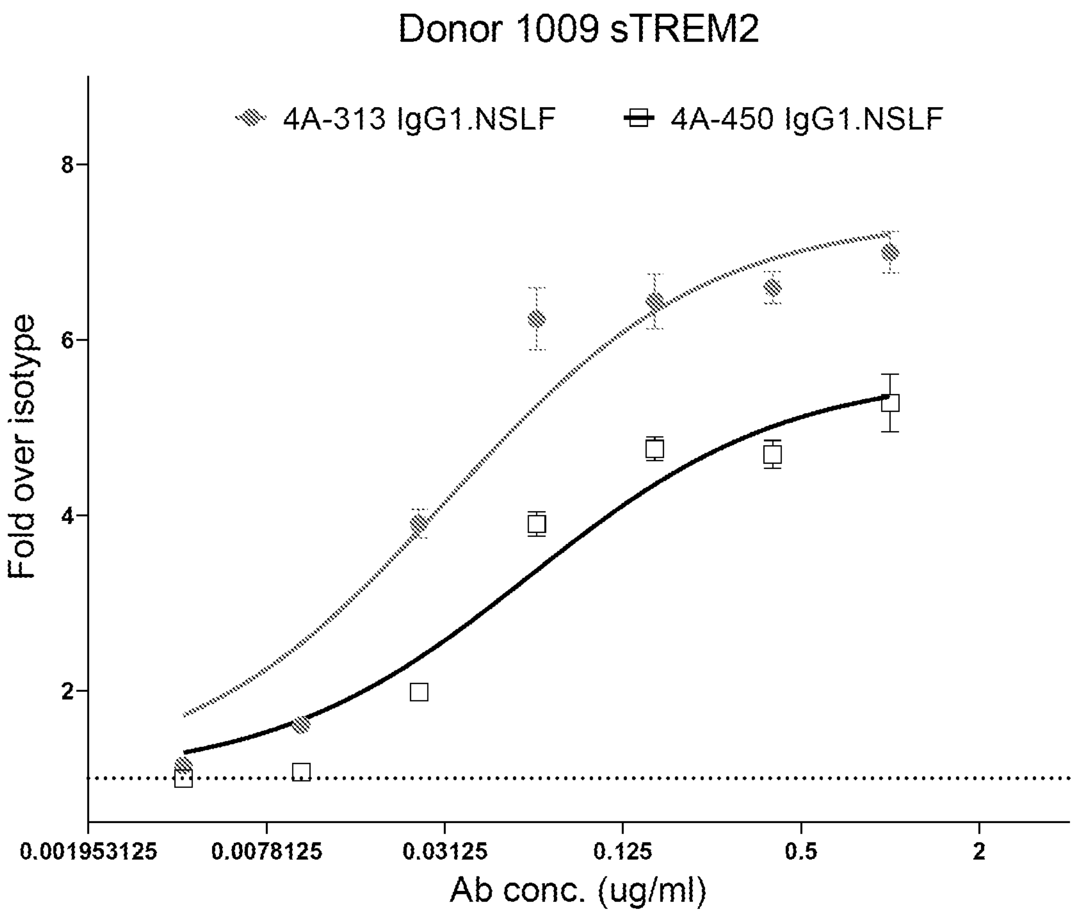
FIGS. 26A, 26B, and 26C set forth data showing a dose-dependent increase in soluble TREM2 levels in primary human macrophages from three different donors following addition of anti-MS4A4A antibodies of the present disclosure.
Figure 26B:
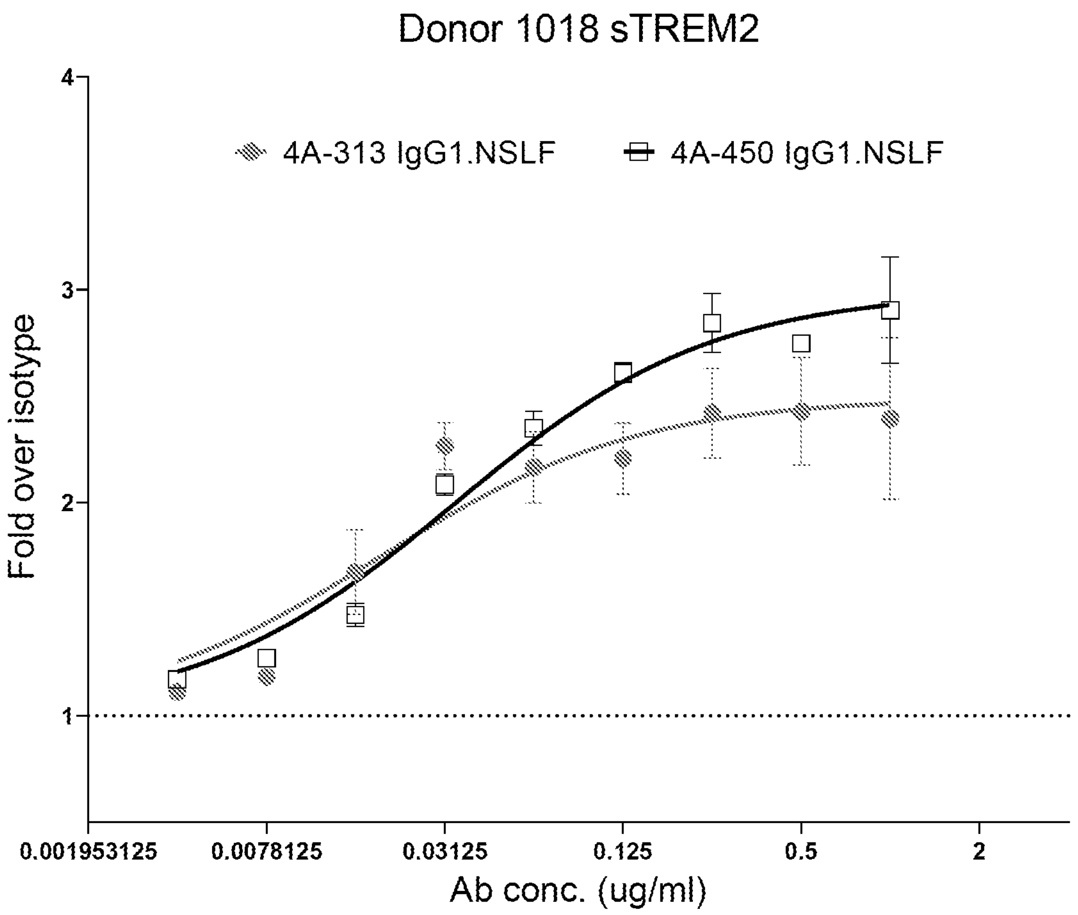
Figure 26C:
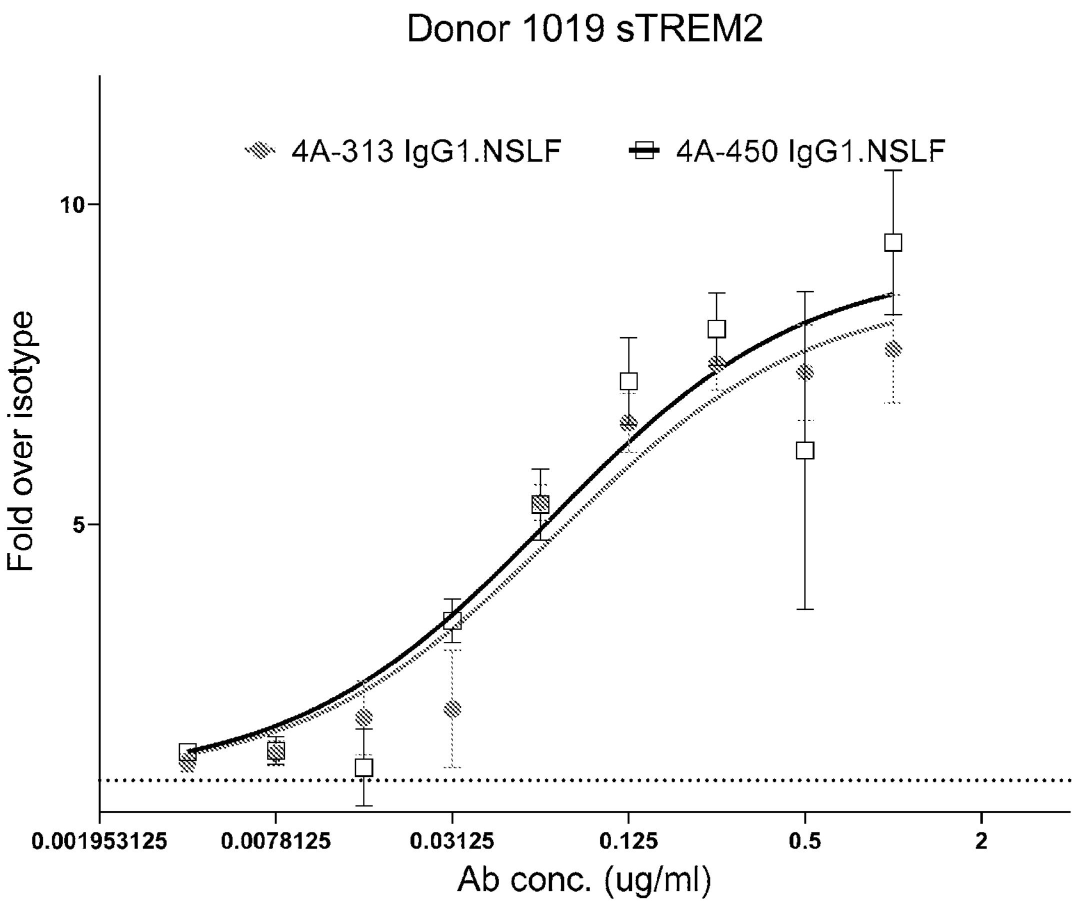

As shown in FIG. 26A, FIG. 26B, and FIG. 26C, anti-MS4A4A antibody 4A-313.NSLF and anti-MS4A4A antibody 4A-450.NSLF increased levels of sTREM2 in a dose-dependent manner in primary human macrophages obtained from three different donors, respectively. Data in FIG. 26A, FIG. 26B, and FIG. 26C is presented as fold-increase in the levels of sTREM2 over that observed using an isotype control antibody (the x-axis shows antibody concentrations Wimp and the y-axis shows fold-increase above control, which was set at 1.0). Data from these graphs were analyzed to determine EC50 values and maximum response; these results are shown below in Table 42 (shown as mean+/−SEM).

TABLE 42

| Antibody | EC50 (μg/ml) | Max sTREM2 Response (fold increase over isotype control) |
|---|---|---|
| 4A-313.NSLF | 0.025 +/− 0.007 | 6.17 +/− 1.90 |
| 4A-450.NSLF | 0.069 +/− 0.006 | 5.74 +/− 1.65 |

Figure 27A:
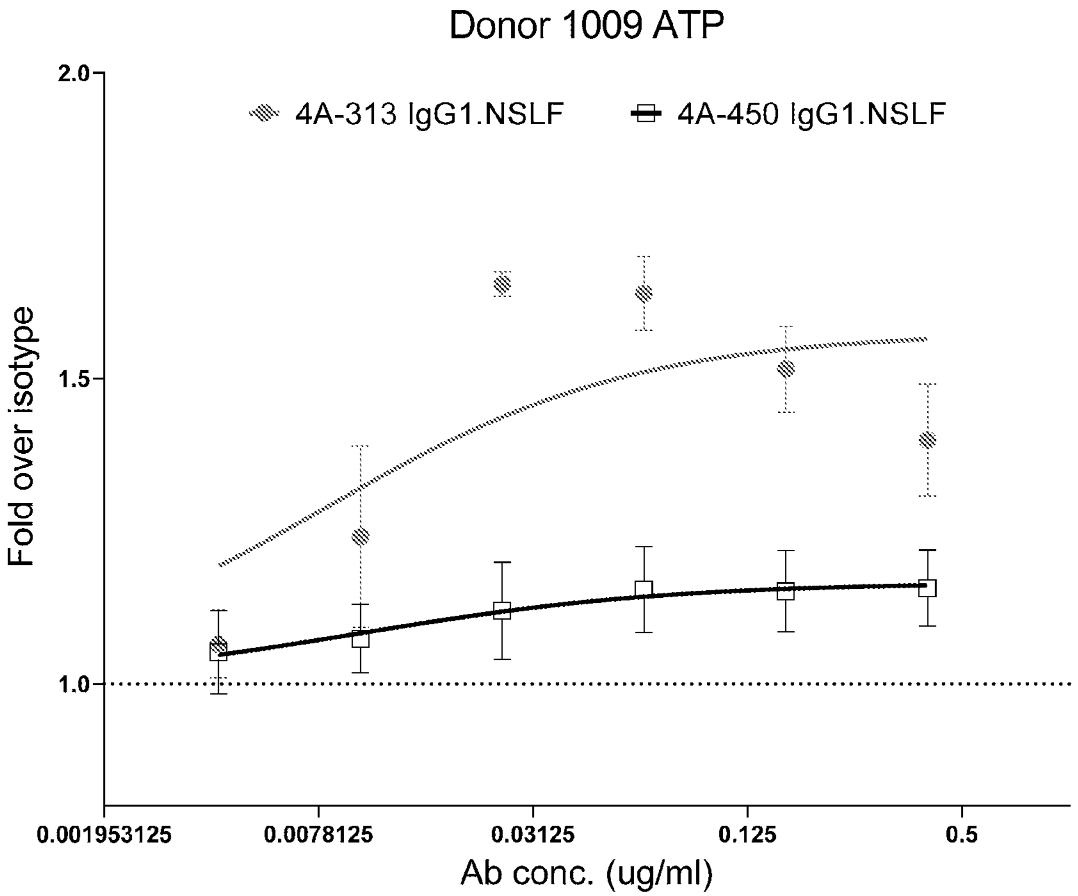
FIGS. 27A, 27B, and 27C set forth data showing a dose-dependent increase in ATP levels in primary human macrophages from three different donors following addition of anti-MS4A4A antibodies of the present disclosure.
Figure 27B:
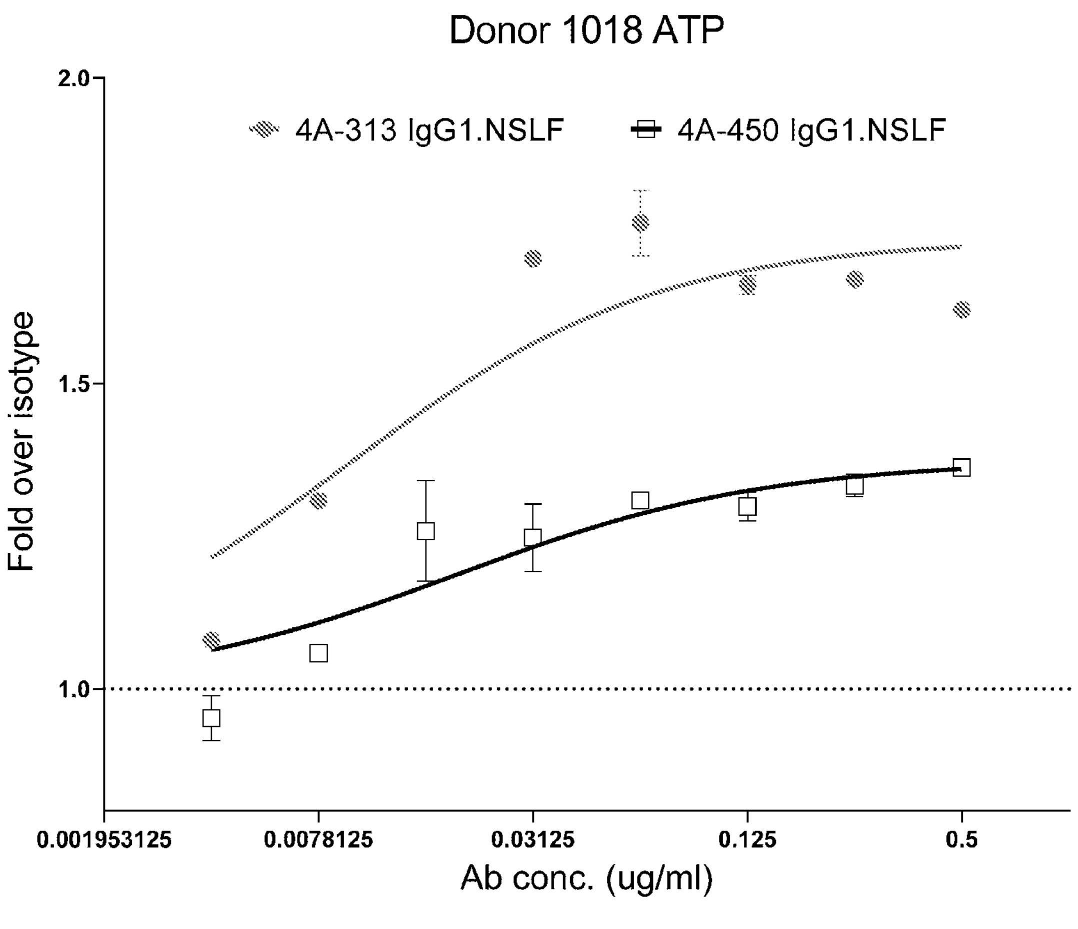
Figure 27C:
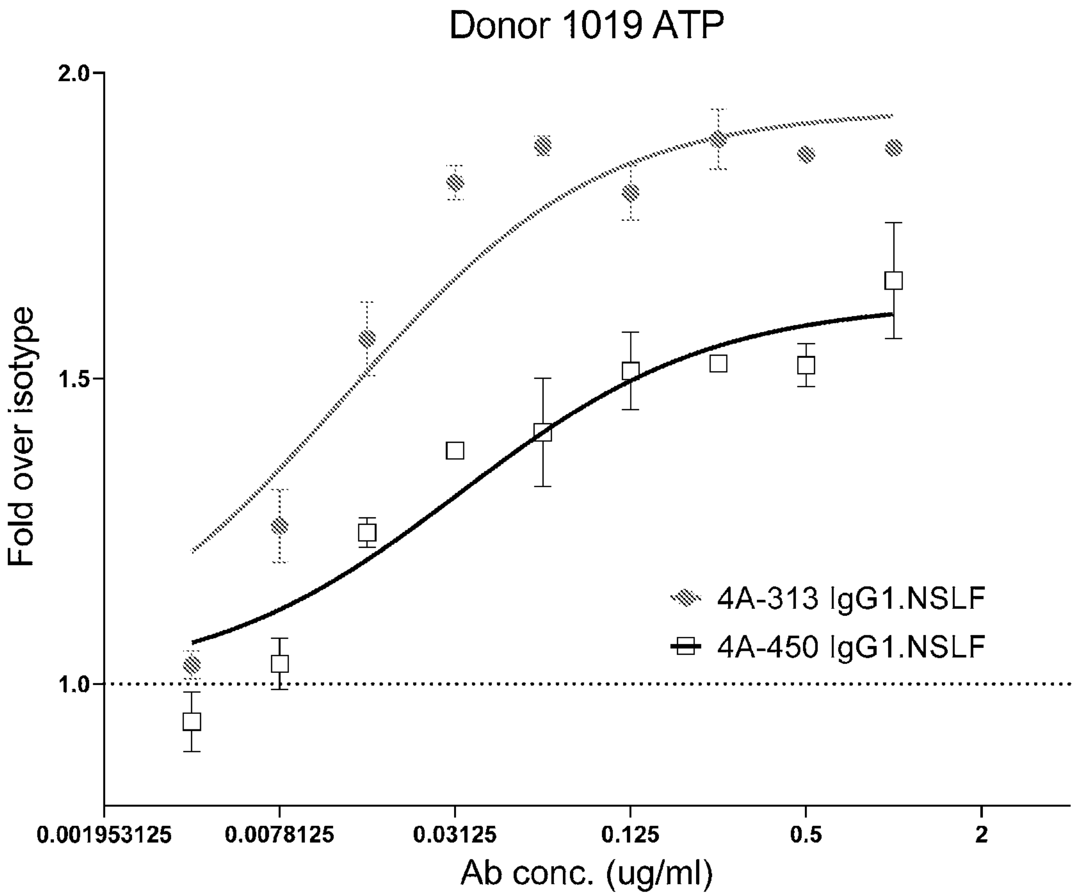

As shown in FIG. 27A, FIG. 27B, and FIG. 27C, anti-MS4A4A antibody 4A-313.NSLF and anti-MS4A4A antibody 4A-450.NSLF increased levels of cellular ATP in a dose-dependent manner in primary human macrophages obtained from three different donors, respectively. Data in FIG. 27A, FIG. 27B, and FIG. 27C is presented as fold-increase in the levels of cellular ATP over that observed using an isotype control antibody (the x-axis shows antibody concentrations Wimp and the y-axis shows fold-increase above control, which was set at 1.0). Data from these graphs were analyzed to determine EC50 values and maximum response; these results are shown below in Table 43 (shown as mean+/−SEM).

TABLE 43

| Antibody | EC50 (μg/ml) | Max Cellular ATP Response (fold increase over isotype control) |
|---|---|---|
| 4A-313.NSLF | 0.010 +/− 0.001 | 1.76 +/− 0.10 |
| 4A-450.NSLF | 0.021 +/− 0.006 | 1.43 +/− 0.10 |

Taken together, these results showed that anti-MS4A4A antibodies of the present disclosure induced functional changes in primary human macrophages as evidenced by increased levels of mTREM2, sTREM2, and cellular ATP following antibody addition.

Example 36: Anti-MS4A4A Antibodies Rescue CSF1R Inhibition Induced Cell Death To evaluate the ability of MS4A4A to sustain survival of human macrophages after CSF1R inhibition, anti-MS4A4A antibodies of the present disclosure were studied for their ability to enhance cell survival in the presence of a CSF1R inhibitor, PLX3397 (See DeNardo et al., Cancer Discov (2011) 1(1):54-67. 22039576); Peng, et al., J. of Exp Canc Res (2019) 38(1):372. PMID: 31438996).

Human monocytes were isolated from whole blood using RosetteSep Human Monocyte Enrichment Protocol (Stem Cell Technologies). To prepare human monocyte derived macrophages, monocytes were counted and plated in complete RPMI media (RPMI supplemented with Glutamax, penicillin/streptomycin, non-essential amino acids, sodium-pyruvate, and 10% heat inactivated fetal bovine serum) and 50 ng/ml MCSF (Peprotech). After 6 days, differentiated monocytes (macrophages) were harvested and plated onto 96-well plates at a density of $0.1\times10^6$ cells/well in complete RPMI media with 50 ng/ml M-CSF. Macrophages were allowed to recover overnight. On Day 7, anti-MS4A4A antibodies 4A-313.NSLF and 4A-450.NSLF were added to the cultured macrophages with and without PLX3397 (1 μM). All antibodies were added at a final concentration of 1 μg/ml. Cell viability was determined using cytotox red reagent, a DNA dye that labels dying cells (Essen Bioscience). The level of cytotox red reagent was determined by measuring fluorescence signal over several days using the IncuCyte Live Cell imaging system (Essen Bioscience).

Figure 28A:
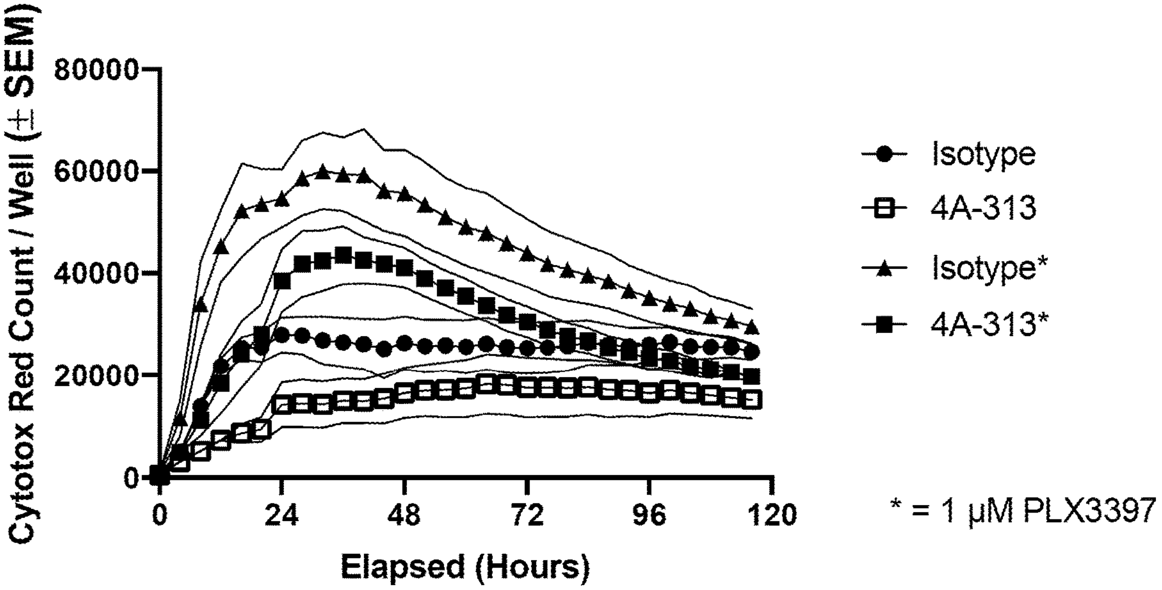
FIGS. 28A and 28B set forth data showing anti-MS4A4A antibodies of the present disclosure are effective at rescuing CSF1R inhibition-induced cell death.

As shown in FIG. 28A, human macrophages treated with PLX3397 and anti-MS4A4A antibody 4A-313.NSLF showed a decrease in cytotox red count compared to that observed in cells treated with PLX3397 plus isotype control antibody. Data in FIG. 28A are graphed as mean±SEM; N=3 from three human donors.

Figure 28B:
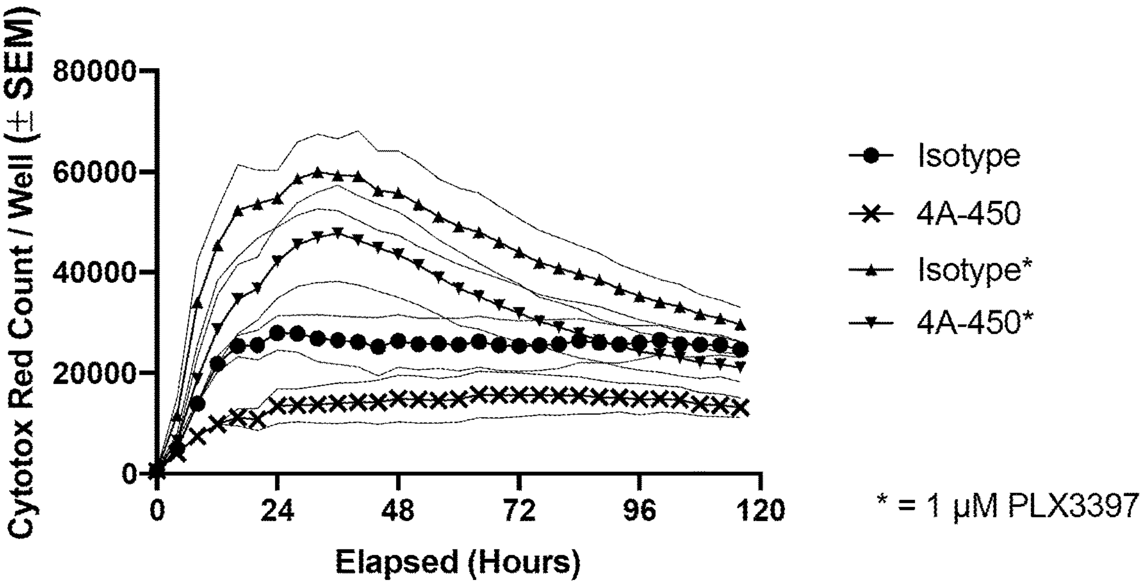

As shown in FIG. 28B, human macrophages treated with PLX3397 and anti-MS4A4A antibody 4A-450.NSLF showed a decrease in cytotox red count compared to that observed in cells treated with PLX3397 plus isotype control antibody. Data in FIG. 28B are graphed as mean±SEM; N=3 from three human donors.

Taken together, these results showed that anti-MS4A4A antibodies of the present disclosure reduced cell death and sustained survival of human macrophages following CSF1R inhibition. Accordingly, the anti-MS4A4A antibodies of the present disclosure are useful for treating an individual having a CSF1R-deficient disease or disorder, such as ALSP or HDLS.

Example 37: Pharmacokinetics of Anti-MS4A4A Antibodies in Cynomolgus Monkey Serum To examine the pharmacokinetics (PK) of anti-MS4A4A antibodies of the present disclosure in serum in vivo, the following studies were performed.

Cynomolgus monkeys (cyno) were administered anti-MS4A4A antibodies 4A-21.WT, 4A-25.WT, 4A-18.WT, or isotype control (huIgG1) at doses of 80 mg/kg by intravenous bolus injection. Each animal group was administered a total of five doses; the first and second doses separated by an interval of 28 days and the remaining four doses were separated by an interval of 7 days between each dose.

Serum samples were collected from the animals at pre-dose, 0.5, 4, 6, 10, 12, 24, 48, 96, 168, 192, 264, 312, 336, 480, 504, 648, 672, 672.5, 684, 720, 840, 840.5, 852, 888, 1008, 1008.5, 1014, 1020, 1032, 1056, 1104, 1176, 1188, and 1224 hours post administration of antibody.

Levels of anti-MS4A4A antibodies 4A-21.WT, 4A-25.WT, and 4A-18.WTin cynornolgus monkey serum were measured using a custom Gyrolab assay based on a stepwise sandwich format with a biotin labeled Goat anti-human IgG (Cat no. NBP1-74983; Novus Biologicals) as the capturing reagent and an Alexa fluor® 647 labeled anti-human IgG (Cat no. 2049-31; Southern Biotech) as the detection reagent. Standards, quality controls, and samples were diluted in Rexxip HN buffer (Cat no. P0004996, Gyrolab). Anti-MS4A4A antibodies present in samples were captured by the biotinylated anti-human IgG bound to the streptavidin coated affinity column of the gyrolab bioaffy 200 CD. Captured anti-MS4A4A antibodies were detected by the fluorescently labelled anti-human IgG antibody. The intensity of the fluorescent signals produced were proportional to the amount of anti-MS4A4A antibodies present in the sample. Data was analyzed using Gyrolab xP and Excel.

Following administration of an 80 mg/kg dose to the animals, anti-MS4A4A antibody concentrations in the serum steadily declined after reaching mean maximum observed concentration ($C_{max}$), with an average half-life ($t_{1/2}$) value (mean±SD) of 140±54.5 hours for anti-MS4A4A antibody 4A-21.WT, 269±114 hours for anti-MS4A4A antibody 4A-25.WT, and 193±26.8 hours for anti-MS4A4A antibody 4A-18.WT after day 1 (day of first dose) administration. The clearance (CL) was inversely proportional to $t_{1/2}$ with an average CL (mean±SD) of 0.625±0.107 mL/hr/kg for antibody 4A-21.WT, 0.124±0.025 mL/hr/kg for antibody 4A-25.WT, and 0.402±0.09 mL/hr/kg for antibody 4A-18.WT on Day 1. The steady state volume of distribution (Vss) values on day 1 ranged from 30.8 to 51.4 mL/kg, 22.6 to 41.7 mL/kg, and 24.9 to 41.3 mL/kg for antibody 4A-21.WT, 4A-25.WT, 4A-18.WT groups, respectively.

Exposure was assessed by $C_{max}$ and area under the concentration-time curve from 0 to 168 hours post dose ($AUC_{0-168}$). On day 1, antibody 4A-25.WT had the highest mean $C_{max}$ ($6.26\times10^6$ ng/mL), followed by antibody 4A-18.WT ($4.81\times10^6$ ng/mL). Anti-MS4A4A antibody 4A-21.WT ($3.53\times10^6$ ng/mL) had the lowest $C_{max}$ amongst the test articles.

Anti-MS4A4A antibodies 4A-25.WT and 4A-18.WT had similar $AUC_{0-168}$($3.47\times10^8$ ng*hr/mL and $3.35\times10^8$ ng*hr/mL, respectively), that was significantly higher than that of antibody 4A-21 ($1.15\times10^8$ ng*hr/mL).

Example 38: Anti-MS4A4A Antibodies Increase Serum and CSF sTREM2 Levels In Vivo To examine the effect of anti-MS4A4A antibodies of the present disclosure on sTREM2 levels in serum and cerebrospinal fluid (CSF) in vivo, the following studies were performed.

Cynomolgus monkeys were administered anti-MS4A4A antibodies 4A-21.WT, 4A-25.WT, 4A-18.WT, or isotype control (huIgG1) at doses of 80 mg/kg by intravenous bolus injection. Each group was administered a total of five doses; the first and second doses separated by an interval of 28 days and the remaining four doses were separated by an interval of 7 days between each dose.

Serum samples were collected from the animals at pre-dose, 0.5, 4, 6, 10, 12, 24, 48, 96, 168, 192, 264, 312, 336, 480, 504, 648, 672, 672.5, 684, 720, 840, 840.5, 852, 888, 1008, 1008.5, 1014, 1020, 1032, 1056, 1104, 1176, 1188, and 1224 hours post administration of antibody. CSF samples were also collected from the animals at pre-dose, 0.5, 4, 6, 10, 12, 24, 48, 96, 168, 192, 264, 312, 336, 480, 504, 648, 672, 672.5, 684, 720, 840, 840.5, 852, 888, 1008, 1008.5, 1014, 1020, 1032, 1056, 1104, 1176, 1188, and 1224 hours post administration of antibody.

In serum, following the administration of anti-MS4A4A antibodies 4A-25.WT, 4A-18.WT, and 4A-21.WT, sTREM2 levels increased greater than 2-fold from baseline, with peak levels of 232%, 261%, and 287%, respectively, of their pre-dose baseline levels, 48 to 96 hours after administration of the first antibody dose. Furthermore, the levels of sTREM2 in the serum remained elevated with repeated weekly dosing of anti-MS4A4A antibodies on days 29, 36, 43, and 50 with average sTREM2 levels approximately 2-fold (214%, 4A-25.WT; 226%, 4A-18.WT; 199%, 4A-21.WT) above that observed at pre dose baseline levels. The isotype control remained close to predose levels (107% of baseline) throughout the dosing period.

In the CSF, sTREM2 levels significantly increased at 24 and 96 hours following the administration of anti-MS4A4A antibodies 4A.21.WT (p=0.0008, 2-way ANOVA) and 4A-25.WT (p=0.004, 2-way ANOVA), respectively, compared to that observed in isotype control treated animals.

The sTREM2 levels in the 4A-18.WT treated group remained similar to that observed in the isotype control group.

Taken together, these results showed that anti-MS4A4A antibodies of the present disclosure are effective at increasing sTREM2 levels in both serum and CSF in vivo.

Example 39: Anti-MS4A4A Antibodies Increase CSF Osteopontin Levels In Vivo

To examine the effect of anti-MS4A4A antibodies of the present disclosure on osteopontin levels in CSF in vivo, the following studies were performed.

Cynomolgus monkeys were administered anti-MS4A4A antibodies 4A-21.WT, 4A-25.WT, 4A-18.WT, or isotype control (huIgG1) at doses of 80 mg/kg by intravenous bolus injection. Each group was administered a total of five doses; the first and second doses separated by an interval of 28 days and the remaining four doses were separated by an interval of 7 days between each dose. CSF samples were collected from the animals at pre-dose, 0.5, 4, 6, 10, 12, 24, 48, 96, 168, 192, 264, 312, 336, 480, 504, 648, 672, 672.5, 684, 720, 840, 840.5, 852, 888, 1008, 1008.5, 1014, 1020, 1032, 1056, 1104, 1176, 1188, and 1224 hours post administration of antibody.

Anti-MS4A4A antibodies 4A-25.WT, 4A-18.WT, and 4A-21.WT significantly increased osteopontin levels in the CSF compared to that observed with isotype control antibody.

Repeat administration of anti-MS4A4A antibody 4A-21.WT resulted in significantly increased CSF osteopontin levels that peaked at 12 hours post first dose to approximately 280 ng/ml ($p<0.0001$, 2-way ANOVA) compared to the isotype control and continued to show peak levels at 12 to 24 hours post subsequent doses. Repeat administration of anti-MS4A4A antibody 4A-25.WT and antibody 4A-18.WT showed a trend in increased CSF osteopontin levels 12 to 24 hours (to levels of approximately 50-80 ng/ml) after each dose compared to the isotype control.

These results showed that anti-MS4A4A antibodies of the present disclosure are effective at increasing osteopontin levels in CSF in vivo.

Example 40: Anti-MS4A4A Antibodies Increase Osteopontin Levels in Various Brain Regions In Vivo To examine the effect of anti-MS4A4A antibodies of the present disclosure on osteopontin levels in the frontal cortex and hippocampus of cynomolgus monkeys in vivo, the following studies were performed.

Cynomolgus monkeys were administered anti-MS4A4A antibodies 4A-21.WT, 4A-25.WT, 4A-18.WT, or isotype control (huIgG1) at doses of 80 mg/ml by intravenous bolus injection. Each group was administered a total of five doses; the first and second doses were separated by an interval of 28 days between each dose, and the remaining four doses were separated by an interval of 7 days between each dose. The animals were euthanized 48 hours after the fifth dose and the frontal cortex and hippocampus were removed and frozen.

Osteopontin levels in brain tissue were measured as follows. Frozen brain samples were lysed with N-Per Neuronal Protein Extraction Reagent (cat #87792, Thermo Scientific) and Halt Protease inhibitor (cat #1861278) on ice for 20 minutes according to manufacturer instructions. Samples were centrifuged and supernatants were transferred to a new tube and stored at −80° C. until further analysis. The total protein concentration in each sample was measured by BCA protein analysis kit (cat #23225, Thermo Scientific) according to manufacturer instructions. The protein concentration values were used to normalize analyte concentrations measured in brain tissues.

Osteopontin levels in the brain tissue of cynomolgus monkeys increased after treatment with anti-MS4A4A antibody 4A-21.WT. Repeat administration of anti-MS4A4A antibody 4A-21.WT to cynomolgus monkeys resulted in significantly increased ($p<0.035$ and $p=0.0003$, respectively; 1-way ANOVA) osteopontin levels in the frontal cortex of cynomolgus monkeys when compared to that observed with isotype control antibody. In particular, mean osteopontin levels measured in the frontal cortex following antibody administration were as follows: approximately 0.6 ng/mg (isotype control antibody); approximately 1.2 ng/mg (4A-21.WT); approximately 0.7 ng/mg (4A-25.WT and 4A-18.WT). Repeat administration of anti-MS4A4A antibodies resulted in a trend in increased osteopontin levels in the hippocampus of cynomolgus monkeys when compared to that observed with isotype control antibody. In particular, mean osteopontin levels measured in the hippocampus following antibody administration were as follows: approximately 1.3 ng/mg (isotype control antibody); approximately 1.8 ng/mg (4A-21.WT and 4A-18.WT); and approximately 2.4 ng/mg (4A-25.WT). These results showed that anti-MS4A4A antibodies of the present disclosure are effective at increasing osteopontin levels in the frontal cortex and hippocampus in non-human primates.

Example 41: Effect of Anti-MS4A4A Antibodies on CSF Protein Biomarkers

Cerebral spinal fluid obtained from cynomolgus monkeys administered a peripheral injection of anti-MS4A4A antibody 4A-21.WT (80 mg/kg) was further analysed for changes in protein biomarker expression in vivo. In these studies, changes in protein expression levels in CSF were measured using Somalogic Somascan 1.3k assay performed on CSF samples obtained from the animals 24-hours following injection of the antibody.

Figure 29:
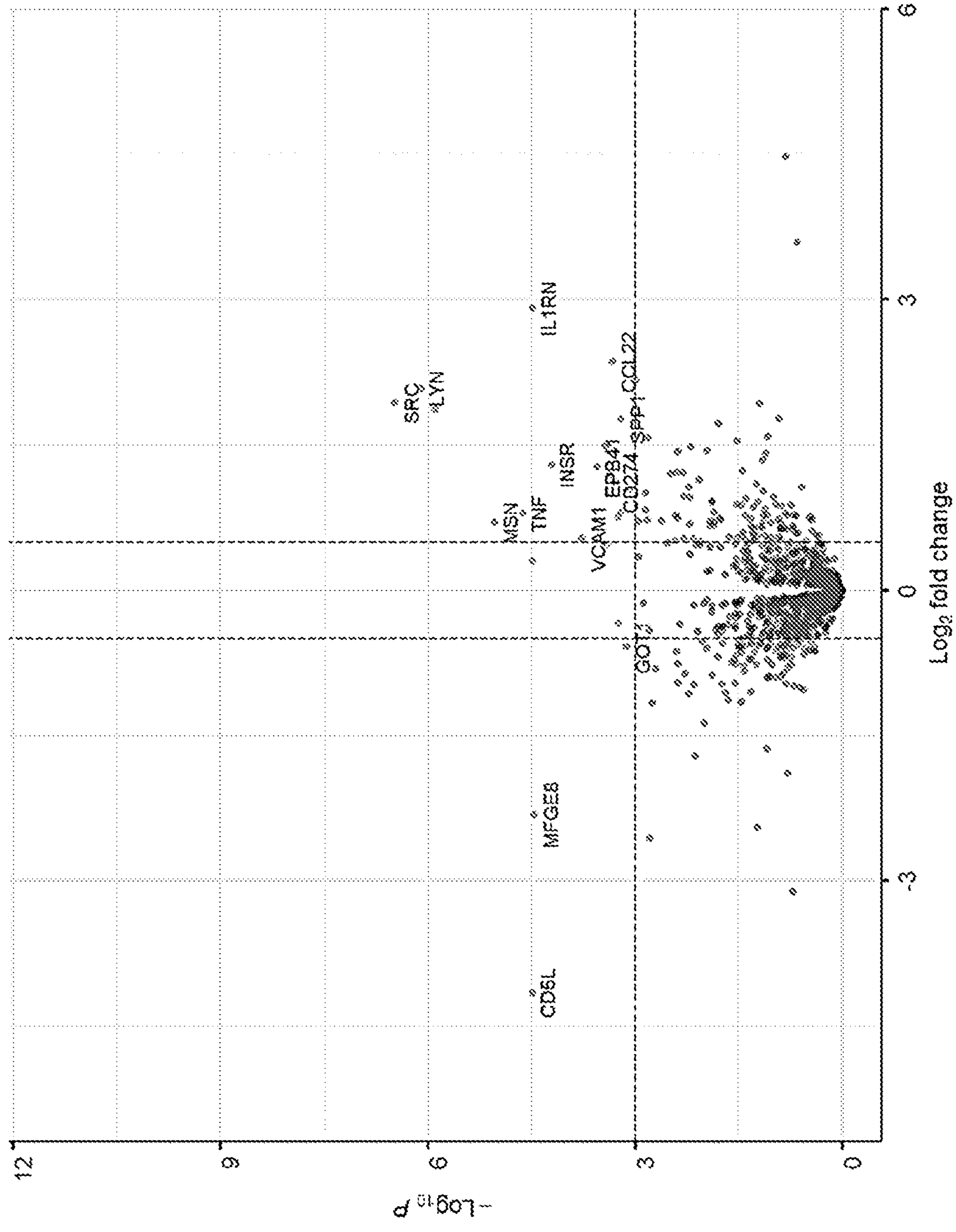
FIG. 29 shows a volcano plot of proteome-wide effects in cynomolgus monkey CSF following administration of an anti-MS4A4A antibody of the present disclosure.

Protein changes in CSF were observed following administration of anti-MS4A4A antibody 4A-21.WT to cynomolgus monkeys. FIG. 29 is a volcano plot presenting the proteome-wide effects from three CSF samples taken from cynomolgus monkeys after peripheral injection of anti-MS4A4A antibody 4A-21.WT (80 mg/kg). Each dot in the volcano plot represents 1 protein. For each measured protein, values on the x-axis represent the fold-change difference in a protein's levels in CSF between antibody treated animals and control animals; values on the y-axis represents the significance of these observed differences, expressed as the minus log 10 of the p-value for differential expression, assessed by ANOVA. Protein symbols in FIG. 29 are presented for proteins differentially expressed in antibody-treated vs control animals with a p-value of <1E-3.

As shown in FIG. 29, an increase in CSF levels of osteopontin (SSP1) and IL1RN (2 microglial markers) was observed in animals administered anti-MS4A4A antibody. Taken together, these results showed that anti-MS4A4A antibodies of the present disclosure increased IL1RN and osteopontin protein levels in both CSF and serum of non-human primates.

Example 42: Anti-MS4A4A Antibodies Increase Serum sTREM2 Levels In Vivo

The effect of anti-MS4A4A antibodies of the present disclosure on sTREM2 levels in serum and cerebrospinal fluid (CSF) in vivo was examined further in another series of experiments performed in non-human primates.

Cynomolgus monkeys were administered anti-MS4A4A antibodies 4A-313.NSLF, 4A-313.WT, and 4A-450.NSLF at doses of 80 mg/ml; anti-MS4A4A antibody 4A-313.NSLF at doses of 250 mg/ml, or vehicle control by intravenous bolus injection. Each group was administered a total of four doses; the first and second doses separated by an interval of 7 days, the second and third doses separated by an interval of 14 days, and the third and fourth doses separated by an interval of 28 days.

Serum samples were collected from the animals at pre-dose, 0.5, 2, 6, 10, 24, 34, 48, 72, 96, 168, 168.5, 170, 174, 178, 192, 216, 240, 264, 336, 408, 504, 504.5, 506, 510, 514, 528, 552, 576, 600, 672, 744, 840, 912, 1008, 1176, 1186, 1200, and 1224 hours post administration of antibody; CSF samples were also collected from the animals at pre-dose, 0.5, 2, 6, 10, 24, 34, 48, 72, 96, 168, 168.5, 170, 174, 178, 192, 216, 240, 264, 336, 408, 504, 504.5, 506, 510, 514, 528, 552, 576, 600, 672, 744, 840, 912, 1008, 1176, 1186, 1200, and 1224 hours post administration of antibody.

sTREM levels in serum were measured as follows. Single spot Meso Scale Discovery (MSD) plates (Rockville, MD) were coated with a capture antibody in PBS at 4° C. overnight. Monkey serum samples (as well as monkey TREM2-Fc standards) were diluted in binding buffer and added to the wells for 1 hour at room temperature. Biotinylated goat anti-human TREM2 polyclonal antibody (R&D Systems) was added at a 1:2,000 dilution in binding buffer and incubated for 1 hour at room temperature, followed by detection with sulfo tag streptavidin (MSD). 150 μl of 1× Read Buffer was added to the plates, and the plates were then analyzed.

Figure 30:
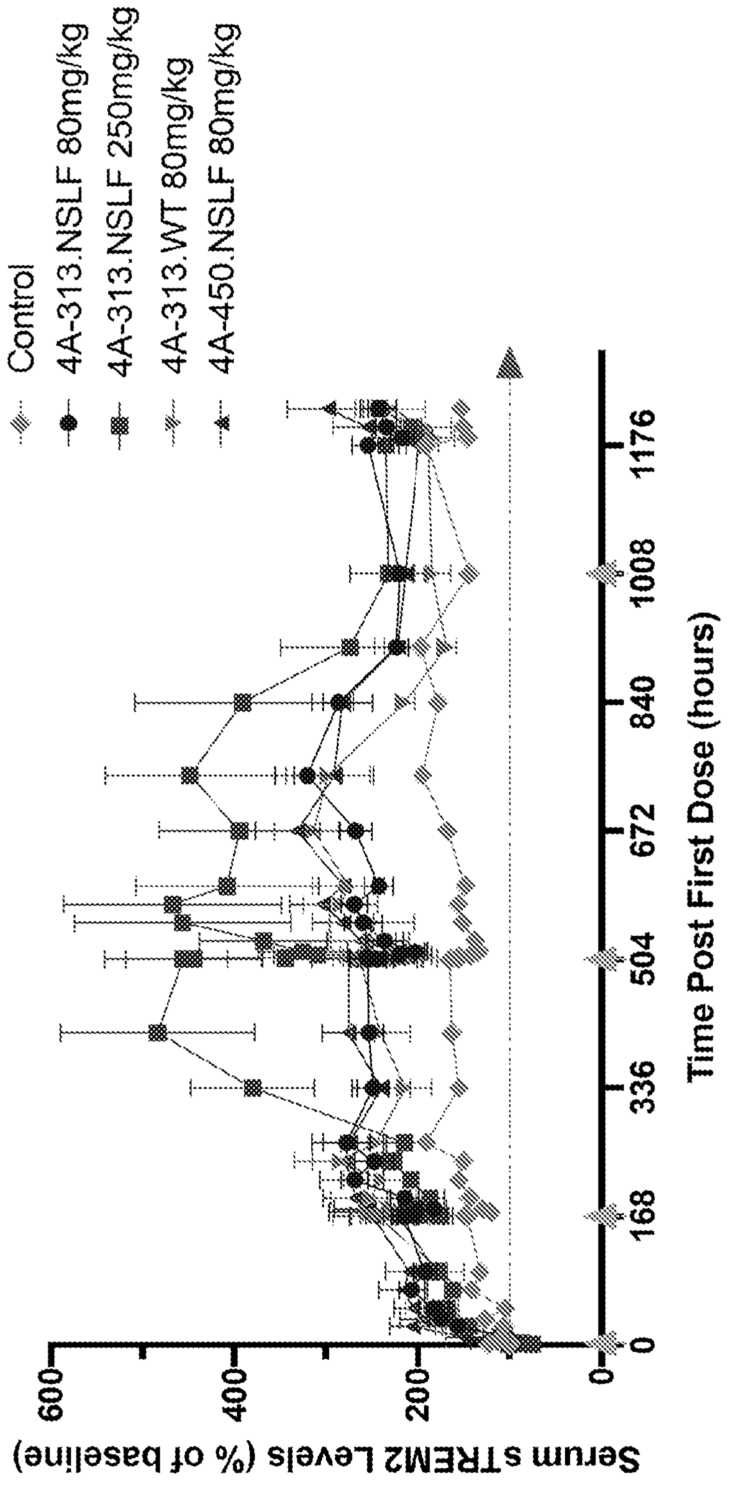
FIG. 30 sets forth data showing increased sTREM2 levels in cynomolgus monkey serum following administration of anti-MS4A4A antibodies of the present disclosure.

Results of these studies are shown in FIG. 30. In serum, sTREM2 levels increased approximately 1.5-fold above that observed at baseline (~150% of predose baseline levels) following administration of anti-MS4A4A antibody 4A-313.NSLF at 80 mg/kg, at 24 hours post dose. Levels of sTREM2 continued increasing over time, reaching maximum levels of 3-fold above that observed at baseline (~300% of predose baseline levels) after multiple doses at 80 mg/kg.

At doses of 250 mg/kg of anti-MS4A4A antibody 4A-313.NSLF, serum sTREM2 levels increased approximately 1.5-fold from that observed at baseline at 24 hours post dose and continued increasing with time, reaching maximum levels of 4.8-fold from that observed at baseline after multiple doses at 250 mg/kg.

Following administration of anti-MS4A4A antibody 4A-313.WT at 80 mg/kg, serum sTREM2 levels increased approximately 1.5-fold from that observed at baseline starting 24 hours post dose. With repeated doses of 4A-313.WT at 80 mg/kg, serum sTREM2 levels increased up to a maximum of 3-fold from that observed at baseline.

Following administration of anti-MS4A4A antibody 4A-450.NSLF at 80 mg/kg, serum sTREM2 levels increased approximately 2-fold from that observed at baseline at 24 hours post dose and continued increasing with time, reaching maximum levels of 3-fold from that observed at baseline after multiple doses of 4A-450.NSLF at 80 mg/kg.

Taken together, these results showed that anti-MS4A4A antibodies of the present invention were effective at increasing sTREM2 levels in serum in non-human primates.

Example 43: Anti-MS4A4A Antibodies Increase CSF Osteopontin Levels In Vivo

To examine the effect of anti-MS4A4A antibodies of the present disclosure on osteopontin levels in cerebrospinal fluid (CSF) in vivo, the following studies were performed.

Cynomolgus monkeys were administered anti-MS4A4A antibodies 4A-313.NSLF, 4A-313.WT, 4A-450.NSLF at doses of 80 mg/ml, 4A-313.NSLF at doses of 250 mg/ml, or vehicle control by intravenous bolus injection. Each group was administered a total of four doses; the first and second doses separated by an interval of 7 days, the second and third doses separated by an interval of 14 days, and the third and fourth doses separated by an interval of 28 days.

CSF samples were collected from the animals at pre-dose, 0.5, 2, 6, 10, 24, 34, 48, 72, 96, 168, 168.5, 170, 174, 178, 192, 216, 240, 264, 336, 408, 504, 504.5, 506, 510, 514, 528, 552, 576, 600, 672, 744, 840, 912, 1008, 1176, 1186, 1200, and 1224 hours post administration of antibody.

Osteopontin levels in CSF were measured as follows. Single spot Meso Scale Discovery (MSD) plates (Rockville, MD) were coated with a capture antibody in PBS at 4° C. overnight. Monkey CSF samples were diluted in binding buffer and added to the wells for 1 hour at room temperature. Biotinylated goat anti-human Osteopontin polyclonal antibody (R&D Systems) was added at a 1:2,000 dilution in binding buffer and incubated for 1 hour at room temperature, followed by detection with sulfo tag streptavidin (MSD). 150 μl of 1× Read Buffer was added to the plates, and the plates were then analyzed on a Sector Imager (MSD).

Figure 31A:
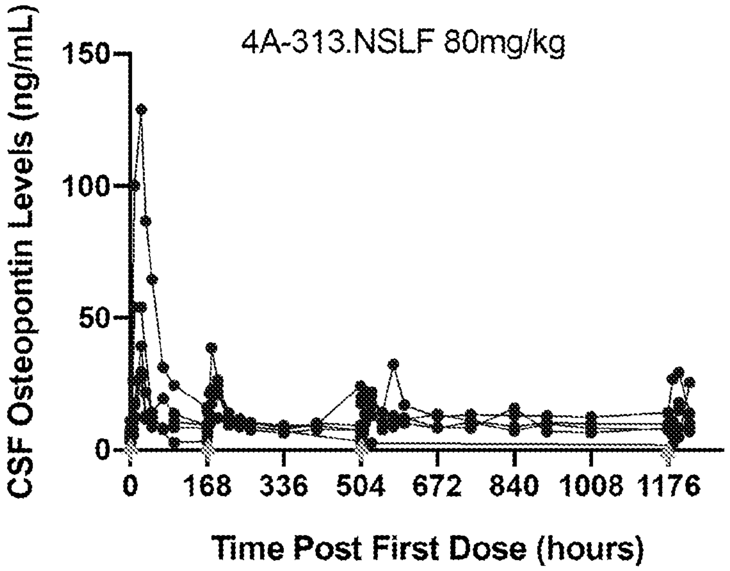
FIGS. 31A, 31B, 31C, and 31D set forth data showing increased osteopontin levels in cynomolgus monkey CSF following administration of anti-MS4A4A antibodies of the present disclosure.
Figure 31B:
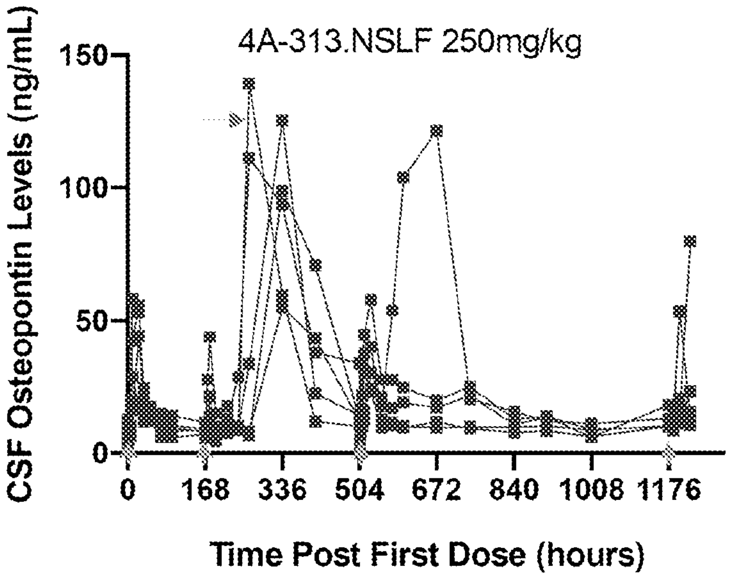

Osteopontin levels in the CSF of cynomolgus monkeys increased after administration of anti-MS4A4A antibodies of the present disclosure. Following administration of anti-MS4A4A antibody 4A-313.NSLF at doses 80 mg/kg and 250 mg/kg, CSF osteopontin levels peaked on average approximately 13-fold and 6-fold from that observed at baseline, respectively, 24 hours post first dose followed by a decline to 1.5-fold of baseline levels (FIGS. 31A and 31B). With repeated dosing of anti-MS4A4A antibody 4A-313.NSLF at 80 mg/kg, CSF osteopontin levels peaked at 10 to 24 hours after each dose, reaching peak levels of 3-fold to 5-fold of that observed at baseline levels (FIG. 31A). With repeated dosing at 250 mg/kg of anti-MS4A4A antibody 4A-313.NSLF, CSF osteopontin levels increased, and reached peak levels of 14-fold from that observed at baseline 168 hours post second dose (FIG. 31B) and peak levels of 4-fold to 5-fold from that observed at baseline 24 to 48 hours post subsequent doses (FIG. 31B).

Figure 31C:
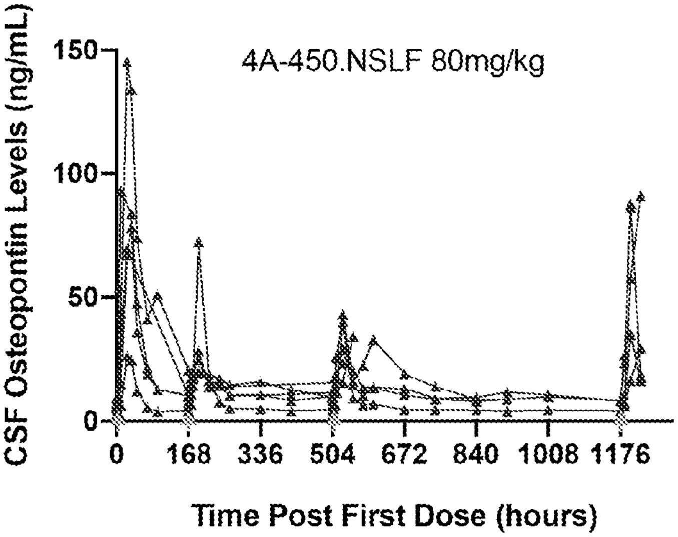
Figure 31D:
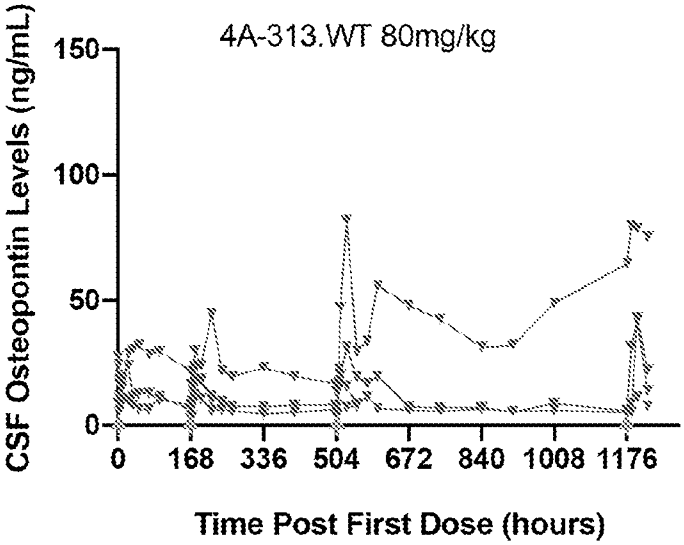

Following administration of anti-MS4A4A antibody 4A-450.NSLF at 80 mg/kg, CSF osteopontin levels peaked approximately 13-fold from that observed at baseline, 24 hours post first dose followed by a decline to baseline levels (FIGS. 31C and 31D). With repeated dosing of 4A-450.NSLF at 80 mg/kg, CSF osteopontin levels peaked at 24 hours after each dose, reaching peak levels of 6-fold to 9-fold from that observed at baseline levels (FIG. 31C).

Following repeated administration of anti-MS4A4A antibody 4A-313.WT at 80 mg/kg, CSF osteopontin levels peaked approximately 1.5-fold from that observed at baseline, 24 hours after each dose followed by a decline to baseline levels (FIG. 31D).

Taken together, these results showed that anti-MS4A4A antibodies of the present disclosure are effective at increasing osteopontin levels in CSF in non-human primates.

Example 44: Anti-MS4A4A Antibodies Increase Osteopontin Levels in Various Brain Regions In Vivo To examine the effect of anti-MS4A4A antibodies of the present disclosure on osteopontin levels in frontal cortex and hippocampus in vivo, the following studies were performed.

Cynomolgus monkeys were administered anti-MS4A4A antibodies 4A-313.NSLF, 4A-313.WT, and 4A-450.NSLF at doses of 80 mg/kg, and anti-MS4A4A antibody 4A-313.NSLF at doses of 250 mg/kg, or vehicle control by intravenous bolus injection. Each group was administered a total of four doses; the first and second doses separated by an interval of 7 days, the second and third doses separated by an interval of 14 days, and the third and fourth doses separated by an interval of 28 days. The animals were euthanized 48 hours after the fourth dose and the frontal cortex and hippocampus were removed and frozen.

Osteopontin levels in brain tissue were measured as follows. Frozen brain samples were lysed with N-Per Neuronal Protein Extraction Reagent (cat #87792, Thermo Scientific) and Halt Protease inhibitor (cat #1861278) on ice for 20 minutes according to manufacturer instructions. Samples were centrifuged and supernatants were transferred to a new tube and stored at −80° C. until further analysis. The total protein concentration in each sample was measured by BCA protein analysis kit (cat #23225, Thermo Scientific) according to manufacturer instructions. The protein concentration values were used to normalize analyte concentrations measured in brain tissues.

Figure 32A:
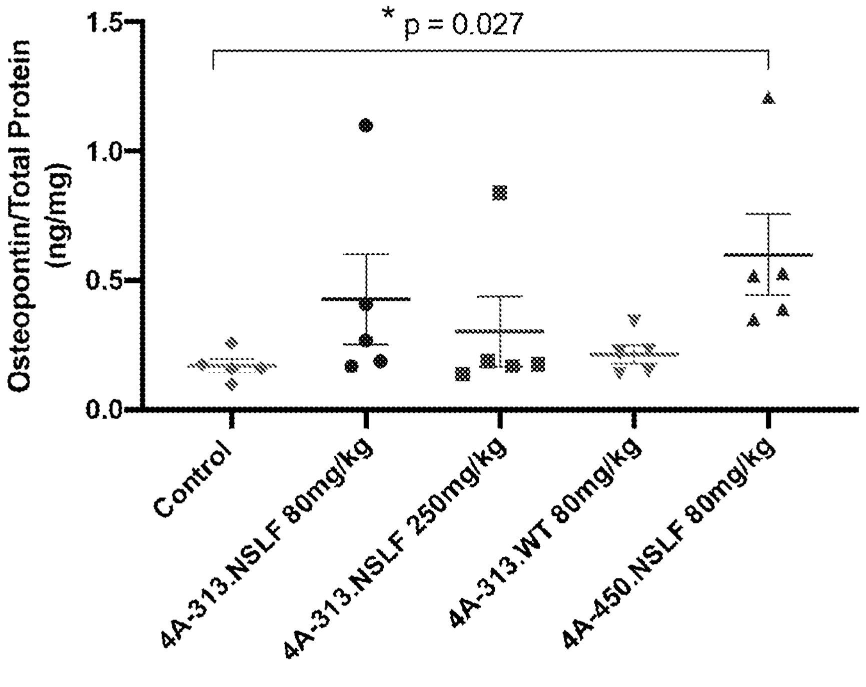
FIGS. 32A and 32B set forth data showing increased osteopontin levels in frontal cortex and hippocampus, respectively, in cynomolgus monkey brains following administration of anti-MS4A4A antibodies of the present disclosure.
Figure 32B:
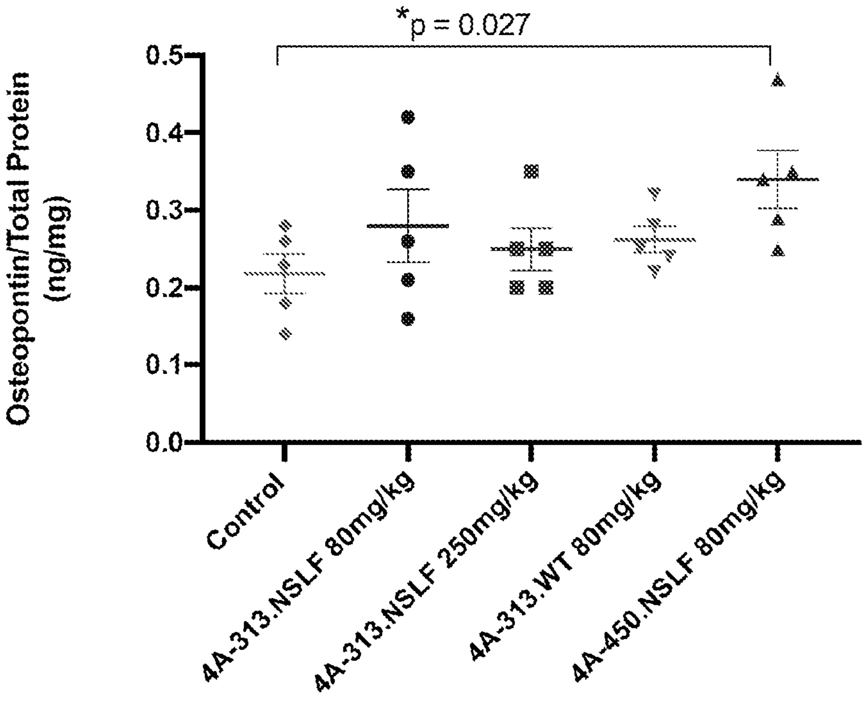

Osteopontin levels in the brain tissue of cynomolgus monkeys increased after administration of anti-MS4A4A antibody 4A-450.NSLF. Repeat administration of antibody 4A-450.NSLF at 80 mg/kg, resulted in significantly increased (p=0.027, t-test) osteopontin levels in the frontal cortex of cynomolgus monkeys when compared to that observed in control animals (FIG. 32A). Similarly, repeat administration of anti-MS4A4A antibody 4A-450.NSLF at 80 mg/kg resulted in significantly increased (p=0.027, t-test) osteopontin levels in the hippocampus of cynomolgus monkeys when compared to that observed in control treated animals (FIG. 32B).

Taken together, these results showed that anti-MS4A4A antibodies of the present disclosure are effective at increasing osteopontin levels in brain tissue (e.g., frontal cortex and hippocampus) in non-human primates.

Example 45: Anti-MS4A4A Antibodies Increase CSF1R Levels in Various Brain Regions In Vivo To examine the effect of anti-MS4A4A antibodies of the present disclosure on Colony stimulating factor 1 receptor (CSF1R) levels in the frontal cortex and hippocampus in vivo, the following studies were performed.

Cynomolgus monkeys were administered anti-MS4A4A antibodies 4A-313.NSLF, 4A-313.WT, and 4A-450.NSLF at doses of 80 mg/kg, anti-MS4A4A antibody 4A-313.NSLF at doses of 250 mg/kg, or vehicle control by intravenous infusion. Each group was administered a total of four doses; the first and second doses separated by an interval of 7 days, the second and third doses separated by an interval of 14 days, and the third and fourth doses separated by an interval of 28 days. The animals were euthanized 48 hours after the fourth dose and the frontal cortex and hippocampus were removed and frozen.

CSF1R levels in brain tissue were measured as follows. Frozen brain samples were lysed with N-Per Neuronal Protein Extraction Reagent (cat #87792, Thermo Scientific) and Halt Protease inhibitor (cat #1861278) on ice for 20 minutes according to manufacturer instructions. Samples were centrifuged and supernatants were transferred to a new tube and stored at −80° C. until further analysis. The total protein concentration in each sample was measured by BCA protein analysis kit (cat #23225, Thermo Scientific) according to manufacturer instructions. The protein concentration values were used to normalize analyte concentrations measured in brain tissues.

Figure 33A:
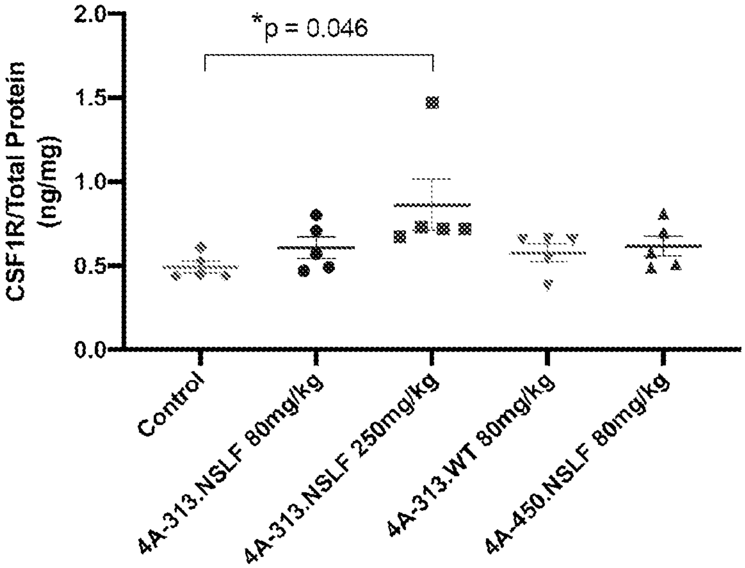
FIGS. 33A and 33B set forth data showing increased CSF1R levels in frontal cortex and hippocampus, respectively, in cynomolgus monkey brains following administration of anti-MS4A4A antibodies of the present disclosure.
Figure 33B:
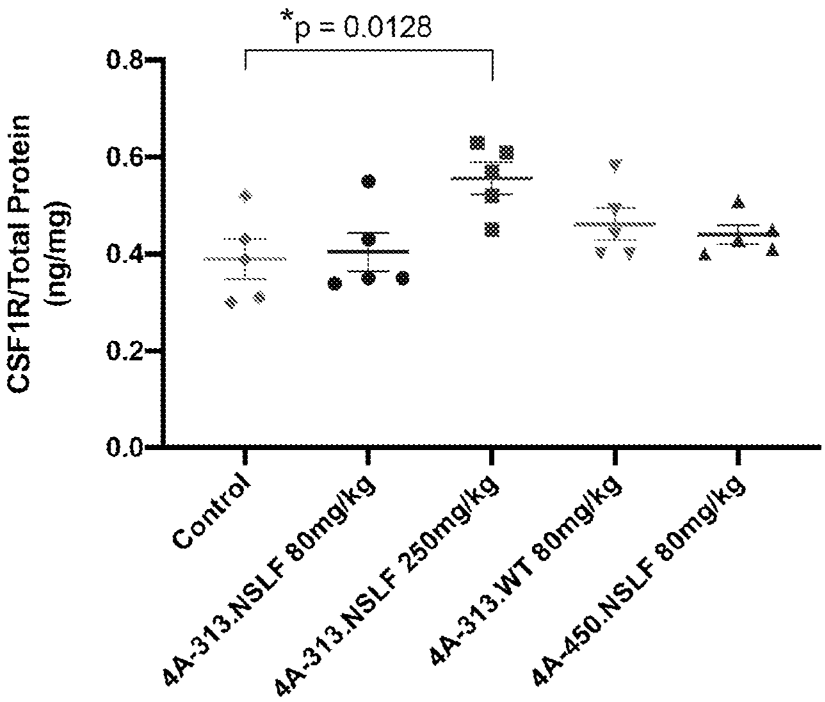

CSF1R levels in the brain tissue of cynomolgus monkeys increased after administration with anti-MS4A4A antibody 4A-313.NSLF. Repeat administration of antibody 4A-313.NSLF at 250 mg/kg resulted in significantly increased (p=0.046, t-test) CSF1R levels in the frontal cortex of cynomolgus monkeys when compared to that observed in control treated animals (FIG. 33A). Similarly, repeat administration of anti-MS4A4A antibody 4A-450.NSLF at 80 mg/kg resulted in significantly increased (p=0.013, t-test) CSF1R levels in the hippocampus of cynomolgus monkeys when compared to that observed in control animals (FIG. 33B).

Taken together, these results showed that anti-MS4A4A antibodies of the present disclosure are effective at increasing CSF1R levels in brain tissue (e.g., frontal cortex and hippocampus) in non-human primates.

Example 46: Anti-MS4A4A Antibodies Increase Total TREM2 Levels in Various Brain Regions In Vivo To examine the effect of anti-MS4A4A antibodies of the present disclosure on soluble TREM2 and membrane TREM2 (total TREM2) levels in frontal cortex and hippocampus in vivo, the following studies were performed.

Cynomolgus monkeys were administered anti-MS4A4A antibodies, 4A-313.NSLF, 4A-313.WT, 4A-450.NSLF at doses of 80 mg/kg, 4A-313.NSLF at doses of 250 mg/kg, or vehicle control by intravenous bolus injection. Each group was administered a total of four doses; the first and second doses separated by an interval of 7 days, the second and third doses separated by an interval of 14 days, and the third and fourth doses separated by an interval of 28 days. The animals were euthanized 48 hours after the fourth dose and the frontal cortex and hippocampus were removed and frozen. The total TREM2 levels were measured in these brain regions.

Figure 34A:
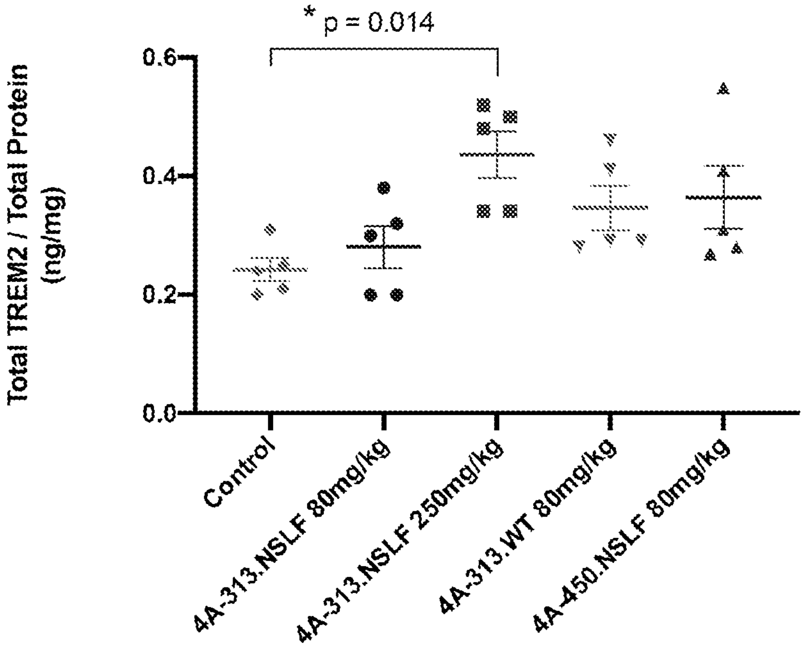
FIGS. 34A and 34B set forth data showing increased total TREM2 protein levels in frontal cortex and hippocampus, respectively, in cynomolgus monkey brains following administration of anti-MS4A4A antibodies of the present disclosure.
Figure 34B:
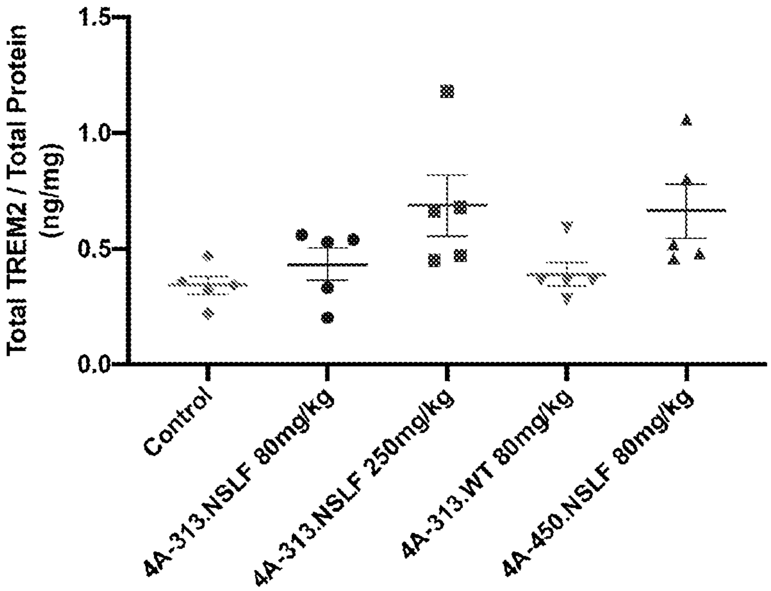

Total TREM2 levels in the brain tissue of cynomolgus monkeys increased after treatment with anti-MS4A4A antibodies, 4A-313.NSLF, 4A-313.WT, and 4A-450.NSLF. Repeat administration of antibody 4A-313.NSLF at 250 mg/kg resulted in a statistically significant increase (p=0.014, 1-way ANOVA) in total TREM2 levels in the hippocampus of cynomolgus monkeys compared to that observed in control treated animals (FIG. 34A). Repeat administration of antibody 4A-313.NSLF at 250 mg/kg and antibody 4A-313.WT at 80 mg/kg resulted in a trend in increased TREM2 levels in the frontal cortex of cynomolgus monkeys when compared to that observed in control treated animals (FIG. 34B).

Taken together, these results showed that anti-MS4A4A antibodies of the present disclosure are effective at increasing TREM2 levels in brain tissue (e.g., frontal cortex and hippocampus) in non-human primates.

Example 47: Effect of Anti-MS4A4A Antibodies on Gene Expression Profile in Microglia In Vivo Changes in gene expression as measured by microglia RNAseq analysis following administration of anti-MS4A4A antibodies of the present disclosure to cynomolgus monkeys as described above was performed as follows. The anti-MS4A4A antibodies included antibody 4A-313.WT (80 mg/kg), 4A-313.NSLF (80 mg/kg and 250 mg/kg), and 4A-450.NSLF (80 mg/kg). After terminal take down of the animals, frontal cortex samples were dissociated using a gentle manual dissociation protocol followed by Percoll gradient separation to remove debris. Cell pellet was stained with CdIIb antibodies for 20 minutes, washed, labeled with DAPI and processed for FACS isolation of microglia. $DAPI^{-}$:$CD11b^{+}$ cells were sorted directly into 350 ul or RLT plus buffer (Qiagen) and cells were processed immediately for RNA isolation. RNA quality was determined using tape station and libraries were generated using the low input protocol for Lexogen QuantSeq with mild modifications. Libraries were quantitated using tape station and sequenced using Next Seq. Sequenced data was demultiplexed using Lexogen multiple error correction tool and analyzed.

Figure 35A:
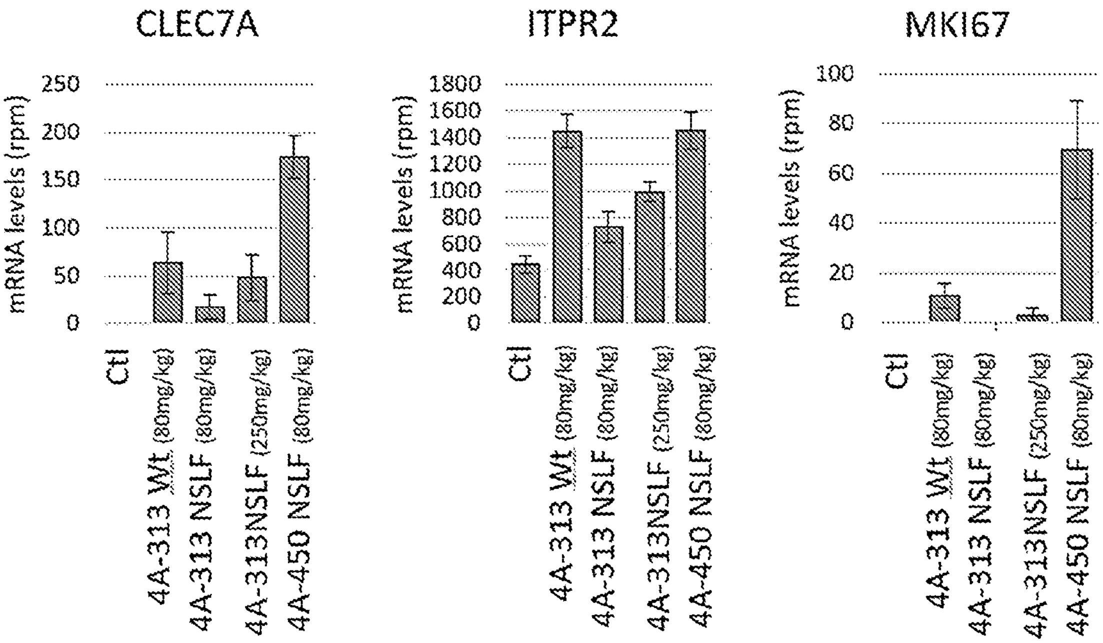
FIGS. 35A, 35B, and 35C set forth data showing changes in mRNA levels in markers of microglia activation, migration, and proliferation in microglia isolated from the brains of cynomolgus monkeys administered anti-MS4A4A antibodies of the present disclosure.
Figure 35B:
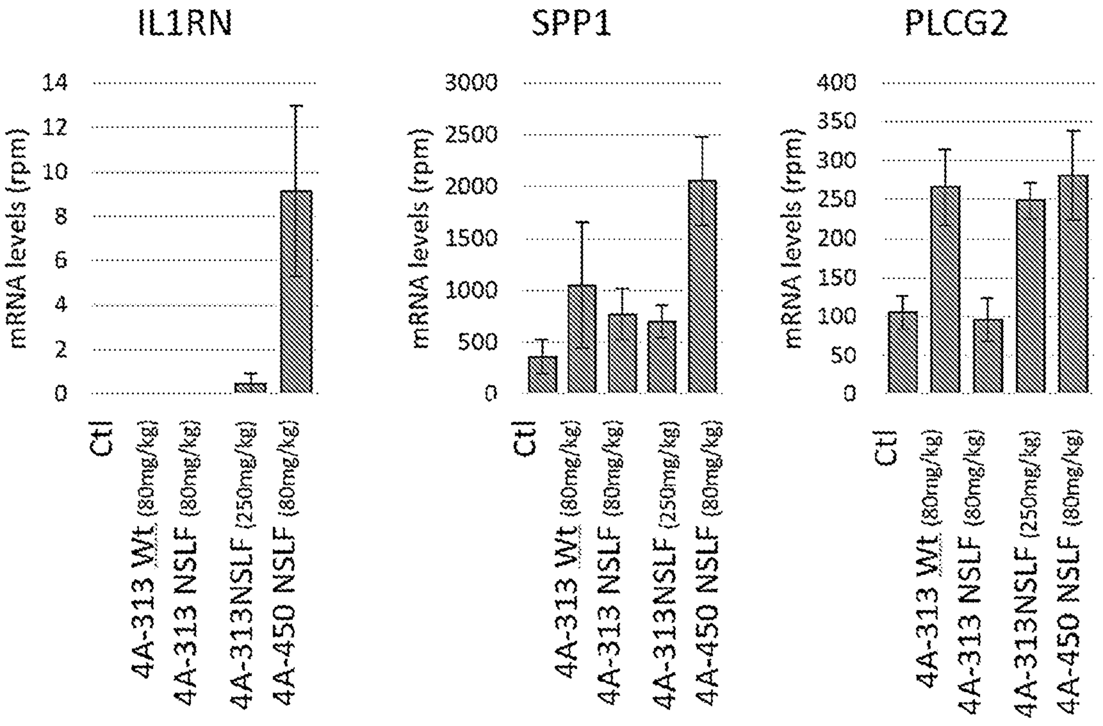
Figure 35C:
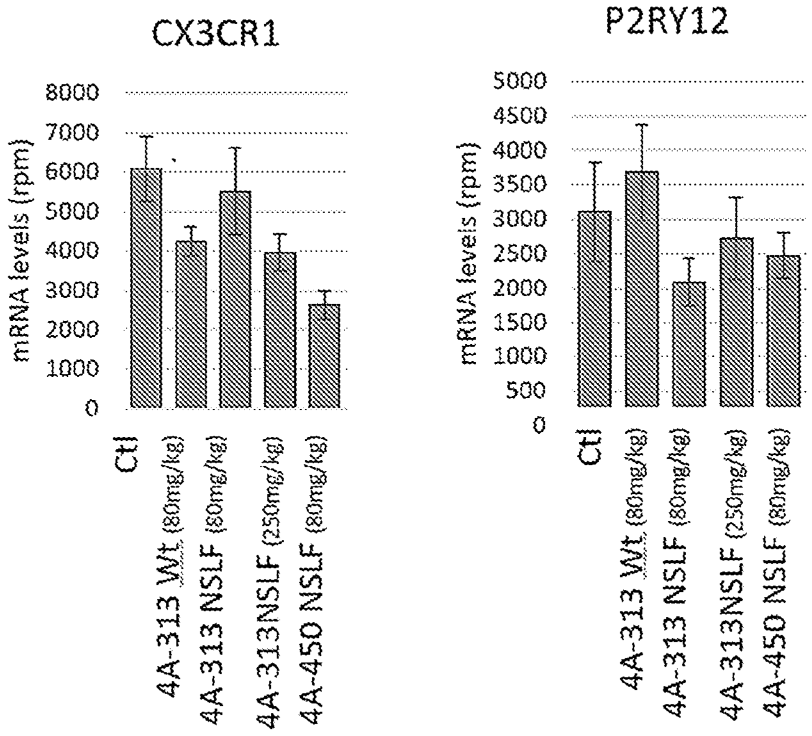

As shown in FIGS. 35A, 35B, and 35C, peripheral injection of anti-MS4A4A antibodies of the present disclosure in cynomolgus monkeys resulted in gene expression changes in microglia as measured by RNAseq analysis in FACS-sorted microglia isolated from the frontal cortex of these non-human primates. Among the genes showing a strong induction by anti-MS4A4A antibody treatment in microglia are markers of microglia activation (C-type lectin domain family 7 member A, CLEC7A), microglia migration (inositol 1,4,5-triphosphate receptor 2, ITPR2), and microglia proliferation (antigen KI-67 (MKI67)) (FIG. 35A). Changes in additional markers of microglia activation were also observed, and included microglia activation markers IL1RN, SPP1, and 1-phosphatidylinositol-4,5-bisphosphate phosphodiesterase gamma-2 (PLCG2) as shown in FIG. 35B. FIG. 35C. The effect of anti-MS4A4A antibodies of the present disclosure on two homeostatic microglia markers (purinergic receptor P2RY12 and CX3C chemokine receptor 1 (CX3CR1)) is shown in FIG. 35C, where the expression levels of these two homeostatic microglia makers decreased following anti-MS4A4A antibody treatment. Data in FIGS. 35A, 35B, and 35C are presented as means on log 2 scale, error bars are SEM, and N=5 per experimental group and per timepoint.

Taken together, these results showed that anti-MS4A4A antibodies of the present disclosure are effective at activating microglia in vivo as evidenced by increases in various mRNA levels of proteins associated with microglia activation, migration, and proliferation; and by decreases in various mRNA levels of proteins associated with microglia homeostasis.

Example 48: Anti-MS4A4A Antibodies Decrease Surface Expression of HA-Snorkel-Tagged MS4A4A on U937 Cells U937 cells (ATCC CRL-1593.2) were transfected with an expression plasmid encoding for human MS4A4A tagged with a snorkel tag (a transmembrane domain followed by a HA-tag was attached to the cytoplasmic C-terminus of the human MS4A4A). In this way the tag is displayed extracellularly, but structurally separate from the membrane protein. Transfected U937 cells were viable after plasmid transfection and antibiotic selection. The cells were then screened for human MS4A4A protein cell surface expression using flow cytometry, and only the 5% most positive cells were collected for use in the following studies.

U937 cells overexpressing recombinant human MS4A4A-snorkel, generated as described above, were used as target cells in these studies. Cells were pretreated for 24 hours with PMA (25 ng/ml), then harvested and seeded at 100,000 cells/well in round-bottom 96 well plates, in RPMI 1640 media complete, with PMA and anti-MS4A4A antibodies and isotype control antibody at the final concentrations of 0.01, 0.1, and 1 ug/ml. Cells were incubated for 48 hours. Cells were washed with cold FACS buffer (PBS+2% FBS) and 50 μL of 1:200 diluted anti-HA Tag Monoclonal Antibody (ThermoFisher, A-21287) was added per well and incubated on ice for 30 minutes, cells were also labeled with Aqua Live/Dead for viability discrimination. Cells were washed 2× with cold FACS buffer and resuspended in 2004 of FACS buffer. Flow cytometry analysis was performed on a FACSCanto system (BD Biosciences). Binding data was analyzed using Median fluorescent intensity.

Figure 36:
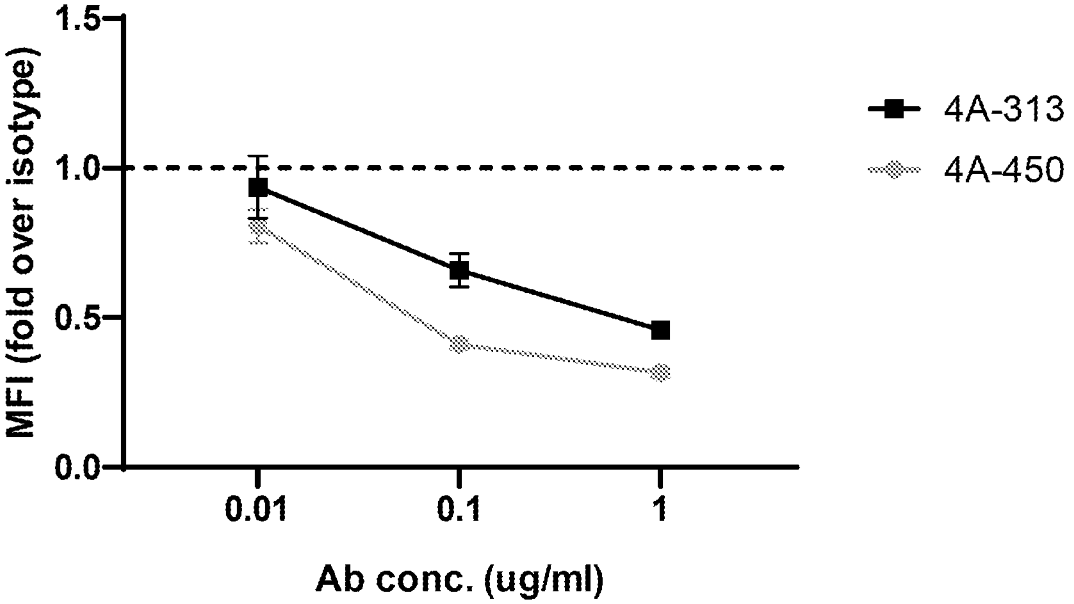
FIG. 36 sets forth data showing anti-MS4A4A antibodies of the present disclosure decrease cell surface expression of HA-Snorkel-tagged MS4A4A protein recombinantly expressed in U937 cells.

As shown in FIG. 36, anti-MS4A4A antibodies 4A-313.NSLF an d4A-450.NSLF decreased the level of plasma membrane MS4A4A in U937 cells expressing human MS4A4A-snorkel-tagged protein in a dose related fashion. At the highest anti-MS4A4A antibody concentration of 1 μg/ml, anti-MS4A4A antibodies 4A-313.NSLF and 4A-450.NSLF decreased surface MS4A4A levels by approximately 50% compared to that observed in cells treated with isotype control antibody. These results showed that the anti-MS4A4A antibodies of the present disclosure decreased or downregulated cell surface MS4A4A levels in U937 cells expressing recombinant human MS4A4A-snorkel.

Example 49: Anti-MS4A4A Antibodies Modulate Glycoprotein Nonmetastatic Melanoma Protein B (GPNMB) Protein Levels in Primary Human Myeloid Cells GPNMB is a surface glycoprotein expressed in multiple cell types including tissue macrophages and microglia. Several genetic variants have been associated with Parkinson's disease (PD) risk. GPNMB protein levels are elevated in the substantia nigra of PD patients and GPNMB levels are increased following lysosomal stress (Moloney et. al., 2018, Neurobio Dis. 120: 1-11). Additionally, increased expression of GPNMB was linked to SNP rs199347, this risk SNP being located withing the GPNMB gene (Murthy et al, 2017, 18:121-133). To determine whether MS4A4A may modulate the expression levels of GPNMB, human primary macrophages from two donors (donor #1117 and #1118) were treated with various concentrations of anti-MS4A4A antibody 4A-313.NSLF for 48 hours. Cell surface (membrane bound) GPNMB was measured by flow cytometry after cells were stained with an anti-GPNMB antibody conjugated with fluorophores.

Figure 37:
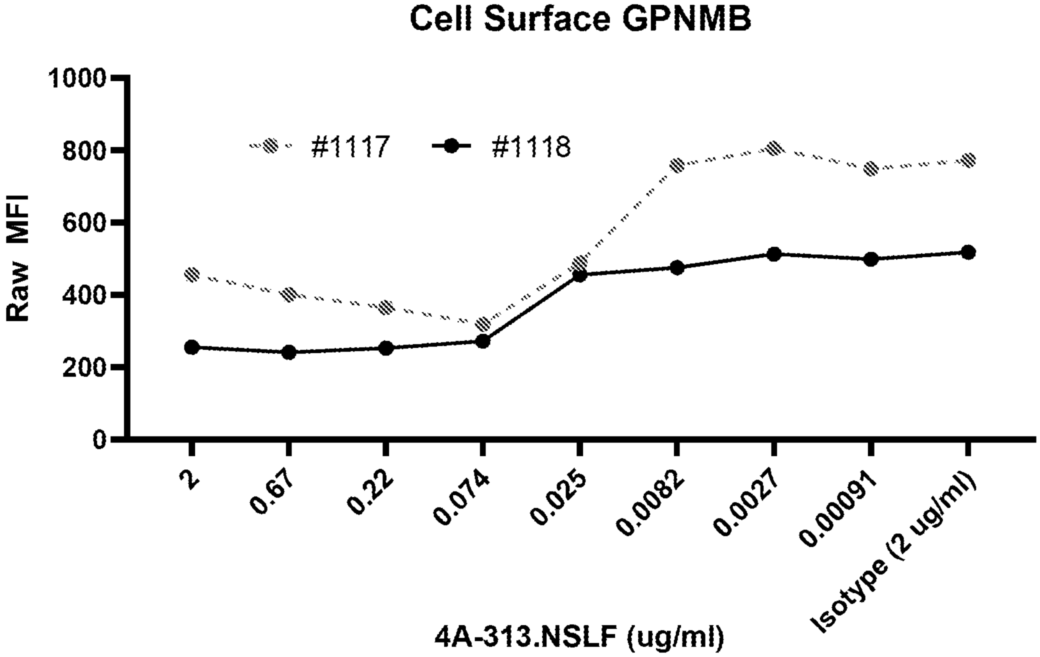
FIG. 37 sets forth data showing anti-MS4A4A antibody of the present disclosure reduced GPNMB cell surface expression in primary human macrophages.

As shown in FIG. 37, membrane GPNMB levels decreased in human primary macrophages following addition to the cells of anti-MS4A4A antibody 4A.313.NSLF. The decrease in GPNMB levels in response to anti-MS4A4A antibody treatment was dose-dependent manner. These results showed that anti-MS4A4A antibodies of the present disclosure are effective at decreasing cell surface expression levels of GPNMB in myeloid cells, e.g., macrophages.

Exemplary anti-MS4A4A antibody heavy chain amino acid sequences having wildtype huIgG1 or Fc variants of wildtype huIgG1:

4A-450 (huIgG1 heavy chain)
(SEQ ID NO: 320)
QVQLVQSGSELKKPGASVKVSCKASGYAFTSYGLSWVRQAPGQGLEWMGWINTYSGVPTYAQGFTGRFV
FSLDTSVSTAYLQISSLKAEDTAVYYCARTMADYWGQGTLVTVSSASTKGPSVFPLAPSSKSTSGGTAALG
CLVKDYFPEPVTVSWNSGALTSGVHTFPAVLQSSGLYSLSSVVTVPSSSLGTQTYICNVNHKPSNTKVDKK
VEPKSCDKTHTCPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPREPQVYTLPPSRD
ELTKNQVSLTCLVKGFYPSDIAVEWESNGQPENNYKTTPPVLDSDGSFFLYSKLTVDKSRWQQGNVFSCSV
MHEALHNHYTQKSLSLSPGK 4A-450 (huIgG1 heavy chain without C-terminal K)
(SEQ ID NO: 321)
QVQLVQSGSELKKPGASVKVSCKASGYAFTSYGLSWVRQAPGQGLEWMGWINTYSGVPTYAQGFTGRFV
FSLDTSVSTAYLQISSLKAEDTAVYYCARTMADYWGQGTLVTVSSASTKGPSVFPLAPSSKSTSGGTAALG
CLVKDYFPEPVTVSWNSGALTSGVHTFPAVLQSSGLYSLSSVVTVPSSSLGTQTYICNVNHKPSNTKVDKK
VEPKSCDKTHTCPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPREPQVYTLPPSRD
ELTKNQVSLTCLVKGFYPSDIAVEWESNGQPENNYKTTPPVLDSDGSFFLYSKLTVDKSRWQQGNVFSCSV
MHEALHNHYTQKSLSLSPG 4A-450 (hIgG1 heavy chain; P331S)
(SEQ ID NO: 322)
QVQLVQSGSELKKPGASVKVSCKASGYAFTSYGLSWVRQAPGQGLEWMGWINTYSGVPTYAQGFTGRFV
FSLDTSVSTAYLQISSLKAEDTAVYYCARTMADYWGQGTLVTVSSASTKGPSVFPLAPSSKSTSGGTAALG
CLVKDYFPEPVTVSWNSGALTSGVHTFPAVLQSSGLYSLSSVVTVPSSSLGTQTYICNVNHKPSNTKVDKK
VEPKSCDKTHTCPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPASIEKTISKAKGQPREPQVYTLPPSRD
ELTKNQVSLTCLVKGFYPSDIAVEWESNGQPENNYKTTPPVLDSDGSFFLYSKLTVDKSRWQQGNVFSCSV
MHEALHNHYTQKSLSLSPGK 4A-450 (hIgG1 heavy chain P331S without C-terminal K)
(SEQ ID NO: 323)
QVQLVQSGSELKKPGASVKVSCKASGYAFTSYGLSWVRQAPGQGLEWMGWINTYSGVPTYAQGFTGRFV
FSLDTSVSTAYLQISSLKAEDTAVYYCARTMADYWGQGTLVTVSSASTKGPSVFPLAPSSKSTSGGTAALG
CLVKDYFPEPVTVSWNSGALTSGVHTFPAVLQSSGLYSLSSVVTVPSSSLGTQTYICNVNHKPSNTKVDKK
VEPKSCDKTHTCPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPASIEKTISKAKGQPREPQVYTLPPSRD
ELTKNQVSLTCLVKGFYPSDIAVEWESNGQPENNYKTTPPVLDSDGSFFLYSKLTVDKSRWQQGNVFSCSV
MHEALHNHYTQKSLSLSPG 4A-450 (huIgG1 heavy chain N325S/L328F)
(SEQ ID NO: 324)
QVQLVQSGSELKKPGASVKVSCKASGYAFTSYGLSWVRQAPGQGLEWMGWINTYSGVPTYAQGFTGRFV
FSLDTSVSTAYLQISSLKAEDTAVYYCARTMADYWGQGTLVTVSSASTKGPSVFPLAPSSKSTSGGTAALG
CLVKDYFPEPVTVSWNSGALTSGVHTFPAVLQSSGLYSLSSVVTVPSSSLGTQTYICNVNHKPSNTKVDKK
VEPKSCDKTHTCPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSSKAFPAPIEKTISKAKGQPREPQVYTLPPSRD
ELTKNQVSLTCLVKGFYPSDIAVEWESNGQPENNYKTTPPVLDSDGSFFLYSKLTVDKSRWQQGNVFSCSV
MHEALHNHYTQKSLSLSPGK -continued 4A-450 (hIgG1 heavy chain N325S/L328F without C-terminal K)
(SEQ ID NO: 325)
QVQLVQSGSELKKPGASVKVSCKASGYAFTSYGLSWVRQAPGQGLEWMGWINTYSGVPTYAQGFTGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSSKAFPAPIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPG 4A-450 (huIgG1 heavy chain K322A)
(SEQ ID NO: 326)
QVQLVQSGSELKKPGASVKVSCKASGYAFTSYGLSWVRQAPGQGLEWMGWINTYSGVPTYAQGFTGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCAVSNKALPAPIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPGK 4A-450 (huIgG1 heavy chain K322A without C-terminal K)
(SEQ ID NO: 327)
QVQLVQSGSELKKPGASVKVSCKASGYAFTSYGLSWVRQAPGQGLEWMGWINTYSGVPTYAQGFTGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCAVSNKALPAPIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPG

********

4A-419 (huIgG1 heavy chain)
(SEQ ID NO: 328)
QVQLVQSGSELKKPGASVKVSCKASGYRFTSYGLSWVRQAPGQGLEWMGWINTYSGVPTYAQGFKGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPGK 4A-419 (huIgG1 heavy chain without C-terminal K)
(SEQ ID NO: 329)
QVQLVQSGSELKKPGASVKVSCKASGYRFTSYGLSWVRQAPGQGLEWMGWINTYSGVPTYAQGFKGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

-continued

NAKTKPREEQYNSTYRVVSVLTVLHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPG 4A-419 (hIgG1 heavy chain P331S)
(SEQ ID NO: 330)
QVQLVQSGSELKKPGASVKVSCKASGYRFTSYGLSWVRQAPGQGLEWMGWINTYSGVPTYAQGFKGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPASIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPGK 4A-419 (hIgG1 heavy chain P331S without C-terminal K)
(SEQ ID NO: 331)
QVQLVQSGSELKKPGASVKVSCKASGYRFTSYGLSWVRQAPGQGLEWMGWINTYSGVPTYAQGFKGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPASIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPG 4A-419 (huIgG1 heavy chain N325S/L328F)
(SEQ ID NO: 332)
QVQLVQSGSELKKPGASVKVSCKASGYRFTSYGLSWVRQAPGQGLEWMGWINTYSGVPTYAQGFKGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSSKAFPAPIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPGK 4A-419 (hIgG1 heavy chain N325S/L328F without C-terminal K)
(SEQ ID NO: 333)
QVQLVQSGSELKKPGASVKVSCKASGYRFTSYGLSWVRQAPGQGLEWMGWINTYSGVPTYAQGFKGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSSKAFPAPIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPG 4A-419 (huIgG1 heavy chain K322A)
(SEQ ID NO: 334)
QVQLVQSGSELKKPGASVKVSCKASGYRFTSYGLSWVRQAPGQGLEWMGWINTYSGVPTYAQGFKGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

-continued

NAKTKPREEQYNSTYRVVSVLTVLHQDWLNGKEYKCAVSNKALPAPIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPGK 4A-419 (huIgG1 heavy chain K322A without C-terminal K)
(SEQ ID NO: 335)
QVQLVQSGSELKKPGASVKVSCKASGYRFTSYGLSWVRQAPGQGLEWMGWINTYSGVPTYAQGFKGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCAVSNKALPAPIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPG

********

4A-313 (huIgG1 heavy chain constant region)
(SEQ ID NO: 336)
ASTKGPSVFPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK 4A-313 (huIgG1 heavy chain constant region without C-terminal K)
(SEQ ID NO: 337)
ASTKGPSVFPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPG 4A-313 (hIgG1 heavy chain constant region P331S)
(SEQ ID NO: 338)
ASTKGPSVFPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEYKCKVSNKALPA

SIEKTISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK 4A-313 (hIgG1 heavy chain constant region P331S without C-terminal K)
(SEQ ID NO: 339)
ASTKGPSVFPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEYKCKVSNKALPA

SIEKTISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPG 4A-313 (huIgG1 heavy chain constant region N325S/L328F)
(SEQ ID NO: 340)
ASTKGPSVFPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEYKCKVSSKAFPA

-continued

PIEKTISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK 4A-313 (hIgG1 heavy chain constant region N325S/L328F without C-terminal K)

(SEQ ID NO: 341)

ASTKGPSVFPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEYKCKVSSKAFPA

PIEKTISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPG 4A-313 (huIgG1 heavy chain constant region K322A)

(SEQ ID NO: 342)

ASTKGPSVFPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEYKCAVSNKALPA

PIEKTISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK 4A-313 (huIgG1 heavy chain constant region K322A without C-terminal K)

(SEQ ID NO: 343)

ASTKGPSVFPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEYKCAVSNKALPA

PIEKTISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPG

********

Human IgG1 Light Chain Constant Region (SEQ ID NO: 344)

RTVAAPSVFIFPPSDEQLKSGTASVVCLLNNFYPREAKVQWKVDNALQSGNSQESVTEQDSKDS

TYSLSSTLTLSKADYEKHKVYACEVTHQGLSSPVTKSFNRGEC

********

4A-313 (huIgG1 heavy chain)

(SEQ ID NO: 355)

QVQLVQSGAEVKKPGASVKVSCKASGYTFTNYWMQWVRQAPGQGLEWMGATHPGHGDTRYAQKFQGR

VTMTRDTSTSTVYMELSSLRSEDTAVYYCAREEVYYGFRSYWYFDLWGRGTLVTVSSASTKGPSVFPLAP

SSKSTSGGTAALGCLVKDYFPEPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVSNKALPAPIEKTISKAKGQP

REPQVYTLPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPGK 4A-313 (huIgG1 heavy chain without C-terminal K)

(SEQ ID NO: 356)

QVQLVQSGAEVKKPGASVKVSCKASGYTFTNYWMQWVRQAPGQGLEWMGATHPGHGDTRYAQKFQGR

VTMTRDTSTSTVYMELSSLRSEDTAVYYCAREEVYYGFRSYWYFDLWGRGTLVTVSSASTKGPSVFPLAP

SSKSTSGGTAALGCLVKDYFPEPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVSNKALPAPIEKTISKAKGQP

-continued

REPQVYTLPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPG 4A-313 (hIgG1 heavy chain P331S)

(SEQ ID NO: 357)

QVQLVQSGAEVKKPGASVKVSCKASGYTFTNYWMQWVRQAPGQGLEWMGATHPGHGDTRYAQKFQGR

VTMTRDTSTSTVYMELSSLRSEDTAVYYCAREEVYYGFRSYWYFDLWGRGTLVTVSSASTKGPSVFPLAP

SSKSTSGGTAALGCLVKDYFPEPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVSNKALPASIEKTISKAKGQP

REPQVYTLPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPGK 4A-313 (hIgG1 heavy chain P331S without C-terminal K)

(SEQ ID NO: 358)

QVQLVQSGAEVKKPGASVKVSCKASGYTFTNYWMQWVRQAPGQGLEWMGATHPGHGDTRYAQKFQGR

VTMTRDTSTSTVYMELSSLRSEDTAVYYCAREEVYYGFRSYWYFDLWGRGTLVTVSSASTKGPSVFPLAP

SSKSTSGGTAALGCLVKDYFPEPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVSNKALPASIEKTISKAKGQP

REPQVYTLPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPG 4A-313 (huIgG1 heavy chain N325S/L328F)

(SEQ ID NO: 359)

QVQLVQSGAEVKKPGASVKVSCKASGYTFTNYWMQWVRQAPGQGLEWMGATHPGHGDTRYAQKFQGR

VTMTRDTSTSTVYMELSSLRSEDTAVYYCAREEVYYGFRSYWYFDLWGRGTLVTVSSASTKGPSVFPLAP

SSKSTSGGTAALGCLVKDYFPEPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVSSKAFPAPIEKTISKAKGQP

REPQVYTLPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPGK 4A-313 (hIgG1 heavy chain N325S/L328F without C-terminal K)

(SEQ ID NO: 360)

QVQLVQSGAEVKKPGASVKVSCKASGYTFTNYWMQWVRQAPGQGLEWMGATHPGHGDTRYAQKFQGR

VTMTRDTSTSTVYMELSSLRSEDTAVYYCAREEVYYGFRSYWYFDLWGRGTLVTVSSASTKGPSVFPLAP

SSKSTSGGTAALGCLVKDYFPEPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVSSKAFPAPIEKTISKAKGQP

REPQVYTLPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPG 4A-313 (huIgG1 heavy chain K322A)

(SEQ ID NO: 361)

QVQLVQSGAEVKKPGASVKVSCKASGYTFTNYWMQWVRQAPGQGLEWMGATHPGHGDTRYAQKFQGR

VTMTRDTSTSTVYMELSSLRSEDTAVYYCAREEVYYGFRSYWYFDLWGRGTLVTVSSASTKGPSVFPLAP

SSKSTSGGTAALGCLVKDYFPEPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCAVSNKALPAPIEKTISKAKGQP

-continued

REPEQVYTLPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPGK 4A-313 (huIgG1 heavy chain K322A without C-terminal K)

(SEQ ID NO: 362)

QVQLVQSGAEVKKPGASVKVSCKASGYTFTNYWMQWVRQAPGQGLEWMGATHPGHGDTRYAQKFQGR

VTMTRDTSTSTVYMELSSLRSEDTAVYYCAREEVYYGFRSYWYFDLWGRGTLVTVSSASTKGPSVFPLAP

SSKSTSGGTAALGCLVKDYFPEPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCAVSNKALPAPIEKTISKAKGQP

REPQVYTLPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPG

********

4A-450 - full length light chain (SEQ ID NO: 363)

DVVMTQSPLSLPVTLGQPASISCKSSRSLLYSAGKTYLSWFQQRPGQSPRRLIYLVSKLDSGVPDR

FSGSGSGTDFTLKISRVEAEDVGVYYCWQGIDFHQTFGGGTKVEIKRTVAAPSVFIFPPSDEQLKS

GTASVVCLLNNFYPREAKVQWKVDNALQSGNSQESVTEQDSKDSTYSLSSTLTLSKADYEKHK

VYACEVTHQGLSSPVTKSFNRGEC 4A-419 - full length light chain (SEQ ID NO: 364)

DVVMTQSPLSLPVTLGQPASISCKSSRSLLYSAGKTYLSWFQQRPGQSPRRLIYLVSKLDSGVPDR

FSGSGSGTDFTLKISRVEAEDVGVYYCWQGIDFHQTFGGGTKVEIKRTVAAPSVFIFPPSDEQLKS

GTASVVCLLNNFYPREAKVQWKVDNALQSGNSQESVTEQDSKDSTYSLSSTLTLSKADYEKHK

VYACEVTHQGLSSPVTKSFNRGEC 4A-313 - full length light chain (SEQ ID NO: 365)

EIVLTQSPATLSLSPGERATLSCRASESVDNYGVSRMNWYQQKPGQAPRLLIYGASNQGSGIPAR

FSGSGSGTDFTLTISSLEPEDFAVYYCQQSKEVPPTFGGGTKVEIKRTVAAPSVFIFPPSDEQLKSG

TASVVCLLNNFYPREAKVQWKVDNALQSGNSQESVTEQDSKDSTYSLSSTLTLSKADYEKHKV

YACEVTHQGLSSPVTKSFNRGEC

---

What is claimed is:

1. A method of detecting MS4A4A protein in an individual or in a tissue sample derived from an individual comprising contacting the individual or the tissue sample derived from an individual with an isolated antibody that binds to the MS4A4A protein, wherein the antibody comprises a heavy chain variable region and a light chain variable region, wherein the heavy chain variable region comprises: an HVR-H1 comprising an amino acid sequence of SEQ ID NO: 308; an HVR-H2 comprising an amino acid sequence of SEQ ID NO: 309; and an HVR-H3 comprising an amino acid sequence of SEQ ID NO: 310; and the light chain variable region comprises: an HVR-L1 comprising an amino acid sequence of SEQ ID NO: 314; an HVR-L2 comprising an amino acid sequence of SEQ ID NO: 315; and an HVR-L3 comprising an amino acid sequence of SEQ ID NO: 316.

2. The method of claim 1, wherein the individual is a human.

3. The method of claim 1, wherein the detecting comprises quantifying antigen-bound antibody.

4. The method of claim 1, wherein the detecting in the tissue sample is performed by immunofluorescence microscopy, immunocytochemistry, immunohistochemistry, ELISA, FACS analysis, immunoprecipitation, or micro-positron emission tomography.

5. The method of claim 1, wherein the detecting in the individual is performed by positron emission tomography (PET), X-ray computed tomography, single-photon emission computed tomography (SPECT), computed tomography (CT), or computed axial tomography (CAT).

6. The method of claim 1, wherein the antibody is radiolabeled.

7. The method of claim 1, wherein the antibody comprises a heavy chain variable region comprising the amino acid sequence of SEQ ID NO: 304, and a light chain variable region comprising the amino acid sequence of SEQ ID NO: 305.

8. The antibody method of claim 1, wherein the antibody is an antibody fragment.

9. The antibody method of claim 8, wherein the antibody fragment is a Fab, Fab', Fab'-SH, F(ab')2, Fv or scFv fragment.

10. A method of detecting MS4A4A protein in an individual or in a tissue sample derived from an individual comprising contacting the individual or the tissue sample derived from an individual with an isolated antibody that binds to the MS4A4A protein, wherein the antibody comprises a heavy chain variable region and a light chain variable region, wherein the heavy chain variable region comprises: an HVR-H1 comprising the amino acid sequence of SEQ ID NO: 94; an HVR-H2 comprising the amino acid sequence of SEQ ID NO: 96; and an HVR-H3 comprising the amino acid sequence of SEQ ID NO: 102; and the light chain variable region comprises: an HVR-L1 comprising the amino acid sequence of SEQ ID NO: 104; an HVR-L2 comprising the amino acid sequence of SEQ ID NO: 105; and an HVR-L3 comprising the amino acid sequence of SEQ ID NO: 107.

11. The method of claim 10, wherein the individual is a human.

12. The method of claim 10, wherein the detecting comprises quantifying antigen-bound antibody.

13. The method of claim 10, wherein the detecting in the tissue sample is performed by immunofluorescence microscopy, immunocytochemistry, immunohistochemistry, ELISA, FACS analysis, immunoprecipitation, or micro-positron emission tomography.

14. The method of claim 10, wherein the detecting in the individual is performed by positron emission tomography (PET), X-ray computed tomography, single-photon emission computed tomography (SPECT), computed tomography (CT), or computed axial tomography (CAT).

15. The method of claim 10, wherein the antibody is radiolabeled.

16. The method of claim 10, wherein the antibody comprises a heavy chain variable region comprising the amino acid sequence of SEQ ID NO: 14, and a light chain variable region comprising the amino acid sequence of SEQ ID NO: 22.

17. The antibody method of claim 10, wherein the antibody is an antibody fragment.

18. The antibody method of claim 17, wherein the antibody fragment is a Fab, Fab', Fab'-SH, F(ab')2, Fv or scFv fragment.

19. A method of detecting MS4A4A protein in an individual or in a tissue sample derived from an individual comprising contacting the individual or the tissue sample derived from an individual with an isolated antibody that binds to the MS4A4A protein, wherein the antibody comprises a heavy chain variable region comprising an HVR-H1, HVR-H2, and HVR-H3 and a light chain variable region comprising an HVR-L1, HVR-L2, and HVR-L3, wherein the antibody comprises the HVR-H1, HVR-H2, HVR-H3, HVR-L1, HVR-L2, and HVR-L3 of SEQ ID NOs: 94, 98, 100, 103, 105, and 107, respectively; SEQ ID NOs: 94, 96, 101, 103, 106, and 107, respectively; SEQ ID NOs: 94, 99, 100, 104, 105, and 107, respectively; SEQ ID NOs: 116, 118, 124, 130, 139, and 144, respectively; SEQ ID NOs: 116, 118, 124, 132, 139, and 144, respectively; SEQ ID NOs: 116, 118, 124, 133, 139, and 144, respectively; SEQ ID NOs: 116, 118, 124, 136, 139, and 144, respectively; SEQ ID NOs: 116, 118, 124, 130, 139, and 145, respectively; SEQ ID NOs: 116, 118, 124, 138, 141, and 144, respectively; SEQ ID NOs: 116, 118, 124, 130, 141, and 144, respectively; SEQ ID NOs: 116, 118, 125, 130, 139, and 145, respectively; SEQ ID NOs: 116, 118, 127, 131, 139, and 144, respectively; SEQ ID NOs: 116, 118, 129, 131, 139, and 144, respectively; SEQ ID NOs: 116, 118, 129, 132, 139, and 144, respectively; SEQ ID NOs: 116, 118, 129, 133, 139, and 144, respectively; SEQ ID NOs: 116, 118, 129, 134, 139, and 144, respectively; SEQ ID NOs: 116, 118, 129, 135, 139, and 144, respectively; SEQ ID NOs: 116, 118, 129, 136, 139, and 144, respectively; SEQ ID NOs: 147, 149, 154, 156, 160, and 163, respectively; SEQ ID NOs: 146, 150, 154, 156, 160, and 163, respectively; SEQ ID NOs: 147, 149, 154, 157, 159, and 163, respectively; SEQ ID NOs: 147, 151, 154, 156, 160, and 163, respectively; SEQ ID NOs: 147, 151, 154, 158, 159, and 163, respectively; SEQ ID NOs: 146, 152, 154, 156, 161, and 163, respectively; SEQ ID NOs: 146, 153, 154, 158, 159, and 163, respectively; or SEQ ID NOs: 311, 312, 313, 317, 318, and 319, respectively.

20. The method of claim 19, wherein the individual is a human.

21. The method of claim 19, wherein the detecting comprises quantifying antigen-bound antibody.

22. The method of claim 19, wherein the detecting in the tissue sample is performed by immunofluorescence microscopy, immunocytochemistry, immunohistochemistry, ELISA, FACS analysis, immunoprecipitation, or micro-positron emission tomography.

23. The method of claim 19, wherein the detecting in the individual is performed by positron emission tomography (PET), X-ray computed tomography, single-photon emission computed tomography (SPECT), computed tomography (CT), or computed axial tomography (CAT).

24. The method of claim 19, wherein the antibody is radiolabeled.

25. The antibody of claim 19, wherein the antibody comprises a heavy chain variable region and a light chain variable region, wherein the heavy chain variable region and the light chain variable region comprise the amino acid sequences of SEQ ID NOs: 12 and 17, respectively; SEQ ID NOs: 13 and 21, respectively; SEQ ID NOs: 15 and 22, respectively; SEQ ID NOs: 47 and 55, respectively; SEQ ID NOs: 47 and 63, respectively; SEQ ID NOs: 47 and 64, respectively; SEQ ID NOs: 47 and 67, respectively; SEQ ID NOs: 47 and 69, respectively; SEQ ID NOs: 47 and 71, respectively; SEQ ID NOs: 47 and 73, respectively; SEQ ID NOs: 48 and 69, respectively; SEQ ID NOs: 50 and 62, respectively; SEQ ID NOs: 53 and 62, respectively; SEQ ID NOs: 53 and 63, respectively; SEQ ID NOs: 53 and 64, respectively; SEQ ID NOs: 53 and 65, respectively; SEQ ID NOs: 53 and 66, respectively; SEQ ID NOs: 53 and 67, respectively; SEQ ID NOs: 76 and 86, respectively; SEQ ID NOs: 77 and 87, respectively; SEQ ID NOs: 78 and 88, respectively; SEQ ID NOs: 79 and 89, respectively; SEQ ID NOs: 80 and 90, respectively; SEQ ID NOs: 81 and 91, respectively; SEQ ID NOs: 82 and 91, respectively; SEQ ID NOs: 83 and 92, respectively; SEQ ID NOs: 84 and 93, respectively; or SEQ ID NOs: 306 and 307, respectively.

26. The antibody method of claim 19, wherein the antibody is an antibody fragment.

27. The antibody method of claim 26, wherein the antibody fragment is a Fab, Fab', Fab'-SH, F(ab')2, Fv or scFv fragment.

* * * * *